US011002729B2

(12) United States Patent
Li et al.

(10) Patent No.: US 11,002,729 B2
(45) Date of Patent: May 11, 2021

(54) CD2-ASSOCIATED PROTEIN (CD2AP) AND ITS INTERACTIVE PROTEINS

(71) Applicant: WUHAN INSTITUTE OF VIROLOGY, CHINESE ACADEMY OF SCIENCES, Wuhan (CN)

(72) Inventors: Chaoyang Li, Wuhan (CN); Huixia Zhang, Wuhan (CN)

(73) Assignee: WUHAN INSTITUTE OF VIROLOGY, CHINESE ACADEMY OF SCIENCES, Wuhan (CN)

( * ) Notice: Subject to any disclaimer, the term of this patent is extended or adjusted under 35 U.S.C. 154(b) by 0 days.

(21) Appl. No.: 16/345,719

(22) PCT Filed: Jun. 14, 2017

(86) PCT No.: PCT/CN2017/088258
§ 371 (c)(1),
(2) Date: Apr. 28, 2019

(87) PCT Pub. No.: WO2018/227432
PCT Pub. Date: Dec. 20, 2018

(65) Prior Publication Data
US 2019/0353642 A1    Nov. 21, 2019

(51) Int. Cl.
| | |
|---|---|
| C07H 21/04 | (2006.01) |
| G01N 33/50 | (2006.01) |
| A61K 38/08 | (2019.01) |
| A61K 38/10 | (2006.01) |
| A61K 38/17 | (2006.01) |
| C12N 15/113 | (2010.01) |

(52) U.S. Cl.
CPC ......... *G01N 33/5041* (2013.01); *A61K 38/08* (2013.01); *A61K 38/10* (2013.01); *A61K 38/17* (2013.01); *C12N 15/113* (2013.01); *C12N 2310/14* (2013.01); *C12N 2310/20* (2017.05)

(58) Field of Classification Search
None
See application file for complete search history.

(56) References Cited

PUBLICATIONS

Li ("CD2AP facilitates HCV production by targeting NS5A to lipid droplets and regulating lipid droplet biogenesis," FASEB Journal, vol. 31, No. 1 supplement, Abstract 184.1, Apr. 2017) (Year: 2017).*
Hyvönen, Mervi E., et al. ("CD2AP is associated with end-stage renal disease in patients with type 1 diabetes." Acta diabetologica 50.6 (2013): 887-897).*
Park, Hye-Young, et al. ("CD2-associated protein/phosphoinositide 3-kinase signaling has a preventive role in angiotensin II-induced podocyte apoptosis." The international journal of biochemistry & cell biology 79 (2016): 370-381).*
Choo QL, Kuo G, Weiner AJ, Overby LR, Bradley DW, Houghton M. 1989. Isolation of a cDNA clone derived from a blood-borne non-A, non-B viral hepatitis genome. Science 244:359-362.
Rosen HR. 2011. Clinical practice. Chronic hepatitis C infection. The New England journal of medicine 364:2429-2438.
Lohmann V, Korner F, Koch J, Herian U, Theilmann L, Bartenschlager R. 1999. Replication of subgenomic hepatitis C virus RNAs in a hepatoma cell line. Science 285:110-113.
Romero-Brey I, Merz A, Chiramel A, Lee JY, Chlanda P, Haselman U, Santarella-Mellwig R, Habermann A, Hoppe S, Kallis S, Walther P, Antony C, Krijnse-Locker J, Bartenschlager R. 2012. Three-dimensional architecture and biogenesis of membrane structures associated with hepatitis C virus replication. PLoS pathogens 8:e1003056.
Ferraris P, Beaumont E, Uzbekov R, Brand D, Gaillard J, Blanchard E, Roingeard P. 2013. Sequential biogenesis of host cell membrane rearrangements induced by hepatitis C virus infection. Cellular and molecular life sciences : CMLS 70:1297-1306.
Appel N, Zayas M, Miller S, Krijnse-Locker J, Schaller T, Friebe P, Kallis S, Engel U, Bartenschlager R. 2008. Essential role of domain III of nonstructural protein 5A for hepatitis C virus infectious particle assembly. PLoS pathogens 4:e1000035.
Miyanari Y, Atsuzawa K, Usuda N, Watashi K, Hishiki T, Zayas M, Bartenschlager R, Wakita T, Hijikata M, Shimotohno K. 2007. The lipid droplet is an important organelle for hepatitis C virus production. Nature cell biology 9:1089-1097.
Shi ST, Polyak SJ, Tu H, Taylor DR, Gretch DR, Lai MM. 2002. Hepatitis C virus NS5A colocalizes with the core protein on lipid droplets and interacts with apolipoproteins. Virology 292:198-210.
Abid K, Pazienza V, de Gottardi A, Rubbia-Brandt L, Conne B, Pugnale P, Rossi C, Mangia A, Negro F. 2005. An in vitro model of hepatitis C virus genotype 3a-associated triglycerides accumulation. Journal of hepatology 42:744-751.
Hinson ER, Cresswell P. 2009. The antiviral protein, viperin, localizes to lipid droplets via its N-terminal amphipathic alpha-helix. Proceedings of the National Academy of Sciences of the United States of America 106:20452-20457.
Masaki T, Suzuki R, Murakami K, Aizaki H, Ishii K, Murayama A, Date T, Matsuura Y, Miyamura T, Wakita T. 2008. Interaction of hepatitis C virus nonstructural protein 5A with core protein is critical for the production of infectious virus particles. Journal of virology 82:7964-7976.
Lai CK, Jeng KS, Machida K, Lai MM. 2008. Association of hepatitis C virus replication complexes with microtubules and actin filaments is dependent on the interaction of NS3 and NS5A. Journal of virology 82:8838-8848.
Eyre NS, Fiches GN, Aloia AL, Helbig KJ, McCartney EM, McErlean CS, Li K, Aggarwal A, Turville SG, Beard MR. 2014. Dynamic imaging of the hepatitis C virus NS5A protein during a productive infection. Journal of virology 88:3636-3652.

(Continued)

*Primary Examiner* — Kimberly Chong
(74) *Attorney, Agent, or Firm* — YIHE Intellectual Property Service Company

(57) ABSTRACT

A method for down-regulating CD2AP expression in a subject comprises administering a CD2AP down-regulation composition to the subject, wherein the CD2AP down regulation composition is workable by way of siRNA/shRNA, CRISPR/Cas9, Talen or ZFNs; thereby the CD2AP expression in liver tissues of the subject is down-regulated.

6 Claims, 29 Drawing Sheets

Specification includes a Sequence Listing.

(56) References Cited

PUBLICATIONS

Lai C-K, Saxena V, Tseng C-H, Jeng K-S, Kohara M, Lai MM. 2014. Nonstructural protein 5A is incorporated into hepatitis C virus low-density particle through interaction with core protein and microtubules during intracellular transport. PloS one 9:e99022.

Tilg H, Moschen AR, Roden M. 2017. NAFLD and diabetes mellitus. Nature Reviews Gastroenterology & Hepatology 14:32-42.

Anai M, Funaki M, Ogihara T, Terasaki J, Inukai K, Katagiri H, Fukushima Y, Yazaki Y, Kikuchi M, Oka Y. 1998. Altered expression levels and impaired steps in the pathway to phosphatidylinositol 3-kinase activation via insulin receptor substrates 1 and 2 in Zucker fatty rats. Diabetes 47:13-23.

Araki E, Llpes MA, Patti M-E. 1994. signalling in mice with targeted disruption. Nature 372.

Bruning JC, Winnay J, Bonner-Weir S, Taylor SI, Accili D, Kahn CR. 1997. Development of a novel polygenic model of NIDDM in mice heterozygous for IR and IRS-1 null alleles. Cell 88:561-572.

Jiang ZY, Lin Y-W, Clemont A, Feener EP, Hein KD, Igarashi M, Yamauchi T, White MF, King GL. 1999. Characterization of selective resistance to insulin signaling in the vasculature of obese Zucker (fa/fa) rats. The Journal of clinical investigation 104:447-457.

Kerouz NJ, Hörsch D, Pons S, Kahn CR. 1997. Differential regulation of insulin receptor substrates-1 and-2 (IRS-1 and IRS-2) and phosphatidylinositol 3-kinase isoforms in liver and muscle of the obese diabetic (ob/ob) mouse. Journal of Clinical Investigation 100:3164.

Tamemoto H, Kadowaki T, Tobe K, Yagi T, Sakura H, Hayakawa T, Terauchi Y, Ueki K, Kaburagi Y, Satoh S. 1994. Insulin resistance and growth retardation in mice lacking insulin receptor substrate-1.

Withers DJ, Gutierrez JS, Towery H, Burks DJ, Ren JM, Previs S, Zhang Y, Bernal D, Pons S, Shulman GI, Bonner-Weir S, White MF. 1998. Disruption of IRS-2 causes type 2 diabetes in mice. Nature 391:900-904.

Stephens JM, Lee J, Pilch PF. 1997. Tumor necrosis factor-α-induced insulin resistance in 3T3-L1 adipocytes is accompanied by a loss of insulin receptor substrate-1 and GLUT4 expression without a loss of insulin receptor-mediated signal transduction. Journal of Biological Chemistry 272:971-976.

Egawa K, Nakashima N, Sharma PM, Maegawa H, Nagai Y, Kashiwagi A, Kikkawa R, Olefsky JM. 2000. Persistent Activation of Phosphatidylinositol 3-Kinase Causes Insulin Resistance Due to Accelerated Insulin-Induced Insulin Receptor Substrate-1 Degradation in 3T3-L1 Adipocytes 1. Endocrinology 141:1930-1935.

Sun XJ, Goldberg JL, Qiao L, Mitchell JJ. 1999. Insulin-induced insulin receptor substrate-1 degradation is mediated by the proteasome degradation pathway. Diabetes 48:1359-1364.

Haruta T, Uno T, Kawahara J, Takano A, Egawa K, Sharma PM, Olefsky JM, Kobayashi M. 2000. A rapamycin-sensitive pathway down-regulates insulin signaling via phosphorylation and proteasomal degradation of insulin receptor substrate-1. Molecular endocrinology 14:783-794.

Lee AV, Gooch JL, Oesterreich S, Guler RL, Yee D. 2000. Insulin-like growth factor I-induced degradation of insulin receptor substrate 1 is mediated by the 26S proteasome and blocked by phosphatidylinositol 3'-kinase inhibition. Molecular and cellular biology 20:1489-1496.

Zhande R, Mitchell JJ, Wu J, Sun XJ. 2002. Molecular mechanism of insulin-induced degradation of insulin receptor substrate 1. Molecular and cellular biology 22:1016-1026.

Bose SK, Ray R. 2014. Hepatitis C virus infection and insulin resistance. World J Diabetes 5:52-58.

John J. Sambrook DDWR. 1989. Molecular Cloning: A Laboratory Mannual, second edition. CSHL Press.

Ausubel FM. 1987. Current Protocols in Molecular Biology.

Rosenberg IM. 1996. Protein Analysis and Purification—Benchtop Techniques.

Copeland RA. 2013. Methods for Protein Analysis: A Practical Guide for Laboratory Protocols.

John E. Coligan BB. 1999 Current Protocols in Immunology.

Kim JM, Wu H, Green G, Winkler CA, Kopp JB, Miner JH, Unanue ER, Shaw AS. 2003. CD2-associated protein haploinsufficiency is linked to glomerular disease susceptibility. Science 300:1298-1300.

Kobayashi S, Sawano A, Nojima Y, Shibuya M, Maru Y. 2004. The c-Cbl/CD2AP complex regulates VEGF-induced endocytosis and degradation of Flt-1 (VEGFR-1). The FASEB journal 18:929-931.

Bao M, Hanabuchi S, Facchinetti V, Du Q, Bover L, Plumas J, Chaperot L, Cao W, Qin J, Sun S-C. 2012. CD2AP/SHIP1 complex positively regulates plasmacytoid dendritic cell receptor signaling by inhibiting the E3 ubiquitin ligase Cbl. The Journal of Immunology 189:786-792.

Calco GN, Stephens OR, Donahue LM, Tsui CC, Pierchala BA. 2014. CD2-associated protein (CD2AP) enhances casitas B lineage lymphoma-3/c (Cbl-3/c)-mediated Ret isoform-specific ubiquitination and degradation via its amino-terminal Src homology 3 domains. Journal of Biological Chemistry 289:7307-7319.

Kowanetz K, Szymkiewicz I, Haglund K, Kowanetz M, Husnjak K, Taylor JD, Soubeyran P, Engstrom U, Ladbury JE, Dikic I. 2003. Identification of a novel proline-arginine motif involved in CIN85-dependent clustering of Cbl and down-regulation of epidermal growth factor receptors. Journal of Biological Chemistry 278:39735-39746.

Gout I, Middleton G, Adu J, Ninkina NN, Drobot LB, Filonenko V, Matsuka G, Davies AM, Waterfield M, Buchman VL. 2000. Negative regulation of PI 3-kinase by Ruk, a novel adaptor protein. The EMBO journal 19:4015-4025.

Huber TB, Hartleben B, Kim J, Schmidts M, Schermer B, Keil A, Egger L, Lecha RL, Borner C, Pavenstädt H. 2003. Nephrin and CD2AP associate with phosphoinositide 3-OH kinase and stimulate AKT-dependent signaling. Molecular and cellular biology 23:4917-4928.

Oprea C, Ianache I, Radoi R, Erscoiu S, Tardei G, Nicolaescu O, Nica M, Calistru P, Ruta S, Ceausu E. 2014. Alarming increase in tuberculosis and hepatitis C virus (HCV) among HIV infected intravenous drug users. Journal of the International AIDS Society 17:19625.

Chamond N, Cosson A, Coatnoan N, Minoprio P. 2009. Proline racemases are conserved mitogens: characterization of a Trypanosoma vivax proline racemase. Molecular and biochemical parasitology 165:170-179.

Zehmer JK, Bartz R, Liu P, Anderson RG. 2008. Identification of a novel N-terminal hydrophobic sequence that targets proteins to lipid droplets. Journal of cell science 121:1852-1860.

Wu Y, Liao Q, Yang R, Chen X, Chen X. 2011. A novel luciferase and GFP dual reporter virus for rapid and convenient evaluation of hepatitis C virus replication. Virus research 155:406-414.

Lindenbach BD, Evans MJ, Syder AJ, Wolk B, Tellinghuisen TL, Liu CC, Maruyama T, Hynes RO, Burton DR, McKeating JA, Rice CM. 2005. Complete replication of hepatitis C virus in cell culture. Science 309:623-626.

\* cited by examiner (A)

(B)

US 11,002,729 B2

CD2-ASSOCIATED PROTEIN (CD2AP) AND ITS INTERACTIVE PROTEINS

FIELD OF THE INVENTION

The present invention generally relates to CD2 associated protein (CD2AP) and its interactive proteins, and more particularly to the interaction between CD2AP and NS5A of Hepatitis C virus (HCV), to the interaction between CD2AP and insulin receptor substrate 1 (IRS1), and to the interaction between Cbl-b/Cbl and IRS1, and further to an agent and method for down-regulating CD2AP expression, an agent and method for manipulating the interaction between CD2AP and NS5A for inhibiting the assembly of HCV, an agent and method for manipulating the interaction between CD2AP and IRS1 for modulating insulin insensitive diabetes for treating diabetics, and an agent and method for manipulating the interaction between Cbl-b/Cbl and IRS1 for modulating insulin insensitive diabetes for treating diabetics.

BACKGROUND OF THE INVENTION

Hepatitis C virus (HCV), a member of Flavivirus, is a positive sense, single-stranded RNA virus with a 9.6 kb genome (1). HCV infects approximately 180 million people worldwide causing serious chronic liver diseases (2). The normal target of HCV is hepatocyte. Upon entering a host cell, HCV uncoats its genome RNA, and translates a polyprotein precursor that is then cleaved by host and viral proteases to generate three structural proteins and seven non-structural proteins that are important in viral RNA replication, assembly and release (3).

Chronic HCV infection usually results in hepatosteatosis characterized by large vacuoles of neutral lipid, which is also the component of lipid droplets (LDs), the hub for virus assembly (4, 5). LDs are ubiquitous and unique cellular organelles, with a single phosphor-lipid layer. LDs participate in many biological processes such as energy storage, lipid metabolism, immunity as well as signal transduction. In HCV infected cell, the surface of LDs is coated with core protein and NS5A, with NS5A on the outer surface (5-7), and attachment of both core protein and NS5A on LDs is essential for the assembly and release of infectious HCV particles (6, 8, 9).

NS5A can be divided into three domains, Domain1, Domain2 and Domain3. Domain1 and Domain2 are required for RNA replication, and Domain3 contributes to viral assembly and release. In addition, NS5A Domain1 is thought to be responsible for targeting to LDs, and D3 responsible for binding core protein (10, 11).

Transportation of the HCV replication complexes (RCs) containing NS5A to LDs depends on the interactions between NS5A/core and cytoskeletal filaments. The movement of RCs is inhibited by treatment with inhibitors of microtubules and actin filaments (12). Long-range motility of NS5A-positive structures to LDs was significantly reduced when microtubule motor protein dynein was silenced (13, 14). However, a direct interaction between dynein and NS5A was not shown. Therefore the nature of the host proteins interacting with NS5A for the transfer process remains not completely understood.

The liver constitutes a key organ in systemic metabolism, contributing substantially to the development of insulin resistance and type 2 diabetes mellitus (T2DM)(15). Among the molecules contributing to insulin resistance, IRS-1, a scaffold protein, plays an important role in the insulin cascade. Many in vitro and in vivo studies suggested that lowering of IRS cellular levels may be a mechanism of insulin resistance (15-22). A major target for the insulin receptor tyrosine kinase, IRS1 stability is mainly regulated at protein level through proteasome dependent degradation. Studies suggest that proteasome-mediated degradation of IRS-1 might be involved in the down-regulation of signaling by insulin and IGF-1 and contribute to insulin resistance (23-27). Ubiquitination of IRS-1 was shown to be a prerequisite for insulin-induced IRS-1 proteasome degradation and the N-terminal region of IRS-1 including the PH and PTB domains was identified as essential for targeting IRS-1 to the ubiquitin-proteasome degradation pathway (28).

Insulin resistance often results in hepatic fibrosis and steatosis, especially under HCV infection condition (29). Insulin drives macronutrient storage and tissue growth by inducing trans-autophosphorylation of its receptor, which is a dimeric transmembrane receptor tyrosine kinase (RTK). This results in phosphorylation of insulin receptor substrates (IRSs) 1 and 2 and activation of a widely ramifying signaling network including, but not limited to, the phosphatidylinositol-2-kinase/AKT/mTOR and RAS/MEK/ERK pathways.

IRS-1 is a signaling adapter protein that in humans is encoded by the IRS-1 gene. It is a 131 kDa protein with amino acid sequence of 1242 residues. It contains a single pleckstrin homology (PH) domain at the N-terminus and a PTB domain, 40 residues downstream of this, followed by a poorly conserved C-terminus tail. IRS-1 plays a key role in transmitting signals from the insulin and insulin-like growth factor-1 (IGF-1) receptors to intracellular pathways PI3K/Akt and Erk MAP kinase pathways. Tyrosine phosphorylation of IRS-1 by insulin receptor (IR) introduces multiple binding sites for proteins bearing SH2 homology domain, such as PI3K, Grb-2/Sos complex and SHP2.

SUMMARY OF THE INVENTION

The present invention provides a method for down-regulating CD2AP expression in a subject. In certain embodiments, the method comprises administering a CD2AP down-regulation composition to the subject, wherein the CD2AP down regulation composition is workable by way of siRNA/shRNA, CRISPR/Cas9, Talen or ZFNs; thereby the CD2AP expression in liver tissues of the subject is down-regulated. In another embodiment of the method, the CD2AP down-regulation composition comprises at least one siRNA/shRNAi polynucleotide that is selected from the group consisting of SEQ ID NOS 3-20 when the subject is human or SEQ ID NOS 59-76 when the subject is dog, or at least one CRISPR/Cas9 vector comprising a guide polynucleotide selected from the group consisting of SEQ IS NOS 21-56 when the subject is human or SEQ ID NOS 77-103 when the subject is dog.

The present invention provides a pharmaceutical composition for down-regulating CD2AP expression in liver tissue of a subject, comprising at least one siRNA/shRNAi polynucleotide that is selected from the group consisting of SEQ ID NOS 3-20 when the subject is human or SEQ ID NOS 59-76 when the subject is dog, or at least one CRISPR/Cas9 vector comprising a guide polynucleotide selected from the group consisting of SEQ IS NOS 21-56 when the subject is human or SEQ ID NOS 77-103 when the subject is dog.

The present invention provides a method for screening a candidate agent that is capable of reducing the interaction between CD2AP and HCV non-structural protein NS5A. In certain embodiments, the method comprises providing cells expressing both CD2AP and NS5A; contacting a candidate agent with the cells expressing both CD2AP and NS5A; and assaying the effects of the candidate agent on the interaction between CD2AP and NS5A; wherein the candidate agent is identified if it reduces the interaction between CD2AP and NS5A to a predefined threshold; and wherein the predefined threshold is defined as at least 70%, more preferably 80%, reduction of the interaction between CD2AP and NS5A.

The present invention provides a pharmaceutical composition for reducing interaction between CD2AP and NS5A, comprising at least one peptide with 5-40 amino acids, preferably 10-30 amino acids, more preferably 15-25 amino acids, wherein the peptide is a derivative of amino acids 3-58 of SEQ ID NO 2, amino acids 111-165 of SEQ ID NO 2, amino acids 271-327 of SEQ ID NO 2, and amino acids 353-466 of SEQ ID NO 105.

The present invention provides a method for screening a candidate agent that is capable of reducing the interaction between CD2AP and IRS1. The method comprises providing cells expressing both CD2AP and IRS1; contacting a candidate agent with the cells expressing both CD2AP and IRS1; and assaying the effects of the candidate agent on the interaction between CD2AP and IRS1; wherein the candidate agent is identified if it reduces the interaction between CD2AP and IRS1 to a predefined threshold; and wherein the predefined threshold is defined as at least 70%, more preferably 80%, reduction of the interaction between CD2AP and IRS1.

The present invention provides a pharmaceutical composition for reducing the interaction between CD2AP and IRS1, comprising at least one peptide with 5-40 amino acids, preferably 10-30 amino acids, more preferably 15-25 amino acids, wherein the peptide is a derivative of amino acids 3-58 of SEQ ID NO 2 or 58, amino acids 111-165 of SEQ ID NO 2 or 58, and amino acids 271-327 of SEQ ID NO 2 or 58.

The present invention provides a method for screening a candidate agent that is capable of reducing the interaction between Cbl-b/Cbl and IRS1. In certain embodiments, the method comprises providing cells expressing both Cbl-b/Cbl and IRS1; contacting a candidate agent with the cells expressing both Cbl-b/Cbl and IRS1; and assaying the effects of the candidate agent on the interaction between Cbl-b/Cbl and IRS1; wherein the candidate agent is identified if it reduces the interaction between Cbl-b/Cbl and IRS1 to a predefined threshold, and wherein the predefined threshold is defined as at least 70%, more preferably 80%, reduction of the interaction between Cbl-b/Cbl and IRS1.

The present invention provides a method for down-regulating Cbl-b/Cbl expression in liver tissues of a subject. In certain embodiments, the method comprises administering a Cbl-b/Cbl down-regulation composition to the subject, wherein the Cbl-b/Cbl down regulation composition is workable by way of siRNA/shRNA, CRISPR/Cas9, Talen or ZFNs; thereby the Cbl-b/Cbl expression in liver tissues of the subject is down-regulated. In certain embodiments, the Cbl-b/Cbl down-regulation composition comprises at least one siRNA/shRNAi polynucleotide that is selected from the group consisting of SEQ ID NOS 112-124 and 195-208 when the subject is human or SEQ ID NOS 161-170 and 246-255 when the subject is dog or at least one CRISPR/Cas9 vector comprising a guide polynucleotide selected from the group consisting of SEQ IS NOS 125-158 and 209-243 when the subject is human or SEQ ID NOS 171-192 or 256-280 when the subject is dog.

The present invention provides a pharmaceutical composition for down-regulating Cbl-b/Cbl expression in a subject, comprising at least one siRNA/shRNAi polynucleotide that is selected from the group consisting of SEQ ID NOS 112-124 and 195-208 when the subject is human or SEQ ID NOS 161-170 and 246-255 when the subject is dog or at least one CRISPR/Cas9 vector comprising a guide polynucleotide selected from the group consisting of SEQ IS NOS 125-158 and 209-243 when the subject is human or SEQ ID NOS 171-192 or 256-280 when the subject is dog.

The present invention provides treatment for HCV infection in a subject. In certain embodiments, the treatment comprises administering a composition comprising at least one siRNA/shRNAi nucleotide sequence selected from the group consisting of sequences represented by SEQ ID NOS 3-20; administering a CRISPR/Cas9 vector comprising a guide nucleotide sequence selected from the group consisting of the nucleotide sequences represented by SEQ ID NOS 21-56; or administering a composition comprising an agent that reduces the interactions between CD2AP and NS5A.

The present invention provides treatment for diabetics in a subject. In certain embodiments, the treatment comprises administering a composition comprising at least one siRNA/shRNAi nucleotide sequence selected from the group consisting of sequences represented by SEQ ID NOS 3-20 when the subject is human) or SEQ ID NOS 59-76 when the subject is dog; administering a CRISPR/Cas9 vector comprising a guide nucleotide sequence selected from the group consisting of the nucleotide sequences represented by SEQ ID NOS 21-56 when the subject is human or SEQ ID NOS 77-103 when the subject is dog; or administering a composition comprising an agent that can reduce the interactions between CD2AP and IRS1 as afore described.

The present invention provides treatment for diabetics in a subject. In certain embodiments, the treatment comprises administering a composition comprising at least one siRNA/shRNAi nucleotide sequence selected from the group consisting of sequences represented by SEQ ID NOS 112-124 and 195-208 when the subject is human or SEQ ID NOS 161-170 and 246-255 when the subject is dog; administering a CRISPR/Cas9 vector comprising a guide nucleotide sequence selected from the group consisting of the nucleotide sequences represented by SEQ IS NOS 125-158 and 209-243 when the subject is human or SEQ ID NOS 171-192 or 256-280 when the subject is dog; or administering a composition comprising an agent that can reduce the interactions between Cbl-b/Cbl and IRS1.

The present invention provides a diagnostic method for detecting abnormalities in live sample of a subject. In certain embodiments, the method comprises providing a liver sample from the subject; contacting the liver sample with a detecting agent for detecting expression of CD2AP; thereby, when a CD2AP expression is detected, the subject is indicated with liver abnormalities. The abnormalities include HCV infection and diabetes.

The present invention provides a diagnostic kit for detecting abnormalities in liver sample of a subject. In certain embodiments, the kit comprises an antibody specific for CD2AP protein or a polynucleotide probe specific for mRNA of CD2AP; and a secondary agent that can detect the antibody bound to CD2AP protein or signal from the mRNA of CD2AP.

The objectives and advantages of the invention will become apparent from the following detailed description of preferred embodiments thereof in connection with the accompanying drawings.

BRIEF DESCRIPTION OF THE DRAWINGS

Preferred embodiments according to the present invention will now be described with reference to the Figures, in which like reference numerals denote like elements.

However, the expression level of NS5A was not affected by CD2Ap down regulation (top right panel). The lipid droplets fractions were isolated 48 hpt. Protein levels of NS5A on LD fractions were detected by WB. ADRP (second panels) and calnexin (the third panels) served as markers for LD and ER respectively.

Figure 17:
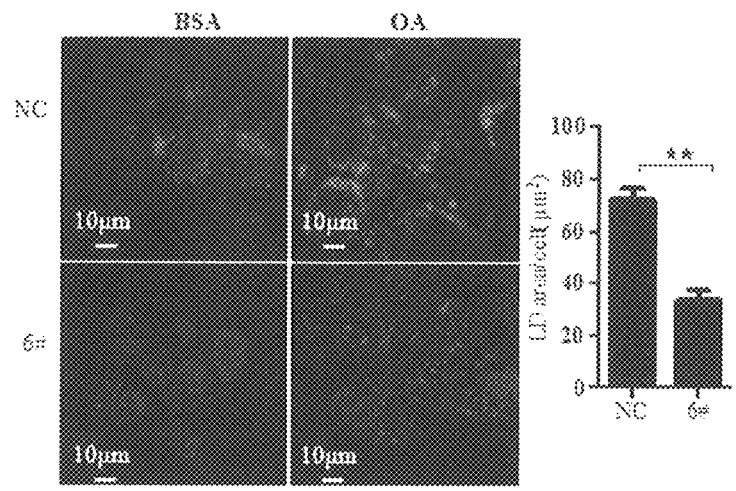

FIG. 17 are photographs showing that down regulation of CD2AP reduced LDs biogenesis. CD2AP knocking down (6 #) and control (NC) Huh7.5.1 cells were treated with BSA alone (left panels) or with 0.5 mM of oleic acid (OA)-BSA complexes (right panels) for 16 hours. The cells were then performed LD staining using HCS LipidTOX Deep Red neutral lipid stains. Knocking down CD2AP significantly curtails the OA stimulated LDs formation. Quantification of more than 200 cells to count LD area in single cell supported there was significant difference between control cells and CD2AP down regulated cells (black box, p<0.01).

Figure 18:
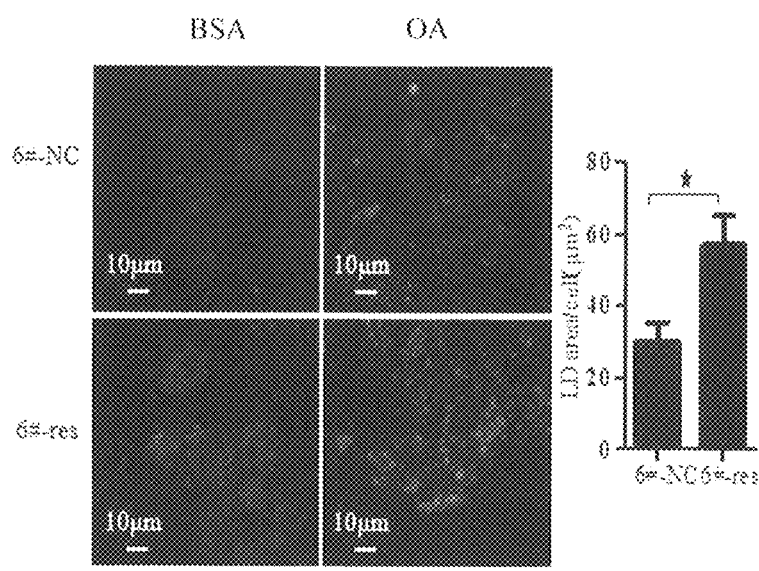

FIG. 18 are photographs showing that reduction of LDs biogenesis could be functionally rescued by over-expressing CD2AP. CD2AP knocking down cells (6 #) were transduced with CD2AP rescue mutant (6 #-res) or empty vector (6 #-NC). The cells were then treated with BSA alone (left panels) or with 0.5 mM of OA-BSA complexes (right panels) for 16 hours. The cells were then stained for LDs. Quantification of more than 200 cells to count LD area in single cell supported that LDs biogenesis was substantially recovered after CD2AP rescuing (black box, p<0.05).

Figure 19:
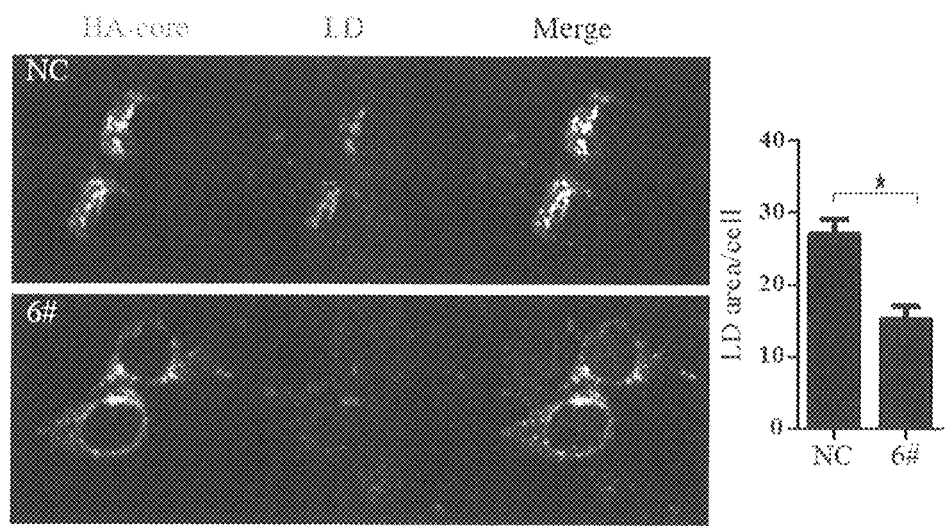

FIG. 19 are photographs showing that expression of HCV core protein in CD2AP down-regulated cells (6 #) did not rescue the accumulation of lipid droplets. HA-tagged Core was transfected into control (NC) or CD2AP down regulated (6 #) cells and stained for LDs. HCV core was stained with anti-HA antibodies (green). LDs were stained as above (red). Quantification of more than 200 cells to count LD area in single cell supported that LDs biogenesis was not rescued by Core expressing in CD2AP down regulated cells (black box, p<0.05).

Figure 20:
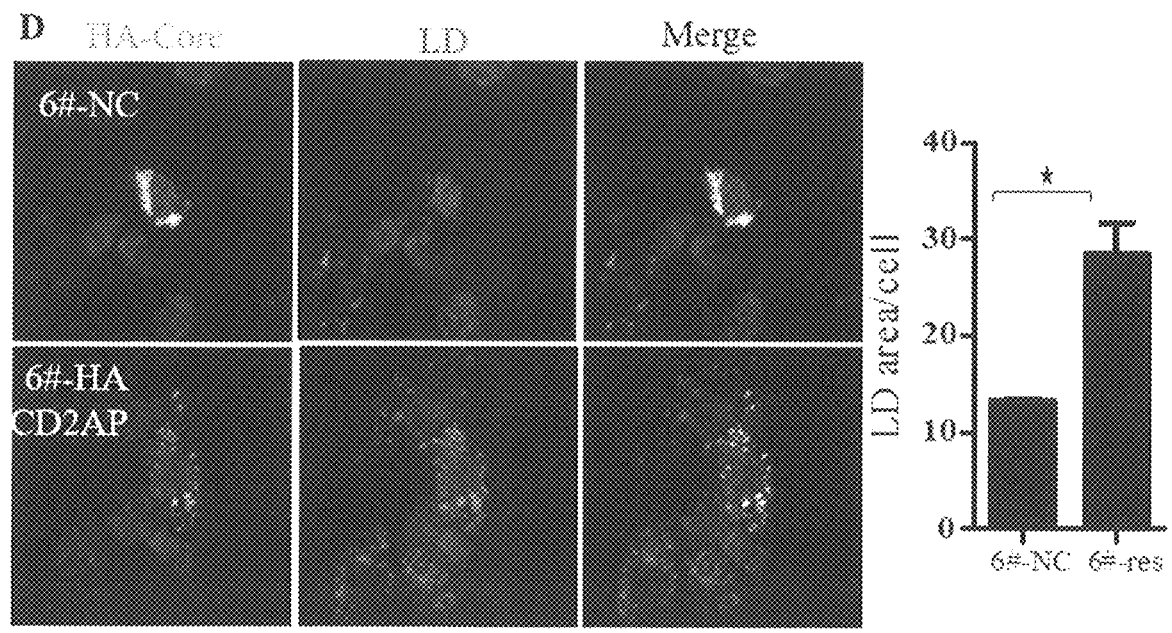

FIG. 20 are photographs showing that CD2AP rescuing cells showed significant more LD accumulation than control cell. HA-tagged CD2AP (6 #-HA-CD2AP) or control (6 #-NC) plasmid were transfected into CD2AP down regulated cells, significantly more LD biogenesis was detected in HA-CD2AP cells than in control vector cells. Quantification of more than 200 cells to count LD area in single cell supported that LDs biogenesis was recovered after CD2AP expression (black box, p<0.05).

Figure 21:
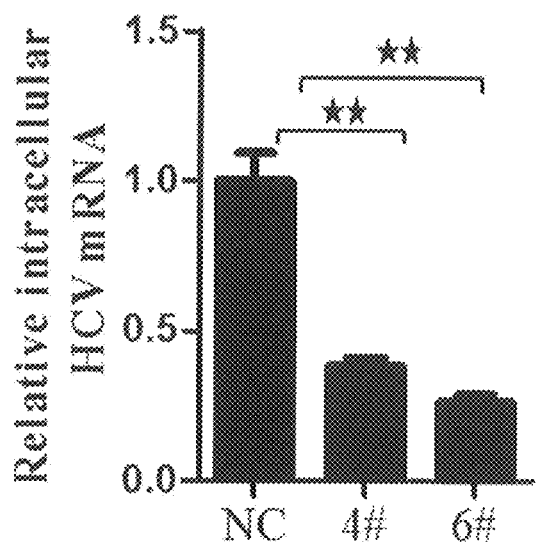

FIG. 21 is a bar graph showing that knocking-down CD2AP reduced HCV mRNA level compared to control cells 72 hpi. CD2AP down-regulated (4 # & 6 #) or control (NC) huh 7.5.1 cells were infected with HCV JFH1 for 72 hours. Total intracellular RNAs were extracted and subjected for quantitative RT-PCR to detect HCV mRNA. All the results shown were from at least three independent experiments (mean±SE). The bars indicate the standard error of the mean. P value is considered significantly if p<0.05. Statistical analysis differences of the different groups were shown as *(P<0.05), **(P<0.01), and n.s. (no significant difference).

Figure 22:
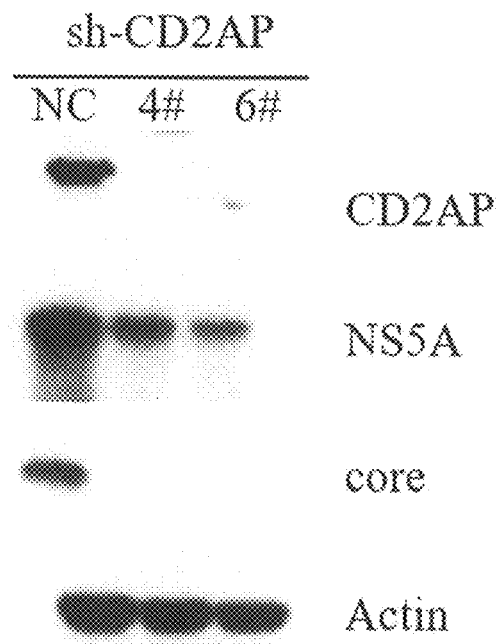

FIG. 22 shows photographs of western blots. Total cell lysates were immunoblotted for CD2AP, HCV NS5A, core and β-actin to show that down regulation of CD2AP and reduction of NS5A and core.

Figure 23:
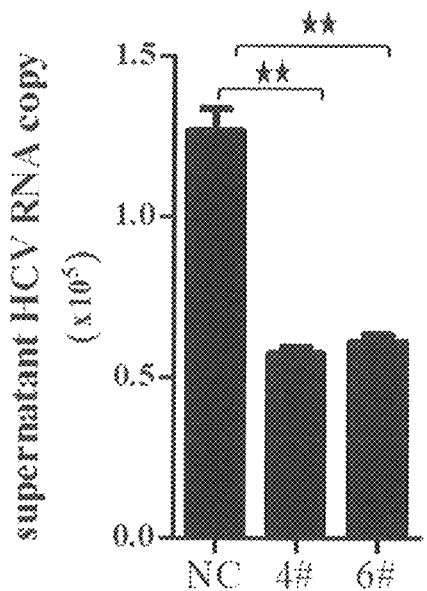

FIG. 23 is a bar graph showing that knocking-down CD2AP significantly reduces supernatant HCV RNA copy. Supernatant HCV RNA copy numbers from CD2AP knocking down (4 # & 6 #) and control (NC) cells were quantified by RT-PCR. All the results shown were from at least three independent experiments (mean±SE). The bars indicate the standard error of the mean. P value is considered significantly if p<0.05. Statistical analysis differences of the different groups were shown as *(P<0.05), **(P<0.01), and n.s. (no significant difference).

Figure 24:
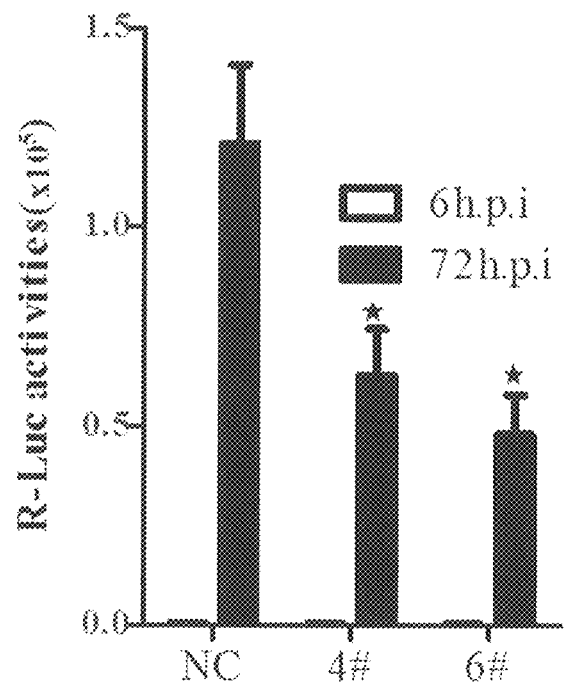

FIG. 24 is a bar graph showing that knocking-down CD2AP significantly suppresses luciferase activity of the report gene. The CD2AP knocking down (4 # & 6 #) and control (NC) cells were infected with a reporter virus J399EM+LM with a renila luciferase gene. The luciferase activities were assessed 72 hours later. All the results shown were from at least three independent experiments (mean±SE). The bars indicate the standard error of the mean. P value is considered significantly if p<0.05. Statistical analysis differences of the different groups were shown as *(P<0.05), **(P<0.01), and n.s. (no significant difference).

Figure 25:
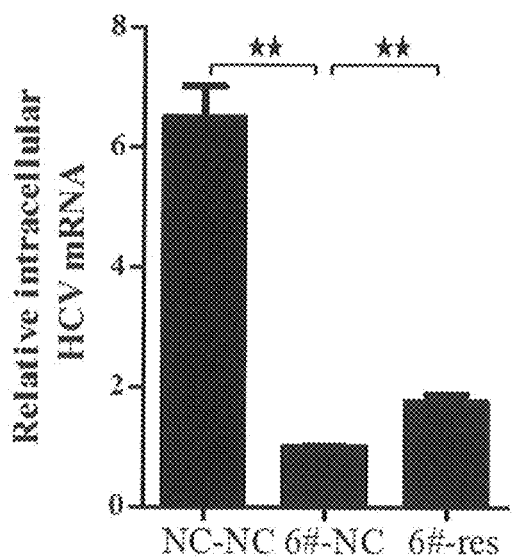

FIG. 25 is a bar graph showing that CD2AP rescuing cells partially recovered intracellular HCV mRNA. Huh7.5.1 cells down regulated CD2AP (6 #) were transduced with CD2AP rescue mutant (6 #-res) or control plasmid (6 #-NC) and then infected with JFH1 at a MOI of 0.1. Significantly increased intracellular HCV RNA levels were detected in CD2AP rescuing cells than control cells by relative qRT-PCR analysis 72 hpi. All the results shown were from at least three independent experiments (mean±SE). The bars indicate the standard error of the mean. P value is considered significantly if p<0.05. Statistical analysis differences of the different groups were shown as *(P<0.05), **(P<0.01), and n.s. (no significant difference).

Figure 26:
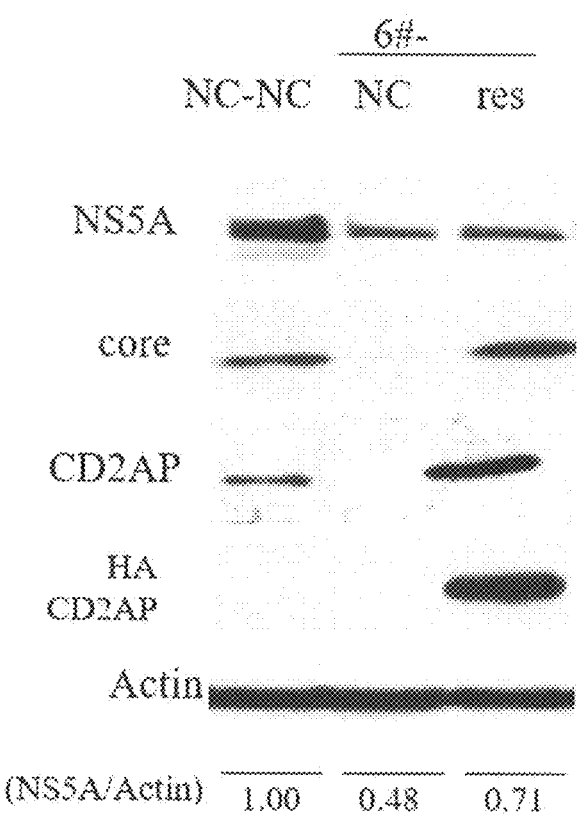

FIG. 26 shows photographs of western blots. CD2AP rescuing cells partially recovered HCV proteins. Cell lysates from CD2AP rescuing cells infected with HCV JFH1 were immunoblotted with CD2AP, core, NS5A to show partial rescue of NS5A and core.

Figure 27:
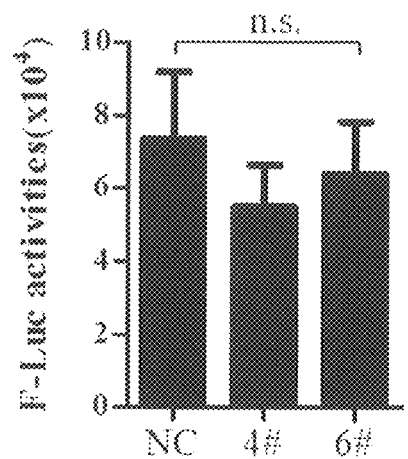

FIG. 27 is a bar graph showing that CD2AP knocking down (4 # & 6 #) did not affect HCVpp entry compared to control cells (NC). Cells were transduced with HCVpp and luciferase activities were measured 48 hours later. There were no significant effects on HCV entry after CD2AP down regulated. All the results shown were from at least three independent experiments (means±SE). The bars indicate the standard error of three experiments. Statistical analysis differences of the different groups were shown as *(P<0.05), **(P<0.01), and n.s. (no significant difference).

Figure 28:
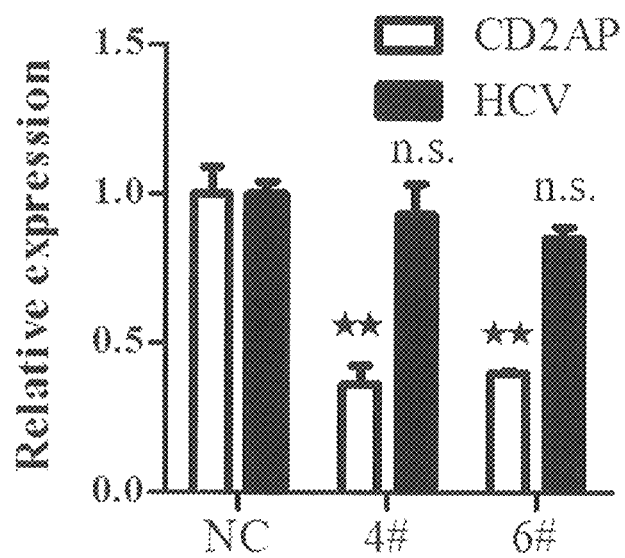

FIG. 28 is a bar graph showing that down-regulation CD2AP (4 # & 6 #) did not reduce HCV subgenomic replication in replicon Con1 cells compared to control cells (NC). Compare to control plasmid, knocking down CD2AP significantly reduces the mRNA of CD2AP as measured by RT-PCR (empty boxes, p<0.01). Knocking down CD2AP did not reduce intracellular HCV RNA levels (black boxes). All the results shown were from at least three independent experiments (means±SE). The bars indicate the standard error of three experiments. Statistical analysis differences of the different groups were shown as *(P<0.05), **(P<0.01), and n.s. (no significant difference).

Figure 29:
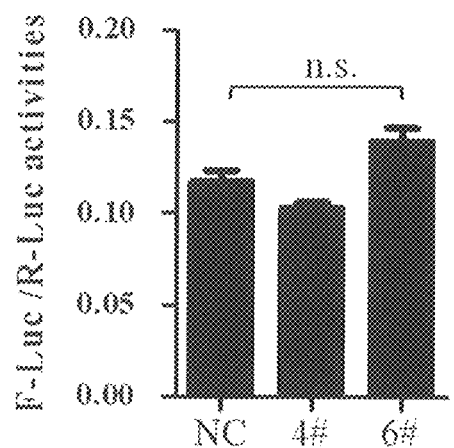

FIG. 29 is a bar graph showing that knocking-down CD2AP (4 # & 6 #) did not influence HCV-IRES dependent translation compared to control cells (NC). Cells were transfected with pHCV-IRES. Dual-luciferase luciferase activities were measured with a dual-luciferase reporter assay system (Promega) 48 hours later. Translation efficiency was determined by the ratio of firefly luciferase (F-Luc) activity to Renilla luciferase (R-Luc) activity. All the results shown were from at least three independent experiments (means±SE). The bars indicate the standard error of three experiments. Statistical analysis differences of the different groups were shown as *(P<0.05), **(P<0.01), and n.s. (no significant difference).

Figure 30:
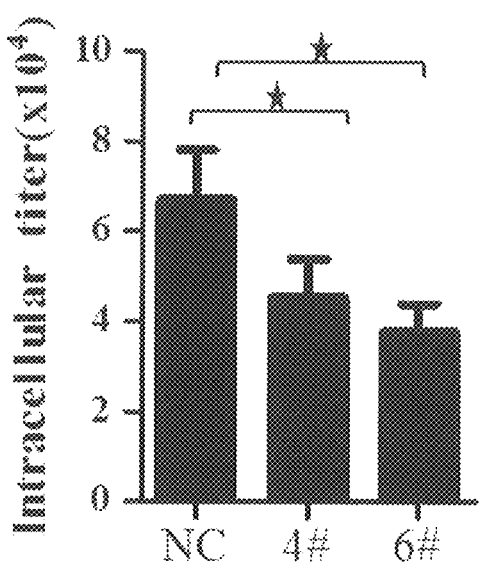

FIG. 30 is a bar graph showing that down regulation of CD2AP significantly reduced intracellular HCV titer (p<0.05). CD2AP down regulated (4 # & 6 #) or control (NC) Huh7.5.1 cells were infected with J399EM at an MOI of 1. Cell pellet was collected for quantitation of intracellular virus titer. All the results shown were from at least three independent experiments (means±SE). The bars indicate the standard error of three experiments. Statistical analysis differences of the different groups were shown as *(P<0.05), **(P<0.01), and n.s. (no significant difference).

Figure 31:
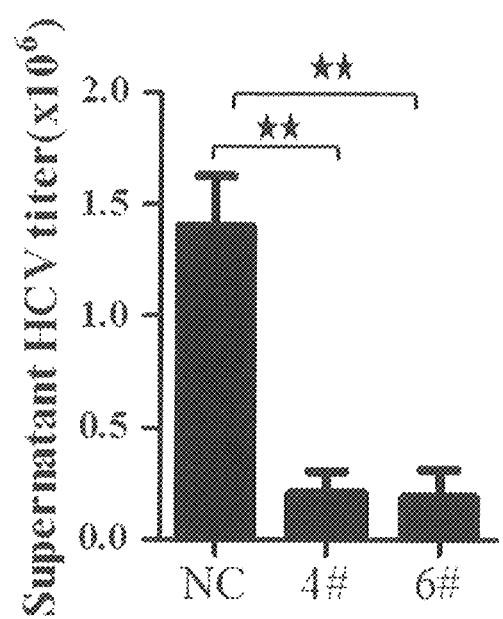

FIG. 31 is a bar graph showing that down regulation of CD2AP also significantly reduced supernatant HCV titer (p<0.01). The culture supernatant was collected 72 hours later to quantify released extracellular virus titer as described in material and methods. All the results shown were from at least three independent experiments (means±SE). The bars indicate the standard error of three experiments. Statistical analysis differences of the different groups were shown as *(P<0.05), **(P<0.01), and n.s. (no significant difference).

Figure 32:
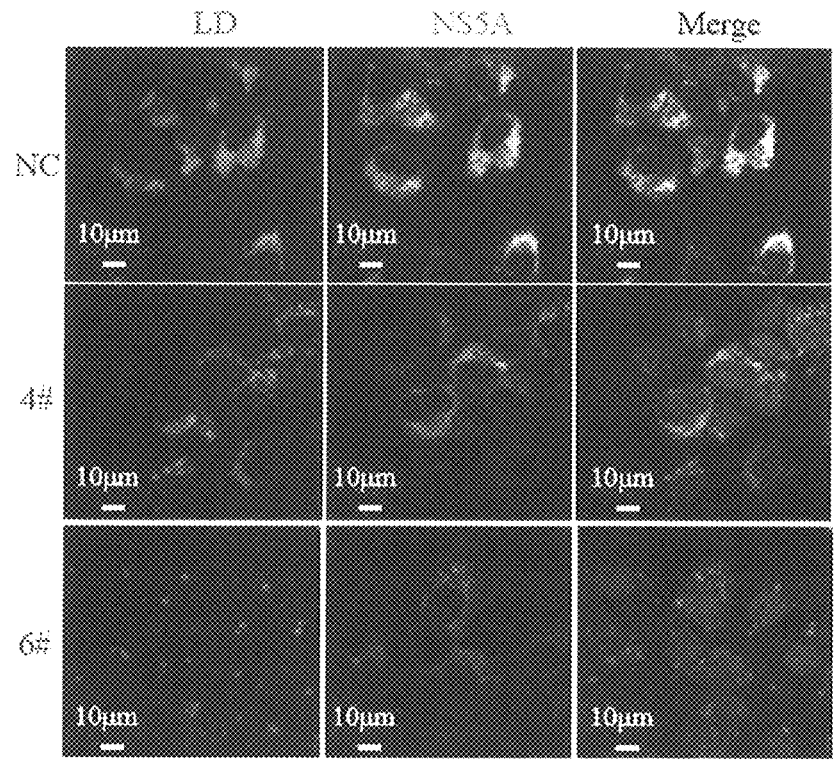
Figure 32:
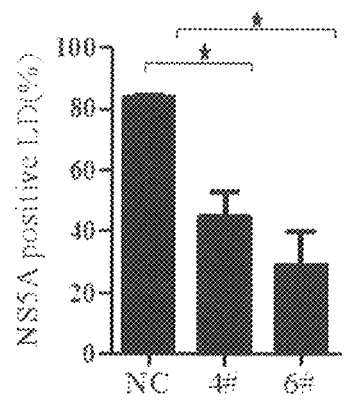

FIG. 32 shows (A) photographs of association of HCV NS5A with lipid droplets (LD), and (B) a bar graph of NS5A positive LD. For (A), stable CD2AP knocking down (4 # and 6 #) and control cells (NC) were infected with JFH-1 and then immunostained for LDs (red) and HCV NS5A (green). Nuclei were counter stained with DAPI (blue). Knocking down CD2AP significantly reduces co-localization of lipid droplets with HCV proteins NS5A. For (B), quantification of NS5A positive LDs showed that down regulation of CD2AP significantly reduced NS5A locating on LDs in HCV-infected cells. A total of 161, 104, and 87 cells were counted from control (NC) and CD2AP down regulated (4 # & 6 #) cells, respectively. Statistical analysis differences of the different groups were shown as *(P<0.05), **(P<0.01).

Figure 33:
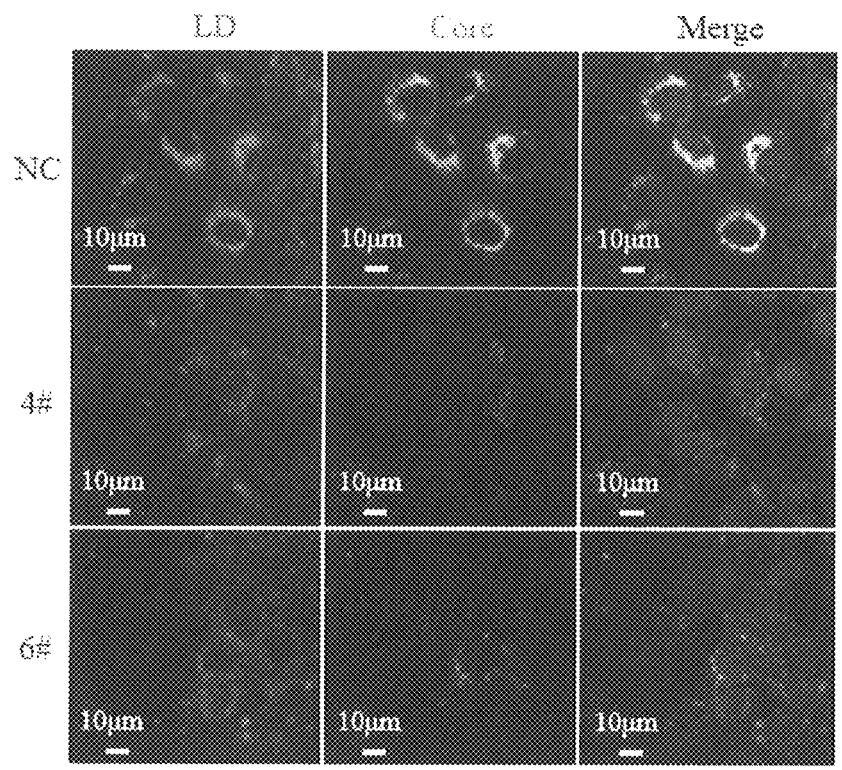
Figure 33:
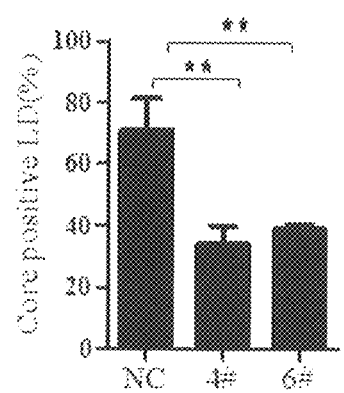

FIG. 33 shows (A) photographs of association of HCV core protein with LD, and (B) a bar graph of core protein positive LD. Stable CD2AP knocking down (4 # and 6 #) and control cells (NC) were infected with JFH-1 and then immunostained for LDs (red) and HCV core protein (green). Nuclei were counter stained with DAPI (blue). Knocking down CD2AP significantly reduces co-localization of lipid droplets with HCV core protein. For (B), quantification of core positive LDs showed that down regulation of CD2AP significantly reduced core locating on LDs in HCV-infected cells. A total of 161, 104, and 87 cells were counted from control (NC) and CD2AP down regulated (4 # & 6 #) cells, respectively. Statistical analysis differences of the different groups were shown as *(P<0.05), **(P<0.01).

Figure 34:
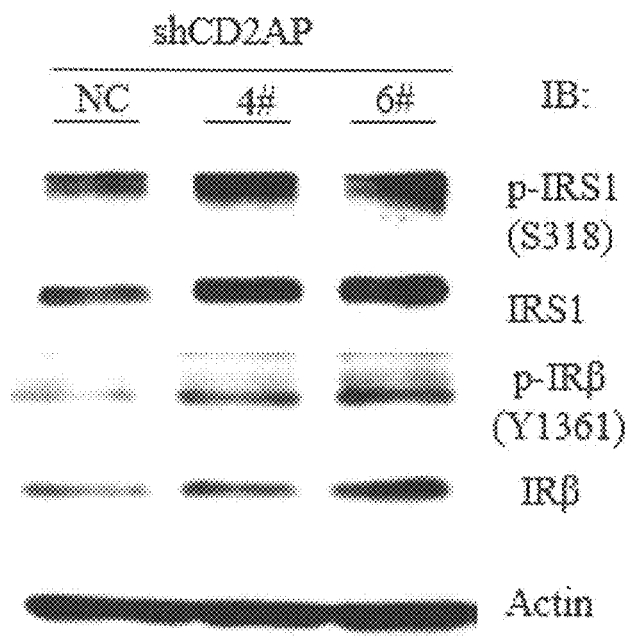

FIG. 34 shows photographs of western blots. The expression insulin receptor substrate 1 (IRS1) in CD2AP knocking down cells is significantly up-regulated. CD2AP down-regulated (4 # & 6 #) and control (NC) cells were infected with JFH-1. Total cell lysates were immunoblotted against IRS1 or insulin receptor (IR) and their phosphorylated forms 72 hpi. Significantly more IRS1 and p-IRS1 were detected in CD2AP down-regulated cells than in control cells. There were modestly increases of IR and p-IR in CD2AP down-regulated cells in comparison with control cells.

Figure 35:
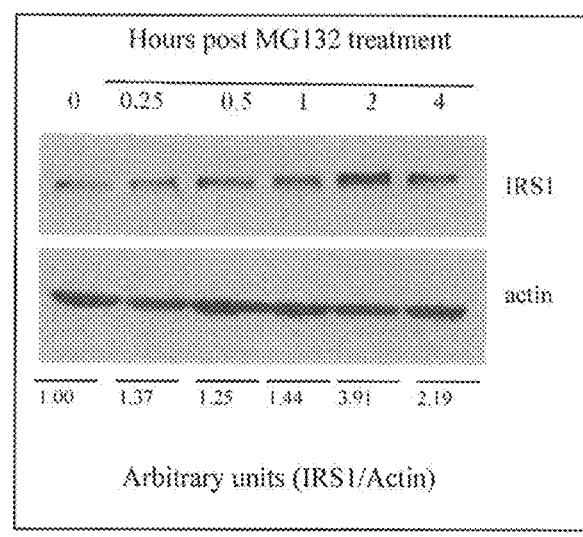

FIG. 35 shows photographs of western blots. Degradation of IRS1 was proteasome-dependent. Time course of MG132 treated Huh7.5.1 cells were immunoblotted with specific antibody to detect the expression level of IRS1 after different time of treatment (0, 0.25, 0.5, 1, 2, 4 h 10 μM MG132 treatment).

Figure 36:
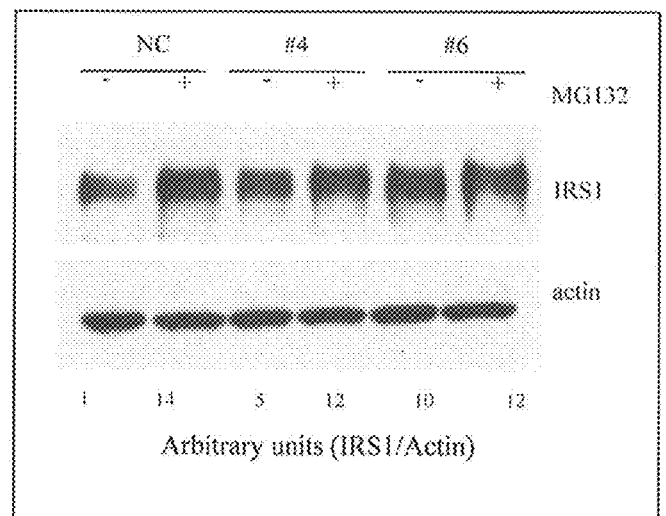

FIG. 36 shows photographs of western blots. CD2AP down-regulated cells were less sensitive to proteasome inhibitor treatment. CD2AP down-regulated (4 # & 6 #) and control (NC) cells were treated with DMSO (−) or 10 μM MG132 (+) for two hours. Total cell lysates were immunoblotted with IRS1 specific antibody.

Figure 37:
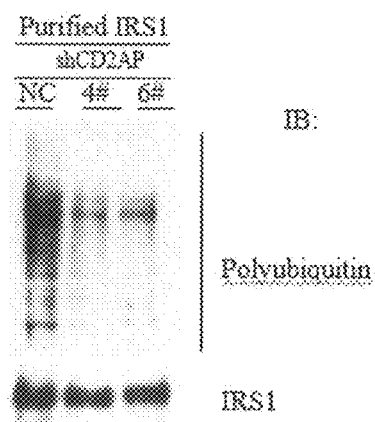

FIG. 37 shows photographs of western blots. Less ubiquitination of IRS1 in CD2AP down-regulated cells (4 # & 6 #) than in control (NC) cells. Cells were cultured in complete medium for 48 hours and then harvested. Cell lysates were purified with anti-IRS1 antibody. The purified protein was then immunoblotted for polyubiquitin and IRS1.

Figure 38:
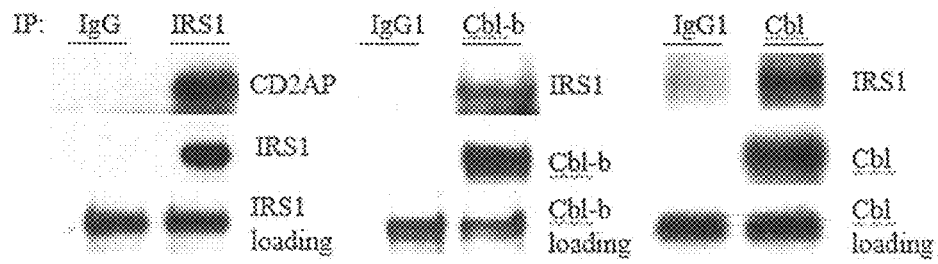

FIG. 38 shows photographs of western blots. IRS1, CD2AP and cbl-b/cbl existed in the same protein complex. Huh7.5.1 Cell lysates were co-IPed with anti-IRS1 (left panel) antibody. CD2AP was co-purified with IRS1. Huh7.5.1 cell lysates were co-IPed with anti-cbl-b antibody (mid panel) or with anti-cbl antibody (right panel). IRS1 was co-purified with cbl-b/cbl.

Figure 39:
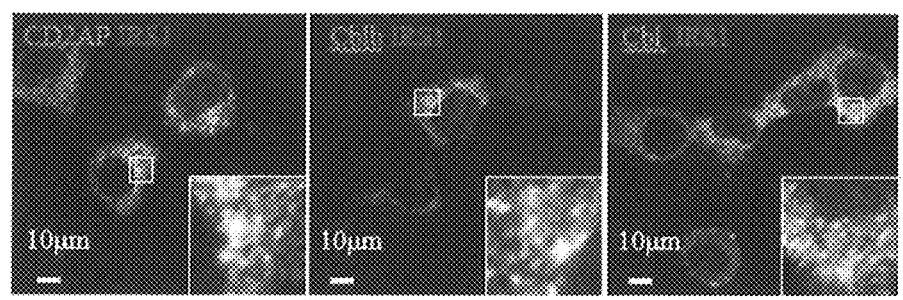

FIG. 39 shows photographs of co-localization of IRS1, CD2AP and cbl-b/cbl in Huh7.5.1 Cells. The cells were stained with anti-IRS1 antibody (red) and anti-CD2AP antibody (green). Co-localization of CD2AP and IRS1 was observed in the cytosol (left panel). The cells were stained with anti-IRS1 antibody (red) and anti-cbl-b antibody (green) (mid panel) or anti-cbl antibody (green) (right panel). Co-localization of IRS1 and cbl-b or cbl was observed in the cytosol.

Figure 40:
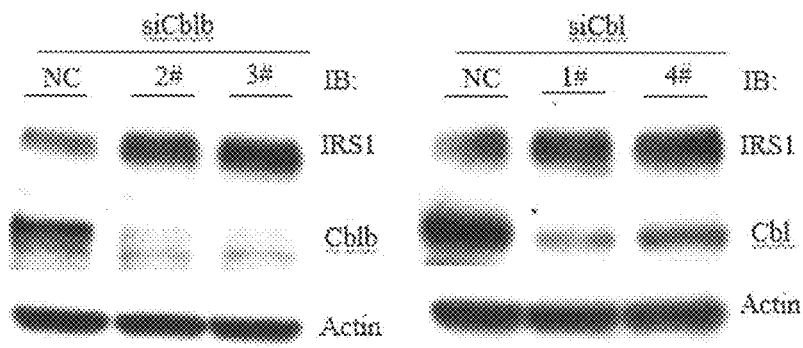

FIG. 40 shows photographs of western blots. Cbl-b/cbl expressions in Huh7.5.1 cells were down-regulated with siRNA specific for cbl-b or cbl, and IRS1 and cbl-b/cbl proteins were immunoblotted with corresponding antibodies. Actin from the treatment was blotted as loading control. 2 # and 3 # were two different siRNAs specific for cbl-b, and 1 # and 4 # were two different siRNAs specific for cbl. NC is a negative control siRNA. The data show that IRS1 level in Huh7.5.1 cells is significantly up-regulated in cbl-b down-regulated cells (left panel) or cbl down-regulated cells (right panel).

Figure 41:
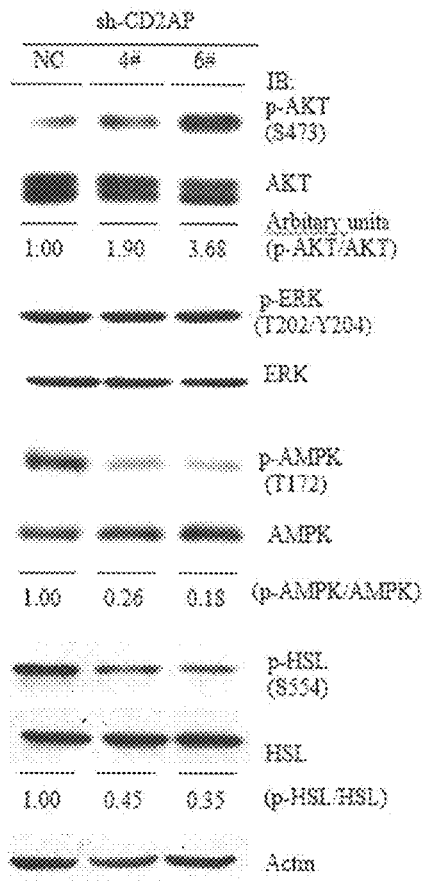

FIG. 41 shows photographs of western blots. Akt-AMPK-HSL axis was activated in CD2AP down-regulated cells (4 # & 6 #) compared to control (NC) cells. Total cell lysates were immunoblotted with different antibodies targeting AMPK signaling pathway. P-Akt (s473) but not total Akt was increased; p-AMPK (T172) but not total AMPK was reduced; p-HSL (S554) but not total HSL was reduced; no change in p-Erk or total Erk was observed.

Figure 42:
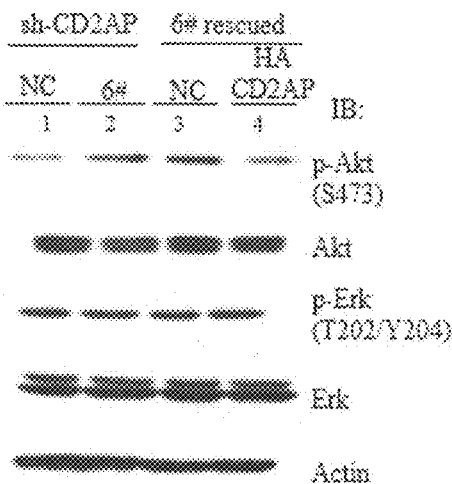

FIG. 42 shows photographs of western blots. P-Akt expression level was recovered in CD2AP-rescued cells compared to control cells. Lysates from CD2AP-rescued cells and control cells were immunoblotted with anti-p-Akt (S473) and anti-Akt antibodies. More p-Akt was detected in CD2AP down-regulated cells (6 #) than in control cells. When CD2AP was rescued in CD2AP down-regulated cells, less p-Akt was detected in CD2AP-rescued cells than in control cells.

Figure 43:
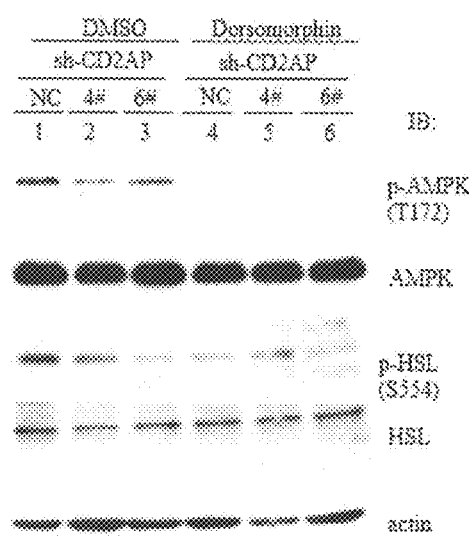

FIG. 43 shows photographs of western blots. Dorsomophin (an inhibitor for AMPK) treatment of CD2AP down-regulated cells (4 # & 6 #) reduced p-AMPK and p-HSL levels compared to control cells (NC). Cells were cultured in complete medium for 48 hours and then treated with DMSO or dorsomorphin (5 μM) for four hours. Total cell lysates were immunoblotted with specific antibodies.

Figure 44:
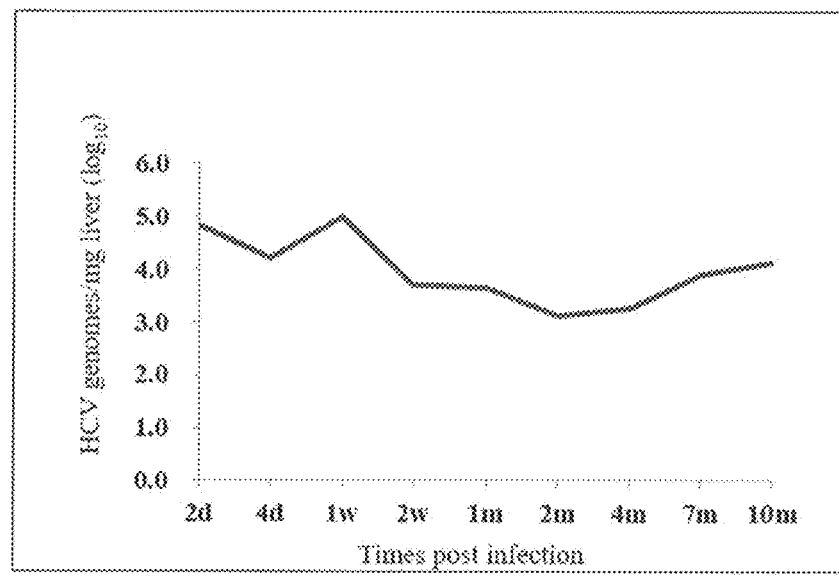

FIG. 44 is a curve graph showing the time course of liver HCV titers in an HCV infection mouse model. Liver HCV titers were quantified by QPCR at different time points after infection. The first two weeks are the acute period of HCV infection whereas the other time points are the chronic infection period of HCV infection.

Figure 45:
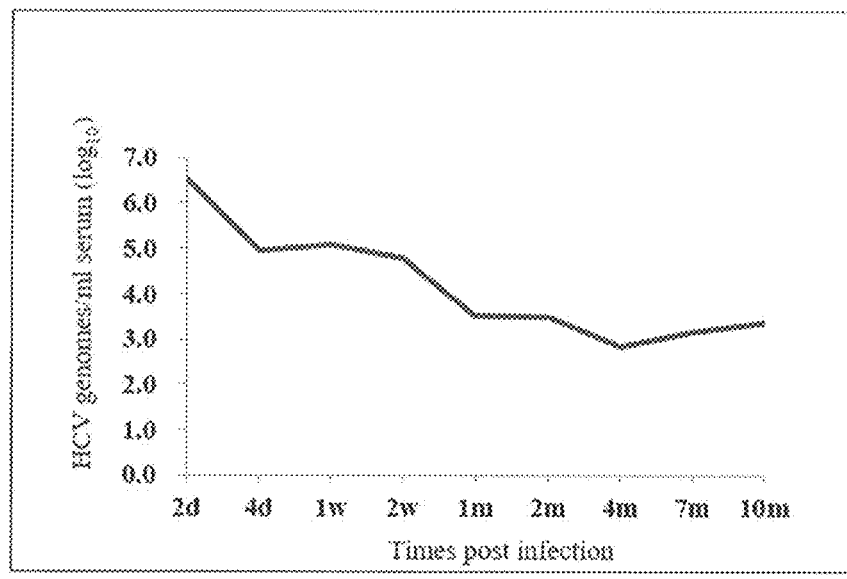

FIG. 45 is a curve graph showing the time course of serum HCV titers in the HCV infection mouse model. Serum HCV titers were quantified QPCR at different time points after infection.

Figure 46:
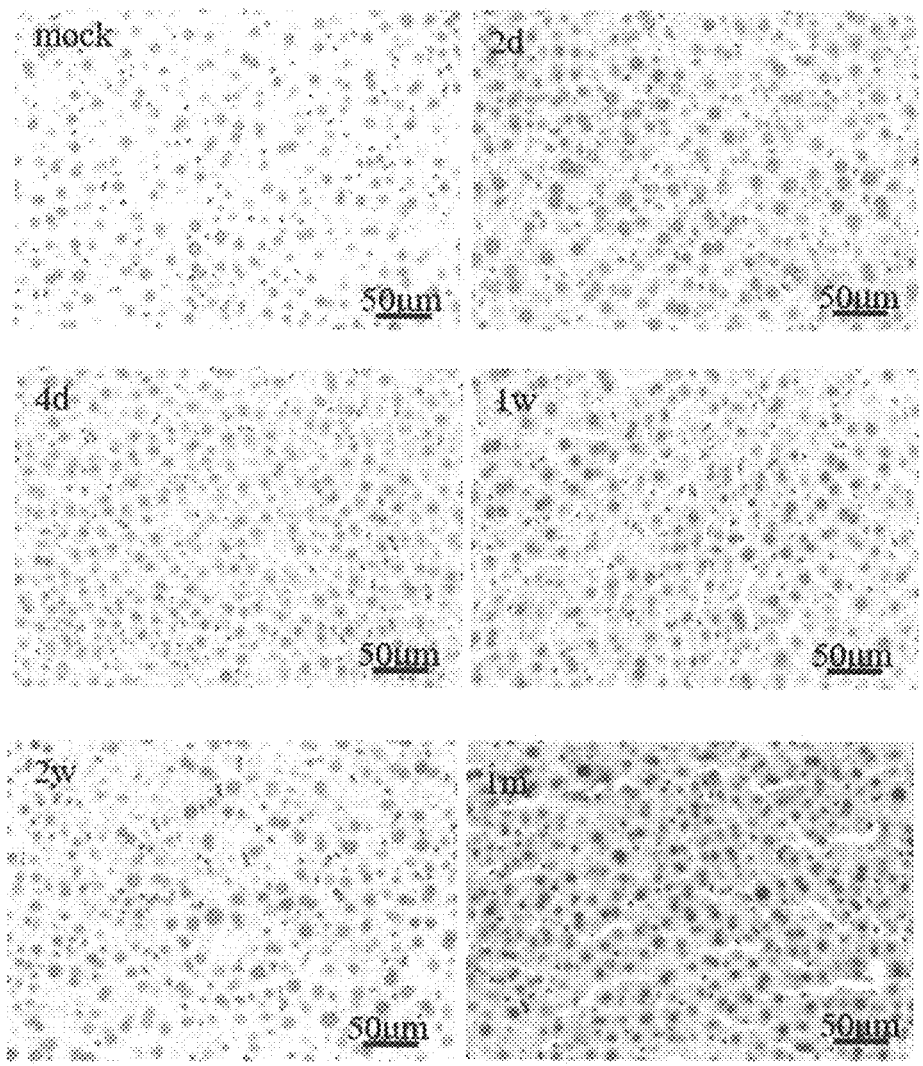
Figure 46:
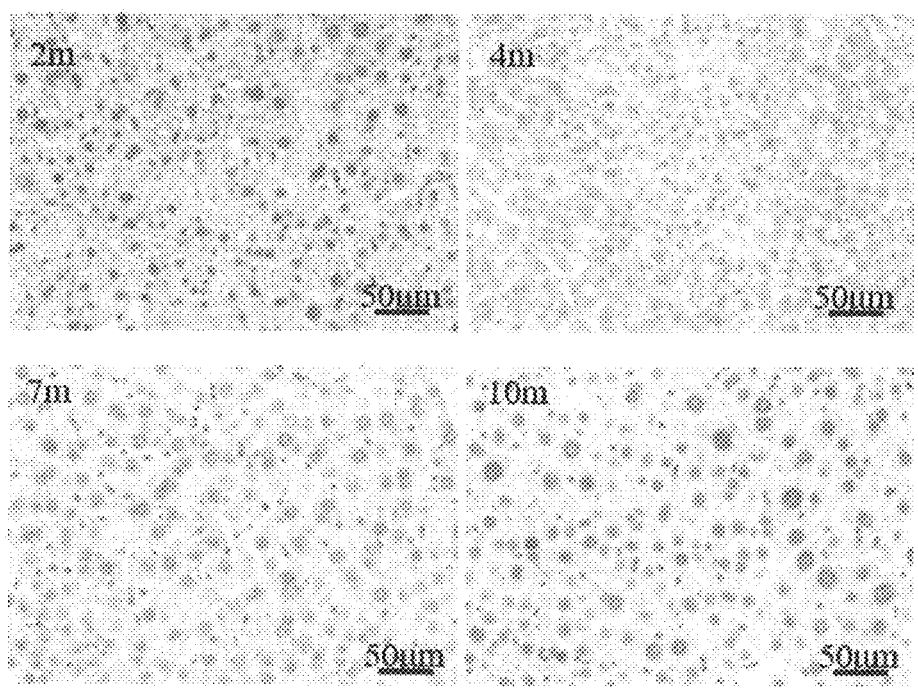

FIG. 46 shows photographs of CD2AP-stained mouse liver sections from HCV infected mice at different post-infection time points. HCV infection induced CD2AP expression. CD2AP immunostaining was observed in the liver sections at post HCV infection time of 1 month, 2 months, and 4 months, which corresponds well with the appearance of steatosis.

Figure 47:
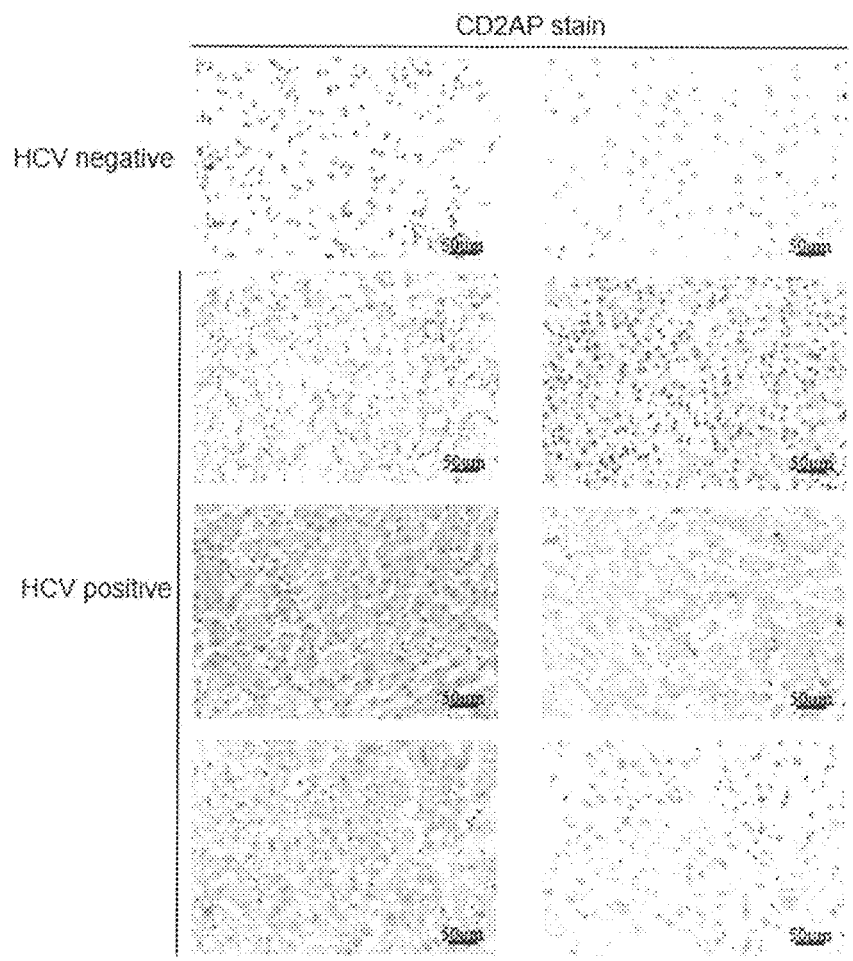

FIG. 47 shows photographs of CD2AP-stained liver biopsies from HCV-infected and non-HCV-infected patients. The liver biopsies from non-HCV-infected controls showed no CD2AP staining, but the liver biopsies from HCV-infected patients showed positive CD2AP staining.

Figure 48:
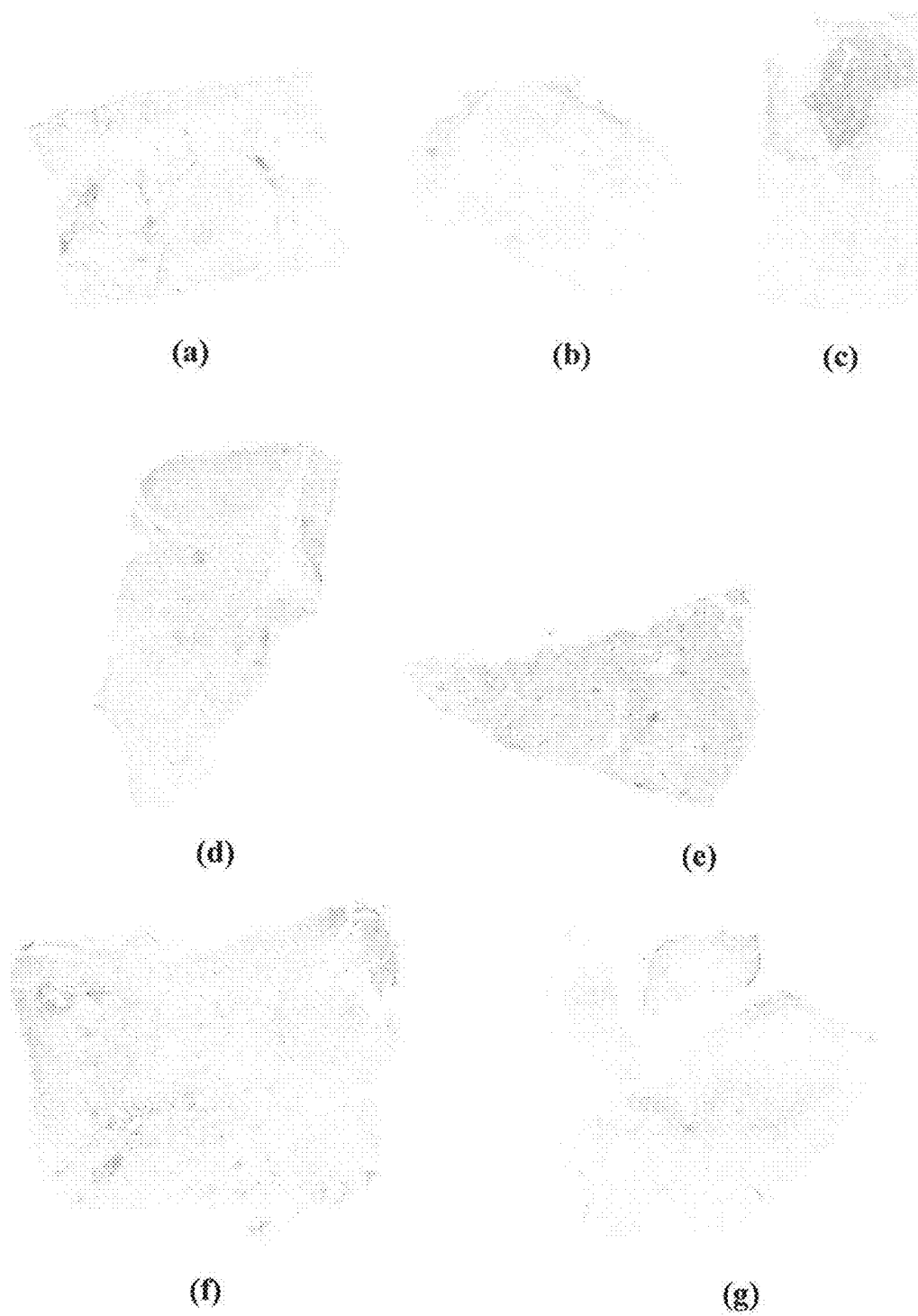

FIG. 48 shows photographs of CD2AP-stained liver biopsies from diabetic patients. All 7 patients showed CD2AP immunostaining in their liver tissues.

DETAILED DESCRIPTION OF THE INVENTION

The present invention may be understood more readily by reference to the following detailed description of certain embodiments of the invention.

Throughout this application, where publications are referenced, the disclosures of these publications are hereby incorporated by reference, in their entireties, into this application in order to more fully describe the state of art to which this invention pertains.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, for example, *Molecular Cloning: A Laboratory Mannual*, second edition (Sambrook et al., 1989)(30); *Current Protocols in Molecular Biology* (F. M. Ausubel et al., eds., 1987)(31); *Protein Analysis and Purification-Benchtop Techniques* (Ian M. Rosenberg, 1996) (32); *Methods for Protein Analysis: a Practical Guide for Laboratory Protocols* (Robert A Copeland, 2013)(33); *Current Protocols in Immunology* (John E. Coligan, Barbara Bierer et al., 1999)(34).

The present invention discovers that CD2 associated protein (CD2AP), a scaffolding molecule that regulates the actin cytoskeleton, is required for HCV assembly. CD2AP interacts with HCV non-structural protein NS5A, and transfers NS5A via an actin dependent manner to a cellular machinery which is then targeting to LDs via a microtubule dependent manner. The interaction between NS5A and CD2AP requires the SH3 domains of CD2AP and the domain III of NS5A. Normal hepatocyte cells do not express CD2AP, but HCV infection induces CD2AP expression. In CD2AP-expression cells, down-regulation of CD2AP expression significantly reduces HCV assembly and propagation.

CD2AP is an adaptor protein with three SH3 domains, and its haploinsufficiency is a determinant of human glomerular disease susceptibility (35). CD2AP was shown to down regulate cell surface receptor tyrosine kinase activity via E3 ligase (36-39). In addition to regulate cell surface receptor signaling, CD2A has been shown to positively stimulate PI3K signaling (40, 41), a pathway involved in lipid metabolism.

The present invention also discovers that CD2AP interacts with IRS1. In CD2AP-expression hepatic cells, down-regulation of CD2AP increases the level of IRS1 proteins. CD2AP expression is observed in the liver tissues from diabetic patients.

The present invention also discovers that CD2AP, cbl-b/cbl, and IRS1 are co-localized in the same protein complex. Cbl-b/cbl are the E3 ligase. Cbl-b/cbl is known to interact with CD2AP. The present invention discovers that cbl-b/cbl interacts with IRS1 by showing that Cbl-b/cbl could be co-purified with IRS1 and co-localized with IRS1. When cbl-b/cbl level was down-regulated by siRNA, the level of IRS1 was up-regulated.

In certain embodiments, the present invention provides a method for down-regulating CD2AP expression in a subject. The subject is a human being or dog. In certain embodiments, the CD2AP expression is preferably down-regulated in hepatic cells in the liver tissues of the subject. The method for down-regulating CD2AP expression comprises: administering a CD2AP down-regulation composition to the subject, thereby the CD2AP expression in the liver tissues of the subject is down-regulated. In certain embodiments, the CD2AP down-regulation composition comprises siRNA/shRNAi polynucleotides specific for CD2AP (SEQ ID NO 1 for human or SEQ ID NO 57 for dog) encoding an amino acid sequence represented by SEQ ID NOS 2 or 58 respectively. In certain embodiments, the CD2AP-specific siRNA/shRNAi polynucleotides are complementary to the nucleotide sequences selected from the group consisting of SEQ ID NOS 3-20 for human (Table 1) or SEQ ID NOS 59-76 for dog (Table 3). In certain embodiments, the CD2AP down-regulation composition comprises a CRISPR/Cas9 vector that specifically targets the CD2AP in the subject. The CD2AP-specific CRISPR/Cas9 vector comprises a guide polynucleotide selected from the group consisting of SEQ ID NOS 21-56 for human (Table 2) or SEQ ID NOS 77-103 for dog (Table 4). In addition, Transcription Activator-Like Effector Nuclease (Talen) and Zinc-finger nucleases (ZFNs) can also be used to down-regulate CD2AP expression.

TABLE 1 siRNA/shRNAi sequences for down-regulating CD2AP expression

| SEQ ID NO # | Nucleotide sequences |
|---|---|
| SEQ ID NO 3 | GCTGGAAGGAGAACTAAATGG |
| SEQ ID NO 4 | GGAGAACTAAATGGGAGAAGA |
| SEQ ID NO 5 | GGACTTCCAGCTGGAGGAATT |
| SEQ ID NO 6 | GGAGCTGAAAGTGGGAGATAT |
| SEQ ID NO 7 | GCTGAAAGTGGGAGATATTAT |
| SEQ ID NO 8 | GCTGAAAGTGGGAGATATTAT |
| SEQ ID NO 9 | GCCCAGGACGATTCAGAAACT |
| SEQ ID NO 10 | GCTGGGCCTACTTCACCTATA |
| SEQ ID NO 11 | GCCAGTAATTTACTGAGATCT |
| SEQ ID NO 12 | GCTTCATCTCACTGCAAATAG |
| SEQ ID NO 13 | GGAAGTTTCCAGCAGATTTCA |

TABLE 1-continued siRNA/shRNAi sequences for down-regulating CD2AP expression

| SEQ ID NO # | Nucleotide sequences |
|---|---|
| SEQ ID NO 14 | AGCCGAGGGTCTGGGCAAA |
| SEQ ID NO 15 | AGCCGAGGGTCTGGGCAAA |
| SEQ ID NO 16 | TGAAGAGACTGGTAGGAGA |
| SEQ ID NO 17 | CTAAATGGGAGAAGAGGAA |
| SEQ ID NO 18 | AGGATGAACTGGAGCTGAA |
| SEQ ID NO 19 | GGTAACAGATGATGGTGAA |
| SEQ ID NO 20 | GGAAACAGATGATGTGAAA |

TABLE 2

CRISPR/CAS9 target sequences for down-regulating CD2AP expression

| SEQ ID NO # | Nucleotide sequences |
|---|---|
| SEQ ID NO 21 | AAAGGCGACACCGTAGACTA |
| SEQ ID NO 22 | CGACACCGTAGACTAAGGTG |
| SEQ ID NO 23 | GTGGGAAAACCGCGGTCGGG |
| SEQ ID NO 24 | GGCGACACCGTAGACTAAGG |
| SEQ ID NO 25 | AGGGTGGGAAAACCGCGGTC |
| SEQ ID NO 26 | TGGGAAAACCGCGGTCGGGC |
| SEQ ID NO 27 | GCGACACCGTAGACTAAGGT |
| SEQ ID NO 28 | CAGGGTGGGAAAACCGCGGT |
| SEQ ID NO 29 | CGACCGCGGTTTTCCCACCC |
| SEQ ID NO 30 | AAAACCGCGGTCGGGCGGGC |
| SEQ ID NO 31 | CGAGGCTAGGCGGGCGCTCG |
| SEQ ID NO 32 | GAAAACCGCGGTCGGGCGGG |
| SEQ ID NO 33 | GAGGGTCTGGGCAAACCGGT |
| SEQ ID NO 34 | TGGGTCCCCACCTTAGTCTA |
| SEQ ID NO 35 | CGAGGGTCTGGGCAAACCGG |
| SEQ ID NO 36 | GCGCTCGGGGTTGGAGCCGA |
| SEQ ID NO 37 | TCCGAGGCTAGGCGGGCGCT |
| SEQ ID NO 38 | TTTTCTAACTGCGAGTGCTA |
| SEQ ID NO 39 | CCGAGGCTAGGCGGGCGCTC |
| SEQ ID NO 40 | AAACCGCGGTCGGGCGGGCG |
| SEQ ID NO 41 | TTAGCACTCGCAGTTAGAAA |
| SEQ ID NO 42 | GCTAGGCGGGCGCTCGGGGT |
| SEQ ID NO 43 | TCCCCACTGCGGGAGCGGCC |
| SEQ ID NO 44 | CCCGAGCGCCCGCCTAGCCT |
| SEQ ID NO 45 | ACCCTGGCCGCTCCCGCAGT |

TABLE 2-continued

CRISPR/CAS9 target sequences for down-regulating CD2AP expression

| SEQ ID NO # | Nucleotide sequences |
|---|---|
| SEQ ID NO 46 | CGGCCAGGGTGGGAAAACCG |
| SEQ ID NO 47 | CGAGTGCTAAGGAAGAGGCG |
| SEQ ID NO 48 | AACTGCGAGTGCTAAGGAAG |
| SEQ ID NO 49 | GGCGGGCTCCGAGGCTAGGC |
| SEQ ID NO 50 | TCCCCAGGAGCCACGGCGGC |
| SEQ ID NO 51 | CTACCCCGCCCGCCCGACCG |
| SEQ ID NO 52 | GTAGGGCCCTCCCGCCGCCG |
| SEQ ID NO 53 | CACCGGTTTGCCCAGACCCT |
| SEQ ID NO 54 | CCCTGGCCGCTCCCGCAGTG |
| SEQ ID NO 55 | AGCCGAGGGTCTGGGCAAAC |
| SEQ ID NO 56 | TGGCCGCTCCCGCAGTGGGG |

TABLE 3 siRNA sequences for down-regulating canine CD2AP expression

| SEQ ID NO # | Nucleotide sequence |
|---|---|
| SEQ ID NO 59 | GAGGAATGTTTCCTGATAA |
| SEQ ID NO 60 | TCAGTAGACCTAGATTCAT |
| SEQ ID NO 61 | GCGTCAGTGTAAAGTTCTC |
| SEQ ID NO 62 | TAGCTACAGAGAAGAAGTA |
| SEQ ID NO 63 | AGAGGGAGAGATAATTCAC |
| SEQ ID NO 64 | ATCAGTAGACCTAGATTCA |
| SEQ ID NO 65 | GGTACTAATGAAGACGAGC |
| SEQ ID NO 66 | AGAAGAAGATAGTGCCAAC |
| SEQ ID NO 67 | CTCATGAAGCCAAGAGGA |
| SEQ ID NO 68 | CGAATAAGCACCTATGGAC |
| SEQ ID NO 69 | CTGGAATGGAGACAACCAA |
| SEQ ID NO 70 | GCAAGCTCAGAAAGTGTCT |
| SEQ ID NO 71 | GCTCAGAAAGTGTCTACAA |
| SEQ ID NO 72 | CAGAAAGTGTCTACAACTT |
| SEQ ID NO 73 | GTCTACAACTTCTCCGGTG |
| SEQ ID NO 74 | GGAGTCGGATTTCTGGTCA |
| SEQ ID NO 75 | GTCACGGGTCAGTTGACTA |
| SEQ ID NO 76 | ACGGGTCAGTTGACTATAT |

TABLE 4

CRISPR/CAS9 target sequences for down-regulating canine CD2AP expression

| SEQ ID NO # | Nucleotide sequence |
| --- | --- |
| SEQ ID NO 77 | AAAGGCAGACACTCAACCGCCGG |
| SEQ ID NO 78 | ATGTATTGAAGTGAGACACCTGG |
| SEQ ID NO 79 | ATGATGTGGGACTCCATCCCAGG |
| SEQ ID NO 80 | AGGGCGTGACCCCCAAGTCCTGG |
| SEQ ID NO 81 | TGTATTGAAGTGAGACACCTGGG |
| SEQ ID NO 82 | GGGCGTGACCCCCAAGTCCTGGG |
| SEQ ID NO 83 | CCATGCAGGAAGCATGATGTGGG |
| SEQ ID NO 84 | GGGGTCACGCCCTGAGCCAAAGG |
| SEQ ID NO 85 | TCCATGCAGGAAGCATGATGTGG |
| SEQ ID NO 86 | ATTGAAGTGAGACACCTGGGTGG |
| SEQ ID NO 87 | GACTCCATCCCAGGACTTGGGGG |
| SEQ ID NO 88 | GAGTGTCTGCCTTTGGCTCAGGG |
| SEQ ID NO 89 | TGGGACTCCATCCCAGGACTTGG |
| SEQ ID NO 90 | AGACACCTGGGTGGCTCCGGCGG |
| SEQ ID NO 91 | TGAGTGTCTGCCTTTGGCTCAGG |
| SEQ ID NO 92 | GGACTCCATCCCAGGACTTGGGG |
| SEQ ID NO 93 | GTGACCCCAAGTCCTGGGATGG |
| SEQ ID NO 94 | GGCGGTTGAGTGTCTGCCTTTGG |
| SEQ ID NO 95 | GTGAGACACCTGGGTGGCTCCGG |
| SEQ ID NO 96 | CCCACATCATGCTTCCTGCATGG |
| SEQ ID NO 97 | GGGACTCCATCCCAGGACTTGGG |
| SEQ ID NO 98 | TAACGCAACTTTCTATTTTTTGG |
| SEQ ID NO 99 | CTCACTTCAATACATTTTTAAGG |
| SEQ ID NO 100 | CCAGTTAAAAAGAAAATCTAAGG |
| SEQ ID NO 101 | CTCAACCGCCGGAGCCACCCAGG |
| SEQ ID NO 102 | TAAAGCAACTTTCTATTTTTTGG |
| SEQ ID NO 103 | CCTTAGATTTTCTTTTTAACTGG |

In certain embodiments, the present invention provides a pharmaceutical composition for down-regulating CD2AP expression in a subject. The subject is a human being or dog. In certain embodiments, the CD2AP expression is preferably down-regulated in hepatic cells in the liver tissues of the subject. In certain embodiments, the CD2AP down-regulation composition comprises siRNA/shRNAi polynucleotides specific for CD2AP (SEQ ID NO 1 for human or SEQ ID NO 57 for dog) encoding an amino acid sequence represented by SEQ ID NOS 2 or 58 respectively. In certain embodiments, the CD2AP-specific siRNA/shRNAi polynucleotides are complementary to the nucleotide sequences selected from the group consisting of SEQ ID NOS 3-20 for human (Table 1) or SEQ ID NOS 59-76 (Table 3). In certain embodiments, the CD2AP down-regulation composition comprises a CRISPR/Cas9 system that specifically targets the CD2AP in the subject. The CD2AP-specific CRISPR/Cas9 system comprises a guide polynucleotide selected from the group consisting of SEQ IS NOS 21-56 for human (Table 2) or SEQ ID NOS 77-103 for dog (Table 4).

In certain embodiments, the present invention provides a method for screening a candidate agent that is capable of reducing the interaction between CD2AP and HCV nonstructural protein NS5A. The CD2AP has an amino acid sequence represented by SEQ ID NO 2 or a variant thereof, where the variant is defined as an amino acid sequence that shares the identity of at least 80%, more preferably 90%, or even more preferably 95% with SEQ ID NO 2. SEQ ID NO 2 is encoded by a nucleic acid sequence represented by SEQ ID NO 1, where a CD2AP variant can be encoded by a nucleic acid sequence that shares the identity of at least 80%, more preferably 90%, or even more preferably 95% with SEQ ID NO 1. The NS5A has an amino acid sequence represented by SEQ ID NO 105 or a variant thereof, where the variant is defined as an amino acid sequence that shares the identity of at least 80%, more preferably 90%, or even more preferably 95% with SEQ ID NO 105. SEQ ID NO 105 is encoded by a nucleic acid sequence represented by SEQ ID NO 104, where a NS5A variant can be encoded by a nucleic acid sequence that shares the identity of at least 80%, more preferably 90%, or even more preferably 95% with SEQ ID NO 104. The method comprises providing cells expressing both CD2AP and NS5A, contacting a candidate agent with the cells expressing both CD2AP and NS5A, and then assaying the effects of the candidate agent on the interaction between CD2AP and NS5A, where the candidate agent is identified if it reduces the interaction between CD2AP and NS5A to a predefined threshold.

The cells expressing both CD2AP and NS5A can be any suitable primary cell or cell line. In certain embodiments, the suitable cells are cell lines that express CD2AP intrinsically, and NS5A expression can be achieved by transfection of NS5A expression vectors; and the cell lines are preferably hepatic tumor cell lines. In certain embodiments, the suitable cells are hepatic cells with HCV infection.

The assay for assaying the interaction between CD2AP and NS5A is any suitable one that can measure or determine the interaction between CD2AP and NS5A. In certain embodiments, the assay is co-immunoprecipitation, co-localization, and confocal time-lapsed live cell imaging of CD2AP and NS5A co-movement; how to perform these assays is well known in the art; thus, no details are provided herein. The predefined threshold for determining whether a candidate agent is effective in reducing the interaction between CD2AP and NS5A is defined as at least 70%, more preferably 80%, reduction of the interaction between CD2AP and NS5A. For example, in the co-immunoprecipitation assay, the predetermined threshold is that the co-immunoprecipitated amount of either CD2AP or NS5A from the cells treated with the candidate agent is reduced at least 70%, more preferably 80%, compared to the cells without treatment of the candidate agent.

In certain embodiments, the present invention provides a pharmaceutical composition for reducing the interaction between CD2AP and NS5A. In certain embodiments, the pharmaceutical composition comprises a peptide with 5-40 amino acids, preferably 10-30 amino acids, more preferably 15-25 amino acids, where the peptide is a derivative of amino acids 3-58 of SEQ ID NO 2, amino acids 111-165 of SEQ ID NO 2, amino acids 271-327 of SEQ ID NO 2, and amino acids 353-466 of SEQ ID NO 105. A derivative is defined as a peptide that shares the identity of at least 80%, more preferably 90%, or even more preferably 95% with the corresponding sequences.

In certain embodiments, the present invention provides a method for screening a candidate agent that is capable of reducing the interaction between CD2AP and IRS1 The CD2AP has an amino acid sequence represented by SEQ ID NOS 2 or 58 or a variant thereof, where the variant is defined as an amino acid sequence that shares the identity of at least 80%, more preferably 90%, or even more preferably 95% with SEQ ID NOS 2 or 58. SEQ ID NOS 2 or 58 are encoded by a nucleic acid sequence represented by SEQ ID NOS 1 or 57, respectively, where a CD2AP variant can be encoded by a nucleic acid sequence that shares the identity of at least 80%, more preferably 90%, or even more preferably 95% with SEQ ID NOS 1 or 57. The IRS1 has an amino acid sequence represented by SEQ ID NOS 107 (for human) or 109 (for dog) or a variant thereof, where the variant is defined as an amino acid sequence that shares the identity of at least 80%, more preferably 90%, or even more preferably 95% with SEQ ID NOS 107 or 109. SEQ ID NO 107 or 109 is encoded by a nucleic acid sequence represented by SEQ ID NO 106 or 108 respectively, where an IRS1 variant can be encoded by a nucleic acid sequence that shares the identity of at least 80%, more preferably 90%, or even more preferably 95% with SEQ ID NOS 106 or 108. The method comprises providing cells expressing both CD2AP and IRS1, contacting a candidate agent with the cells expressing both CD2AP and IRS1, and then assaying the effects of the candidate agent on the interaction between CD2AP and IRS1, where the candidate agent is identified if it reduces the interaction between CD2AP and IRS1 to a predefined threshold.

The cells expressing both CD2AP and IRS1 can be any suitable primary cell or cell line. In certain embodiments, the suitable cells are cell lines that express CD2AP and IRS1.

The assay for assaying the interaction between CD2AP and IRS1 is any suitable one that can measure or determine the interaction between CD2AP and IRS1. In certain embodiments, the assay is co-immunoprecipitation, and co-localization; how to perform these assays is well known in the art; thus, no details are provided herein. The predefined threshold for determining whether a candidate agent is effective in reducing the interaction between CD2AP and IRS1 is defined as at least 70%, more preferably 80%, reduction of the interaction between CD2AP and IRS1. For example, in the co-immunoprecipitation assay, the predetermined threshold is that the co-immunoprecipitated amount of either CD2AP or IRS1 from the cells treated with the candidate agent is reduced at least 70%, more preferably 80%, compared to the cells without treatment of the candidate agent.

In certain embodiments, the present invention provides a pharmaceutical composition for reducing the interaction between CD2AP and IRS1. In certain embodiments, the pharmaceutical composition comprises a peptide with 5-40 amino acids, preferably 10-30 amino acids, more preferably 15-25 amino acids, where the peptide is a derivative of amino acids 3-58 of SEQ ID NO 2 or 58, amino acids 111-165 of SEQ ID NO 2 or 58, and amino acids 271-327 of SEQ ID NO 2 or 58. A derivative is defined as a peptide that shares the identity of at least 80%, more preferably 90%, or even more preferably 95% with the corresponding sequences.

In certain embodiments, the present invention provides a method for screening a candidate agent that is capable of reducing the interaction between Cbl-b/Cbl and IRS1. The Cbl-b has an amino acid sequence represented by SEQ ID NO 111 or 160 or a variant thereof, where the variant is defined as an amino acid sequence that shares the identity of at least 80%, more preferably 90%, or even more preferably 95% with SEQ ID NO 111 or 160. SEQ ID NO 111 or 160 is encoded by a nucleic acid sequence represented by SEQ ID NO 110 or 159 respectively, where a Cbl-b variant can be encoded by a nucleic acid sequence that shares the identity of at least 80%, more preferably 90%, or even more preferably 95% with SEQ ID NO 110 or 159. The Cbl has an amino acid sequence represented by SEQ ID NO194 or 245 or a variant thereof, where the variant is defined as an amino acid sequence that shares the identity of at least 80%, more preferably 90%, or even more preferably 95% with SEQ ID NO 194 or 245. SEQ ID NO 194 or 245 is encoded by a nucleic acid sequence represented by SEQ ID NO 193 or 244, respectively, where a Cbl-b/Cbl variant can be encoded by a nucleic acid sequence that shares the identity of at least 80%, more preferably 90%, or even more preferably 95% with SEQ ID NO 193 or 244. The IRS1 has an amino acid sequence represented by SEQ ID NO 107 or 109 or a variant thereof, where the variant is defined as an amino acid sequence that shares the identity of at least 80%, more preferably 90%, or even more preferably 95% with SEQ ID NO 107 or 109. SEQ ID NO 107 or 109 is encoded by a nucleic acid sequence represented by SEQ ID NO 106 or 108, respectively, where an IRS1 variant can be encoded by a nucleic acid sequence that shares the identity of at least 80%, more preferably 90%, or even more preferably 95% with SEQ ID NO 106 or 108. The method comprises providing cells expressing both Cbl-b/Cbl and IRS1, contacting a candidate agent with the cells expressing both Cbl-b/Cbl and IRS1, and then assaying the effects of the candidate agent on the interaction between Cbl-b/Cbl and IRS1, where the candidate agent is identified if it reduces the interaction between Cbl-b/Cbl and IRS1 to a predefined threshold.

The cells expressing both Cbl-b/Cbl and IRS1 can be any suitable primary cell or cell line. In certain embodiments, the suitable cells are cell lines that express Cbl-b/Cbl and IRS 1.

The assay for assaying the interaction between Cbl-b/Cbl and IRS1 is any suitable one that can measure or determine the interaction between Cbl-b/Cbl and IRS1. In certain embodiments, the assay is co-immunoprecipitation, and co-localization; how to perform these assays is well known in the art; thus, no details are provided herein. The predefined threshold for determining whether a candidate agent is effective in reducing the interaction between Cbl-b/Cbl and IRS1 is defined as at least 70%, more preferably 80%, reduction of the interaction between Cbl-b/Cbl and IRS1. For example, in the co-immunoprecipitation assay, the predetermined threshold is that the co-immunoprecipitated amount of either Cbl-b/Cbl or IRS1 from the cells treated with the candidate agent is reduced at least 70%, more preferably 80%, compared to the cells without treatment of the candidate agent.

In certain embodiments, the present invention provides a method for down-regulating Cbl-b/Cbl expression in a subject. The subject is a human being or dog. In certain embodiments, the Cbl-b/Cbl expression is preferably down-regulated in hepatic cells in the liver tissues of the subject. The method for down-regulating Cbl-b/Cbl expression comprises: administering a Cbl-b/Cbl down-regulation composition to the subject, thereby the Cbl-b/Cbl expression in the liver tissues of the subject is down-regulated. In certain embodiments, the Cbl-b/Cbl down-regulation composition comprises siRNA/shRNAi polynucleotides specific for Cbl-b/Cbl (SEQ ID NO 110 or 159 or SEQ ID NO 193 or 244) encoding an amino acid sequence represented by SEQ ID NO 111 or 160 or SEQ ID NO 110 or 245, respectively. In certain embodiments, the Cbl-b/Cbl-specific siRNA/shRNAi polynucleotides are complementary to the nucleotide sequences selected from the group consisting of SEQ ID NOS 112-124 (Table 5) or 161-170 (Table 7) and SEQ ID NOS 195-208 (Table 9) or 246-255 (Table 11). In certain embodiments, the Cbl-b/Cbl down-regulation composition comprises a CRISPR/Cas9 vector that specifically targets the Cbl-b/Cbl in the subject. The Cbl-b/Cbl-specific CRISPR/Cas9 vector comprises a guide polynucleotide selected from the group consisting of SEQ ID NOS 125-158 (Table 6) or 171-192 (Table 8)) and SEQ ID NOS 209-243 (Table 10) or 256-280 (Table 12). In addition, Transcription Activator-Like Effector Nuclease (Talen) and Zinc-finger nucleases (ZFNs) can also be used to down-regulate Cbl-b/Cbl expression.

TABLE 5 siRNA/shRNAi sequences for down-regulating human Cbl-b expression

| SEQ ID NO # | Nucleotide sequence |
|---|---|
| SEQ ID NO 112 | GCCTGATACATATCAGCAT |
| SEQ ID NO 113 | GCGGAATTGGAATTTCTTA |
| SEQ ID NO 114 | GCATGCCGATGCTAGACTT |
| SEQ ID NO 115 | GCCTGATACATATCAGCAT |
| SEQ ID NO 116 | GGAGAGAATGTATGAAGAACA |
| SEQ ID NO 117 | GCGGAATTGGAATTTCTTAGC |
| SEQ ID NO 118 | GCACGACTACAGAAATATAGC |
| SEQ ID NO 119 | GGAATATCTTACAGACCATAC |
| SEQ ID NO 120 | GCACCAAACCCGGAAGCTATA |
| SEQ ID NO 121 | GCCTGGATCTAATTCAGAAAG |
| SEQ ID NO 122 | GGAATCACAGCGAGTTCAAAT |
| SEQ ID NO 123 | GGAACACATGGTCCATCTTCA |
| SEQ ID NO 124 | GCATAGTCTCATTGAACATTC |

TABLE 6

CRISPR/CAS9 target sequences for down-regulating human Cbl-b expression

| SEQ ID NO # | Nucleotide sequence |
|---|---|
| SEQ ID NO 125 | GTTGCGTTTCCACGTCTCGG |
| SEQ ID NO 126 | GAACAGCTCGCTCCCGAAGA |
| SEQ ID NO 127 | ATTGTTGCGTTTCCACGTCT |
| SEQ ID NO 128 | AGTGCTGCTGCGGCGTCCCG |
| SEQ ID NO 129 | AGGAGGAGGAGACCGCTCGC |
| SEQ ID NO 130 | GAAGGAGCAACCCAGCGCGC |
| SEQ ID NO 131 | GCGCGCAGGCCTCCGAGACG |
| SEQ ID NO 132 | CGTCTCGGAGGCCTGCGCGC |
| SEQ ID NO 133 | GTCCCGCGGCCTCCCCGAGT |
| SEQ ID NO 134 | CTCCCCTCCCGCCCGACTCG |

TABLE 6-continued

CRISPR/CAS9 target sequences for down-regulating human Cbl-b expression

| SEQ ID NO # | Nucleotide sequence |
|---|---|
| SEQ ID NO 135 | GACGCCGCAGCAGCACTAGC |
| SEQ ID NO 136 | GTCTCGGAGGCCTGCGCGCT |
| SEQ ID NO 137 | GCGGCCTCCCCGAGTCGGGC |
| SEQ ID NO 138 | CCCTCCCGCCCGACTCGGGG |
| SEQ ID NO 139 | CGCGGCCTCCCCGAGTCGGG |
| SEQ ID NO 140 | CTCCCCGAGTCGGGCGGGAG |
| SEQ ID NO 141 | CGGGTGTGGATTTGTCTTGA |
| SEQ ID NO 142 | GCCTCCCCGAGTCGGGCGGG |
| SEQ ID NO 143 | TCCCGCGGCCTCCCCGAGTC |
| SEQ ID NO 144 | CGCCCGACTCGGGGAGGCCG |
| SEQ ID NO 145 | CTCTCCCCTCCCGCCCGACT |
| SEQ ID NO 146 | TCTCCCCTCCCGCCCGACTC |
| SEQ ID NO 147 | AGCGATCCCACTCCCAGCCG |
| SEQ ID NO 148 | TCAGCGATCCCACTCCCAGC |
| SEQ ID NO 149 | CGCTGGGTTGCTCCTTCTTC |
| SEQ ID NO 150 | GCCCGACTCGGGGAGGCCGC |
| SEQ ID NO 151 | GCGCTGGGTTGCTCCTTCTT |
| SEQ ID NO 152 | CCTCCCCGAGTCGGGCGGGA |
| SEQ ID NO 153 | TGTGTGTGGGGAGCCCCGGC |
| SEQ ID NO 154 | GTGTGTGGGGAGCCCCGGCT |
| SEQ ID NO 155 | CGCTGGACACCCCACCCCTG |
| SEQ ID NO 156 | GCCGCAGCAGCACTAGCAGG |
| SEQ ID NO 157 | CGGGGCTCCCCACACACACT |
| SEQ ID NO 158 | CTGGGTCCTGTGTGTGCCAC |

TABLE 7 siRNA/shRNAi sequences for down-regulating canine Cbl-b expression

| SEQ ID NO # | Nucleotide sequence |
|---|---|
| SEQ ID NO 161 | CCCACCATATATACTTGAT |
| SEQ ID NO 162 | CCTGATACATATCAGCATT |
| SEQ ID NO 163 | GCGGGCAATAAGACTCTTT |
| SEQ ID NO 164 | GCAGAAATACAGCACCAAA |
| SEQ ID NO 165 | GCACCAAACCTGGAAGCTA |
| SEQ ID NO 166 | GCAATATCTTACAGACCAT |
| SEQ ID NO 167 | CCACACCACATGACCTATAT |
| SEQ ID NO 168 | GCCTCCTCCCTTAAGAGAT |

TABLE 7-continued siRNA/shRNAi sequences for down-regulating canine Cbl-b expression

| SEQ ID NO # | Nucleotide sequence |
|---|---|
| SEQ ID NO 169 | CCTTCATCCCATCCTGTTT |
| SEQ ID NO 170 | CCTCTGATCCAGTGCCATT |

TABLE 8

CRISPR/CAS9 target sequences for down-regulating canine Cbl-b expression

| SEQ ID NO # | Nucleotide sequence |
|---|---|
| SEQ ID NO 171 | CCCCCGAAAAGGACGGATTTTGG |
| SEQ ID NO 172 | CCCCGAAAAGGACGGATTTTGGG |
| SEQ ID NO 173 | CCAAAATCCGTCCTTTTCGGGGG |
| SEQ ID NO 174 | CCCAAAATCCGTCCTTTTCGGGG |
| SEQ ID NO 175 | CGAGGAGGAAACCCCCGAAAAGG |
| SEQ ID NO 176 | GGGTTTCCTCCTCGACCACCAGG |
| SEQ ID NO 177 | TACCCAAAATCCGTCCTTTTCGG |
| SEQ ID NO 178 | AGCAAGCAGCAGCAGATCGCAGG |
| SEQ ID NO 179 | ACCCAAAATCCGTCCTTTTCGGG |
| SEQ ID NO 180 | GGTTTCCTCCTCGACCACCAGGG |
| SEQ ID NO 181 | TCTGCTGCTGCTTGCTTCGGAGG |
| SEQ ID NO 182 | AGAAACCCTGGTGGTCGAGGAGG |
| SEQ ID NO 183 | GGCAGAAACCCTGGTGGTCGAGG |
| SEQ ID NO 184 | AGCAGCAGCAGATCGCAGGACGG |
| SEQ ID NO 185 | AGCAGCAGATCGCAGGACGGTGG |
| SEQ ID NO 186 | GAGGAAACCCCCGAAAAGGACGG |
| SEQ ID NO 187 | GATGCTATTCAAGATGCAGTTGG |
| SEQ ID NO 188 | TCTATGAATGGCAGAAACCCTGG |
| SEQ ID NO 189 | CGATCTGCTGCTGCTTGCTTCGG |
| SEQ ID NO 190 | GCAGGACGGTGGAGAAAACTTGG |
| SEQ ID NO 191 | ATGAATGGCAGAAACCCTGGTGG |
| SEQ ID NO 192 | GGAGAAAACTTGGAAACTCATGG |

TABLE 9 siRNA/shRNAi sequences for down-regulating human Cbl expression

| SEQ ID NO # | Nucleotide sequence |
|---|---|
| SEQ ID NO 195 | CCAGACAATCCCTCACAAT |
| SEQ ID NO 196 | GGACACCTCATGTGCACAT |
| SEQ ID NO 197 | CCAGGCCTCTACGGCCTTT |
| SEQ ID NO 198 | CCAGAAAGCTTTGGTCATT |

TABLE 9-continued siRNA/shRNAi sequences for down-regulating human Cbl expression

| SEQ ID NO # | Nucleotide sequence |
|---|---|
| SEQ ID NO 199 | GCCTGATTGGGCTCATGAAGG |
| SEQ ID NO 200 | GGGAACATTCTCCAGACAATC |
| SEQ ID NO 201 | GCTTCAGGGAAGGCTTCTATT |
| SEQ ID NO 202 | GGGAAGGCTTCTATTTGTTTC |
| SEQ ID NO 203 | GGACACCTCATGTGCACATCC |
| SEQ ID NO 204 | GCAGAATCCCGACCTCAAAGA |
| SEQ ID NO 205 | GGAGCAATGTGAGGGTGAAGA |
| SEQ ID NO 206 | GCCTCTACGGCCTTTGGATAC |
| SEQ ID NO 207 | GCTGTACGTATGAAGCAATGT |
| SEQ ID NO 208 | GGTACTCCTACCAGGACATCC |

TABLE 10

CRISPR/CAS9 target sequences for down-regulating human Cbl expression.

| SEQ ID NO # | Nucleotide sequence |
|---|---|
| SEQ ID NO 209 | CTCGGCTCGACTGCGAGCGA |
| SEQ ID NO 210 | GCCGCCGCCGGCTATCCGGG |
| SEQ ID NO 211 | TCCGCCCGGATAGCCGGCGG |
| SEQ ID NO 212 | GCTCGGCTCGACTGCGAGCG |
| SEQ ID NO 213 | TCGCAGTCGAGCCGAGCCGG |
| SEQ ID NO 214 | CTTCTTCACGTTGCCGGCCA |
| SEQ ID NO 215 | CGGGTTCGGGTGGCCTGATT |
| SEQ ID NO 216 | CGCTCGCAGTCGAGCCGAGC |
| SEQ ID NO 217 | CCGAGCCGGCGGACCCGCCT |
| SEQ ID NO 218 | TCGGGTTCGGGTGGCCTGAT |
| SEQ ID NO 219 | GCCGAGCCGGCGGACCCGCC |
| SEQ ID NO 220 | AGAGCTCTTCTTCACGTTGC |
| SEQ ID NO 221 | GCCGCCGCCGCCGGCTATCC |
| SEQ ID NO 222 | CCCAGGCGGGTCCGCCGGCT |
| SEQ ID NO 223 | CGTCCTTCATGAGCCCAATC |
| SEQ ID NO 224 | CGGAGCCCAGGCGGGTCCGC |
| SEQ ID NO 225 | TGGCCTGATTGGGCTCATGA |
| SEQ ID NO 226 | TCACGTTGCCGGCCATGGCC |
| SEQ ID NO 227 | CGCCGCCGCCGCCGGCTATC |
| SEQ ID NO 228 | GGCAACGTGAAGAAGAGCTC |
| SEQ ID NO 229 | CGGCTCCGGGGGCTCGGGTT |
| SEQ ID NO 230 | TCCGGGGGCTCGGGTTCGGG |
| SEQ ID NO 231 | GGCTCCGGGGGCTCGGGTTC |

TABLE 10-continued

CRISPR/CAS9 target sequences for down-regulating human Cbl expression.

| SEQ ID NO # | Nucleotide sequence |
|---|---|
| SEQ ID NO 232 | GCAACGTGAAGAAGAGCTCT |
| SEQ ID NO 233 | GCAACGTGAAGAAGAGCTCT |
| SEQ ID NO 234 | GCCACCCGAACCCGAGCCCC |
| SEQ ID NO 235 | CACGTTGCCGGCCATGGCCT |
| SEQ ID NO 236 | GCCCGGATAGCCGGCGGCGG |
| SEQ ID NO 237 | GAAGAAGAGCTCTGGGGCCG |
| SEQ ID NO 238 | CAACGTGAAGAAGAGCTCTG |
| SEQ ID NO 239 | AAGAAGAGCTCTGGGGCCGG |
| SEQ ID NO 240 | GGGAGAGAAGCAGGGCGTGA |
| SEQ ID NO 241 | CGGCAGCGGCTCCGGGGGCT |
| SEQ ID NO 242 | CCTGGGCAGGGTCGGAGCCC |
| SEQ ID NO 243 | AGAGAAGCAGGGCGTGAAGG |

TABLE 11 siRNA/shRNAi sequences for down-regulating canine Cbl expression

| SEQ ID NO # | Nucleotide sequence |
|---|---|
| SEQ ID NO 246 | CCAGAAGTTCATTCACAAA |
| SEQ ID NO 247 | GGAACATCCTCCAGACGAT |
| SEQ ID NO 248 | CCAGACGATCCCTCACAAT |
| SEQ ID NO 249 | GCTTCAGGGAAGGCTTCTA |
| SEQ ID NO 250 | GCAGGAATCAGAAGGCCAA |
| SEQ ID NO 251 | CCTTTCTGCCGATGTGAAA |
| SEQ ID NO 252 | GCTGATGATTCTCTCTTTA |
| SEQ ID NO 253 | GCTTCTGGCTCCCTTCATA |
| SEQ ID NO 254 | GCATCTGCCAATGCCATTT |
| SEQ ID NO 255 | GCTGCACATATGAAGCAAT |

TABLE 12

CRISPR/CAS9 target sequences for down-regulating canine Cbl expression

| SEQ ID NO # | Nucleotide sequence |
|---|---|
| SEQ ID NO 256 | CCCGGAGCCGCCGCCGCCCCGG |
| SEQ ID NO 257 | TGCCGGGCGGGTGGGGCTGAGG |
| SEQ ID NO 258 | CGGCCTCATCGGGCTCATGAAGG |
| SEQ ID NO 259 | GGAGCTCTTCTTCACGTTGCCGG |
| SEQ ID NO 260 | CAACGTGAAGAAGAGCTCCGGG |
| SEQ ID NO 261 | GGGGCTCGGGCGGCCTCATCGGG |

TABLE 12-continued

CRISPR/CAS9 target sequences for down-regulating canine Cbl expression

| SEQ ID NO # | Nucleotide sequence |
|---|---|
| SEQ ID NO 262 | GGCAACGTGAAGAAGAGCTCCGG |
| SEQ ID NO 263 | GCAACGTGAAGAAGAGCTCCGGG |
| SEQ ID NO 264 | GGGGGCTCGGGCGGCCTCATCGG |
| SEQ ID NO 265 | GTGAAGAAGAGCTCCGGGGCCGG |
| SEQ ID NO 266 | TGAAGAAGAGCTCCGGGGCCGGG |
| SEQ ID NO 267 | CGTCCTTCATGAGCCCGATGAGG |
| SEQ ID NO 268 | AAGAAGAGCTCCGGGGCCGGGGG |
| SEQ ID NO 269 | GAAGAAGAGCTCCGGGGCCGGGG |
| SEQ ID NO 270 | GATGAGGCCGCCCGAGCCCCCGG |
| SEQ ID NO 271 | GTGGTGGTGGTGCGGCTGGAAGG |
| SEQ ID NO 272 | AAGAGCTCCGGGGCCGGGGCGG |
| SEQ ID NO 273 | CACCTCAGCCCCCACCCGCCCGG |
| SEQ ID NO 274 | CGGCGGCGGCTCCGGGGGCTCGG |
| SEQ ID NO 275 | AGCTCCGGGGCCGGGGCGGCGG |
| SEQ ID NO 276 | GCGGGTGGGGGCTGAGGTGGTGG |
| SEQ ID NO 277 | TCCGGGGCCGGGGCGGCGGCGG |
| SEQ ID NO 278 | GCCGCCGCCGCCCCGGCCCCGG |
| SEQ ID NO 279 | CGGGCGGGTGGGGGCTGAGGTGG |
| SEQ ID NO 280 | GCCGGGGCGGCGGCGGCTCCGG |

In certain embodiments, the present invention provides a pharmaceutical composition for down-regulating Cbl-b/Cbl expression in a subject. The subject is a human being or dog. In certain embodiments, the Cbl-b/Cbl expression is preferably down-regulated in hepatic cells in the liver tissues of the subject. In certain embodiments, the Cbl-b/Cbl down-regulation composition comprises siRNA/shRNAi polynucleotides specific for Cbl-b/Cbl (SEQ ID NO 110 or 159 or SEQ ID NO 193 or 244) encoding an amino acid sequence represented by SEQ ID NO 111 or 160 or SEQ ID NO 110 or 245, respectively. In certain embodiments, the Cbl-b/Cbl-specific siRNA/shRNAi polynucleotides are complementary to the nucleotide sequences selected from the group consisting of SEQ ID NOS 112-124 (Table 5) or 161-170 (Table 7) and SEQ ID NOS 195-208 (Table 9) or 246-255 (Table 11). In certain embodiments, the Cbl-b/Cbl down-regulation composition comprises a CRISPR/Cas9 vector that specifically targets the Cbl-b/Cbl in the subject. The Cbl-b/Cbl-specific CRISPR/Cas9 vector comprises a guide polynucleotide selected from the group consisting of SEQ ID NOS 125-158 (Table 6) or 171-192 (Table 8)) and SEQ ID NOS 209-243 (Table 10) or 256-280 (Table 12).

In certain embodiments, the present invention provides the treatments for HCV infection in a subject. In certain embodiments, the subject is a human. In certain embodiments, the treatment is to specifically down-regulate CD2AP expression in hepatocytes of liver tissues of the subject by administering a composition comprising at least one siRNA/shRNAi nucleotide sequence that is complementary to the nucleotide sequences selected from the group consisting of sequences represented by SEQ ID NOS 3-20 or 59-76. In certain embodiments, the treatment is to specifically down-regulate CD2AP expression in hepatocytes of liver tissues of the subject by administering a CRISPR/Cas9 vector comprising a guide nucleotide sequence selected from the group consisting of the nucleotide sequences represented by SEQ ID NOS 21-56 or 77-103. In certain embodiments, the treatment is to specifically reduce the interaction between CD2AP and NS5A in hepatocytes of liver tissues of the subject by administering a composition comprising the agent that can reduce the interactions between CD2AP and NS5A.

In certain embodiments, the present invention provides the treatments for diabetics in a subject. In certain embodiments, the subject is a human or dog. In certain embodiments, the treatment is to specifically down-regulate CD2AP expression in hepatocytes of liver tissues of the subject by administering a composition comprising at least one siRNA/shRNAi nucleotide sequence that is complementary to the nucleotide sequence selected from the group consisting of sequences represented by SEQ ID NOS 3-20 or 59-76. In certain embodiments, the treatment is to specifically down-regulate CD2AP expression in hepatocytes of liver tissues of the subject by administering a CRISPR/Cas9 vector comprising a guide nucleotide sequence selected from the group consisting of the nucleotide sequences represented by SEQ ID NOS 21-56 or 77-103. In certain embodiments, the treatment is to specifically reduce the interaction between CD2AP and IRS1 in hepatocytes of liver tissues of the subject by administering a composition comprising the agent that can reduce the interactions between CD2AP and IRS1 as afore described.

In certain embodiments, the present invention provides the treatments for diabetics in a subject. In certain embodiments, the subject is a human. In certain embodiments, the treatment is to specifically down-regulate Cbl-b/Cbl expression in hepatocytes of liver tissues of the subject by administering a composition comprising at least one siRNA/shRNAi nucleotide sequence that is complementary to the nucleotide sequences selected from the group consisting of sequences represented by SEQ ID NOS 112-124 or 161-170 and SEQ ID NOS 195-208 or 246-255. In certain embodiments, the treatment is to specifically down-regulate Cbl-b/Cbl expression in hepatocytes of liver tissues of the subject by administering a CRISPR/Cas9 vector comprising a guide nucleotide sequence selected from the group consisting of the nucleotide sequences represented by SEQ ID NOS 125-158 or 171-192 and SEQ ID NOS 209-243 or 256-280. In certain embodiments, the treatment is to specifically reduce the interaction between Cbl-b/Cbl and IRS1 in hepatocytes of liver tissues of the subject by administering a composition comprising the agent that can reduce the interactions between Cbl-b/Cbl and IRS1 as afore described.

In certain embodiments, the present invention provides a diagnostic method for liver abnormalities. The diagnostic method comprises providing a liver sample from a subject, and contacting the liver sample with a detecting agent for detecting expression of CD2AP; thereby indicating liver abnormalities when a CD2AP expression is detected in the liver sample. The abnormalities include HCV infection and diabetes. The assays for detecting the expression of CD2AP can be any suitable ones including PCR and immunostaining.

In certain embodiments, the present invention provides a diagnostic kit for detecting abnormalities in liver sample of a subject. The kit comprises an antibody specific for CD2AP protein or a polynucleotide probe specific for mRNA of CD2AP; and a secondary agent that can detect the antibody bound to CD2AP protein or signal from the mRNA of CD2AP.

The following examples are provided for the purpose of illustrating the application of the principles of the present invention; they are by no means intended to be the coverage of the present invention.

EXAMPLES

1. Materials and Methods 1.1 Cell Lines and Virus

Human hepatoma cells Huh7, its derivative Huh7-Lunet cells and Huh7.5.1 cells and HEK293T cells were cultured in Dulbecco's Modified Eagle Medium (DMEM) (Gibco, cat #11965-092, USA) supplemented with 3.17 g/l sodium bicarbonate, 10% FBS (Gibco, cat #10099-141), 3 g/l HEPES, 100 U/ml of penicillin and streptomycin in a humidified atmosphere with 5% $CO_2$. The Con1 cells harboring the HCV 1b subgenomic HCV replicon pFKI389neo/NS3-3' was derived from Huh7-Lunet cells and maintained in the same medium as Huh7-Lunet cells with addition of 0.5 mg/ml G418 (Merck, 345810) (42). Infectious HCV JFH1 virus contains the HCV genotype 2a strain full-length genomic cDNA sequence (43). The HCV J399EM virus was derived from the JFH-1 virus by inserting the EGFP gene after amino acid 399 of NS5A and introducing five adaptive mutations into the JFH1 genome to enhance the viral production capability (44). The JFH1-luc reporter virus was kindly provided by Professor Xulin Chen at Wuhan Institute of Virology (45). To generate viral stocks, the original HCV viruses were diluted in DMEM and used to inoculate naive Huh7.5.1 cells at a multiplicity of infection (MOI) of 0.1. Infected cells were passaged once at 72 hpi. Then the supernatants were harvested at 7 or 8 days post-infection, aliquoted and stored at −80° C.

1.2 Plasmid Construction and Reagents

Human CD2AP (GenBank #NM_012120) (SEQ ID NO 1; SEQ ID NO 2 for amino acid sequence) and HCV NS5A from genotype 2a (AB047639 JFH1) (SEQ ID NO. 57; SEQ ID NO 58 for amino acid sequence) were cloned into mammalian expression vector pRK-7 HA and pRK-7 Flag plasmids (Addgene) with the corresponding primers. Total RNA from Huh7.5.1 cells infected with HCV JFH1 or uninfected Huh7.5.1 cells was used as template. The truncated NS5A and CD2AP were amplified by polymerase chain reaction (PCR) using full-length NS5A and CD2AP as templates. Mammalian expression plasmid pcDNA3.1 BirA (R118G)-HA (BirA*) was purchased (Addgene). HCV NS5A was subcloned into the N terminus of BirA*. The entire NS5A-BirA*-HA sequence was removed from pcDNA3.1 with restriction enzymes SalI and NotI and inserted into pMSCV-puro. Mouse monoclonal antibodies (mAbs) against Flag, HA, or β-actin were purchased from Tianjin Sungene Biotech (Tianjin, China); mouse polyclonal antibodies against HCV core and rabbit polyclone antibodies against CD2AP (H-290) were purchased from Santa Cruz Biotechnology; mAbs (7B5 and 2F6) against HCV 2a NS5A were purchased from BioFront; mAb 9E10 anti-NS5A was kindly provided by Professor Charles Rice (Rockefeller University, New York, N.Y.) (46). Rabbit mAbs against Phospho (p)-Akt (Ser473) (4060), Akt(4691), p-Erk(91065), Erk(4695P) and PI3K-Akt inhibitor LY294002 (9901) were purchased from Cell Signaling Technology (Massachusetts, USA); rabbit polyclonal antibody anti-ADRP (ab52355) from abcam; rabbit polyclonal antibody against calnexin (RLT0613) from Ruiyingbio (Suzhou, China); HCS Lipid-TOX Deep Red neutral lipid stains and alexa fluor conjugated secondary antibodies from Invitrogen (Carlsbad, USA); horseradish peroxidase (HRP)-conjugated secondary antibody from AntGene Biotech (Wuhan, China); mouse IgG1 isotype control and HRP-streptavidin from Biolegend (San Diego, Calif., USA); 4',6-Diamidine-2'-phenylindole dihydro-chloride (DAPI) from Roche (Mannheim, Germany). All the other reagents were purchased from Amresco (Ohio, USA).

1.3 Cell Lysate Preparation and Western Blotting (WB)

Cells were rinsed gently with ice-cold phosphate buffered saline (PBS) and then solubilized in lysis buffer (20 mM Tris-HCl (pH 7.5), 150 mM NaCl, 1 mM EDTA, 1 mM EGTA, 1% Triton X-100, 2.5 mM sodium pyrophosphate, 1 mM β-glycerol phosphate, 1 mM $Na_3VO_4$, 1 mM PMSF) according to Li et al (47). Protein concentration was determined by BCA assay. Proteins were separated on a 10% SDS-PAGE, and then transferred to nitrocellulose membrane (#9004700, Billerica, Mass., USA). After blocking in 5% non-fat milk in TBST (tris buffered saline (TBS) with 0.1% Tween-20)), the separated proteins were probed with specific primary antibodies, followed by HRP-conjugated secondary antibody.

1.4 Co-Immunoprecipitation (Co-IP)

To perform co-IP, HEK293T cells were seeded in 10 cm cell culture dishes 12 hours before transfection. The plasmids were transfected by calcium phosphate precipitation. Cells were lysed in 1 ml IP buffer containing 50 mM Tris, pH 7.5, 1 mM EDTA, 1% NP40, 150 mM NaCl, 1 mM phenylmethylsulfonyl fluoride (PMSF), and a protease inhibitor cocktail (Complete Mini; Roche). An equal volume of supernatants was incubated with 1.2 μg of the indicated antibody or isotype control antibody and 20 μl of 50% slurry of Protein G sepharose (GE Healthcare Life Sciences) at 4° C. for 3 hours. Co-IPed proteins were separated on a 10% SDS-PAGE. For endogenous co-IP analysis, Huh7.5.1 cells infected with JFH1 for 72 hours were directly lysed, and co-IP was performed as described above.

1.5 Immunofluorescence Staining

Cells were cultured on 20 mm glass bottom confocal dishes (NEST). 72 hours post infection, the cells were then fixed in 4% (w/v) paraformaldehyde (PFA) for 15 minutes at room temperature (RT). After blocking the cells with 10% goat serum plus 1% BSA in PBST, the cells were incubated with indicated primary Abs in blocking buffer. Bound antibodies were probed with alexa fluor conjugated secondary Abs. The nuclei were counterstained with DAPI. LDs were stained with HCS LipidTOX Deep Red neutral lipid stains. After adding anti-fade fluorescence medium, pictures were taken by confocal microscope (Perkin Elmer UltraView Vox confocal microscope).

1.6 RNA Extraction and Quantitative Real-Time RT-PCR (QPCR)

Total RNAs from cultured cells and in culture supernatants were extracted using RNA pure Tissue Composition and RNA pure Virus Composition (#CW0584 and CW0586, CWBiotech, Beijing, China) respectively according to the manufacturer's instructions. First-strand cDNA was synthesized from 1 μg of total RNA using the PrimeScript RT reagent composition (#DRR047A, Takara Bio, Japan). RNA quantification was carried out using SYBR Green Supermix (#170-8882AP, Bio-Rad, USA) on a Bio-Rad Connect™ QPCR instrument (CFX Connect™ Optics Module). The quantities of intracellular HCV RNA and cellular RNA levels were normalized to GAPDH RNA levels. HCV RNA levels in culture supernatants were determined relative to a standard curve comprised of serial dilutions of plasmid containing the HCV JFH-1 cDNA.

1.7 Retrovirus Production and Transduction

To establish a stably knockdown cell line, the short hairpin RNA interference (shRNAi) against target gene was subcloned into pSuper retro puro plasmid (Oligoengine) according to the manufacturer's instructions. Vesicular stomatitis virus glycoprotein (VSV-G)-pseudotyped retroviral particles were produced in 293T cells using calcium phosphate method. Briefly, HEK293T cells were co-transfected with pSuper retro puro constructs and the packaging plasmids pGag-pol and pVSV-G. The shRNA retroviral stocks were used to transduce Huh7.5.1 with 7.5 μg/ml polybrene. The knockdown cells were selected with 2 mg/ml puromycin (Amersco) for at least 7 days. The interference effects of surviving colonies were confirmed by QPCR or western blot analysis. The siRNA/shRNAi sequences targeting CD2AP mRNA were listed in Table 1.

1.8 Functional Rescuing of CD2AP in CD2AP Down Regulated Cells

To functionally rescue CD2AP interference, the CD2AP down-regulated Huh7.5.1 cells (shCD2AP-6 #) was transiently transduced by a lentiviral vector pHAGE expressing exogenous wobble mutant HA-CD2AP (sh-CD2AP 6 #-HA-CD2AP) by altering targeted CD2AP sequence GGAAACAGATGATGTGAAA (2175-2193 of SEQ ID NO 1) to GGAGACGGACGACGTAAAG (SEQ ID NO 281). Lentivirus production was performed as described previously (48). Lentiviral particles containing an empty vector were transduced into shCD2AP-6 # cells as control.

1.9 Affinity Capture of Biotinylated Proteins

Biotinylated proteins were isolated at 4° C. using a previous procedure with modifications (49). In brief, huh7 cells stably expressing NS5A BirA* were incubated for 24 hours in complete media supplemented with 50 μM biotin. Cells from five confluent 10 cm cell culture plates were lysed in cell lysis buffer as described above. Biotinylated proteins were pulled down with 100 μl of streptavidin-agarose beads with rocking at 4° C. overnight. The beads were then washed extensively (49). NS5A interacting proteins were subjected to mass spectrometry analysis and confirmed by immunoblotting.

1.10 HCVpp Entry and HCV IRES-Dependent Translation Assay

HCVpp was generated as described with minor modifications (50). Briefly, HEK 293T cells were co-transfected with pNL4.3.lucRE and pcDNA3.1-E1E2 plasmids. Pseudotyped virus was then used to infect CD2AP knocking down Huh7.5.1 cells to assay the Luciferase activity with Reporter Assay composition (Promega) according to the manufacturer's instructions. To assay IRES dependent translation, CD2AP down regulated Huh7.5.1 cells were transfected with the pHCV-IRES plasmids using Lipofectamine 2000 (Invitrogen). After 48 hours, firefly luciferase (F-Luc) and renilla luciferase (R-Luc) activities were measured using a dual-luciferase reporter assay composition (Promega, #E1910) according to the manufacturer's instructions. Assays were performed in triplicates, and the data are expressed as the mean±standard error (SEM) of luciferase activity.

1.11 Isolation of Lipid Droplets

Preparation of lipid droplets-enriched fractions was performed by density gradient centrifugation (51). Briefly, cells at ~95% confluency were scraped in PBS, pelleted by centrifugation at 1000×g for 5 minutes, then lysed in 1 ml hypotonic buffer (50 mM HEPES, 1 mM EDTA and 2 mM $MgCl_2$ at pH 7.4, 1 mM PMSF and protease inhibitor mixture). The suspension was incubated for 20 minutes at 4° C. and sonicated with 20 strokes in a tight-fitting Dounce homogenizer. The nuclei were removed by centrifugation at 1000×g for 5 min at 4° C. 1 ml supernatant was collected and mixed with equal volumes of 1.5 M sucrose in isotonic buffer (50 mM HEPES, 100 mM KCl, 2 mM MgCl2) and set at the bottom of SW55 Ti (Beckman) ultracentrifuge tubes, then 3 ml isotonic buffer containing 1 mM PMSF was placed onto the mixture. The sample was centrifuged at 10,000 g for 2 hours at 4° C. The LD fraction on top layer was collected, precipitated with 10% trichloroacetic acid (TCA), washed once with ether:ethanol (1:1) and boiled in 2×SDS loading buffer before subjected to SDS-PAGE.

1.12 OA Stimulation

To determine the accumulation of LDs induced by OA stimulation, $1.5 \times 10^5$ cells were seeded in confocal dish and cultured for 16 hours in complete culture medium. The cells were then incubated with serum-free DMEM containing 0.5 mM OA complexed with 2% BSA (w/v) for 12 hours before LD staining.

1.13 HCV Titration (TCID50)

To determine the intracellular and extracellular infectious virus titers, CD2AP down-regulated Huh7.5.1 cells were infected with J399EM at an MOI of 1. At 72 hpi, supernatants containing extracellular virus were harvested. Infected cells were rinsed to remove residual extracellular virus and then collected by centrifugation at 1,000 g for 5 minutes. The cell pellets were resuspended in the same volume of DMEM as the extracellular virus supernatants. After three rounds of freeze-thawing treatment, the sample was centrifuged to remove cell debris. The extracellular virus and intracellular virus titers were measured by a modified endpoint dilution assay (52). Briefly, 10-folds serially diluted virus samples were used to infect the naive Huh7.5.1 cells in a 96-well plate (six wells per dilution). Viral titers were calculated with the EGFP-positive wells counted under a fluorescence microscope (52).

1.14 Detection of Cell Viability

Cell viability of CD2AP down-regulated cells was determined by MTS assay (Promega). Briefly, cells were seeded in 96-well plates at a density of $5 \times 10^3$ cells per well and cultured for the indicated periods (24, 48, 72, 96 hs). MTS reagent (20 µl) was added to the media and incubated for 1 hour at 37° C. Absorbance at 490 nm was measured using the Multimode Plate Readers (PerkinElmer, USA).

1.15 Statistical Analysis

The results were statistically analyzed by the two-tailed Student's t-tests. Mean±Standard Error of the mean (SEM) were determined for at least three independent experiments. NS: not significant; $p<0.05$ (*) was considered to be statistically significant, $p<0.01$ () and $p<0.001$ (*) were considered to be highly significant.

1.16 IRS-1 Ubiquitination Assays

CD2AP silenced and control cells were cultured in complete medium for 48 h. Cell lysates (1 ml) were incubated with 2 µg rabbit polyclonal antibody (pAb) against IRS1 along with 20 µl Protein G Sepharose beads at 4° C. for 4 h. The bound proteins were eluted with 30 µl 2×SDS loading buffer. An aliquot (10 µl) of the sample was immunoblotted for IRS1 to confirm the purity of IRS1. Purified IRS1 from CD2AP silenced and control cells were adjusted to the same amount to quantify the levels of polyubiquitinated IRS1 with specific anti-ubiquitin polyclonal antibodies.

1.17 Insulin Signaling Cascade Assays

The molecules of insulin signaling cascade were probed with corresponding antibodies specific for these molecules for cell lysates from control and CD2AP down-regulated huh7.5.1 cells.

1.18 RNA Interference

Huh7.5.1 cells were seeded at 50% confluence and transfected with small interfering RNAs (siRNAs) specific to Cbl-b or Cbl, or negative control siRNA. Transfections of siRNA were carried out with PepMute reagent (SignaGen, USA) according to the manufacturer's instructions. Gene silencing was measured 48 hpt. The specific siRNA sequences were listed in Tables 3 and 5. Effects on IRS1 were probed with antibodies specific for IRS1, cbl-b, cbl and actin.

1.19 Immunohistochemistry (IHC)

For CD2AP staining in HCV infected mouse, right lobe of liver tissues from HCV infected or mock infected mice at the indicated times were sectioned with a thickness of 5 µm. For CD2AP staining of liver biopsies from patients infected with or without HCV, tissues were sectioned with a thickness of 5 µm. Tissue slides were heated for 1 h at 65° C. After deparaffinization, rehydration and 3% $H_2O_2$ treatment for 10 minutes, antigen retrieval was performed. Slides were heated in 10 mM sodium citrate buffer (pH 6.0) at 95-100° C. for 30 minutes and then cooling down to RT in buffer. The slides were then blocked with normal goat serum in 0.02% PBST for 1 h at RT. The slides were incubated with rabbit anti-CD2AP Ab (GeneTex, USA) or isotype control rabbit IgG at 4° C. overnight. HRP-conjugated goat anti-rabbit secondary Ab was applied to detect bound primary Abs for 1 h at RT. Color development was performed using DAB composition (Maxim, China) following the manufacturer's instructions. The slides were counterstained with hematoxylin for 2 minutes. After dehydration and mounting coverslip, slides were pictured by Pannoramic Digital Slide Scanners (3DHISTECH, Hungary). The use of liver sections was approved by the Institutional Review Board of Wuhan Institute of Virology, Chinese Academy of Sciences. The Approval Number:WIVH28201601.

Figure 1:
FIG. 1 shows a schematic domain diagram of a BioID construct, NS5A-BirA*-HA.
Figure 2:
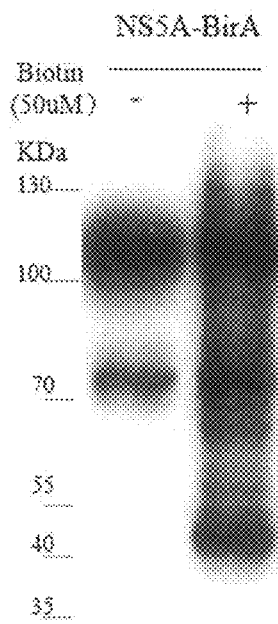
FIG. 2 shows a photograph of western blot. Huh7 cells were transduced with a lentiviral vector expressing NS5A BirA*-HA and then incubated for 24 h in complete media supplemented with or without 50 μM biotin. Whole cell lysates were subjected to 10% SDS-PAGE, separated proteins were then blotted with HRP conjugated streptavidin.

2. Results 2.1 Identification of Novel NS5A-Associated Host Proteins Using a BioID Method in Huh7 Cells Huh7 cells were transfected with the BioID construct, NS5A-BirA*-HA, and cultured in the presence of 50 µM exogenous biotin to label proteins in close association with NS5A (FIG. 1). Cellular proteins labeled with exogenous biotin were then detected by streptavidin-HRP. Increased biotin-labeled proteins were observed in the presence biotin compared to cells without biotin (FIG. 2). For FIG. 2, the NS5A-BirA-HA construct was transfected into Huh7 cells. Expression of the construct was confirmed after immuno-detection of NS5A or HA tag. The cells were then splited into two parts, one treated with 50 uM biotin, the other was not treated. Cell lysates were then subjected for SDS-PAGE. Immunoblotting was performed with streptavidin-HRP to detect the biotinylated cellular proteins. What we found is after biotin treatment, many more proteins were biotin labelled compare to no biotin treated cells.

Figure 3:
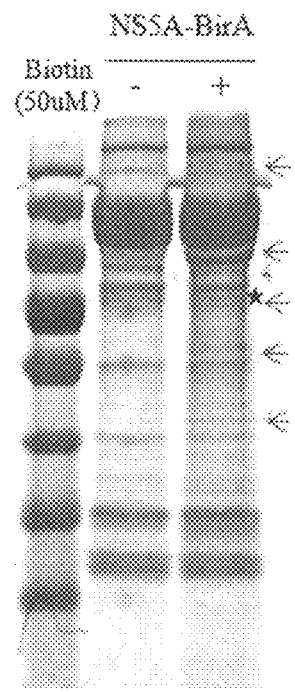
FIG. 3 shows a photograph of SDS-PAGE gel stained with Coommassie blue. Cell lysates were prepared the same as FIG. 2. The lysates were then affinity purified by streptavidin-agarose beads. Purified proteins were subjected to 10% SDS-PAGE and stained by Coommassie Brilliant Blue. The specific bands from biotin treatment samples as indicated by the arrows were subjected to mass spectrometry analysis.

To identify the biotinylated host proteins, streptavidin-purified proteins were separated and stained by Coommassie brilliant blue (FIG. 3). Seven specific bands were subjected to mass spectrometry analysis and the identity of these cellular proteins were revealed. Interestingly, these proteins were either associated with the transport apparatus, such as, COPG2, CD2AP, GOLGA5 and PACE1 or RNA biology, such as RPA34, EF2P and NP1L1. We first concentrated in studying CD2AP, which is an adaptor protein with SH3-containing domain first identified to bind to the cytoplasmic domain of CD2(53). CD2AP also binds actin-capping protein (CP) with high affinity damping the rate of actin polymerization (54, 55), and thus play an important role in actin filament organization.

2.2 HCV NS5A Protein Interacts with CD2AP

Figure 4:
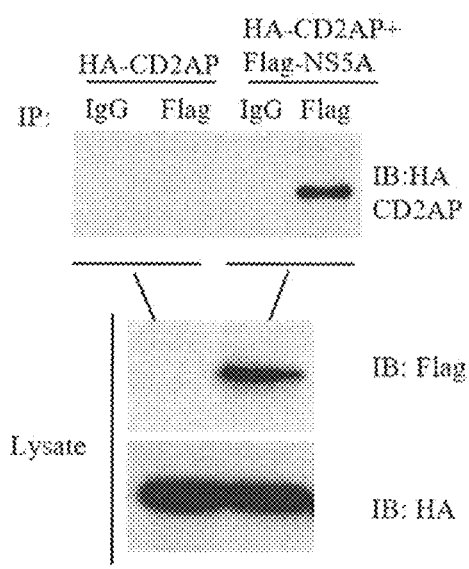
FIG. 4 shows photographs of western blot. Co-IP analysis of the interactions between CD2AP and NS5A in 293T cells. 293T cells were transfected with either HA-tagged CD2AP (pRK-HA-CD2AP) alone or HA-tagged CD2AP (pRK-HA-CD2AP) together with Flag-tagged NS5A derived from HCV genotype 2a strain JFH1 (pRK-Flag-NS5A). At 36 hpt, cell lysates were immunoprecipitated (IP) with rabbit anti-flag (Flag) antibody or control rabbit IgG (IgG). The IP complexes were analyzed by immunoblotting with rabbit anti-HA antibody (upper panel). Cell lysates were blotted with rabbit anti-flag antibody (middle panel) or rabbit anti-HA antibody (bottom panel). The same amount of HA-CD2AP loading was confirmed (bottom panel).
Figure 5:
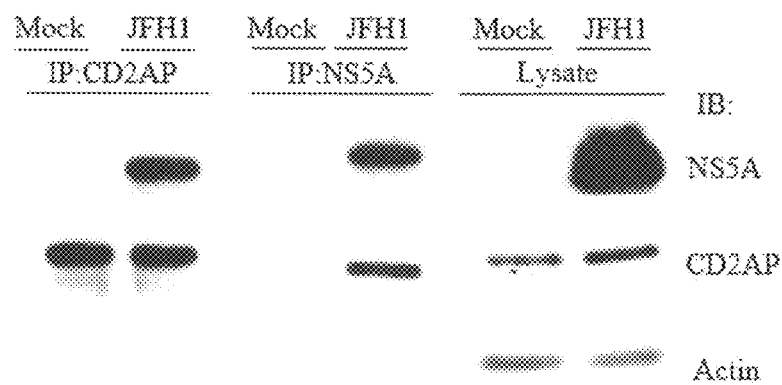
FIG. 5 shows photographs of western blots. Co-IP analysis of the interactions between CD2AP and NS5A during HCV infection. Huh7.5.1 cells were infected with HCV JFH1 or uninfected as mock control. 72 hpi, cells were collected and lysed. Cell lysates were immunoprecipitated with anti-CD2AP antibody (two panels of left column) or anti-NS5A antibody (two panels of middle column). The IP complexes were analyzed by immunoblotting with anti-NS5A antibody and anti-CD2AP antibody. Binding between CD2AP and NS5A was detected. Infection by HCV was confirmed by NS5A blotting (top right panel). The same amount of CD2AP in cells lysates used for co-IP was confirmed (middle right panel), and the equal loading of proteins was verified by actin blotting (bottom right panel).
Figure 6:
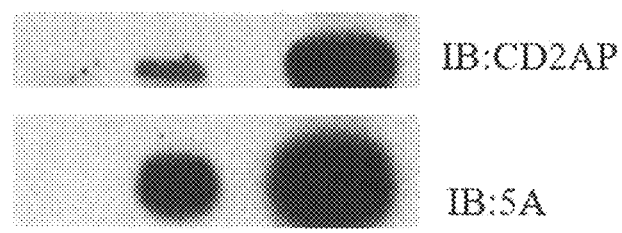
FIG. 6 shows photographs of western blots. Huh7.5.1 cells were infected with HCV JFH1 or left uninfected for 72 hours. Cell lysates were immunoprecipitated with anti-NS5A antibody or isotype control antibody. The IP complexes were analyzed by immunoblotting with anti-CD2AP or anti-NS5A antibodies. Only antibody to NS5A could co-purify CD2AP. Isotype control IgG1 did not co-purify CD2AP.
Figure 7:
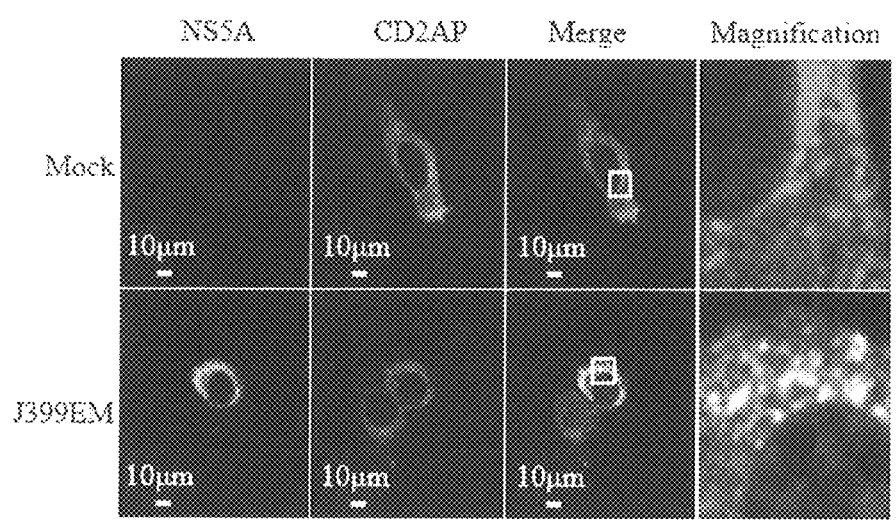
FIG. 7 shows photographs of immunostaining. CD2AP and NS5A were co-localized in HCV-infected Huh7.5.1 cells. Huh7.5.1 cells were infected with HCV J399EM (same HCV2a strain as shown in FIG. 6 but the NS5A is GFP tagged) (lower panel) or left uninfected (upper panel) for 72 hours. Cells were then stained with rabbit anti-CD2AP, bound antibody was further detected with alex fluor 555 conjugated goat anti-rabbit antibody (red).

HCV nonstructural protein NS5A has several proline-rich sequences and specifically binds growth factor receptor-bound protein 2 (Grb2) adaptor protein, which contains SH3 domain (56, 57). Since CD2AP has three SH3 domains (35), we directly tested if CD2AP indeed binds NS5A. When HA-tagged CD2AP was over-expressed together with FLAG-tagged NS5A in HEK 293T cells, we found that CD2AP could be specifically pulled down by NS5A (FIG. 4). To determine whether NS5A binds CD2AP during HCV infection, we performed co-immunoprecipitation (co-IP) analysis in Huh7.5.1 cells infected with or without HCV JFH1. We found that anti-CD2AP antibody indeed co-IPed with NS5A in infected cells, and CD2AP can also be pulled down by antibody specific for NS5A (FIG. 5). To further prove CD2AP interacts with NS5A in infected Huh7.5.1 cells, we applied rabbit IgG isotype control for NS5A antibody and performed the co-IP experiment. We found that CD2AP indeed binds NS5A in cells infected with HCV (FIG. 6). Moreover, by confocal imaging analysis, we observed co-localization of CD2AP and NS5A from HCV-J399EM, the HCV2a strain whose NS5A is GFP tagged, infected cells (FIG. 7). In addition, we double-stained CD2AP and NS5A in huh7.5.1 cells infected with JFH1 and found co-location of CD2AP and NS5A (Results not shown). Together, these results suggest that CD2AP interacts with endogenous NS5A in HCV infected cells.

2.3 Domain III of NS5A Interacts with SH3 Domains of CD2AP

Figure 8:
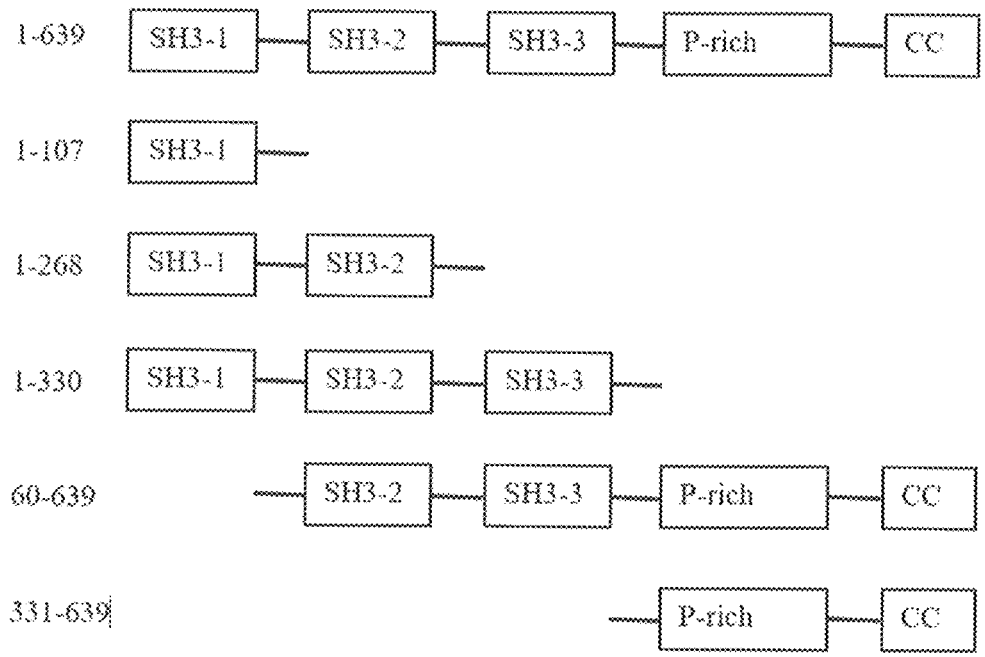
FIG. 8 shows schematic diagrams of full length and truncated CD2AP. The N-terminus of CD2AP contains three SH3 domains, SH3-1, SH3-2 and SH3-3 respectively from the N terminal to C terminal.
Figure 9:
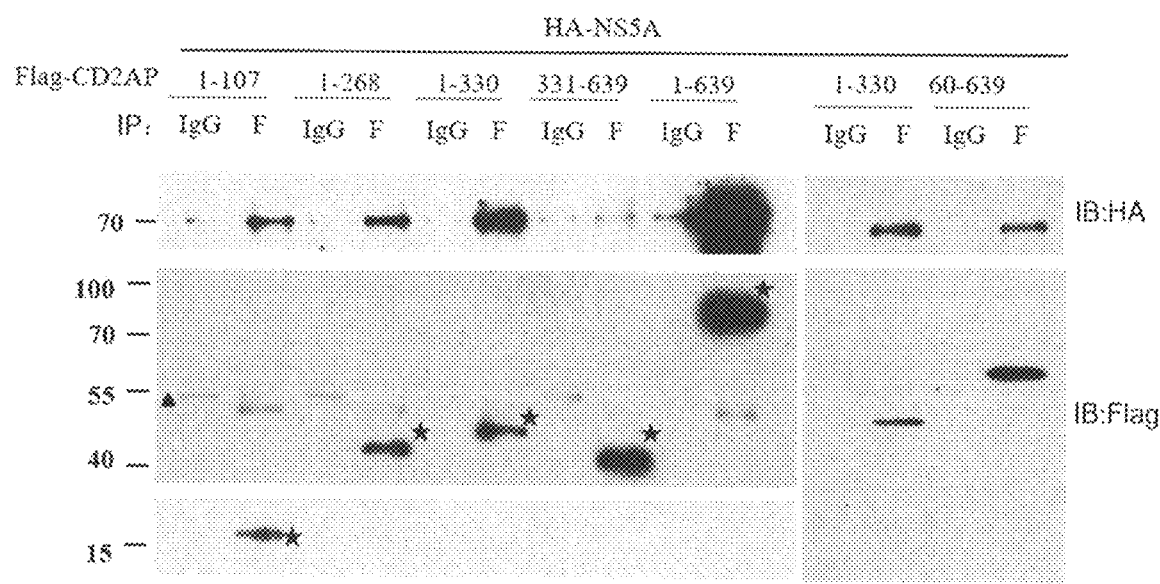
FIG. 9 shows photographs of western blots. Domains of CD2AP binding to NS5A were identified. 293T cells were co-transfected with HA-tagged NS5A and one of the flag-tagged CD2AP and truncates. At 36 hpt, cell lysates were immunoprecipitated with rabbit anti-flag (F) antibody or control rabbit IgG (IgG). The IP complexes were then probed with rabbit anti-HA antibody (upper panel) and rabbit anti-flag antibody (lower panel). Anti-flag antibody purified Flag-tagged CD2AP was labelled with the asterisk. Non-specific bands with molecular weight between 20-35 kDa were not shown here.

Since CD2AP contains three SH3 domains, we further performed experiment to identify whether a specific SH3 domain or all three SH3 domains in CD2AP are responsible for binding NS5A, we generated various truncated CD2AP mutants encoding 1-107aa, 1-268 aa, 1-330 aa, 331-639 aa, 60-639 aa, and 1-639 aa (numbered according to SEQ ID NO.2), which contain the first, second & third, all three SH3 domains, no SH3 domain but retaining all the other CD2AP domain, no first SH3 domain but retaining all the other CD2AP domain, and full length CD2AP, respectively (FIG. 8). We then co-expressed these CD2AP proteins with HA-tagged full length NS5A in HEK 293T cells and preformed co-IP experiments. As shown in FIG. 9, CD2AP mutants lacking the SH3 domain did not interact with NS5A (FIG. 9, see 331-639). On the contrary, Full length CD2AP or CD2AP proteins containing the SH3 domains binds NS5A and the binding is enhanced as more SH3 domain is retained in the CD2AP protein (FIG. 9, comparing 1-107, 1-268, and 1-330). The second and third SH3 domains being also involved in NS5A binding is further supported by the observation that CD2AP lacking the first SH3 domain still binds NS5A (FIG. 9, see 60-639).

Figure 10:
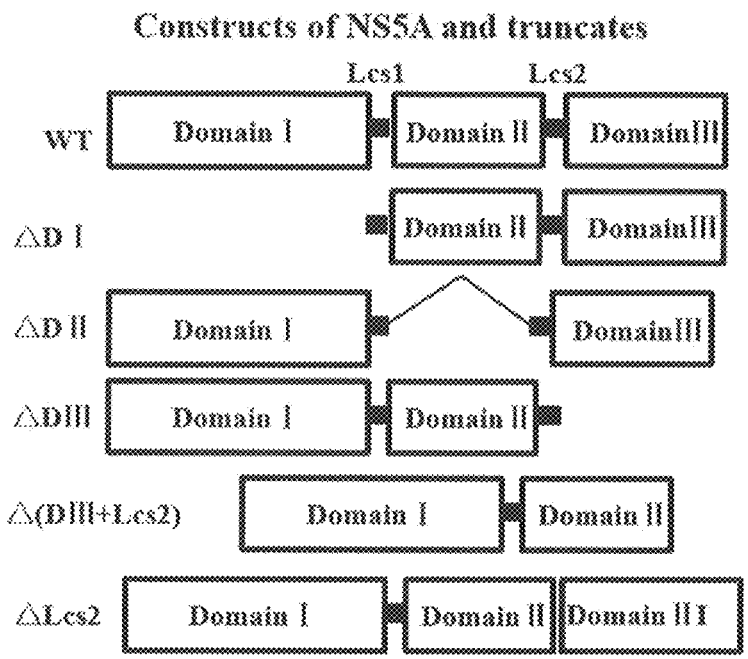
FIG. 10 shows schematic diagrams of full-length and truncated NS5A. NS5A consists of three domains as indicated which are connected by two low-complexity sequences (Lcs1 and Lcs2).
Figure 11:
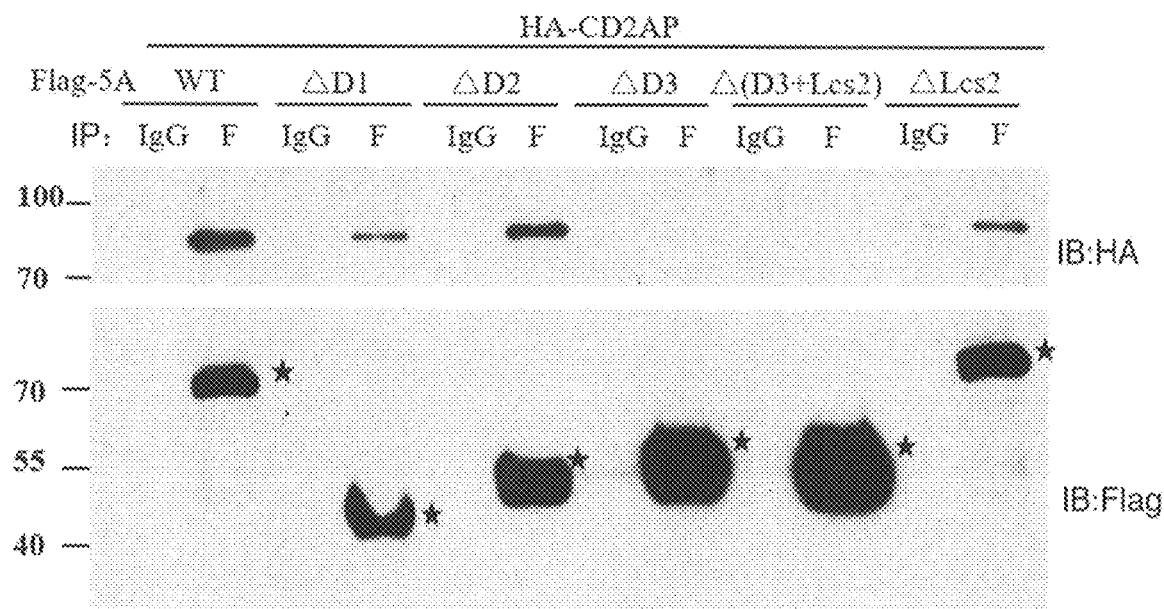
FIG. 11 shows photographs of western blots. NS5A domains interacting with CD2AP were identified. 293T cells were transfected with HA-tagged CD2AP and one of flag-tagged NS5A or truncates. At 36 hpt, cell lysates were immunoprecipitated with rabbit anti-flag (F) antibody or control rabbit IgG (IgG). Domain III of NS5A was found specifically interacting with CD2AP (upper panel). Anti-flag antibody purified NS5A were denoted with the asterisk.

We also mapped the regions in NS5A that are involved in the interaction with CD2AP. NS5A contains an N-terminal amphipathic helix, which anchors the protein to cytoplasmic membrane and three domains (domain I, domain II and domain III) separated by two low-complexity sequences (LCs) (58, 59). We generated full length NS5A and a series NS5A mutants lacking domain I, II, or III, respectively (FIG. 10) and investigated which domain(s) binds CD2AP. We found that CD2AP could not bind NS5A when the first domain of NS5A was deleted (FIG. 11). However, deletion of other NS5A domains did not affect NS5A binding to CD2AP, thus implicating that domain I of NS5A interacts with the SH3 domains of CD2AP.

2.4 CD2AP Transports NS5A Via an Actin Dependent Manner Before Targeting LDs

Figure 12:
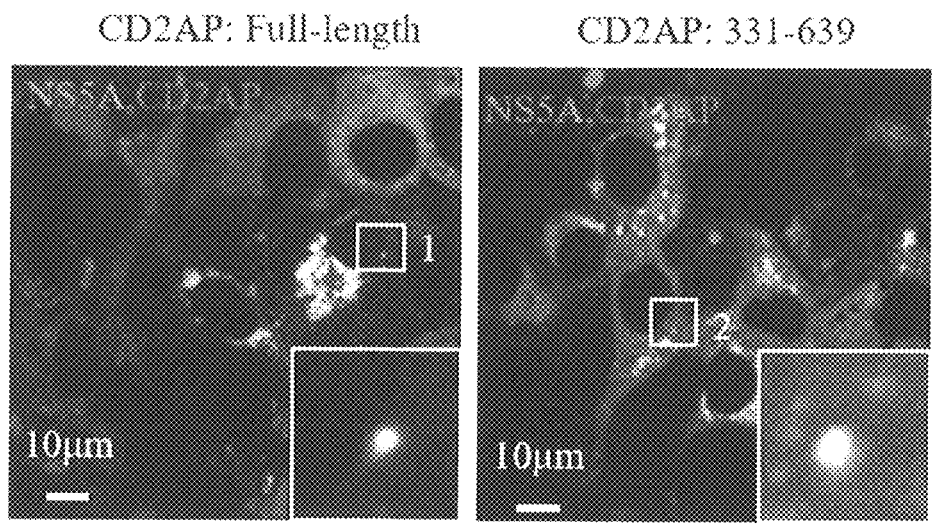
FIG. 12 shows photographs of co-localization of NS5A with full length CD2AP but not truncated CD2AP. Huh7.5.1 cells stably expressing mcherry tagged full length (CD2AP) or SH3 domain deleted CD2AP (ΔCD2AP) were infected with HCV-J399EM. Con-focal immunofluorescence staining of these two proteins was analyzed 72 hpi. NS5A is co-localized with full length CD2AP (left panel), but not with truncated CD2AP (right panel).
Figure 13:
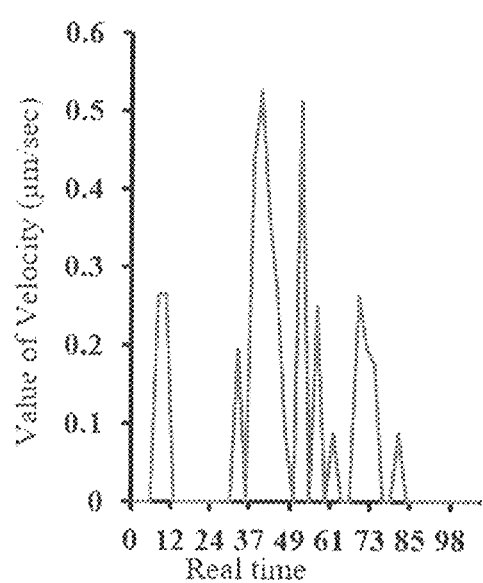
FIG. 13 is a curve graph showing co-movement of one NS5A/CD2AP complex. Live image tracking of CD2AP (red) and NS5A (green) as shown in FIG. 12 showed co-movement (yellow spot) of NS5A and CD2AP 72 hpi. Co-movement curve of one NS5A/CD2AP complex was analyzed with software Volocity (version 2.0) (Perkin Elmer).
Figure 14:
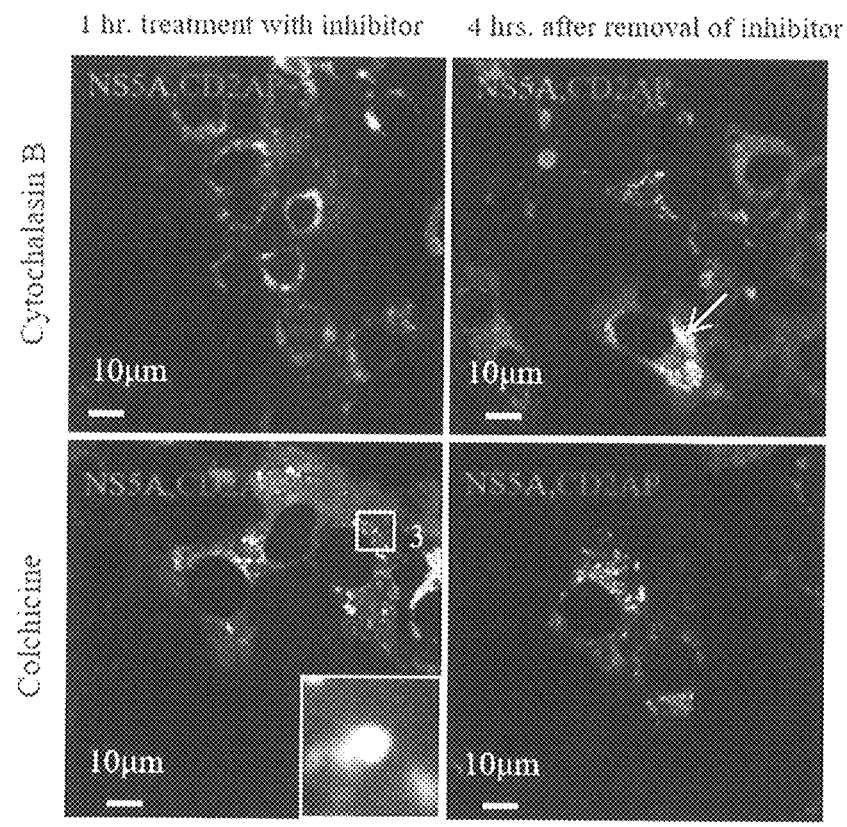
FIG. 14 shows photographs of co-movement of NS5A/CD2AP complex depending on actin polymerization. HCV infected cells as described in FIG. 12 were treated with either cytochalacin B (top panel) or colchicine (bottom panel) for one hour (left two panels) were subjected for confocal immunofluorescence observation. Or after one hour drug treatment, the culture media was replaced with fresh media without drugs for an additional four hours (right panel) and subjected to confocal immunofluorescence staining. There was no co-localization of NS5A and CD2AP after cytochalasin B treatment (top left panel). However, colchicine treatment did not affect the co-location of NS5A and CD2AP (bottom left panel). Four hours after culture medium replacement, co-location of CD2AP and NS5A re-appeared (top right panel) whereas there was no difference for colchicine treated cells after culture medium replacement (bottom right panel).
Figure 15:
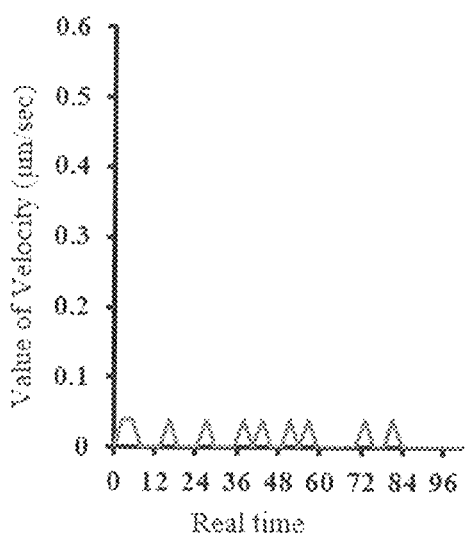
FIG. 15 is a curve graph showing co-movement of one NS5A/CD2AP complex during treatment of cytochalasin B. NS5A showed CD2AP independent agitation. Although there was no co-localization of NS5A and CD2AP after actin polymerization was broken, we observed NS5A agitation independent of CD2AP and actin polymerization by live image tracking of cells treated one hour with cytochalasin B. However, there was no co-movement at all for CD2AP/NS5A complex after microtubule polymerization was inhibited.
Figure 16:
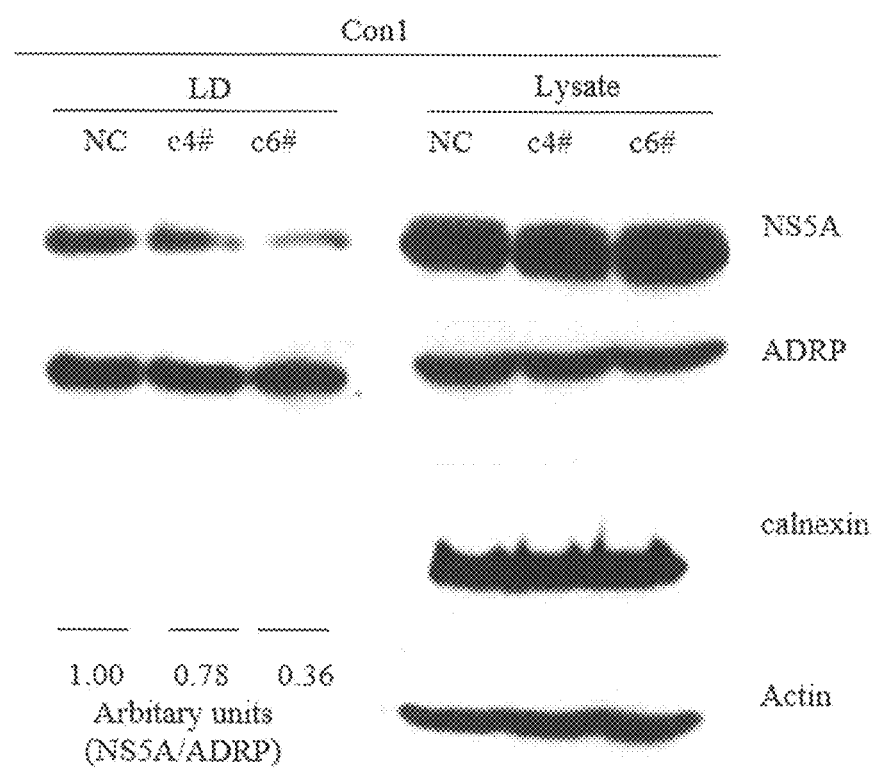
FIG. 16 shows photographs of western blots. Reduced NS5A association with LDs was detected after CD2AP was down regulated. CD2AP expression levels were down regulated in HCV subgenomic replicon cells Con1 with shRNAi (c4 # and c6 #) or unaffected with control sh-RNAi (NC). A reduction of NS5A with LDs was observed (top left panel).

To investigate the functionality of CD2AP interacting with NS5A, Huh7.5.1 cells stably expressing mcherry tagged full length CD2AP or mutant CD2AP lacking all three SH3 domains were infected with HCV-J399EM. By live image tracking, we found that only full length CD2AP co-localizes with GFP-NS5A and co-moves with NS5A while mutant CD2AP without SH3 domain does not co-localize with NS5A (FIG. 12, in left panel, the spot inside the square). Quantification of live image of CD2AP and NS5A further proved that full length CD2AP co-moves with NS5A (FIG. 13). The observation of lacking co-localization between NS5A and mutant CD2AP lacking all three SH3 domains further supports our conclusion that NS5A interacts with the SH3 domains of CD2AP. Since motility of CD2AP spots depends on actin filament polymerization (60), we investigated whether NS5A co-movement with CD2AP is actin or tubulin dependent by treating the infected cells with colchicine (a tubulin polymerization inhibitor) or cytochalacin B (an actin polymerization inhibitor). We found that cytochalacin B but not cochicine treatment significantly reduces co-localization of NS5A and CD2AP (FIG. 14, left panels). However, 4 hours after substituting cytochalasin B with DMSO in the media, the co-localization of CD2AP and NS5A is resumed (FIG. 14, top right panel). These results prove that co-localization of NS5A with CD2AP is actin cytoskeleton dependent. NS5A has to be transported to LDs to assemble via the microtubule system (12) and we find that there is no movement of NS5A/CD2AP complex after the cells are treated with colchicine (FIG. 15). Since colchicine treatment does not affect the co-localization of CD2AP and NS5A but cytochalasin B treatment prevents CD2AP and NS5A co-localization, we assume that actin dependent co-localization of CD2AP and NS5A is a step occurred before the HCV assemble. If this hypothesis is correct, we expect to see less NS5A associated with LDs. To test this hypothesis, we used the Con1 replication system in which LDs is greatly reduced in numbers. We then down-regulated the expression of CD2AP and biochemically tested if NS5A association with LDs fractions is alleviated or not. By knocking down CD2AP in coni replication system (denoted as 4 # and 6 #), we found that NS5A level in Con1 was not affected, however, NS5A association with LDs fractions was significantly reduced (FIG. 16). Successful isolation of LDs without contamination is confirmed by the absence and appearance of calnexin and ADRP, markers for ER and LD respectively, in corresponding fractions (FIG. 16). Since total NS5A expression level is not affected but LDs associated NS5A level is diminished when CD2AP is down regulated in Con1 cells, we come to the conclusion that CD2AP transports NS5A to via the actin cytoskeleton before reaching LDs. These results imply that down regulation of CD2AP does not affect HCV genomic replication but reduce HCV assembly.

2.5 CD2AP Influences LD Biogenesis

Since CD2AP may play a role in HCV assembly and release and we have shown that NS5A transported to LDs is reduced when CD2AP is down regulated, we then investigated if CD2AP plays any other roles in HCV assembly besides transporting NS5A to LDs. We first tested the effect of knocking down CD2AP on LDs biogenesis. Knocking down CD2AP significantly reduces LDs biogenesis and accumulation (FIG. 17, left column under BSA, NC &6 #). Since biogenesis of LDs is very limited under non-infected condition, we further assess the effect of CD2AP knocking down on LDs biogenesis under OA treatment. We found that CD2AP down regulation significantly alleviated LDs biogenesis (FIG. 17, right column under OA). Counting of LDs in more than 200 hundreds cells under OA treatment confirmed that there are significantly fewer LDs per cell when CD2AP is down regulated (FIG. 17, black boxes, comparing NC and 6 #, $p<0.05$). To prove that CD2AP does influence LDs biogenesis, we stained CD2AP rescue cells under OA or BSA treatment, we found that CD2AP over-expressing cells do show significantly more LDs than control cells (FIG. 18). Counting of LDs in more than 200 hundreds cells under OA treatment confirmed that there are significantly more LDs per cell when CD2AP is up regulated (FIG. 18, black boxes, comparing NC and HA-CD2AP, $p<0.05$).

To rule out the possibility that the reduced NS5A and Core expression level resulted in diminished LDs, we then over expressed HA-Core in CD2AP down regulated and control cells. We found that up-regulation of NS5A and Core protein in CD2AP down regulated cells does not significantly increase LDs formation compared to control cells (FIG. 19, right two panels and black boxes indicated significant less LDs after core over expression, $p<0.05$), thus further proving that when CD2AP is down regulated, LDs biogenesis together with HCV NS5A and Core location on LDs is hampered. However, after augmented CD2AP expression in CD2AP down regulated cells, the level of LDs increased significantly, so does the location of Core protein on LDs (FIG. 20, right two panels and black boxes showed significantly more co-location of Core protein on LDs after over expression of CD2AP). These results prove that CD2AP plays an important role for the generation of LDs in the cell and targets HCV components to LDs.

2.6 Knocking Down CD2AP Inhibits HCV Propagation

Since HCV genomic replication was not influenced by interaction between CD2AP and NS5A, we next attempted to examine the effects of such an interaction by silencing CD2AP on HCV propagation. We generated two stable CD2AP knockdown cell lines (Huh7.5.1-sh CD2AP-4, denoted as 4 #; Huh7.5.1-sh CD2AP-6, denoted as 6 #; Huh7.5.1-sh CD2AP negative control, denoted as NC. Knocking down CD2AP does not affect cell growth. However, knocking down CD2AP significantly reduces HCV mRNA level compared to control cells after the cells were infected with HCV-JFH1 for 72 hours (FIG. 21). Western blotting analysis confirmed that NS5A and Core protein expression of HCV were significantly reduced (FIG. 22). In addition, the viral RNA copy number released into the CD2AP knocking down cell supernatant was also significantly alleviated (FIG. 23, $p<0.01$). The effect of CD2AP knocking down on HCV replication was further confirmed by using a reporter virus J399EM+LM with a Renila luciferase reporter gene (FIG. 24). To rule out the possibility that the effect is due to off-target effect of CD2AP down regulation, we performed a rescue experiment. We transiently expressed HA-CD2AP mutant with wobble mutations at the site targeted by shCD2AP-6 # (denoted as 6 #-HA-CD2AP) in CD2AP-knockdown cells. After infection with HCV JFH1, expression of HA-CD2AP mutant (6 #-HA-CD2AP+), but not the empty vector (6 #-HA-CD2AP-), rescued intracellular HCV RNA level (FIG. 25). Consistent with RNA level, Core and NS5A protein levels were also partially restored in 6 #-HA-CD2AP compared to empty vector transfected cells (lane 2 vs lane 3, FIG. 26). Taken together, these results revealed that knocking down of endogenous CD2AP significantly inhibited HCV propagation in Huh7.5.1 cells.

2.7 Knocking Down CD2AP does not Impair HCV Entry, Genomic RNA Replication and IRES Dependent Translation but Inhibits the Production of HCV Infectious Particles Since CD2AP did not affect HCV subgenomic replication but played an important role in HCV propagation, we further investigated the underlying mechanism by which CD2AP affects HCV infection. We first explored if CD2AP influences HCV entry by the transduction of HCV pseudoparticles (HCVpps). CD2AP stably down regulated cells were transduced with HCVpps. Luciferase activities were measured 48 hours after transduction and used as the indicator of HCV entry efficiency. As shown in FIG. 27, no significant difference in HCVpp infection was observed between CD2AP knocking down and control cells, which suggested that HCV entry was not influenced by CD2AP down regulation. We then investigated whether knocking down CD2AP would affect HCV internal ribosome entry site (IRES)-directed translation. HCV IRES activity was monitored with the bi-cistronic reporter plasmid pHCV-IRES in which the translation of the upstream Renilla luciferase gene (Rluc) was mediated by the 5'cap structure and the downstream Firefly luciferase gene (Fluc) was controlled by an HCV IRES element. The HCV IRES-dependent translation level was calculated by the normalization of Fluc activities against the Rluc activities. Compared to the control, silencing of CD2AP had no significant impact on HCV IRES-dependent translation (FIG. 28, empty boxes represent CD2AP relative translation levels whereas blackboxes measure normalized IRES activity of HCV).

We further assessed the effect of CD2AP knocking down on HCV genomic RNA replication in subgenomic replicon Con1 cells. After knocking down CD2AP in Con1 cells, we found no significant difference in HCV RNA and proteins levels between CD2AP knocking down and control Con1 cells (FIG. 29), thus proving that CD2AP does not directly affect the subgenomic replication of HCV. We then tested if CD2AP knocking down affects HCV assembly and release, Huh7.5.1 cells stably expressing sh-CD2AP-4 #, 6 # or sh-NC were infected with J399EM at an MOI of 1. At 72 hours post-infection (hpi), the virus titers in cytosol and culture supernatant were significantly reduced (FIG. 30 and FIG. 31), thus implying that CD2AP is involved in HCV assembly and/or release.

2.8 CD2AP Modulates the Association of Multiple HCV Components with Lipid Droplets Since CD2AP down-regulation alleviates LDs biogenesis in the absence of HCV infection, we then investigated if the phenomenon is the same when the cells were infected by HCV. We infected CD2AP knocking down (4 # and 6 #) and control cells (NC) with JFH1 and stained LDs, NS5A, or HCV Core protein. We found that the formation of LDs was seriously impaired in CD2AP down regulated cells the same as when the cells were not infected by HCV (FIG. 32A and FIG. 33A, 4 # and 6 # panels under LD). In addition, the location of NS5A and Core proteins on LDs decreased significantly (FIG. 32A and FIG. 33A, 4 # and 6 #, panels under Merge). There are significant differences between CD2AP down regulated cell and control cell in percentage of NS5A or Core positive LDs (FIG. 32B and FIG. 33B, comparing NC, 4 #, and 6 #). Since we proved that down regulation of CD2AP in con 1 cell does not affects NS5A expression level, these results further support the conclusion that reduced NS5A location on LDs is due to transportation defects after alleviated CD2AP together with reduced LDs biogenesis.

Down-regulation of CD2AP in Huh7.5.1 cells increased total levels of IRS1 and p-IRS1 (FIG. 34). We found that IRS1 underwent proteasome dependent degradation. When treated with MG132 for 2 hours, the level of IRS1 was significantly up-regulated (FIG. 35). To verify that down-regulation of CD2AP affected IRS1 proteasomal dependent degradation, we compare the IRS1 levels of control and CD2AP down-regulated cells under MG132 treatment. We found that MG132 significantly enhanced the level of IRS1 in control cells but not in CD2AP down-regulated cells (FIG. 36). In addition, by purifying IRS1 from control and CD2AP down-regulated cells, we found that down-regulation of CD2AP significantly reduced the polyubiquitination of IRS1 (FIG. 37). To identify the protein complex with CD2AP, we performed co-IP experiment with anti IRS1 antibody and found that CD2AP was co-purified with IRS1. We also performed co-IP experiment with anti-cbl-b and anti-cbl antibody, we found that IRS1 was co-purified with cbl-b/cbl (FIG. 38). To further prove that CD2AP, IRS1 and cbl-b/cbl are in the protein complex, we double stained CD2AP with IRS1 or IRS1 with cbl-b/cbl, and found that in deed IRS1 and CD2AP, and IRS1 and cbl-b/cbl were co-localized (FIG. 39). To prove that cbl-b/cbl is the E3 ligase for IRS1, we down regulated cbl-b/cbl in huh7.5.1 cells and found a significant up-regulation of IRS1 (FIG. 40). Thus cbl-b/cbl is the E3 ligase for IRS1. These results proved that CD2AP, IRS1 and cbl-b/cbl are in the same protein complex.

Since IRS1 is the gate keeper for insulin signaling pathway, we then assayed whether insulin signaling cascade was affected after CD2AP down-regulation. We found that down-regulation of CD2AP increased the level of p-Akt (s473) but down-regulated the levels of p-AMPK(t172) and p-HSL(s554) (FIG. 41). Accordingly, when CD2AP was rescued in CD2AP down-regulated huh7.5.1 cells, the level of p-Akt is down regulated (FIG. 42). To prove that AMPK is directly responsible for the phosphorylation of HSL, we treated the cells with an AMPK inhibitor dorsomophin and found that indeed dorsomophin reduced the level of p-AMPK and correspondingly reduced the level of HSL (FIG. 43).

The above results were obtained from cancer cell lines. We then investigate whether our results have in vivo significance using an HCV infected mouse model. The HCV titer in the liver and serum of mice was monitored with QPCR at different time points post infection (FIGS. 44 & 45). The trend of the HCV titer is very similar to what has been published (61). We then stained CD2AP in the liver tissues from the HCV infected mice and found that CD2AP was significantly up-regulated at 1, 2 and 4 months post infection. Whereas earlier or later time outside that range there was no obvious CD2AP staining, suggesting that CD2AP expression does not correlated with the titer of HCV but as a consequence of HCV infection (FIG. 46). Interestingly, the period of strong CD2AP staining correlated well with the occurrence of steatosis in this mouse model.

In addition, we investigated if CD2AP could be up-regulated in HCV infected patients. We found that 9/16 liver biopsies from HCV infected patients showed moderate to strong CD2AP staining whereas only 1/12 liver biopsies from non-HCV infected patients showed strong CD2AP staining (FIG. 47).

Finally we investigate if CD2AP immunostaining can be detected in liver biopsies from diabetic patients. We found that most of the diabetic liver tissues showed strong CD2AP staining. Thus in human liver biopsies, CD2AP expression is significantly enhanced in diabetic liver (FIG. 48).

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the scope of the present invention. Accordingly, the scope of the present invention is defined by the appended claims and is supported by the foregoing description.

REFERENCES

1. Choo Q L, Kuo G, Weiner A J, Overby L R, Bradley D W, Houghton M. 1989. Isolation of a cDNA clone derived from a blood-borne non-A, non-B viral hepatitis genome. Science 244:359-362.

2. Rosen H R. 2011. Clinical practice. Chronic hepatitis C infection. The New England journal of medicine 364: 2429-2438.
3. Lohmann V, Korner F, Koch J, Herian U, Theilmann L, Bartenschlager R. 1999. Replication of subgenomic hepatitis C virus RNAs in a hepatoma cell line. Science 285:110-113.
4. Romero-Brey I, Merz A, Chiramel A, Lee J Y, Chlanda P, Haselman U, Santarella-Mellwig R, Habermann A, Hoppe S, Kallis S, Walther P, Antony C, Krijnse-Locker J, Bartenschlager R. 2012. Three-dimensional architecture and biogenesis of membrane structures associated with hepatitis C virus replication. PLoS pathogens 8:e1003056.
5. Ferraris P, Beaumont E, Uzbekov R, Brand D, Gaillard J, Blanchard E, Roingeard P. 2013. Sequential biogenesis of host cell membrane rearrangements induced by hepatitis C virus infection. Cellular and molecular life sciences: CMLS 70:1297-1306.
6. Appel N, Zayas M, Miller S, Krijnse-Locker J, Schaller T, Friebe P, Kallis S, Engel U, Bartenschlager R. 2008. Essential role of domain III of nonstructural protein 5A for hepatitis C virus infectious particle assembly. PLoS pathogens 4:e1000035.
7. Miyanari Y, Atsuzawa K, Usuda N, Watashi K, Hishiki T, Zayas M, Bartenschlager R, Wakita T, Hijikata M, Shimotohno K. 2007. The lipid droplet is an important organelle for hepatitis C virus production. Nature cell biology 9:1089-1097.
8. Shi S T, Polyak S J, Tu H, Taylor D R, Gretch D R, Lai M M. 2002. Hepatitis C virus NS5A colocalizes with the core protein on lipid droplets and interacts with apolipoproteins. Virology 292:198-210.
9. Abid K, Pazienza V, de Gottardi A, Rubbia-Brandt L, Conne B, Pugnale P, Rossi C, Mangia A, Negro F. 2005. An in vitro model of hepatitis C virus genotype 3a-associated triglycerides accumulation. Journal of hepatology 42:744-751.
10. Hinson E R, Cresswell P. 2009. The antiviral protein, viperin, localizes to lipid droplets via its N-terminal amphipathic alpha-helix. Proceedings of the National Academy of Sciences of the United States of America 106:20452-20457.
11. Masaki T, Suzuki R, Murakami K, Aizaki H, Ishii K, Murayama A, Date T, Matsuura Y, Miyamura T, Wakita T. 2008. Interaction of hepatitis C virus nonstructural protein 5A with core protein is critical for the production of infectious virus particles. Journal of virology 82:7964-7976.
12. Lai C K, Jeng K S, Machida K, Lai M M. 2008. Association of hepatitis C virus replication complexes with microtubules and actin filaments is dependent on the interaction of NS3 and NS5A. Journal of virology 82:8838-8848.
13. Eyre N S, Fiches G N, Aloia A L, Helbig K J, McCartney E M, McErlean C S, Li K, Aggarwal A, Turville S G, Beard M R. 2014. Dynamic imaging of the hepatitis C virus NS5A protein during a productive infection. Journal of virology 88:3636-3652.
14. Lai C-K, Saxena V, Tseng C-H, Jeng K-S, Kohara M, Lai M M. 2014. Nonstructural protein 5A is incorporated into hepatitis C virus low-density particle through interaction with core protein and microtubules during intracellular transport. PLoS one 9:e99022.
15. Tilg H, Moschen A R, Roden M. 2017. NAFLD and diabetes mellitus. Nature Reviews Gastroenterology & Hepatology 14:32-42.
16. Anai M, Funaki M, Ogihara T, Terasaki J, Inukai K, Katagiri H, Fukushima Y, Yazaki Y, Kikuchi M, Oka Y. 1998. Altered expression levels and impaired steps in the pathway to phosphatidylinositol 3-kinase activation via insulin receptor substrates 1 and 2 in Zucker fatty rats. Diabetes 47:13-23.
17. Araki E, Llpes M A, Patti M-E. 1994. signalling in mice with targeted disruption. Nature 372.
18. Bruning J C, Winnay J, Bonner-Weir S, Taylor S I, Accili D, Kahn C R. 1997. Development of a novel polygenic model of NIDDM in mice heterozygous for IR and IRS-1 null alleles. Cell 88:561-572.
19. Jiang Z Y, Lin Y-W, Clemont A, Feener E P, Hein K D, Igarashi M, Yamauchi T, White M F, King G L. 1999. Characterization of selective resistance to insulin signaling in the vasculature of obese Zucker (fa/fa) rats. The Journal of clinical investigation 104:447-457.
20. Kerouz N J, Horsch D, Pons S, Kahn C R. 1997. Differential regulation of insulin receptor substrates-1 and -2 (IRS-1 and IRS-2) and phosphatidylinositol 3-kinase isoforms in liver and muscle of the obese diabetic (ob/ob) mouse. Journal of Clinical Investigation 100:3164.
21. Tamemoto H, Kadowaki T, Tobe K, Yagi T, Sakura H, Hayakawa T, Terauchi Y, Ueki K, Kaburagi Y, Satoh S. 1994. Insulin resistance and growth retardation in mice lacking insulin receptor substrate-1.
22. Withers D J, Gutierrez J S, Towery H, Burks D J, Ren J M, Previs S, Zhang Y, Bernal D, Pons S, Shulman G I, Bonner-Weir S, White M F. 1998. Disruption of IRS-2 causes type 2 diabetes in mice. Nature 391:900-904.
23. Stephens J M, Lee J, Pilch P F. 1997. Tumor necrosis factor-a-induced insulin resistance in 3T3-L1 adipocytes is accompanied by a loss of insulin receptor substrate-1 and GLUT4 expression without a loss of insulin receptor-mediated signal transduction. Journal of Biological Chemistry 272:971-976.
24. Egawa K, Nakashima N, Sharma P M, Maegawa H, Nagai Y, Kashiwagi A, Kikkawa R, Olefsky J M. 2000. Persistent Activation of Phosphatidylinositol 3-Kinase Causes Insulin Resistance Due to Accelerated Insulin-Induced Insulin Receptor Substrate-1 Degradation in 3T3-L1 Adipocytes 1. Endocrinology 141:1930-1935.
25. Sun X J, Goldberg J L, Qiao L, Mitchell J J. 1999. Insulin-induced insulin receptor substrate-1 degradation is mediated by the proteasome degradation pathway. Diabetes 48:1359-1364.
26. Haruta T, Uno T, Kawahara J, Takano A, Egawa K, Sharma P M, Olefsky J M, Kobayashi M. 2000. A rapamycin-sensitive pathway down-regulates insulin signaling via phosphorylation and proteasomal degradation of insulin receptor substrate-1. Molecular endocrinology 14:783-794.
27. Lee A V, Gooch J L, Oesterreich S, Guler R L, Yee D. 2000. Insulin-like growth factor I-induced degradation of insulin receptor substrate 1 is mediated by the 26S proteasome and blocked by phosphatidylinositol 3'-kinase inhibition. Molecular and cellular biology 20:1489-1496.
28. Zhande R, Mitchell J J, Wu J, Sun X J. 2002. Molecular mechanism of insulin-induced degradation of insulin receptor substrate 1. Molecular and cellular biology 22:1016-1026.
29. Bose S K, Ray R. 2014. Hepatitis C virus infection and insulin resistance. World J Diabetes 5:52-58.
30. John J. Sambrook D D W R. 1989. Molecular Cloning: A Laboratory Mannual, second edition. CSHL Press.
31. Ausubel F M. 1987. Current Protocols in Molecular Biology 32. Rosenberg I M. 1996. Protein Analysis and Purification-Benchtop Techniques
33. Copeland R A. 2013. Methods for Protein Analysis: a Practical Guide for Laboratory Protocols.
34. John E. Coligan B B. 1999 Current Protocols in Immunology.
35. Kim J M, Wu H, Green G, Winkler C A, Kopp J B, Miner J H, Unanue E R, Shaw A S. 2003. CD2-associated protein haploinsufficiency is linked to glomerular disease susceptibility. Science 300:1298-1300.
36. Kobayashi S, Sawano A, Nojima Y, Shibuya M, Maru Y. 2004. The c-Cbl/CD2AP complex regulates VEGF-induced endocytosis and degradation of Flt-1 (VEGFR-1). The FASEB journal 18:929-931.
37. Bao M, Hanabuchi S, Facchinetti V, Du Q, Bover L, Plumas J, Chaperot L, Cao W, Qin J, Sun S-C. 2012. CD2AP/SHIP1 complex positively regulates plasmacytoid dendritic cell receptor signaling by inhibiting the E3 ubiquitin ligase Cbl. The Journal of Immunology 189:786-792.
38. Calco G N, Stephens O R, Donahue L M, Tsui C C, Pierchala B A. 2014. CD2-associated protein (CD2AP) enhances casitas B lineage lymphoma-3/c (Cbl-3/c)-mediated Ret isoform-specific ubiquitination and degradation via its amino-terminal Src homology 3 domains. Journal of Biological Chemistry 289:7307-7319.
39. Kowanetz K, Szymkiewicz I, Haglund K, Kowanetz M, Husnjak K, Taylor J D, Soubeyran P, Engstrom U, Ladbury J E, Dikic I. 2003. Identification of a novel proline-arginine motif involved in C1N85-dependent clustering of Cbl and down-regulation of epidermal growth factor receptors. Journal of Biological Chemistry 278:39735-39746.
40. Gout I, Middleton G, Adu J, Ninkina N N, Drobot L B, Filonenko V, Matsuka G, Davies A M, Waterfield M, Buchman V L. 2000. Negative regulation of PI 3-kinase by Ruk, a novel adaptor protein. The EMBO journal 19:4015-4025.
41. Huber T B, Hartleben B, Kim J, Schmidts M, Schermer B, Keil A, Egger L, Lecha R L, Bonier C, Pavenstädt H. 2003. Nephrin and CD2AP associate with phosphoinositide 3-OH kinase and stimulate AKT-dependent signaling. Molecular and cellular biology 23:4917-4928.
42. Oprea C, Ianache I, Radoi R, Erscoiu S, Tardei G, Nicolaescu O, Nica M, Calistru P, Ruta S, Ceausu E. 2014. Alarming increase in tuberculosis and hepatitis C virus (HCV) among HIV infected intravenous drug users. Journal of the International AIDS Society 17:19625.
43. Chamond N, Cosson A, Coatnoan N, Minoprio P. 2009. Proline racemases are conserved mitogens: characterization of a Trypanosoma vivax proline racemase. Molecular and biochemical parasitology 165:170-179.
44. Zehmer J K, Bartz R, Liu P, Anderson R G. 2008. Identification of a novel N-terminal hydrophobic sequence that targets proteins to lipid droplets. Journal of cell science 121:1852-1860.
45. Wu Y, Liao Q, Yang R, Chen X, Chen X. 2011. A novel luciferase and GFP dual reporter virus for rapid and convenient evaluation of hepatitis C virus replication. Virus research 155:406-414.
46. Lindenbach B D, Evans M J, Syder A J, Wolk B, Tellinghuisen T L, Liu C C, Maruyama T, Hynes R O, Burton D R, McKeating J A, Rice C M. 2005. Complete replication of hepatitis C virus in cell culture. Science 309:623-626.
47. Li C, Yu S, Nakamura F, Yin S, Xu J, Petrolla A A, Singh N, Tartakoff A, Abbott D W, Xin W, Sy M S. 2009. Binding of pro-prion to filamin A disrupts cytoskeleton and correlates with poor prognosis in pancreatic cancer. The Journal of clinical investigation 119:2725-2736.
48. Yang L, Gao Z, Hu L, Wu G, Yang X, Zhang L, Zhu Y, Wong B-S, Xin W, Sy M-S. 2016. Glycosylphosphatidylinositol Anchor Modification Machinery Deficiency Is Responsible for the Formation of Pro-Prion Protein (PrP) in BxPC-3 Protein and Increases Cancer Cell Motility. Journal of Biological Chemistry 291:3905-3917.
49. Roux K J, Kim D I, Raida M, Burke B. 2012. A promiscuous biotin ligase fusion protein identifies proximal and interacting proteins in mammalian cells. The Journal of cell biology 196:801-810.
50. Xu S, Pei R, Guo M, Han Q, Lai J, Wang Y, Wu C, Zhou Y, Lu M, Chen X. 2012. Cytosolic phospholipase A2 gamma is involved in hepatitis C virus replication and assembly. Journal of virology 86:13025-13037.
51. Vogt D A, Camus G, Herker E, Webster B R, Tsou C L, Greene W C, Yen T S, Ott M. 2013. Lipid droplet-binding protein TIP47 regulates hepatitis C Virus RNA replication through interaction with the viral NS5A protein. PLoS pathogens 9:e1003302.
52. Lindenbach B D. 2009. Measuring HCV infectivity produced in cell culture and in vivo. Methods in molecular biology 510:329-336.
53. Dustin M L, Olszowy M W, Holdorf A D, Li J, Bromley S, Desai N, Widder P, Rosenberger F, van der Merwe P A, Allen P M. 1998. A novel adaptor protein orchestrates receptor patterning and cytoskeletal polarity in T-cell contacts. Cell 94:667-677.
54. Tang V W, Brieher W M. 2013. FSGS3/CD2AP is a barbed-end capping protein that stabilizes actin and strengthens adherens junctions. The Journal of cell biology 203:815-833.
55. Zhao J, Bruck S, Cemerski S, Zhang L, Butler B, Dani A, Cooper J A, Shaw A S. 2013. CD2AP links cortactin and capping protein at the cell periphery to facilitate formation of lamellipodia. Molecular and cellular biology 33:38-47.
56. Macdonald A, Crowder K, Street A, McCormick C, Harris M. 2004. The hepatitis C virus NS5A protein binds to members of the Src family of tyrosine kinases and regulates kinase activity. The Journal of general virology 85:721-729.
57. Brasaemle D L, Dolios G, Shapiro L, Wang R. 2004. Proteomic analysis of proteins associated with lipid droplets of basal and lipolytically stimulated 3T3-L1 adipocytes. The Journal of biological chemistry 279:46835-46842.
58. Brass V, Bieck E, Montserret R, Wolk B, Hellings J A, Blum H E, Penin F, Moradpour D. 2002. An amino-terminal amphipathic a-helix mediates membrane association of the hepatitis C virus nonstructural protein 5A. Journal of Biological Chemistry 277:8130-8139.
59. Tellinghuisen T L, Marcotrigiano J, Gorbalenya A E, Rice C M. 2004. The NS5A protein of hepatitis C virus is a zinc metalloprotein. The Journal of biological chemistry 279:48576-48587.
60. Welsch T, Endlich N, Unice G, Doroshenko E, Simpson J C, Kriz W, Shaw A S, Endlich K. 2005. Association of CD2AP with dynamic actin on vesicles in podocytes. American Journal of Physiology-Renal Physiology 289:F1134-F1143.
61. Chen J, Zhao Y, Zhang C, Chen H, Feng J, Chi X, Pan Y, Du J, Guo M, Cao H, Chen H, Wang Z, Pei R, Wang Q, Pan L, Niu J, Chen X, Tang H. 2014. Persistent hepatitis C virus infections and hepatopathological manifestations in immune-competent humanized mice. Cell research 24:1050-1066.

SEQUENCE LISTING

SEQ ID NO. 1: Human CD2AP Nuclei acid sequence
atgg ttgactatat tgtggagtat gactatgatg ctgtacatga tgatgaatta actattcgag ttggagaaat catcaggaat gtgaaaaagc tacaggagga agggtggctg aaggagaac taaatgggag aagaggaatg ttccctgaca atttcgttaa ggaaattaaa agagacgg aattcaagga tgacagtttg cccatcaaac gggaaaggca tgggaatgta gcaagtcttg tacaacgaat aagcacctat ggacttccag ctggaggaat tcagccacat ccacaaacca aaaacattaa gaagaagacc aagaagcgtc agtgtaaagt tctttttgag tacattccac aaaatgagga tgaactggag ctgaaagtgg gagatattat tgatattaat gaagaggtag aagaaggctg gtggagtgga accctgaata acaagttggg actgtttccc tcaaattttg tgaaagaatt agaggtaaca gatgatggtg aaactcatga agcccaggac gattcagaaa ctgttttggc tgggcctact tcacctatac cttctctggg aaatgtgagt gaaactgcat ctggatcagt tacacagcca aagaaaattc gaggaattgg atttggagac atttttaaag aaggctctgt gaaacttcgg acaagaacat ccagtagtga acagaagag aaaaaaccag aaaagcccct aatcctacag tcactgggac caaaaactca gagtgtggag ataacaaaaa cagataccga aggtaaaatt aaagctaaag aatattgtag aacattattt gcctatgaag gtactaatga agatgaactt acttttaaag agggggagat aatccatttg ataagtaagg agactggaga agctggctgg tgggggcg aacttaatgg taaagaagga gtatttccag acaattttgc tgtccagata aatgaacttg ataaagactt tccaaaacca aagaaccac cacctcctgc taaggctcca gctccaaagc ctgaactgat agctgcagag aagaaatatt tttctttaaa gcctgaagaa aaggatgaaa aatcaacact ggaacagaaa ccttctaaac cagcagctcc acaagtccca cccaagaaac ctactccacc taccaaagcc agtaatttac tgagatcttc tggaacagtg tacccaaagc gacctgaaaa accagttcct ccaccacctc ctatagccaa gattaatggg gaagtttcta gcatttcatc aaaatttgaa actgagccag tatcaaaact aaagctagat tctgaacagc tgcccccttag accaaaatca gtagactttg attcacttac agtaaggacc tccaaagaaa cagatgttgt aaattttgat gacatagctt cctcagaaaa cttgcttcat ctcactgcaa atagaccaaa gatgcctgga agaaggttgc cgggccgttt caatggtgga cattctccaa ctcacagccc cgaaaaaatc ttgaagttac caaaagaaga agacagtgcc aacctgaagc catctgaatt aaaaaagat acatgctact ctccaaagcc atctgtgtac cttccaacac cttccagtgc ttctaaagca aatacaactg cttctcctgac tccattagaa atcaaagcta agtggaaac agatgatgtg aaaaaaaatt ccctggatga acttagagcc cagattattg aattgttgtg cattgtagaa gcactgaaaa aggatcacgg gaaagaactg gaaaaactgc gaaaagattt ggaagaagag aagacaatga gaagtaatct agagatggaa atagagaagc tgaaaaaagc tgtcctg SEQ ID NO 2: human CD2AP amino acid sequence
mvdyiveydy davhddelti rvgeiirnvk klqeegwleg elngrrgmfp dnfvkeikre tefkddslpi krerhgnvas lvqristygl paggiqphpq tknikkktkk rqckvlfeyi pqnedelelk vgdiidinee veegwwsgtl nnklglfpsn fvkelevtdd getheaqdds etvlagptsp ipslgnvset asgsvtqpkk irgigfgdif kegsvklrtr tssseteekk pekplilqsl gpktqsveit ktdtegkika keycrtlfay egtnedeltf kegeiihlis ketgeagwwr gelngkegvf pdnfavqine ldkdfpkpkk ppppakapap kpeliaaekk yfslkpeekd ekstleqkps kpaapqvppk kptpptkasn llrssgtvyp krpekpvppp ppiakingev ssisskfete pvsklkldse qlplrpksvd fdsltvrtsk etdvvnfddi assenllhlt anrpkmpgrr lpgrfngghs pthspekilk lpkeedsanl kpselkkdtc yspkpsvyls tpssaskant tafltpleik akvetddvkk nsldelraqi iellciveal kkdhgkelek lrkdleeekt mrsnlemeie klkkavlss

TABLE 1 siRNA/shRNAi sequences for down-regulating human CD2AP expression

| SEQ ID NO # | Nucleotide sequences |
|---|---|
| SEQ ID NO 3 | GCTGGAAGGAGAACTAAATGG |
| SEQ ID NO 4 | GGAGAACTAAATGGGAGAAGA |
| SEQ ID NO 5 | GGACTTCCAGCTGGAGGAATT |
| SEQ ID NO 6 | GGAGCTGAAAGTGGGAGATAT |
| SEQ ID NO 7 | GCTGAAAGTGGGAGATATTAT |
| SEQ ID NO 8 | GCTGAAAGTGGGAGATATTAT |
| SEQ ID NO 9 | GCCCAGGACGATTCAGAAACT |
| SEQ ID NO 10 | GCTGGGCCTACTTCACCTATA |
| SEQ ID NO 11 | GCCAGTAATTTACTGAGATCT |
| SEQ ID NO 12 | GCTTCATCTCACTGCAAATAG |
| SEQ ID NO 13 | GGAAGTTTCCAGCAGATTTCA |
| SEQ ID NO 14 | AGCCGAGGGTCTGGGCAAA |
| SEQ ID NO 15 | AGCCGAGGGTCTGGGCAAA |
| SEQ ID NO 16 | TGAAGAGACTGGTAGGAGA |
| SEQ ID NO 17 | CTAAATGGGAGAAGAGGAA |
| SEQ ID NO 18 | AGGATGAACTGGAGCTGAA |
| SEQ ID NO 19 | GGTAACAGATGATGGTGAA |
| SEQ ID NO 20 | GGAAACAGATGATGTGAAA |

TABLE 2

CRISPR/CAS9 target sequences for down-regulating human CD2AP expression

| SEQ ID NO # | Nucleotide sequences |
|---|---|
| SEQ ID NO 21 | AAAGGCGACACCGTAGACTA |
| SEQ ID NO 22 | CGACACCGTAGACTAAGGTG |
| SEQ ID NO 23 | GTGGGAAAACCGCGGTCGGG |
| SEQ ID NO 24 | GGCGACACCGTAGACTAAGG |
| SEQ ID NO 25 | AGGGTGGGAAAACCGCGGTC |
| SEQ ID NO 26 | TGGGAAAACCGCGGTCGGGC |
| SEQ ID NO 27 | GCGACACCGTAGACTAAGGT |
| SEQ ID NO 28 | CAGGGTGGGAAAACCGCGGT |
| SEQ ID NO 29 | CGACCGCGGTTTTCCCACCC |
| SEQ ID NO 30 | AAAACCGCGGTCGGGCGGGC |
| SEQ ID NO 31 | CGAGGCTAGGCGGGCGCTCG |
| SEQ ID NO 32 | GAAAACCGCGGTCGGGCGGG |
| SEQ ID NO 33 | GAGGGTCTGGGCAAACCGGT |
| SEQ ID NO 34 | TGGGTCCCCACCTTAGTCTA |
| SEQ ID NO 35 | CGAGGGTCTGGGCAAACCGG |
| SEQ ID NO 36 | GCGCTCGGGGTTGGAGCCGA |
| SEQ ID NO 37 | TCCGAGGCTAGGCGGGCGCT |
| SEQ ID NO 38 | TTTTCTAACTGCGAGTGCTA |
| SEQ ID NO 39 | CCGAGGCTAGGCGGGCGCTC |
| SEQ ID NO 40 | AAACCGCGGTCGGGCGGGCG |
| SEQ ID NO 41 | TTAGCACTCGCAGTTAGAAA |
| SEQ ID NO 42 | GCTAGGCGGGCGCTCGGGGT |
| SEQ ID NO 43 | TCCCCACTGCGGGAGCGGCC |
| SEQ ID NO 44 | CCCGAGCGCCCGCCTAGCCT |
| SEQ ID NO 45 | ACCCTGGCCGCTCCCGCAGT |
| SEQ ID NO 46 | CGGCCAGGGTGGGAAAACCG |
| SEQ ID NO 47 | CGAGTGCTAAGGAAGAGGCG |
| SEQ ID NO 48 | AACTGCGAGTGCTAAGGAAG |
| SEQ ID NO 49 | GGCGGGCTCCGAGGCTAGGC |
| SEQ ID NO 50 | TCCCCAGGAGCCACGGCGG |
| SEQ ID NO 51 | CTACCCCGCCCGCCCGACCG |
| SEQ ID NO 52 | GTAGGGCCCTCCCGCCGCCG |
| SEQ ID NO 53 | CACCGGTTTGCCCAGACCCT |
| SEQ ID NO 54 | CCCTGGCCGCTCCCGCAGTG |
| SEQ ID NO 55 | AGCCGAGGGTCTGGGCAAAC |
| SEQ ID NO 56 | TGGCCGCTCCCGCAGTGGGG |

SEQ ID NO 57: canine CD2AP nucleotide sequence
ATGCATTTTA AAAGTTTGCT GAAAAACCTG GAATGGAGAC AACCAACCAG GAGGAAAAGACACATAGAG

AACATCAGCT GAAAAGGTC AAAGAACTG GGGATGGCAA GCTCAGAAAGTGTCTACAAC TTCTCCGGTG

GAGTCGGATT TCTGGTCACG GGTCAGTTGA CTATATTGTGGAGTATGACT ACGATGCTGT ACATGATGAT

GAATTAACTA TTCGGGTTGG TGAAATAATCAGGAATGTGA AAAACTACA GGAGGAAGGA TGGCTAGAAG

GAGAGCTAAA TGGGAGAAGAGGAATGTTTC CTGATAATTT TGTTAAGGAA ATTAAGAGAG AGACAGAACC

CAAGGATGATAATTTGCCCA TTAAACGGGA AGACATGGG AATGTAGCAA GCCTTGTACA

-continued

```
ACGAATAAGCACCTATGGAC TTCCAGCTGG AGGAATTCAA CCACATCCAC AAACCAAAAA

CATTAAGAAGAAGACCAAGA AGCGTCAGTG TAAAGTTCTC TTTGAGTACC TTCCACAAAA

TGAGGATGAATTGGAGCTGA AAGTGGGAGA TATTATTGAT ATTAATGATG AGGTAGAAGA

AGGCTGGTGGAGTGGAACCC TGAACAACAA GTTGGGACTG TTTCCCTCAA ATTTTGTGAA

AGAATTAGAGGTAACAGATG ATGGTGAAAC TCATGAAGCC AAGAGGATT CAGAAACGGT

TTTTACTGGGCCTACCTCAC CTTTACCGTC TCCGGGGAAT GGGAATGAAA CTGCACCTGG

ATCAGTTACACAGCCAAAGA AAATTCGAGG AATTGGATTT GGAGATATTT TTAAAGAAGG

CTCTGTGAAACTTAGAACAA GAACATCTGG TAGTGAAATA GAAGAGAAGA AAACGGAAAA

GCCCTTAATTATACAGTCAG TAGGATCCAA AACACAGAGT CTGGATGCAA CAAAAACAGA

CACGGAAAATAAAAGTAAAG CAAAGGAATA TTGTAGAACA TTATTTGCCT ATGAAGGTAC

TAATGAAGACGAGCTTTCTT TTAAAGAGGG AGAGATAATT CACTTAATAA GTAAGGAGAC

TGGAGAAGCTGGCTGGTGGA AGGGTGAACT TAATGGTAAA GAAGGAGTAT TTCCAGATAA

TTTTGCTATTCAGATACATG AACTGGATAA AGACTTTCCA AAACCAAAGA AACCACCACC

TCCTGCTAAAGGTCCAGCTC CAAAACCTGA GCTAATAGCT ACAGAGAAGA AGTATTTTCC

TATAAAGCCAGAAGAAAAG ATGAAAAATC AGTACTGGAA CAGAAACCTT CTAAACCAGC

AGCTCCACAAGTCCCACCTA GAAGCCTAC TCCACCCACC AAAGCCAATA ATTTATTGAG

ATCTCCTGGGACAATATACC CAAAGCGACC TGAAAAACCA GTCCCTCCAC CACCTCCTAT

AGCCAAGATTAATGGGGAAG TATCTACCAT TTCATCAAAA TTTGAAACTG AGCCATTATC

AAAACCAAAGCTAGATTCTG AACAATTACC ACTTAGACCA AAATCAGTAG ACCTAGATTC

ATTTACAGTTAGGAGCTCTA AAGAAACAGA TATTGTAAAT TTTGATGACA TAGCTTCCTC

AGAAAACTTGCTACATCTTA CTGCAAACAG ACCGAAGATG CCTGGAAGAA GGTTGCCTGG

ACGCTTCAATGGTGGACATT CTCCAACCCA AAGCCCAGAA AAAACCTTGA AGTTACCAAA

AGAAGAAGATAGTGCCAACT TAAAGCCGTC TGAATTTAAA AAGGATTCAA GCTACTCTCC

AAAGCCATCTCTGTACCTTT CAACACCTTC AAGTGCTTCG AAACCAAATA CAGCTGCTTT

TTTAACTCCATTAGAAATCA AAGCTAAAGT AGAATCAGAT GATGGGAAAA AAAACCCCTT

GGATGAACTTAGAGCTCAGA TTATTGAATT GCTGTGCATT GTAGAAGCAC TGAAAAAGGA

TCATGGGAAAGAACTGGAAA AACTACGAAA GGATTTGAA GAGGAGAAGG CAATGAGAAG

TAATCTAGAGGTGGAAATCG AGAAGCTGAA AAAGGCAGTC CTGTCGTCTT GA
```

SEQ ID NO 58: canine CD2AP amino acid sequence

```
MHFKSLLKNL EWRQPTRRKK THREHQLKKV KRTGDGKLRK CLQLLRWSRI SGHGSVDYIVEYDYDAVHDD

ELTIRVGEII RNVKKLQEEG WLEGELNGRR GMFPDNFVKE IKRETEPKDDNLPIKRERHG NVASLVQRIS

TYGLPAGGIQ PHPQTKNIKK KTKKRQCKVL FEYLPQNEDELELKVGDIID INDEVEEGWW SGTLNNKLGL

FPSNFVKELE VTDDGETHEA QEDSETVFTGPTSPLPSPGN GNETAPGSVT QPKKIRGIGF GDIFKEGSVK

LRTRTSGSEI EEKKTEKPLIIQSVGSKTQS LDATKTDTEN KSKAKEYCRT LFAYEGTNED ELSFKEGEII

HLISKETGEAGWWKGELNGK EGVFPDNFAI QIHELDKDFP KPKKPPPPAK GPAPKPELIA

TEKKYFPIKPEEKDEKSVLE QKPSKPAAPQ VPPKKPTPPT KANNLLRSPG TIYPKRPEKP

VPPPPPIAKINGEVSTISSK FETEPLSKPK LDSEQLPLRP KSVDLDSFTV RSSKETDIVN

FDDIASSENLLHLTANRPKM PGRRLPGRFN GGHSPTQSPE KTLKLPKEED SANLKPSEFK

KDSSYSPKPSLYLSTPSSAS KPNTAAFLTP LEIKAKVESD DGKKNPLDEL RAQIIELLCI

VEALKKDHGKELEKLRKDLE EEKAMRSNLE VEIEKLKKAV LSS
```

TABLE 3 siRNA sequences for down-regulating canine CD2AP expression

| SEQ ID NO # | Nucleotide sequence |
| --- | --- |
| SEQ ID NO 59 | GAGGAATGTTTCCTGATAA |
| SEQ ID NO 60 | TCAGTAGACCTAGATTCAT |
| SEQ ID NO 61 | GCGTCAGTGTAAAGTTCTC |
| SEQ ID NO 62 | TAGCTACAGAGAAGAAGTA |
| SEQ ID NO 63 | AGAGGGAGAGATAATTCAC |
| SEQ ID NO 64 | ATCAGTAGACCTAGATTCA |
| SEQ ID NO 65 | GGTACTAATGAAGACGAGC |
| SEQ ID NO 66 | AGAAGAAGATAGTGCCAAC |
| SEQ ID NO 67 | CTCATGAAGCCCAAGAGGA |
| SEQ ID NO 68 | CGAATAAGCACCTATGGAC |
| SEQ ID NO 69 | CTGGAATGGAGACAACCAA |
| SEQ ID NO 70 | GCAAGCTCAGAAAGTGTCT |
| SEQ ID NO 71 | GCTCAGAAAGTGTCTACAA |
| SEQ ID NO 72 | CAGAAAGTGTCTACAACTT |
| SEQ ID NO 73 | GTCTACAACTTCTCCGGTG |
| SEQ ID NO 74 | GGAGTCGGATTTCTGGTCA |
| SEQ ID NO 75 | GTCACGGGTCAGTTGACTA |
| SEQ ID NO 76 | ACGGGTCAGTTGACTATAT |

TABLE 4

CRISPR/CAS9 target sequences for down-regulating canine CD2AP expression

| SEQ ID NO # | Nucleotide sequence |
| --- | --- |
| SEQ ID NO 77 | AAAGGCAGACACTCAACCGCCGG |
| SEQ ID NO 78 | ATGTATTGAAGTGAGACACCTGG |
| SEQ ID NO 79 | ATGATGTGGGACTCCATCCCAGG |
| SEQ ID NO 80 | AGGGCGTGACCCCAAGTCCTGG |
| SEQ ID NO 81 | TGTATTGAAGTGAGACACCTGGG |
| SEQ ID NO 82 | GGGCGTGACCCCAAGTCCTGGG |
| SEQ ID NO 83 | CCATGCAGGAAGCATGATGTGGG |
| SEQ ID NO 84 | GGGGTCACGCCCTGAGCCAAAGG |
| SEQ ID NO 85 | TCCATGCAGGAAGCATGATGTGG |
| SEQ ID NO 86 | ATTGAAGTGAGACACCTGGGTGG |
| SEQ ID NO 87 | GACTCCATCCCAGGACTTGGGGG |
| SEQ ID NO 88 | GAGTGTCTGCCTTTGGCTCAGGG |
| SEQ ID NO 89 | TGGGACTCCATCCCAGGACTTGG |
| SEQ ID NO 90 | AGACACCTGGGTGGCTCCGGCGG |
| SEQ ID NO 91 | TGAGTGTCTGCCTTTGGCTCAGG |
| SEQ ID NO 92 | GGACTCCATCCCAGGACTTGGGG |
| SEQ ID NO 93 | GTGACCCCAAGTCCTGGGATGG |
| SEQ ID NO 94 | GGCGGTTGAGTGTCTGCCTTTGG |
| SEQ ID NO 95 | GTGAGACACCTGGGTGGCTCCGG |
| SEQ ID NO 96 | CCCACATCATGCTTCCTGCATGG |
| SEQ ID NO 97 | GGGACTCCATCCCAGGACTTGGG |
| SEQ ID NO 98 | TAACGCAACTTTCTATTTTTGG |
| SEQ ID NO 99 | CTCACTTCAATACATTTTTAAGG |
| SEQ ID NO 100 | CCAGTTAAAAAGAAAATCTAAGG |
| SEQ ID NO 101 | CTCAACCGCCGGAGCCACCCAGG |
| SEQ ID NO 102 | TAAAGCAACTTTCTATTTTTGG |
| SEQ ID NO 103 | CCTTAGATTTTCTTTTAACTGG |

SEQ ID NO 104: HCV NS5A nucleic acid sequence
TCCGGATCCT GGCTCCGCGA CGTGTGGGAC TGGGTTTGCA CCATCTTGAC AGACTTCAAA

AATTGGCTGA CCTCTAAATT GTTCCCCAAG CTGCCCGGCC TCCCCTTCAT CTCTTGTCAA

AAGGGGTACA AGGGTGTGTG GGCCGGCACT GGCATCATGA CCACGCGCTG CCCTTGCGGC

GCCAACATCT CTGGCAATGT CCGCCTGGGC TCTATGAGGA TCACAGGGCC TAAAACCTGC

ATGAACACCT GGCAGGGGAC CTTTCCTATC AATTGCTACA CGGAGGGCCA GTGCGCGCCG

AAACCCCCCA CGAACTACAA GACCGCCATC TGGAGGGTGG CGGCCTCGGA GTACGCGGAG

GTGACGCAGC ATGGGTCGTA CTCCTATGTA ACAGGACTGA CCACTGACAA TCTGAAAATT

CCTTGCCAAC TACCTTCTCC AGAGTTTTTC TCCTGGGTGG ACGGTGTGCA GATCCATAGG

TTTGCACCCA CACCAAAGCC GTTTTTCCGG GATGAGGTCT CGTTCTGCGT TGGGCTTAAT

TCCTATGCTG TCGGGTCCCA GCTTCCCTGT GAACCTGAGC CCGACGCAGA CGTATTGAGG

```
TCCATGCTAA CAGATCCGCC CCACATCACG GCGGAGACTG CGGCGCGGCG CTTGGCACGG

GGATCACCTC CATCTGAGGC GAGCTCCTCA GTGAGCCAGC TATCAGCACC GTCGCTGCGG

GCCACCTGCA CCACCCACAG CAACACCTAT GACGTGGACA TGGTCGATGC CAACCTGCTC

ATGGAGGGCG GTGTGGCTCA GACAGAGCCT GAGTCCAGGG TGCCCGTTCT GGACTTTCTC

GAGCCAATGG CCGAGGAAGA GAGCGACCTT GAGCCCTCAA TACCATCGGA GTGCATGCTC

CCCAGGAGCG GGTTTCCACG GCCTTACCG GCTTGGGCAC GGCCTGACTA CAACCCGCCG

CTCGTGGAAT CGTGGAGGAG CCAGATTAC CAACCGCCCA CCGTTGCTGG TTGTGCTCTC

CCCCCCCCA AGAAGGCCCC GACGCCTCCC CCAAGGAGAC GCCGGACAGT GGGTCTGAGC

GAGAGCACCA TATCAGAAGC CCTCCAGCAA CTGGCCATCA AGACCTTTGG CCAGCCCCCC

TCGAGCGGTG ATGCAGGCTC GTCCACGGGG GCGGCGCCG CCGAATCCGG CGGTCCGACG

TCCCCTGGTG AGCCGGCCCC CTCAGAGACA GGTTCCGCCT CCTCTATGCC CCCCCTCGAG

GGGGAGCCTG GAGATCCGGA CCTGGAGTCT GATCAGGTAG AGCTTCAACC TCCCCCCCAG

GGGGGGGGGG TAGCTCCCGG TTCGGGCTCG GGTCTTGGT CTACTTGCTC CGAGGAGGAC

GATACCACCG TGTGCTGC

SEQ ID NO 105: NS5A amino acid sequence
SGSWLRDVWD WVCTILTDFK NWLTSKLFPK LPGLPFISCQ KGYKGVWAGT

GIMTTRCPCG ANISGNVRLG SMRITGPKTC MNTWQGTFPI NCYTEGQCAP

KPPTNYKTAI WRVAASEYAE VTQHGSYSYV TGLTTDNLKI PCQLPSPEFF

SWVDGVQIHR FAPTPKPFFR DEVSFCVGLN SYAVGSQLPC EPEPDADVLR

SMLTDPPHIT AETAARRLAR GSPPSEASSS VSQLSAPSLR ATCTTHSNTY

DVDMVDANLL MEGGVAQTEP ESRVPVLDFL EPMAEEESDL EPSIPSECML

PRSGFPRALP AWARPDYNPP LVESWRRPDY QPPTVAGCAL PPPKKAPTPP

PRRRRTVGLS ESTISEALQQ LAIKTFGQPP SSGDAGSSTG AGAAESGGPT

SPGEPAPSET GSASSMPPLE GEPGDPDLES DQVELQPPPQ GGGVAPGSGS

GSWSTCSEED DTTVCC

SEQ ID NO 106: human IRS1 nucleotide sequence
atggcgag ccctccggag agcgatggct tctcggacgt gcgcaaggtg ggctacctgc gcaaacccaa gagcatgcac aaacgcttct tcgtactgcg cgcggccagc gaggctgggg gcccggcgcg cctcgagtac tacgagaacg agaagaagtg gcggcacaag tcgagcgccc ccaaacgctc gatccccctt gagagctgct tcaacatcaa caagcgggct gactccaaga acaagcacct ggtggctctc tacacccggg acagcacttt tgccatcgcg gcggacagcg aggccgagca agacagctgg taccaggctc tcctacagct gcacaaccgt gctaagggcc accacgacgg agctgcggcc ctcggggcgg gaggtggtgg gggcagctgc agcggcagct ccggccttgg tgaggctggg gaggacttga gctacggtga cgtgccccca ggacccgcat tcaaagaggt ctggcaagtg atcctgaagc ccaagggcct gggtcagaca agaacctga ttggtatcta ccgcctttgc ctgaccagca agaccatcag cttcgtgaag ctgaactcgg aggcagcggc cgtggtgctg cagctgatga acatcaggcg ctgtggccac tcggaaaact tcttcttcat cgaggtgggc cgttctgccg tgacggggcc cggggagttc tggatgcagg tggatgactc tgtggtggcc cagaacatgc acgagaccat cctggaggcc atgcgggcca tgagtgatga gttccgccct cgcagcaaga gccagtcctc gtccaactgc tctaacccca tcagcgtccc cctgcgccgg caccatctca caatcccccc gccagccag gtggggctga cccgccgatc acgcactgag agcatcaccg ccacctcccc ggccagcatg gtgggcggga agccaggctc cttccgtgtc cgcgcctcca
```

-continued

```
gtgacggcga aggcaccatg tcccgcccag cctcggtgga cggcagccct gtgagtccca gcaccaacag aacccacgcc caccggcatc ggggcagcgc ccggctgcac ccccgctca accacagccg ctccatcccc atgccggctt cccgctgctc gccttcggcc accagcccgg tcagtctgtc gtccagtagc accagtggcc atggctccac ctcggattgt ctcttccac ggcgatctag tgcttcggtg tctggttccc ccagcgatgg cggtttcatc tcctcggatg agtatggctc cagtccctgc gatttccgga gttccttccg cagtgtcact ccggattccc tgggccacac cccaccagcc cgcggtgagg aggagctaag caactatatc tgcatgggtg gcaaggggcc ctccaccctg accgccccca acggtcacta cattttgtct cggggtggca atggccaccg ctgcacccca ggaacaggct tgggcacgag tccagccttg gctggggatg aagcagccag tgctgcagat ctggataatc ggttccgaaa gagaactcac tcggcaggca catccctac cattacccac cagaagaccc cgtcccagtc ctcagtggct tccattgagg agtacacaga gatgatgcct gcctaccac caggaggtgg cagtggaggc cgactgccgg gacacaggca ctccgccttc gtgcccaccc gctcctaccc agaggagggt ctggaaatgc accccttgga gcgtcggggg gggcaccacc gcccagacag ctccaccctc cacacggatg atggctacat gcccatgtcc ccaggggtgg ccccagtgcc cagtggccga aagggcagtg gagactatat gcccatgagc cccaagagcg tatctgccca cagcagatc atcaatccca tcagacgcca tcccagaga gtggacccca atggctacat gatgatgtcc cccagcggtg gctgctctcc tgacattgga ggtggcccca gcagcagcagcagcagcage aacgccgtcc cttccgggac cagctatgga aagctgtgga caaacgggt aggggggccac cactctcatg tcttgcctca ccccaaaccc ccagtggaga gcagcggtggtaagctctta ccttgcacag gtgactacat gaacatgtca ccagtgggg actccaacaccagcagcccc tccgactgct actacggccc tgaggacccc cagcacaagc cagtcctctcctactactca ttgccaagat cctttaagca cacccagcgc cccggggagc cggaggagggtgcccggcat cagcacctcc gcctttccac tagctctggt cgccttctct atgctgcaacagcagatgat tcttcctctt ccaccagcag cgacagcctg ggtgggggat actgcggggctaggctggag cccagccttc cacatcccca ccatcaggtt ctgcagcccc atctgcctcgaaaggtggac acagctgctc agaccaatag ccgcctggcc cggcccacga ggctgtccctgggggatccc aaggccagca ccttacctcg ggcccgagag cagcagcagc agcagcagcccttgctgcac cctccagagc ccaagagccc ggggggaatat gtcaatattg aatttgggagtgatcagtct ggctacttgt ctggcccggt ggctttccac agctcacctt ctgtcaggtgtccatcccag ctccagccag ctcccagaga ggaagagact ggcactgagg agtacatgaagatggacctg gggccgggcc ggagggcagc ctggcaggag agcactgggg tcgagatgggcagactgggc cctgcacctc ccggggctgc tagcatttgc aggcctaccc gggcagtgcccagcagccgg ggtgactaca tgaccatgca gatgagttgt ccccgtcaga gctacgtggacacctcgcca gctgccctg taagctatgc tgacatgcga acaggcattg ctgcagaggaggtgagcctg cccagggcca ccatggctgc tgcctcctca tcctcagcag cctctgcttccccgactggg cctcaagggg cagcagagct ggctgcccac tcgtccctgc tgggggccacaaggacct ggggggcatga gcgccttcac ccgggtgaac ctcagtccta accgcaaccagagtgccaaa gtgatccgtg cagacccaca agggtgccgg cggaggcata gctccgagactttctcctca acacccagtg ccacccgggt gggcaacaca gtgcccttttg gagcgggggcagcagtaggg ggcggtggcg gtagcagcag cagcagcgag gatgtgaaac gccacagctctgcttccttt gagaatgtgt ggctgaggcc tggggagctt gggggagccc ccaaggagccagccaaactg tgtggggctg ctgggggttt ggagaatggt cttaactaca tagacctggatttggtcaag gacttcaaac agtgccctca ggagtgcacc cctgaaccgc
```

-continued agcctcccccaccccaccc cctcatcaac ccctgggcag cggtgagagc agctccaccc gccgctcaagtgaggattta agcgcctatg ccagcatcag tttccagaag cagccagagg accgtcagtag SEQ ID NO 107: human IRS1 amino acid sequence
masppesdgf sdvrkvgylr kpksmhkrff vlraaseagg parleyyene kkwrhkssapkrsiplescf ninkradskn khlvalytrd ehfaiaadse aeqdswyqal lqlhnrakghhdgaaalgag gggggscsgss glgeagedls ygdvppgpaf kevwqvilkp kglgqtknli giyrlcltsk tisfvklnse aaavvlqlmn irrcghsenf ffievgrsav tgpgefwmqv ddsvvaqnmh etileamram sdefrprsks qsssncsnpi svplrrhhln npppsqvglt rrsrtesita tspasmvggk pgsfrvrass dgegtmsrpa svdgspvsps tnrthahrhr gsarlhppln hsrsipmpas rcspsatspv slssssstsgh gstsdclfpr rssasvsgsp sdggfissde ygsspcdfrs sfrsvtpdsl ghtppargee elsnyicmgg kgpstltapn ghyilsrggn ghrctpgtgl gtspalagde aasaadldnr frkrthsagt sptithqktp sqssvasiee ytemmpaypp gggsggrlpg hrhsafvptr sypeeglemh plerrgghhr pdsstlhtdd gympmspgva pvpsgrkgsg dympmspksv sapqqiinpi rrhpqrvdpngymmmspsgg cspdigggps sssssssnavp sgtsygklwt ngvgghhshv lphpkppves sggkllpctg dymnmspvgd sntsspsdcy ygpedpqhkp vlsyyslprs fkhtqrpgep eegarhqhlr lstssgrlly aataddssss tssdslgggy cgarlepslp hphhqvlqph lprkvdtaaq tnsrlarptr lslgdpkast lprareqqqq qqpllhppep kspgeyvnie fgsdqsgyls gpvafhssps vrcpsqlqpa preeetgtee ymkmdlgpgr raawqestgvemgrlgpapp gaasicrptr avpssrgdym tmqmscprqs yvdtspaapv syadmrtgiaaeevslprat maaasssssaa sasptgpqga aelaahssll ggpqgpggms aftrvnlspnrnqsakvira dpqgcrrrhs setfsstpsa trvgntvpfg agaavgggg sssssedvkrhssasfenvw lrpgelggap kepaklcgaa gglenglnyi dldlvkdfkq cpqectpepqppppppphqp lgsgessstr rssedlsaya sisfqkqped rq SEQ ID NO 108: canine IRS1 nucleotide sequence
ATGGCGAGCC CTCCGGAGAC CGACGGCTTC TCGGACGTGC GCAAGGTGGG CTACCTGCGC AAACCCAAGA

GCATGCACAA GCGCTTCTTC GTGCTGCGGG CGGCCAGCGA GGCGGGGGCC CGGCGCGCC TCGAGTACTA

CGAGAACGAG AAGAAGTGGC GGCACAAGTC GAGCGCCCCC AAACGCTCGA TCCCCCTCGA GAGCTGCTTC

AACATCAACA AGCGGGCGGA CTCCAAGAAC AAGCACCTGG TGGCCCTTTA CACCCGGGAC GAGCACTTTG

CCATCGCGGC GGACAGCGAG GCCGAGCAGG ACAGCTGGTA CCAGGCCCTC CTGCAGCTGC ACAACCGGGC

CAAGGGCCACCACGACGGCG CCTCGGCCCC CGGGGCGGGA GGCGGCGGGG GCAGCTGCAG

CGGCAGCTCG GGCCTCGGGG AGGCCGGCGA GGACTTGAGC TACGGGGACG TGCCCCCGGG

ACCTGCGTTCAAGGAGGTCT GGCAGGTGAT CCTGAAACCC AAGGGCCTGG GCAGACAAA

GAACCTGATTGGCATCTACC GCCTCTGCCT GACCAGCAAG ACCATCAGCT TCGTGAAGCT

GAACTCCGAGGCGGCGCCG TGGTGCTGCA GCTGATGAAC ATCCGACGTT GCGGCCACTC

GGAGAACTTCTTCTTCATCG AAGTGGGCCG TTCCGCAGTG ACGGGACCCG GCGAGTTCTG

GATGCAGGTGGATGACTCCG TGGTGGCCCA GAACATGCAC GAGACCATCC TGGAGGCCAT

GCGGGCCATGAGCGACGAGT TCCGCCCTCG GAGTAAGAGC CAGTCCTCCT CCAACTGCTC

CAACCCCATCAGCGTCCCCC TGCGCCGGCA CCACCTCAAC AACCCCCCTC CAGCCAGGT

GGGGCTGACGCGCCGCTCGC GCACCGAGAG CATCACCGCC ACCTCTCCGG CCAGCATGGT

GGGCGGGAAGCAGGGCTCCT TCCGTGTGCG CGCGTCCAGC GACGGCGAGG GCACCATGTC

CCGCCCGGCCTCGGTGGACG GCAGCCCCGT GAGCCCGAGC ACCACCAGGA CCCACGCGCA

CCGGCATCGCGGCAGCTCCC GGCTGCACCC CCCGCTCAAC CACAGCCGCT CCATCCCCAT

GCCTTCCTCTCGCTGCTCGC CTTCCGCCAC CAGCCCGGTC AGCCTGTCGT CCAGCAGCAC

CAGTGGCCACGGCTCCACCT CGGACTGCCT CTTCCCCCGG CGCTCTAGTG CCTCTGTGTC

```
GGGTTCCCCCAGCGACGGTG GTTTCATCTC CTCTGACGAG TACGGCTCGA GTCCCTGCGA

TTTCCGAAGTTCCTTCCGCA GTGTCACCCC GGATTCCCTG GGCCACACCC CCCCGGCCCG

CGGCGAGGAGGAGCTGAGCA ACTACATCTG CATGGGAGGC AAAGGGTCCT CCACCCTCAC

CGCCCCAACGGTCACTACA TTTTGCCTCG GGGTGGCAAT GGCCACCGCT ACATCCCGGG

GGCTGGCTTGGGCACCAGCC CGGCCCTGGC TGCGGATGAA GCGGCCGCTG CGGCCGACCT

GGATAACCGGTTCCGAAAGC GGACTCACTC CGCGGGCACA TCCCCTACCA TTTCCCACCA

GAAGACCCCGTCCCAGTCTT CTGTGGCTTC CATTGAGGAG TACACGGAGA TGATGCCTGC

CTACCCGCCAGGAGGTGGCA GTGGAGGCCG ACTGCCTGGC TACCGGCACT CTGCCTTCGT

GCCCACCCACTCCTACCCCG AGGAGGGTCT GGAAATGCAC CCTCTGGACA GGCGTGGGGG

CCACCACCGGCCGGACGCCG CCGCCCTCCA CACGGATGAT GGCTACATGC CCATGTCCCC

GGGAGTGGCACCGGTGCCCA GCAGCCGGAA GGGCAGTGGG GACTATATGC CCATGAGCCC

CAAGAGCGTGTCCGCGCCGC AGCAGATCAT CAACCCCATT GACGCCATC CCCAGAGGGT

GGACCCCAATGGCTACATGA TGATGTCCCC AAGCGGCAGC TGCTCTCCTG ACATTGGAGG

TGGGCCCGGCAGCAGCAGCA GCGGCAGCGC CGCCCCTTCT GGGAGCAGCT ATGGCAAGCT

GTGGACAAACGGGGTAGGGG GCCACCACCC TCACGCCCTG CCGCACCCCA AACTCCCCGT

GGAGAGCGGGAGTGGCAAGC TCCTGTCTTG TACCGGCGAC TACATGAACA TGTCGCCGGT

GGGGGACTCCAACACCAGCA GCCCCTCCGA CGGCTACTAC GGCCCAGAGG ACCCCCAGCA

CAAGCCAGTTCTCTCCTACT ACTCATTGCC AAGGTCCTTT AAGCACACCC AGCGCCCTGG

GGAGCTGGAGGAGAGCGCCC GGCACNAGCA CCTCCGCCTC TCCTCCAGCT CGGGTCGTCT

TCTCTACGCCGCGACGGCGG AAGATTCCTC CTCCTCCACC AGCAGCGACA GCCTGGGCCC

AGGGGGATACTGTGGGGTCA GGCCGGATCC CGGCCTCCCG CATATCCACC ATCAGGTCCT

GCAGCCTCACCTGCCTCGGA AGGTGGACAC GGCCGCGCAG ACCAACAGCC GCCTGGCTCG

GCCCACGAGGCTGTCCCTGG GGGACCCCAA GGCCAGCACC TTACCTCGGG TTCGAGAGCA

GCAGCACCCGCCGCCCCTGC TGCACCCTCC GGAGCCCAAG AGCCCCGGGG AATATGTGAA

TATTGAGTTCGGGAGCGATC AGCCGGGCTA CTTATCGGGG CCGGTGGCTG CCCGCAGCTC

GCCTTCTGTCAGGTGCCCAC CCCAGCTCCA GCCAGCTCCC CGCGAGGAAG AGACTGGCAC

CGAGGAGTACATGAACATGG ACCTGGGGCC TGGCCGGAGG GCAGCCTGGC AGGAGGGTGC

TGGGGTCCAGCCCGGCAGGG TGGGCCCCGC GCCCCCCGGG GCCGCTAGCG TGTGCAGGCC

CACCCGGGCAGTGCCCAGCA GCCGGGGCGA CTACATGACC ATGCAGGTGG GCTGTCCCGG

CCAGGGCTACGTGGACACCT CGCCAGTGGC CCCCATCAGC TACGCTGACA TGCGGACAGG

CATTGTCGTGGAGGAGGCCA GCCTGCCGGG GGCCACAGCG GCCGCCCCCT CCTCGGCCTC

GGCAGCCTCGGCTTCCCCCA CGGCGCCTCC AAAAGCGGGG GAGCTGGTGG CCCGCTCCTC

CCTGCTGGGGGCCCGCAGG GACCCGGGGG CATGAGCGCC TTCACCCGGG TGAACCTCAG

CCCCAACCGCAACCAGAGTG CCAAAGTGAT CCGCGCCGAC CCGCAGGGGT GCCGGAGGCG

GCATAGCTCTGAGACCTTCT CCTCCACGCC CAGTGCCACC GGGCGGGCA ACGCAGTGCC

CTTCGGCGGGGGGCGGCCC TGGGGGGCAG CGGTGGCGGC AGCAGCGCGG AGGATATGAA

ACGCCACAGTTCGGCTTCCT TTGAGAACGT GTGGCTGAGG CCTGGGGAGC TCGGGGGAGC

CCCCAAGGAGCCGGCCCCGC ACGCTGGGGC CGCCGGGGGT TTGGAGAATG GGCTTAACTA

CATAGACCTGGATTTGGTCA AGGACTTCAA ACAGTGCTCT CAGGAGCGCC CCCCTCAACC

GCAGCCGCCCCCGCCCCCGG CCCCTCATCA GCCTCTGGGC AGCAGTGAGA GCAGTTCAAC
```

-continued
```
CAGCCGCTCCAGCGAGGATC TAAGCGCCTA TGCCAGCATC AGTTTCCAGA AGCAGCCAGA

GGACCTCCAGTAG

SEQ ID NO 109: canine IRS1 amino acid sequence
MASPPETDGF SDVRKVGYLR KPKSMHKRFF VLRAASEAGG PARLEYYENE KKWRHKSSAPKRSIPLESCF

NINKRADSKN KHLVALYTRD EHFAIAADSE AEQDSWYQAL LQLHNRAKGHHDGASAPGAG GGGGSCSGSS

GLGEAGEDLS YGDVPPGPAF KEVWQVILKP KGLGQTKNLIGIYRLCLTSK TISFVKLNSE AAAVVLQLMN

IRRCGHSENF FFIEVGRSAV TGPGEFWMQVDDSVVAQNMH ETILEAMRAM SDEFRPRSKS QSSSNCSNPI

SVPLRRHHLN NPPPSQVGLTRRSRTESITA TSPASMVGGK QGSFRVRASS DGEGTMSRPA SVDGSPVSPS

TTRTHAHRHRGSSRLHPPLN HSRSIPMPSS RCSPSATSPV SLSSSSTSGH GSTSDCLFPR

RSSASVSGSPSDGGFISSDE YGSSPCDFRS SFRSVTPDSL GHTPPARGEE ELSNYICMGG

KGSSTLTAPNGHYILPRGGN GHRYIPGAGL GTSPALAADE AAAAADLDNR FRKRTHSAGT

SPTISHQKTPSQSSVASIEE YTEMMPAYPP GGGSGGRLPG YRHSAFVPTH SYPEEGLEMH

PLDRRGGHHRPDAAALHTDD GYMPMSPGVA PVPSSRKGSG DYMPMSPKSV SAPQQIINPI

RRHPQRVDPNGYMMMSPSGS CSPDIGGGPG SSSSGSAAPS GSSYGKLWTN GVGGHHPHAL

PHPKLPVESGSGKLLSCTGD YMNMSPVGDS NTSSPSDGYY GPEDPQHKPV LSYYSLPRSF

KHTQRPGELEESARHXHLRL SSSSGRLLYA ATAEDSSSST SSDSLGPGGY CGVRPDPGLP

HIHHQVLQPHLPRKVDTAAQ TNSRLARPTR LSLGDPKAST LPRVREQQHP PPLLHPPEPK

SPGEYVNIEFGSDQPGYLSG PVAARSSPSV RCPPQLQPAP REEETGTEEY MNMDLGPGRR

AAWQEGAGVQPGRVGPAPPG AASVCRPTRA VPSSRGDYMT MQVGCPGQGY VDTSPVAPIS

YADMRTGIVVEEASLPGATA AAPSSASAAS ASPTAPPKAG ELVARSSLLG GPQGPGGMSA

FTRVNLSPNRNQSAKVIRAD PQGCRRRHSS ETFSSTPSAT RAGNAVPFGG GAALGGSGGG

SSAEDMKRHSSASFENVWLR PGELGGAPKE PAPHAGAAGG LENGLNYIDL DLVKDFKQCS

QERPPQPQPPPPPAPHQPLG SSESSSTSRS SEDLSAYASI SFQKQPEDLQ

SEQ ID NO 110: human Cbl-b nucleotide sequence
ATGGGCTATT TGTGTGTTAA TTTCATTTGG TTCTTGGGAA TAACGACTCA CCGCGTTGATTTAAAGAAAG

AACTAAAATT CCAGATGGCA AACTCAATGA ATGGCAGAAA CCCTGGTGGTCGAGGAGGAA ATCCCCGAAA

AGGTCGAATT TTGGGTATTA TTGATGCTAT TCAGGATGCAGTTGGACCCC TAAGCAAGC TGCCGCAGAT

CGCAGGACCG TGGAGAAGAC TTGGAAGCTCATGGACAAAG TGGTAAGACT GTGCCAAAAT CCCAAACTTC

AGTTGAAAAA TAGCCCACCATATATACTTG ATATTTTGCC TGATACATAT CAGCATTTAC GACTTATATT

GAGTAAATATGATGACAACC AGAAACTTGC CCAACTCAGT GAGAATGAGT ACTTTAAAAT

CTACATTGATAGCCTTATGA AAAAGTCAAA ACGGGCAATA AGACTCTTTA AAGAAGGCAA

GGAGAGAATGTATGAAGAAC AGTCACAGGA CAGACGAAAT CTCACAAAAC TGTCCCTTAT

CTTCAGTCACATGCTGGCAG AAATCAAAGC AATCTTTCCC AATGGTCAAT TCCAGGGAGA

TAACTTTCGTATCACAAAAG CAGATGCTGC TGAATTCTGG AGAAAGTTTT TGGAGACAA

AACTATCGTACCATGGAAAG TATTCAGACA GTGCCTTCAT GAGGTCCACC AGATTAGCTC

TGGCCTGGAAGCAATGGCTC TAAAATCAAC AATTGATTTA ACTTGCAATG ATTACATTTC

AGTTTTTGAATTTGATATTT TTACCAGGCT GTTTCAGCCT TGGGGCTCTA TTTTGCGGAA

TTGGAATTTCTTAGCTGTGA CACATCCAGG TTACATGGCA TTTCTCACAT ATGATGAAGT

TAAAGCACGACTACAGAAAT ATAGCACCAA ACCCGGAAGC TATATTTTCC GGTTAAGTTG

CACTCGATTGGGACAGTGGG CCATTGGCTA TGTGACTGGG ATGGGAATA TCTTACAGAC

CATACCTCATAACAAGCCCT TATTTCAAGC CCTGATTGAT GGCAGCAGGG AAGGATTTTA

TCTTTATCCTGATGGGAGGA GTTATAATCC TGATTTAACT GGATTATGTG AACCTACACC
```

-continued

```
TCATGACCATATAAAAGTTA CACAGGAACA ATATGAATTA TATTGTGAAA TGGGCTCCAC

TTTTCAGCTCTGTAAGATTT GTGCAGAGAA TGACAAAGAT GTCAAGATTG AGCCTTGTGG

GCATTTGATGTGCACCTCTT GCCTTACGGC ATGGCAGGAG TCGGATGGTC AGGGCTGCCC

TTTCTGTCGTTGTGAAATAA AAGGAACTGA GCCCATAATC GTGGACCCCT TTGATCCAAG

AGATGAAGGCTCCAGGTGTT GCAGCATCAT TGACCCCTTT GGCATGCCGA TGCTAGACTT

GGACGACGATGATGATCGTG AGGAGTCCTT GATGATGAAT CGGTTGGCAA ACGTCCGAAA

GTGCACTGACAGGCAGAACT CACCAGTCAC ATCACCAGGA TCCTCTCCCC TTGCCCAGAG

AAGAAAGCCACAGCCTGACC CACTCCAGAT CCCACATCTA AGCCTGCCAC CCGTGCCTCC

TCGCCTGGATCTAATTCAGA AAGGCATAGT TAGATCTCCC TGTGGCAGCC AACGGGTTC

ACCAAAGTCTTCTCCTTGCA TGGTGAGAAA ACAAGATAAA CCACTCCCAG CACCACCTCC

TCCCTTAAGAGATCCTCCTC CACCGCCACC TGAAAGACCT CCACCAATCC CACCAGACAA

TAGACTGAGTAGACACATCC ATCATGTGGA AAGCGTGCCT TCCAGAGACC CGCCAATGCC

TCTTGAAGCATGGTGCCCTC GGGATGTGTT TGGGACTAAT CAGCTTGTGG GATGTCGACT

CCTAGGGGAGGGCTCTCCAA AACCTGGAAT CACAGCGAGT TCAAATGTCA ATGGAAGGCA

CAGTAGAGTGGGCTCTGACC CAGTGCTTAT GCGGAAACAC AGACGCCATG ATTTGCCTTT

AGAAGGAGCTAAGGTCTTTT CCAATGGTCA CCTTGGAAGT GAAGAATATG ATGTTCCTCC

CCGGCTTTCTCCTCCTCCTC CAGTTACCAC CCTCCTCCCT AGCATAAAGT GTACTGGTCC

GTTAGCAAATTCTCTTTCAG AGAAAACAAG AGACCCAGTA GAGGAAGATG ATGATGAATA

CAAGATTCCTTCATCCCACC CTGTTTCCCT GAATTCACAA CCATCTCATT GTCATAATGT

AAAACCTCCTGTTCGGTCTT GTGATAATGG TCACTGTATG CTGAATGGAA CACATGGTCC

ATCTTCAGAGAAGAAATCAA ACATCCCTGA CTTAAGCATA TATTTAAAGG GAGATGTTTT

TGATTCAGCCTCTGATCCCG TGCCATTACC ACCTGCCAGG CCTCCAACTC GGGACAATCC

AAAGCATGGTTCTTCACTCA ACAGGACGCC CTCTGATTAT GATCTTCTCA TCCCTCCATT

AGGTGAAGATGCTTTTGATG CCCTCCCTCC ATCTCTCCCA CCTCCCCCAC CTCCTGCAAG

GCATAGTCTCATTGAACATT CAAAACCTCC TGGCTCCAGT AGCCGGCCAT CCTCAGGACA

GGATCTTTTTCTTCTTCCTT CAGATCCCTT TGTTGATCTA GCAAGTGGCC AAGTTCCTTT

GCCTCCTGCTAGAAGGTTAC CAGGTGAAAA TGTCAAAACT AACAGAACAT CACAGGACTA

TGATCAGCTTCCTTCATGTT CAGATGGTTC ACAGGCACCA GCCAGACCCC CTAAACCACG

ACCGCGCAGGACTGCACCAG AAATTCACCA CAGAAAACCC CATGGGCCTG AGGCGGCATT

GGAAAATGTCGATGCAAAAA TTGCAAAACT CATGGGAGAG GGTTATGCCT TTGAAGAGGT

GAAGAGAGCCTTAGAGATAG CCCAGAATAA TGTCGAAGTT GCCCGGAGCA TCCTCCGAGA

ATTTGCCTTCCCTCCTCCAG TATCCCCACG TCTAAATCTA TAG
```

SEQ ID NO 111: human Cb1-b amino acid sequence
```
MGYLCVNFIW FLGITTHRVD LKKELKFQMA NSMNGRNPGG RGGNPRKGRI LGIIDAIQDAVGPPKQAAAD

RRTVEKTWKL MDKVVRLCQN PKLQLKNSPP YILDILPDTY QHLRLILSKYDDNQKLAQLS ENEYFKIYID

SLMKKSKRAI RLFKEGKERM YEEQSQDRRN LTKLSLIFSHMLAEIKAIFP NGQFQGDNFR ITKADAAEFW

RKFFGDKTIV PWKVFRQCLH EVHQISSGLEAMALKSTIDL TCNDYISVFE FDIFTRLFQP WGSILRNWNF

LAVTHPGYMA FLTYDEVKARLQKYSTKPGS YIFRLSCTRL GQWAIGYVTG DGNILQTIPH NKPLFQALID

GSREGFYLYPDGRSYNPDLT GLCEPTPHDH IKVTQEQYEL YCEMGSTFQL CKICAENDKD

VKIEPCGHLMCTSCLTAWQE SDGQGCPFCR CEIKGTEPII VDPFDPRDEG SRCCSIIDPF

GMPMLDLDDDDREESLMMN RLANVRKCTD RQNSPVTSPG SSPLAQRRKP QPDPLQIPHL
```

SLPPVPPRLDLIQKGIVRSP CGSPTGSPKS SPCMVRKQDK PLPAPPPPLR DPPPPPPERP
PPIPPDNRLSRHIHHVESVP SRDPPMPLEA WCPRDVFGTN QLVGCRLLGE GSPKPGITAS
SNVNGRHSRVGSDPVLMRKH RRHDLPLEGA KVFSNGHLGS EEYDVPPRLS PPPPVTTLLP
SIKCTGPLANSLSEKTRDPV EEDDDEYKIP SSHPVSLNSQ PSHCHNVKPP VRSCDNGHCM
LNGTHGPSSEKKSNIPDLSI YLKGDVFDSA SDPVPLPPAR PPTRDNPKHG SSLNRTPSDY
DLLIPPLGEDAFDALPPSLP PPPPPARHSL IEHSKPPGSS SRPSSGQDLF LLPSDPFVDL
ASGQVPLPPARRLPGENVKT NRTSQDYDQL PSCSDGSQAP ARPPKPRPRR TAPEIHHRKP
HGPEAALENVDAKIAKLMGE GYAFEEVKRA LEIAQNNVEV ARSILREFAF PPPVSPRLNL

TABLE 5

| SEQ ID NO # | siRNA/shRNAi sequences for down-regulating human Cbl-b expression<br>Nucleotide sequence |
|---|---|
| SEQ ID NO 112 | GCCTGATACATATCAGCAT |
| SEQ ID NO 113 | GCGGAATTGGAATTTCTTA |
| SEQ ID NO 114 | GCATGCCGATGCTAGACTT |
| SEQ ID NO 115 | GCCTGATACATATCAGCAT |
| SEQ ID NO 116 | GGAGAGAATGTATGAAGAACA |
| SEQ ID NO 117 | GCGGAATTGGAATTTCTTAGC |
| SEQ ID NO 118 | GCACGACTACAGAAATATAGC |
| SEQ ID NO 119 | GGAATATCTTACAGACCATAC |
| SEQ ID NO 120 | GCACCAAACCCGGAAGCTATA |
| SEQ ID NO 121 | GCCTGGATCTAATTCAGAAAG |
| SEQ ID NO 122 | GGAATCACAGCGAGTTCAAAT |
| SEQ ID NO 123 | GGAACACATGGTCCATCTTCA |
| SEQ ID NO 124 | GCATAGTCTCATTGAACATTC |

TABLE 6

| SEQ ID NO # | CRISPR/CAS9 target sequences for down-regulating human Cbl-b expression<br>Nucleotide sequence |
|---|---|
| SEQ ID NO 125 | GTTGCGTTTCCACGTCTCGG |
| SEQ ID NO 126 | GAACAGCTCGCTCCCGAAGA |
| SEQ ID NO 127 | ATTGTTGCGTTTCCACGTCT |
| SEQ ID NO 128 | AGTGCTGCTGCGGCGTCCCG |
| SEQ ID NO 129 | AGGAGGAGGAGACCGCTCGC |
| SEQ ID NO 130 | GAAGGAGCAACCCAGCGCGC |
| SEQ ID NO 131 | GCGCGCAGGCCTCCGAGACG |
| SEQ ID NO 132 | CGTCTCGGAGGCCTGCGCGC |
| SEQ ID NO 133 | GTCCCGCGGCCTCCCCGAGT |
| SEQ ID NO 134 | CTCCCCTCCCGCCCGACTCG |
| SEQ ID NO 135 | GACGCCGCAGCAGCACTAGC |
| SEQ ID NO 136 | GTCTCGGAGGCCTGCGCGCT |
| SEQ ID NO 137 | GCGGCCTCCCCGAGTCGGGC |
| SEQ ID NO 138 | CCCTCCCGCCCGACTCGGGG |
| SEQ ID NO 139 | CGCGGCCTCCCCGAGTCGGG |
| SEQ ID NO 140 | CTCCCCGAGTCGGGCGGGAG |
| SEQ ID NO 141 | CGGGTGTGGATTTGTCTTGA |
| SEQ ID NO 142 | GCCTCCCCGAGTCGGGCGGG |
| SEQ ID NO 143 | TCCCGCGGCCTCCCCGAGTC |
| SEQ ID NO 144 | CGCCCGACTCGGGGAGGCCG |
| SEQ ID NO 145 | CTCTCCCCTCCCGCCCGACT |
| SEQ ID NO 146 | TCTCCCCTCCCGCCCGACTC |
| SEQ ID NO 147 | AGCGATCCCACTCCCAGCCG |
| SEQ ID NO 148 | TCAGCGATCCCACTCCCAGC |
| SEQ ID NO 149 | CGCTGGGTTGCTCCTTCTTC |
| SEQ ID NO 150 | GCCCGACTCGGGGAGGCCGC |
| SEQ ID NO 151 | GCGCTGGGTTGCTCCTTCTT |
| SEQ ID NO 152 | CCTCCCCGAGTCGGGCGGGA |
| SEQ ID NO 153 | TGTGTGTGGGGAGCCCCGGC |
| SEQ ID NO 154 | GTGTGTGGGGAGCCCCGGCT |
| SEQ ID NO 155 | CGCTGGACACCCCACCCCTG |
| SEQ ID NO 156 | GCCGCAGCAGCACTAGCAGG |
| SEQ ID NO 157 | CGGGGCTCCCCACACACACT |
| SEQ ID NO 158 | CTGGGTCCTGTGTGTGCCAC |

SEQ ID NO 159: canine Cbl-b nucleotide sequence
ATGGCAAATT CTATGAATGG CAGAAACCCT GGTGGTCGAG GAGGAAACCC CCGAAAAGGACGGATTTTGG

GTATCATTGA TGCTATTCAA GATGCAGTTG GACCTCCGAA GCAAGCAGCAGCAGATCGCA GGACGGTGGA

GAAAACTTGG AAACTCATGG ACAAAGTGGT CAGACTGTGTCAAATCCCA AGCTTCAGTT GAAAAATAGC

CCACCATATA TACTTGATAT CTTACCTGATACATATCAGC ATTTACGACT ATACTGAGT AAATATGATG

ACAACCAGAA ACTTGCCCAACTCAGTGAGA ATGAGTATTT TAAAATCTAC ATCGATAGTC TAATGAAAAA

GTCAAAGCGGGCAATAAGAC TCTTTAAAGA AGGCAAGGAG AGGATGTATG AAGAGCAGTC

ACAGGACAGACGAAATCTCA CAAAACTGTC CCTTATCTTC AGTCACATGC TGGCAGAAAT

CAAAGCAATCTTTCCCAATG GGCAGTTCCA GGGAGATAAC TTTCGTATCA CGAAAGCAGA

TGCTGCTGAATTCTGGAGAA AGTTTTTTGG AGACAAAACT ATTGTACCAT GGAAAGTATT

CAGACAGTGCCTTCATGAGG TTCATCAAAT TAGCTCTGGC CTGGAAGCAA TGGCTCTGAA

ATCAACAATTGATTTAACTT GTAATGATTA CATTTCAGTT TTTGAATTTG ATATTTTTAC

CAGGCTCTTTCAGCCTTGGG GCTCTATTTT ACGGAATTGG AATTTCTTAG CTGTAACACA

TCCAGGTTACATGGCATTTC TCACATACGA TGAAGTTAAA GCACGACTGC AGAAATACAG

CACCAAACCTGGAAGCTACA TTTTCCGGTT AAGCTGCACC AGATTGGGAC AGTGGGCCAT

TGGCTATGTGACAGGGGATG GCAATATCTT ACAGACCATA CCACATAACA AGCCCTTGTT

TCAAGCCCTGATTGATGGCA GCAGGGAAGG ATTCTATCTT TATCCTGATG GGAGGAGTTA

TAATCCTGATTTAACTGGAT TATGTGAACC CACACCACAT GACCATATAA AGTTACGCA

GGAACAATATGAATTATATT GTGAAATGGG CTCCACTTTT CAGCTCTGTA AAATTTGTGC

TGAGAACGACAAAGATGTCA AGATTGAGCC CTGTGGGCAT TGATGTGCA CCTCTTGCCT

TACAGCGTGGCAGGAGTCGG ACGGCCAAGG CTGCCCCTTT TGCCGCTGTG AAATAAAAGG

AACAGAGCCCATAATCGTGG ACCCCTTTGA TCCAAGAGAT GAAGGTTCCA GGTGCTGTAG

CATCATTGACCCCTTTGGAA TGCCAATGCT GGACCTGGAT GATGACGATG ACCGAGAAGA

GTCCTTGATGATGAATCGGT TGGCAAATGT TCGAAAGTGC ACTGATAGGC AAAATTCACC

AGTCACATCACCAGGATCCT CTCCCCTTGC ACAGAGAAGA AAGCCACATC CAGATCCTCT

CCAGATCCCACATCTGAGCC TGCCACCAGT ACCTCCTCGC CTGGATCTAA TTCAGAAAGG

CATAGTTCGGTCTCCCTGTG GCAGTCCCAC TGGTTCACCA AAGTCTTCTC CTTGCATGGT

GAGAAAACAAGATAAACCAC TCCCAGCACC GCCTCCTCCC TTAAGAGATC CTCCTCCACC

TCCCCCTGAGAGACCTCCCC CGATCCCACC TGACAACAGA CTGAGTCGAC ACTTCCATCA

CGTGGAAAGTGTGCCTTCTA GAGACCAGCC AATGCCTCTT GAAGCCTGGT GCCCTCGGGA

TGTGTTTGGAACTAATCAGT CAGTGGGTTG TCGACAATTA GGGGATGGCT CTCCAAAGCC

TGGAATCACAGCAAGTTCAA ATGTAAATGG AAGGCACAGT AGAATGGGCT CTGACCCTGT

GCTTCTGCGAAAACACAGAC GCCACGATTT GCCTTTAGAA GGAGCCAAGG TCTTTTCCAA

TGGTCACCTGGGAAGCGAAG AGTACGATGT TCCTCCCCGG CTTTCACCTC CTCCTCCAGC

TGCCACCCTTGTCCCTAGCA TCAAGTGTAC TGGCCCGTTA GCAAATCCCC TTTCAGAGAA

AACCAGAGACCCAGTCGAGG AAGATGATGA TGAATACAAG ATTCCTTCAT CCCATCCTGT

TTCCCTGAATTCACAACCAT CTCATTGCCA TAACGTAAAA CCTCCTCTTA GGTCTTGTGA

TAATGGTCATTGTGTATTGA ATGGAACACA TGGTACATCT TCAGAGGTGA AGAAATCAAA

CATCCCTGAATTAGGCATTT ATTTAAAGGG AGATGTTTTT GATTCAGCCT CTGATCCAGT

GCCATTACCACCTGCCAGGC CTCCAACTCG GGACAATCCA AAGCATGGTT CTTCACTCAA

CAGGACGCCCTCTGATTATG ATCTTCTCAT CCCTCCATTA GGTGAAGATG CTTTTGATGC

-continued

```
CCTCCCCCCATCCCTCCCGC CTCCCCCACC TCCCGCAAGG CACAGCCTCA TCGAACACTC

TAAACCTCCCGGCTCCAATA GCCGACCATC CTCAGGACAG GACCTTTTCC TTCTTCCTTC

AGACCCCTTCTTTGATCCAG TAAGTGGTCA AGTCCCTCTG CCTCCTGCTA GGAGATTACC

AGGGGAAAATGTCAAATCCA ACAGAACATC ACAGGACTAT GATCAGCTTC CTTCAGCTTC

AGATGGTTCGCAGGCACCAG CCCGGCCTCC AAGCCGCGC CCGCGCAGGA CCGCCCCGA

GGTCCAGCACCGGAAGCCCC ACGGGCCCGA GGCAGCGTCG GAAAACGTGG ACGCGAAGAT

CGCCAAACTCATGGGGGAGG GCTACGCCTT CGAGGAAGTG AAGAGGGCGC TGGAGATCGC

CCAGAACAACGTCGAGGTGG CCCGGAGCAT CCTGCGCGAG TTCGCCTACC CGCCGCCCGT

CTCCCCGCGGCTGCACCTCT AG

SEQ ID NO 160: canine Cbl-b amino acid sequence
MANSMNGRNP GGRGGNPRKG RILGIIDAIQ DAVGPPKQAA ADRRTVEKTW KLMDKVVRLCQNPKLQLKNS

PPYILDILPD TYQHLRLILS KYDDNQKLAQ LSENEYFKIY IDSLMKKSKRAIRLFKEGKE RMYEEQSQDR

RNLTKLSLIF SHMLAEIKAI FPNGQFQGDN FRITKADAAEFWRKFFGDKT IVPWKVFRQC LHEVHQISSG

LEAMALKSTI DLTCNDYISV FEFDIFTRLFQPWGSILRNW NFLAVTHPGY MAFLTYDEVK ARLQKYSTKP

GSYIFRLSCT RLGQWAIGYVTGDGNILQTI PHNKPLFQAL IDGSREGFYL YPDGRSYNPD LTGLCEPTPH

DHIKVTQEQYELYCEMGSTF QLCKICAEND KDVKIEPCGH LMCTSCLTAW QESDGQGCPF

CRCEIKGTEPIIVDPFDPRD EGSRCCSIID PFGMPMLDLD DDDDREESLM MNRLANVRKC

TDRQNSPVTSPGSSPLAQRR KPHPDPLQIP HLSLPPVPPR LDLIQKGIVR SPCGSPTGSP

KSSPCMVRKQDKPLPAPPPP LRDPPPPPPE RPPPIPPDNR LSRHFHHVES VPSRDQPMPL

EAWCPRDVFGTNQSVGCRQL GDGSPKPGIT ASSNVNGRHS RMGSDPVLLR KHRRHDLPLE

GAKVFSNGHLGSEEYDVPPR LSPPPPAATL VPSIKCTGPL ANPLSEKTRD PVEEDDDEYK

IPSSHPVSLNSQPSHCHNVK PPLRSCDNGH CVLNGTHGTS SEVKKSNIPE LGIYLKGDVF

DSASDPVPLPPARPPTRDNP KHGSSLNRTP SDYDLLIPPL GEDAFDALPP SLPPPPPPAR

HSLIEHSKPPGSNSRPSSGQ DLFLLPSDPF FDPVSGQVPL PPARRLPGEN VKSNRTSQDY

DQLPSASDGSQAPARPPKPR PRRTAPEVQH RKPHGPEAAS ENVDAKIAKL MGEGYAFEEV

KRALEIAQNNVEVARSILRE FAYPPPVSPR LHL
```

| TABLE 7 | |
|---|---|
| siRNA sequences for down-regulating canine Cbl-b expression | |
| SEQ ID NO # | Nucleotide sequence |
| SEQ ID NO 161 | CCCACCATATATACTTGAT |
| SEQ ID NO 162 | CCTGATACATATCAGCATT |
| SEQ ID NO 163 | GCGGGCAATAAGACTCTTT |
| SEQ ID NO 164 | GCAGAAATACAGCACCAAA |
| SEQ ID NO 165 | GCACCAAACCTGGAAGCTA |
| SEQ ID NO 166 | GCAATATCTTACAGACCAT |
| SEQ ID NO 167 | CCACACCACATGACCATAT |
| SEQ ID NO 168 | GCCTCCTCCCTTAAGAGAT |
| SEQ ID NO 169 | CCTTCATCCCATCCTGTTT |
| SEQ ID NO 170 | CCTCTGATCCAGTGCCATT |

| TABLE 8 | |
|---|---|
| CRISPR/CAS9 target sequences for down-regulating canine Cbl-b expression | |
| SEQ ID NO # | Nucleotide sequence |
| SEQ ID NO 171 | CCCCCGAAAAGGACGGATTTTGG |
| SEQ ID NO 172 | CCCCGAAAAGGACGGATTTTGGG |
| SEQ ID NO 173 | CCAAAATCCGTCCTTTTCGGGGG |
| SEQ ID NO 174 | CCCAAAATCCGTCCTTTTCGGGG |
| SEQ ID NO 175 | CGAGGAGGAAACCCCCGAAAAGG |
| SEQ ID NO 176 | GGGTTTCCTCCTCGACCACCAGG |
| SEQ ID NO 177 | TACCCAAAATCCGTCCTTTTCGG |
| SEQ ID NO 178 | AGCAAGCAGCAGCAGATCGCAGG |
| SEQ ID NO 179 | ACCCAAAATCCGTCCTTTTCGG |
| SEQ ID NO 180 | GGTTTCCTCCTCGACCACCAGG |
| SEQ ID NO 181 | TCTGCTGCTGCTTGCTTCGGAGG |

TABLE 8-continued

CRISPR/CAS9 target sequences
for down-regulating canine Cbl-b expression

| SEQ ID NO # | Nucleotide sequence |
|---|---|
| SEQ ID NO 182 | AGAAACCCTGGTGGTCGAGGAGG |
| SEQ ID NO 183 | GGCAGAAACCCTGGTGGTCGAGG |
| SEQ ID NO 184 | AGCAGCAGCAGATCGCAGGACGG |
| SEQ ID NO 185 | AGCAGCAGATCGCAGGACGGTGG |
| SEQ ID NO 186 | GAGGAAACCCCCGAAAAGGACGG |
| SEQ ID NO 187 | GATGCTATTCAAGATGCAGTTGG |

TABLE 8-continued

CRISPR/CAS9 target sequences
for down-regulating canine Cbl-b expression

| SEQ ID NO # | Nucleotide sequence |
|---|---|
| SEQ ID NO 188 | TCTATGAATGGCAGAAACCCTGG |
| SEQ ID NO 189 | CGATCTGCTGCTGCTTGCTTCGG |
| SEQ ID NO 190 | GCAGGACGGTGGAGAAAACTTGG |
| SEQ ID NO 191 | ATGAATGGCAGAAACCCTGGTGG |
| SEQ ID NO 192 | GGAGAAAACTTGGAAACTCATGG |

```
SEQ ID NO 193: human Cbl nucleotide sequence
ATGGCCGGCA ACGTGAAGAA GAGCTCTGGG GCCGGGGGCG GCAGCGGCTC CGGGGGCTCG GGTTCGGGTG

GCCTGATTGG GCTCATGAAG GACGCCTTCC AGCCGCACCA CCACCACCAC CACCACCTCA GCCCCCACCC

GCCGGGGACG GTGGACAAGA AGATGGTGGA GAAGTGCTGG AAGCTCATGG ACAAGGTGGT GCGGTTGTGT

CAGAACCCAA AGCTGGCGCT AAAGAATAGC CCACCTTATA TCTTAGACCT GCTACCAGAT ACCTACCAGC

ATCTCCGTAC TATCTTGTCA AGATATGAGG GGAAGATGGA GACACTTGGA GAAAATGAGT ATTTTAGGGT

GTTTATGGAG AATTTGATGA AGAAAACTAA GCAAACCATA AGCCTCTTCA AGGAGGGAAA

AGAAAGAATG TATGAGGAGA ATTCTCAGCC TAGGCGAAAC CTAACCAAAC TGTCCCTCAT

CTTCAGCCAC ATGCTGGCAG AACTAAAAGG AATCTTTCCA AGTGGACTCT TTCAGGGAGA

CACATTTCGG ATTACTAAAG CAGATGCTGC GGAATTTTGG AGAAAAGCTT TGGGGAAAA

GACAATAGTC CCTTGGAAGA GCTTTCGACA GGCTCTACAT GAAGTGCATC CCATCAGTTC

TGGGCTGGAG GCCATGGCTC TGAAATCCAC TATTGATCTG ACCTGCAATG ATTATATTTC

GGTTTTTGAA TTTGACATCT TTACCCGACT CTTTCAGCCC TGGTCCTCTT TGCTCAGGAA

TTGGAACAGC CTTGCTGTAA CTCATCCTGG CTACATGGCT TTTTTGACGT ATGACGAAGT

GAAAGCTCGG CTCCAGAAAT TCATTCACAA ACCTGGCAGT TATATCTTCC GGCTGAGCTG

TACTCGTCTG GGTCAGTGGG CTATTGGGTA TGTTACTGCT GATGGGAACA TTCTCCAGAC

AATCCCTCAC AATAAACCTC TCTTCCAAGC ACTGATTGAT GGCTTCAGGG AAGGCTTCTA

TTTGTTTCCT GATGGACGAA ATCAGAATCC TGATCTGACT GGCTTATGTG AACCAACTCC

CCAAGACCAT ATCAAAGTGA CCCAGGAACA ATATGAATTA TACTGTGAGA TGGGCTCCAC

ATTCCAACTA TGTAAAATAT GTGCTGAAAA TGATAAGGAT GTAAAGATTG AGCCCTGTGG

ACACCTCATG TGCACATCCT GTCTTACATC CTGGCAGGAA TCAGAAGGTC AGGGCTGTCC

TTTCTGCCGA TGTGAAATTA AAGGTACTGA ACCCATCGTG GTAGATCCGT TTGATCCTAG

AGGGAGTGGC AGCCTGTTGA GGCAAGGAGC AGAGGGAGCT CCCTCCCCAA ATTATGATGA

TGATGATGAT GAACGAGCTG ATGATACTCT CTTCATGATG AAGGAATTGG CTGGTGCCAA

GGTGGAACGG CCGCCTTCTC CATTCTCCAT GGCCCCACAA GCTTCCCTTC CCCCGGTGCC

ACCACGACTT GACCTTCTGC CGCAGCGAGT ATGTGTTCCC TCAAGTGCTT CTGCTCTTGG

AACTGCTTCT AAGGCTGCTT CTGGCTCCCT TCATAAAGAC AAACCATTGC CAGTACCTCC

CACACTTCGA GATCTTCCAC CACCACCGCC TCCAGACCGG CCATATTCTG TTGGAGCAGA

ATCCCGACCT CAAAGACGCC CCTTGCCTTG TACACCAGGC GACTGTCCCT CCAGAGACAA

ACTGCCCCCT GTCCCCTCTA GCCGCCTTGG AGACTCATGG CTGCCCCGGC CAATCCCCAA
```

-continued

```
AGTACCAGTATCTGCCCCAA GTTCCAGTGA TCCCTGGACA GGAAGAGAAT TAACCAACCG

GCACTCACTTCCATTTTCAT TGCCCTCACA AATGGAGCCC AGACCAGATG TGCCTAGGCT

CGGAAGCACGTTCAGTCTGG ATACCTCCAT GAGTATGAAT AGCAGCCCAT TAGTAGGTCC

AGAGTGTGACCACCCCAAAA TCAAACCTTC CTCATCTGCC AATGCCATTT ATTCTCTGGC

TGCCAGACCTCTTCCTGTGC CAAAACTGCC ACCTGGGGAG CAATGTGAGG GTGAAGAGGA

CACAGAGTACATGACTCCCT CTTCCAGGCC TCTACGGCCT TTGGATACAT CCCAGAGTTC

ACGAGCATGTGATTGCGACC AGCAGATTGA TAGCTGTACG TATGAAGCAA TGTATAATAT

TCAGTCCCAGGCGCCATCTA TCACCGAGAG CAGCACCTTT GGTGAAGGGA ATTTGGCCGC

AGCCCATGCCAACACTGGTC CCGAGGAGTC AGAAAATGAG GATGATGGGT ATGATGTCCC

AAAGCCACCTGTGCCGGCCG TGCTGGCCCG CCGAACTCTC TCAGATATCT CTAATGCCAG

CTCCTCCTTTGGCTGGTTGT CTCTGGATGG TGATCCTACA ACAAATGTCA CTGAAGGTTC

CCAAGTTCCCGAGAGGCCTC CAAAACCATT CCCGCGGAGA ATCAACTCTG AACGGAAAGC

TGGCAGCTGTCAGCAAGGTA GTGGTCCTGC CGCCTCTGCT GCCACCGCCT CACCTCAGCT

CTCCAGTGAGATCGAGAACC TCATGAGTCA GGGGTACTCC TACCAGGACA TCCAGAAAGC

TTTGGTCATTGCCCAGAACA ACATCGAGAT GGCCAAAAAC ATCCTCCGGG AATTTGTTTC

CATTTCTTCTCCTGCCCATG TAGCTACCTA G
```

SEQ ID NO 194: human Cbl amino acid sequence
```
MAGNVKKSSG AGGGSGSGGS GSGGLIGLMK DAFQPHHHHH HHLSPHPPGT VDKKMVEKCWKLMDKVVRLC

QNPKLALKNS PPYILDLLPD TYQHLRTILS RYEGKMETLG ENEYFRVFMENLMKKTKQTI SLFKEGKERM

YEENSQPRRN LTKLSLIFSH MLAELKGIFP SGLFQGDTFRITKADAAEFW RKAFGEKTIV PWKSFRQALH

EVHPISSGLE AMALKSTIDL TCNDYISVFEFDIFTRLFQP WSSLLRNWNS LAVTHPGYMA FLTYDEVKAR

LQKFIHKPGS YIFRLSCTRLGQWAIGYVTA DGNILQTIPH NKPLFQALID GFREGFYLFP DGRNQNPDLT

GLCEPTPQDHIKVTQEQYEL YCEMGSTFQL CKICAENDKD VKIEPCGHLM CTSCLTSWQE

SEGQGCPFCRCEIKGTEPIV VDPFDPRGSG SLLRQGAEGA PSPNYDDDDD ERADDTLFMM

KELAGAKVERPPSPFSMAPQ ASLPPVPPRL DLLPQRVCVP SSASALGTAS KAASGSLHKD

KPLPVPPTLRDLPPPPPPDR PYSVGAESRP QRRPLPCTPG DCPSRDKLPP VPSSRLGDSW

LPRPIPKVPVSAPSSSDPWT GRELTNRHSL PFSLPSQMEP RPDVPRLGST FSLDTSMSMN

SSPLVGPECDHPKIKPSSSA NAIYSLAARP LPVPKLPPGE QCEGEEDTEY MTPSSRPLRP

LDTSQSSRACDCDQQIDSCT YEAMYNIQSQ APSITESSTF GEGNLAAAHA NTGPEESENE

DDGYDVPKPPVPAVLARRTL SDISNASSSF GWLSLDGDPT TNVTEGSQVP ERPPKPFPRR

INSERKAGSCQQGSGPAASA ATASPQLSSE IENLMSQGYS YQDIQKALVI AQNNIEMAKN

ILREFVSISSPAHVAT
```

| TABLE 9 | |
|---|---|
| siRNA/shRNAi sequences for down-regulating human Cbl expression | |
| SEQ ID NO # | Nucleotide sequence |
| SEQ ID NO 195 | CCAGACAATCCCTCACAAT |
| SEQ ID NO 196 | GGACACCTCATGTGCACAT |
| SEQ ID NO 197 | CCAGGCCTCTACGGCCTTT |
| SEQ ID NO 198 | CCAGAAAGCTTTGGTCATT |
| SEQ ID NO 199 | GCCTGATTGGGCTCATGAAGG |
| SEQ ID NO 200 | GGGAACATTCTCCAGACAATC |
| SEQ ID NO 201 | GCTTCAGGGAAGGCTTCTATT |
| SEQ ID NO 202 | GGGAAGGCTTCTATTTGTTTC |
| SEQ ID NO 203 | GGACACCTCATGTGCACATCC |

TABLE 9-continued siRNA/shRNAi sequences for down-regulating human Cbl expression

| SEQ ID NO # | Nucleotide sequence |
|---|---|
| SEQ ID NO 204 | GCAGAATCCCGACCTCAAAGA |
| SEQ ID NO 205 | GGAGCAATGTGAGGGTGAAGA |
| SEQ ID NO 206 | GCCTCTACGGCCTTTGGATAC |
| SEQ ID NO 207 | GCTGTACGTATGAAGCAATGT |
| SEQ ID NO 208 | GGTACTCCTACCAGGACATCC |

TABLE 10

CRISPR/CAS9 target sequences for down-regulating human Cbl expression

| SEQ ID NO # | Nucleotide sequence |
|---|---|
| SEQ ID NO 209 | CTCGGCTCGACTGCGAGCGA |
| SEQ ID NO 210 | GCCGCCGCCGGCTATCCGGG |
| SEQ ID NO 211 | TCCGCCCGGATAGCCGGCGG |
| SEQ ID NO 212 | GCTCGGCTCGACTGCGAGCG |
| SEQ ID NO 213 | TCGCAGTCGAGCCGAGCCGG |
| SEQ ID NO 214 | CTTCTTCACGTTGCCGGCCA |
| SEQ ID NO 215 | CGGGTTCGGGTGGCCTGATT |
| SEQ ID NO 216 | CGCTCGCAGTCGAGCCGAGC |
| SEQ ID NO 217 | CCGAGCCGGCGGACCCGCCT |
| SEQ ID NO 218 | TCGGGTTCGGGTGGCCTGAT |
| SEQ ID NO 219 | GCCGAGCCGGCGGACCCGCC |
| SEQ ID NO 220 | AGAGCTCTTCTTCACGTTGC |
| SEQ ID NO 221 | GCCGCCGCCGCCGGCTATCC |
| SEQ ID NO 222 | CCCAGGCGGGTCCGCCGGCT |
| SEQ ID NO 223 | CGTCCTTCATGAGCCCAATC |
| SEQ ID NO 224 | CGGAGCCCAGGCGGGTCCGC |
| SEQ ID NO 225 | TGGCCTGATTGGGCTCATGA |
| SEQ ID NO 226 | TCACGTTGCCGGCCATGGCC |
| SEQ ID NO 227 | CGCCGCCGCCGCCGGCTATC |
| SEQ ID NO 228 | GGCAACGTGAAGAAGAGCTC |
| SEQ ID NO 229 | CGGCTCCGGGGGCTCGGGTT |
| SEQ ID NO 230 | TCCGGGGGCTCGGGTTCGGG |
| SEQ ID NO 231 | GGCTCCGGGGGCTCGGGTTC |
| SEQ ID NO 232 | GCAACGTGAAGAAGAGCTCT |
| SEQ ID NO 233 | GCAACGTGAAGAAGAGCTCT |
| SEQ ID NO 234 | GCCACCCGAACCCGAGCCCC |
| SEQ ID NO 235 | CACGTTGCCGGCCATGGCCT |
| SEQ ID NO 236 | GCCCGGATAGCCGGCGGCGG |
| SEQ ID NO 237 | GAAGAAGAGCTCTGGGGCCG |
| SEQ ID NO 238 | CAACGTGAAGAAGAGCTCTG |
| SEQ ID NO 239 | AAGAAGAGCTCTGGGGCCGG |
| SEQ ID NO 240 | GGGAGAGAAGCAGGGCGTGA |
| SEQ ID NO 241 | CGGCAGCGGCTCCGGGGGCT |
| SEQ ID NO 242 | CCTGGGCAGGGTCGGAGCCC |
| SEQ ID NO 243 | AGAGAAGCAGGGCGTGAAGG |

```
SEQ ID NO 244: canine Cbl nucleotide sequence
ATGGCCGGCA ACGTGAAGAA GAGCTCCGGG GCCGGGGGCG GCGGCGGCTC CGGGGGCTCGGGCGGCCTCA

TCGGGCTCAT GAAGGACGCC TTCCAGCCGC ACCACCACCA CCACCACCTCAGCCCCCACC CGCCCGGCAC

CNGTGACAAG AAGATGGTGG AGAAGTGCTG GAAGCTCATGGACAAGGTGG TGCGGTTGTG TCAGAACCCA

AAGCTGGCGC TAAAGAATAG CCCACCTTATATCTTAGACC TGCTGCCAGA TACCTACCAG CATCTCCGCA

CTATCTTGTC AAGATATGAGGGGAAGATGG AGACACTTGG AGAAAATGAG TATTTTAGGG TGTTCATGGA

GAATTTGATGAAGAAAACTA AGCAGACCAT AAGCCTCTTC AAGGAGGGGA AAGAAAGAAT

GTATGAGGAGAATTCTCAGC CTAGGCGAAA CCTAACCAAA TTGTCCCTGA TCTTCAGCCA

CATGCTGGCAGAACTAAAAG GAATCTTTCC AAGTGGACTC TTTCAAGGAG ACACATTTCG

GATTACTAAAGCAGATGCTG CAGAATTTTG GAGGAAAGCT TTTGGGGAAA AGACAATCGT

CCCTTGGAAGAGTTTCCGCC AGGCCCTTCA TGAAGTGCAT CCCATCAGTT CTGGGCTCGA

GGCCATGGCTCTGAAATCCA CTATTGATCT GACCTGCAAT GATTATATTT CTGTTTTTGA

ATTTGACATCTTCACACGAC TCTTTCAGCC CTGGTCCTCT TTGCTCAGGA ACTGGAACAG

TCTTGCTGTAACTCATCCTG GTTACATGGC TTTCCTGACG TATGATGAAG TGAAAGCTCG
```

-continued

```
GCTCCAGAAGTTCATTCACA AACCTGGCAG TTACATTTTC CGGTTGAGCT GTACTCGTTT
GGGACAGTGGGCTATTGGGT ATGTCACTGC TGATGGGAAC ATCCTCCAGA CGATCCCTCA
CAATAAACCTCTCTTCCAAG CCCTGATTGA CGGCTTCAGG GAAGGCTTCT ATTTGTTTCC
AGATGGACGGAATCAGAATC CTGACCTGAC AGGCCTATGT GAACCAACTC CCCAAGACCA
CATCAAAGTGACCCAGGAAC AATATGAATT ATACTGTGAG AT GGGCTCCA CCTTCCAACT
GTGTAAAATATGTGCTGAGA ACGATAAGGA TGTGAAAATT GAGCCCTGTG GACACCTCAT
GTGCACATCCTGTCTTACAT CCTGGCAGGA ATCAGAAGGC CAAGGCTGCC CTTTCTGCCG
ATGTGAAATTAAAGGTACTG AGCCCATTGT GGTAGATCCG TTTGACCCTC GAGGAAGTGG
CAGCCTACTGAGGCAAGGAG CTGAGGGAGC TCCCTCCCCA AATTATGAAG ATGATGACGA
TGAACGAGCTGATGATTCTC TCTTTATGAT GAAGGAACTG GCTGGTGCCA AGGTGGAACG
GCCTCCTTCTCCGTTCTCGA TGGCCCCACA GGCTCCCCTG CCCCCAGTAC CACCACGTCT
TGACCTCCTACAACAGCGAG TGTCTGTTCC TTCTAGTGCT TCTGGTCTTG GAACTGCTTC
TAAGGTAGCTTCTGGCTCCC TTCATAAGGA CAAACCATTA CCAATACCCC CCACACTTCG
AGATCTTCCACCACCACCCC CTCCAGACCG ACCATATTCT GTTGGAACAG ACACCCGGCC
TCAGAGACGTCCCTTGCCTT GTACACCGGG CGACTGTCCA TCCAGGGACA AACTGCCGCC
TGTTCCCTCTAGCCGTCTCG GGGAATCATG GCTGCCTCGG CCAATCCCCA AAGTACCAGT
GGTTGCTCCAAACTCGAGTG ACCCCTGGAC CTCTGGTAGA GAATTAACCA ACAGGCACTC
ACTTCCATTTTCATTGCCCT CACAANATGA ACCCAGAACA GATGTGCCTA GGCTTGGAGG
CACATTCAATGTGGATACTT CCATGAATGT GAATAACAGC CCACTAGCAA GTTCTGAGTG
TGAGCACCCCAAAATCAAAC CTTCCGCATC TGCCAATGCC ATTTATTCTC TGGCTGCCAG
GCCTCTTCCTGTGCCAAAGC TGCCCCCTGG GGAGCAGTGT GAAGGTGAGG AGGACACAGA
GTATATGACCCCCTCCTCTA GACCTCTAGG GCTTCCAAAG CCAGATGGGA AACGGCCTTT
GGAGACAACCCAGAGTTCAC GAGCATGTGA TTGTGACCAG CAGATCGATA GCTGCACATA
TGAAGCAATGTATAATATTC AGTCCCAAGC GACACCATCT GTCACAGAGA GCAGCACCTT
TGGTGAAGGGAGTCTGGCTG CAGCCCACAT CAGCACCGGC CCCGAGGAAT CAGAAAATGA
GGAGGACGGGTATGATGTCC CTAAGCCGCC CATGCCAGCA GTGCTGGCCC GCCGGACTCT
CTCAGACATCTCCAATGCCA GTTCCTCCTT TGGCTGGTTG TCTCTGGAAG GCGATCCCAC
CACAAACTTCACTGAGGGTT CCCAAGTTCC TGAAAGGCCT CCCAAACCGT TCCCTCGGAG
AATCAACTCTGAACGAAAAG CAGGCAGCTG TCAGCAGGGT GGTGCCGCTG CTGCCTCACC
ACAGCTCTCCAGTGAGATTG AGAACCTCCT GAGCCAGGGA TACTCCTACC AGGACATTCA
GAAAGCTCTGGTCATTGCCC ACAACAACAT TGAAATGGCC AAGAACATCC TCCGGGAATT
TGTTTCTATCTCTTCTCCCG CCCACGTAGC CACCTAG
```

SEQ ID NO 245: canine Cbl amino acid sequence
MAGNVKKSSG AGGGGGSGGS GGLIGLMKDA FQPHHHHHHL SPHPPGTXDK KMVEKCWKLMDKVVRLCQNP
KLALKNSPPY ILDLLPDTYQ HLRTILSRYE GKMETLGENE YFRVFMENLMKKTKQTISLF KEGKERMYEE
NSQPRRNLTK LSLIFSHMLA ELKGIFPSGL FQGDTFRITKADAAEFWRKA FGEKTIVPWK SFRQALHEVH
PISSGLEAMA LKSTIDLTCN DYISVFEFDIFTRLFQPWSS LLRNWNSLAV THPGYMAFLT YDEVKARLQK
FIHKPGSYIF RLSCTRLGQWAIGYVTADGN ILQTIPHNKP LFQALIDGFR EGFYLFPDGR NQNPDLTGLC
EPTPQDHIKVTQEQYELYCE MGSTFQLCKI CAENDKDVKI EPCGHLMCTS CLTSWQESEG
QGCPFCRCEIKGTEPIVVDP FDPRGSGSLL RQGAEGAPSP NYEDDDDERA DDSLFMMKEL
AGAKVERPPSPFSMAPQAPL PPVPPRLDLL QQRVSVPSSA SGLGTASKVA SGSLHKDKPL -continued

PIPPTLRDLPPPPPPDRPYS VGTDTRPQRR PLPCTPGDCP SRDKLPPVPS SRLGESWLPR

PIPKVPVVAPNSSDPWTSGR ELTNRHSLPF SLPSQXEPRT DVPRLGGTFN VDTSMNVNNS

PLASSECEHPKIKPSASANA IYSLAARPLP VPKLPPGEQC EGEEDTEYMT PSSRPLGLPK

PDGKRPLETTQSSRACDCDQ QIDSCTYEAM YNIQSQATPS VTESSTFGEG SLAAAHISTG

PEESENEEDGYDVPKPPMPA VLARRTLSDI SNASSSFGWL SLEGDPTTNF TEGSQVPERP

PKPFPRRINSERKAGSCQQG GAAAASPQLS SEIENLLSQG YSYQDIQKAL VIAHNNIEMA

KNILREFVSISSPAHVAT

TABLE 11 siRNA sequences for down-regulating canine Cbl expression

| SEQ ID NO # | Nucleotide sequence |
|---|---|
| SEQ ID NO 246 | CCAGAAGTTCATTCACAAA |
| SEQ ID NO 247 | GGAACATCCTCCAGACGAT |
| SEQ ID NO 248 | CCAGACGATCCCTCACAAT |
| SEQ ID NO 249 | GCTTCAGGGAAGGCTTCTA |
| SEQ ID NO 250 | GCAGGAATCAGAAGGCCAA |
| SEQ ID NO 251 | CCTTTCTGCCGATGTGAAA |
| SEQ ID NO 252 | GCTGATGATTCTCTCTTTA |
| SEQ ID NO 253 | GCTTCTGGCTCCCTTCATA |
| SEQ ID NO 254 | GCATCTGCCAATGCCATTT |
| SEQ ID NO 255 | GCTGCACATATGAAGCAAT |

TABLE 12

CRISPR/CAS9 target sequences for down-regulating canine Cbl expression

| SEQ ID NO # | Nucleotide sequence |
|---|---|
| SEQ ID NO 256 | CCCGGAGCCGCCGCCGCCCCCGG |
| SEQ ID NO 257 | TGCCGGGCGGGTGGGGGCTGAGG |
| SEQ ID NO 258 | CGGCCTCATCGGGCTCATGAAGG |
| SEQ ID NO 259 | GGAGCTCTTCTTCACGTTGCCGG |
| SEQ ID NO 260 | CAACGTGAAGAAGAGCTCCGGGG |
| SEQ ID NO 261 | GGGGCTCGGGCGGCCTCATCGGG |
| SEQ ID NO 262 | GGCAACGTGAAGAAGAGCTCCGG |
| SEQ ID NO 263 | GCAACGTGAAGAAGAGCTCCGGG |
| SEQ ID NO 264 | GGGGGCTCGGGCGGCCTCATCGG |
| SEQ ID NO 265 | GTGAAGAAGAGCTCCGGGGCCGG |
| SEQ ID NO 266 | TGAAGAAGAGCTCCGGGGCCGGG |
| SEQ ID NO 267 | CGTCCTTCATGAGCCCGATGAGG |
| SEQ ID NO 268 | AAGAAGAGCTCCGGGGCCGGGGG |
| SEQ ID NO 269 | GAAGAAGAGCTCCGGGGCCGGGG |
| SEQ ID NO 270 | GATGAGGCCGCCCGAGCCCCCGG |
| SEQ ID NO 271 | GTGGTGGTGGTGCGGCTGGAAGG |
| SEQ ID NO 272 | AAGAGCTCCGGGGCCGGGGGCGG |
| SEQ ID NO 273 | CACCTCAGCCCCCACCCGCCCGG |
| SEQ ID NO 274 | CGGCGGCGGCTCCGGGGGCTCGG |
| SEQ ID NO 275 | AGCTCCGGGGCCGGGGCGGCGG |
| SEQ ID NO 276 | GCGGGTGGGGGCTGAGGTGGTGG |
| SEQ ID NO 277 | TCCGGGGCCGGGGCGGCGGCGG |
| SEQ ID NO 278 | GCCGCCGCCGCCCCCGGCCCCGG |
| SEQ ID NO 279 | CGGGCGGGTGGGGGCTGAGGTGG |
| SEQ ID NO 280 | GCCGGGGCGGCGGCGGCTCCGG |

| SEQ ID NO 281: human CD2AP wobble mutant sequence GGAGACGGACGACGTAAAG | |

What is claimed is:

1. Treatment for CD2AP-mediated insulin resistance in a human subject, comprising:
   administering a composition comprising at least one siRNA/shRNAi nucleotide sequence selected from the group consisting of sequences represented by SEQ ID NOS 3-20.

2. The treatment of claim 1, wherein the at least one siRNA/shRNAi nucleotide sequence is represented by SEQ ID NO. 3.

3. A method of increasing intracellular IRS1 contents in human CD2AP-expressing cells, comprising:
   introducing into human CD2AP-expressing cells a composition comprising at least one siRNA/shRNAi nucleotide sequence selected from the group consisting of sequences represented by SEQ ID NOS 3-20;
   thereby the at least one siRNA/shRNAi nucleotide sequence down-regulates expression of CD2AP so as to increase intracellular IRS1 contents in the human CD2AP-expressing cells.

4. The method of claim 3, wherein the at least one siRNA/shRNAi nucleotide sequence is represented by SEQ ID NO. 3.

5. The method of claim 3, wherein the human CD2AP-expressing cells are human hepatic cells.

6. The method of claim 4, wherein the human CD2AP-expressing cells are human hepatic cells.

* * * * *

SEQUENCE LISTING

<160> NUMBER OF SEQ ID NOS: 281

<210> SEQ ID NO 1
<211> LENGTH: 1911
<212> TYPE: DNA
<213> ORGANISM: Homo sapiens

<400> SEQUENCE: 1

-continued

```
atggttgact atattgtgga gtatgactat gatgctgtac atgatgatga attaactatt      60
cgagttggag aaatcatcag gaatgtgaaa aagctacagg aggaagggtg gctggaagga     120
gaactaaatg ggagaagagg aatgttccct gacaatttcg ttaaggaaat taaaagagag     180
acggaattca aggatgacag tttgcccatc aaacggaaaa ggcatgggaa tgtagcaagt     240
cttgtacaac gaataagcac ctatggactt ccagctggag gaattcagcc acatccacaa     300
accaaaaaca ttaagaagaa gaccaagaag cgtcagtgta agttctttt tgagtacatt      360
ccacaaaatg aggatgaact ggagctgaaa gtgggagata ttattgatat taatgaagag     420
gtagaagaag gctggtggag tggaaccctg aataacaagt tgggactgtt ccctcaaat      480
tttgtgaaag aattagaggt aacagatgat ggtgaaactc atgaagccca ggacgattca     540
gaaactgttt tggctgggcc tacttcacct ataccttctc tggaaatgt gagtgaaact      600
gcatctggat cagttacaca gccaagaaa attcgaggaa ttggatttgg agacattttt      660
aaagaaggct ctgtgaaact tcggacaaga acatccagta gtgaaacaga agagaaaaa      720
ccagaaaagc ccttaatcct acagtcactg ggacccaaaa ctcagagtgt ggagataaca     780
aaaacagata ccgaaggtaa aattaaagct aaagaatatt gtagaacatt atttgcctat     840
gaaggtacta atgaagatga acttactttt aaagagggg agataatcca tttgataagt      900
aaggagactg gagaagctgg ctggtggagg ggcgaactta atggtaaaga aggagtattt     960
ccagacaatt ttgctgtcca gataaatgaa cttgataaag actttccaaa accaaagaaa    1020
ccaccacctc ctgctaaggc tccagctcca agcctgaac tgatagctgc agagaagaaa     1080
tatttttctt taaagcctga agaaaaggat gaaaaatcaa cactggaaca gaaaccttct    1140
aaaccagcag ctccacaagt ccccacccaag aaacctactc cacctaccaa agccagtaat    1200
ttactgagat cttctggaac agtgtaccca aagcgacctg aaaaaccagt tcctccacca    1260
cctcctatag ccaagattaa tggggaagtt tctagcattt catcaaaatt tgaaactgag    1320
ccagtatcaa aactaaagct agattctgaa cagctgcccc ttagaccaaa atcagtagac    1380
tttgattcac ttacagtaag gacctccaaa gaaacagatg ttgtaaattt tgatgacata    1440
gcttcctcag aaaacttgct tcatctcact gcaaatagac caaagatgcc tggaagaagg    1500
ttgccgggcc gtttcaatgg tggacattct ccaactcaca gccccgaaaa atcttgaag     1560
ttaccaaaag aagaagacag tgccaacctg aagccatctg aattaaaaaa agatacatgc    1620
tactctccaa agccatctgt gtacctttca acaccttcca gtgcttctaa agcaaataca    1680
actgctttcc tgactccatt agaaatcaaa gctaaagtgg aaacagatga tgtgaaaaaa    1740
aattccctgg atgaacttag agcccagatt attgaattgt tgtgcattgt agaagcactg    1800
aaaaaggatc acgggaaaga actggaaaaa ctgcgaaaag attttgaaga agagaagaca    1860
atgagaagta atctagagat ggaaatagag aagctgaaaa aagctgtcct g             1911
```

<210> SEQ ID NO 2
<211> LENGTH: 639
<212> TYPE: PRT
<213> ORGANISM: Homo sapiens

<400> SEQUENCE: 2

Met Val Asp Tyr Ile Val Glu Tyr Asp Tyr Asp Ala Val His Asp Asp
1               5                   10                  15

Glu Leu Thr Ile Arg Val Gly Glu Ile Ile Arg Asn Val Lys Lys Leu
            20                  25                  30

```
Gln Glu Glu Gly Trp Leu Glu Glu Leu Asn Gly Arg Gly Met
         35                  40              45

Phe Pro Asp Asn Phe Val Lys Glu Ile Lys Arg Glu Thr Glu Phe Lys
 50                  55                  60

Asp Asp Ser Leu Pro Ile Lys Arg Glu Arg His Gly Asn Val Ala Ser
 65                  70                  75                  80

Leu Val Gln Arg Ile Ser Thr Tyr Gly Leu Pro Ala Gly Gly Ile Gln
                 85                  90                  95

Pro His Pro Gln Thr Lys Asn Ile Lys Lys Thr Lys Lys Arg Gln
             100                 105                 110

Cys Lys Val Leu Phe Glu Tyr Ile Pro Gln Asn Glu Asp Glu Leu Glu
             115                 120                 125

Leu Lys Val Gly Asp Ile Ile Asp Ile Asn Glu Glu Val Glu Glu Gly
         130                 135                 140

Trp Trp Ser Gly Thr Leu Asn Asn Lys Leu Gly Leu Phe Pro Ser Asn
145                 150                 155                 160

Phe Val Lys Glu Leu Glu Val Thr Asp Asp Gly Glu Thr His Glu Ala
                 165                 170                 175

Gln Asp Asp Ser Glu Thr Val Leu Ala Gly Pro Thr Ser Pro Ile Pro
             180                 185                 190

Ser Leu Gly Asn Val Ser Glu Thr Ala Ser Gly Ser Val Thr Gln Pro
             195                 200                 205

Lys Lys Ile Arg Gly Ile Gly Phe Gly Asp Ile Phe Lys Glu Gly Ser
         210                 215                 220

Val Lys Leu Arg Thr Arg Thr Ser Ser Glu Thr Glu Glu Lys Lys
225                 230                 235                 240

Pro Glu Lys Pro Leu Ile Leu Gln Ser Leu Gly Pro Lys Thr Gln Ser
                 245                 250                 255

Val Glu Ile Thr Lys Thr Asp Thr Glu Gly Lys Ile Lys Ala Lys Glu
             260                 265                 270

Tyr Cys Arg Thr Leu Phe Ala Tyr Glu Gly Thr Asn Glu Asp Glu Leu
             275                 280                 285

Thr Phe Lys Glu Gly Glu Ile Ile His Leu Ile Ser Lys Glu Thr Gly
         290                 295                 300

Glu Ala Gly Trp Trp Arg Gly Glu Leu Asn Gly Lys Glu Gly Val Phe
305                 310                 315                 320

Pro Asp Asn Phe Ala Val Gln Ile Asn Glu Leu Asp Lys Asp Phe Pro
                 325                 330                 335

Lys Pro Lys Lys Pro Pro Pro Ala Lys Ala Pro Ala Pro Lys Pro
             340                 345                 350

Glu Leu Ile Ala Ala Glu Lys Lys Tyr Phe Ser Leu Lys Pro Glu Glu
             355                 360                 365

Lys Asp Glu Lys Ser Thr Leu Glu Gln Lys Pro Ser Lys Pro Ala Ala
         370                 375                 380

Pro Gln Val Pro Pro Lys Lys Pro Thr Pro Thr Lys Ala Ser Asn
385                 390                 395                 400

Leu Leu Arg Ser Ser Gly Thr Val Tyr Pro Lys Arg Pro Glu Lys Pro
                 405                 410                 415

Val Pro Pro Pro Pro Ile Ala Lys Ile Asn Gly Glu Val Ser Ser
             420                 425                 430

Ile Ser Ser Lys Phe Glu Thr Glu Pro Val Ser Lys Leu Lys Leu Asp
             435                 440                 445

Ser Glu Gln Leu Pro Leu Arg Pro Lys Ser Val Asp Phe Asp Ser Leu
```

```
                        450                 455                 460
Thr Val Arg Thr Ser Lys Glu Thr Asp Val Val Asn Phe Asp Ile
465                 470                 475                 480

Ala Ser Ser Glu Asn Leu Leu His Leu Thr Ala Asn Arg Pro Lys Met
                    485                 490                 495

Pro Gly Arg Arg Leu Pro Gly Arg Phe Asn Gly Gly His Ser Pro Thr
                500                 505                 510

His Ser Pro Glu Lys Ile Leu Lys Leu Pro Lys Glu Glu Asp Ser Ala
            515                 520                 525

Asn Leu Lys Pro Ser Glu Leu Lys Lys Asp Thr Cys Tyr Ser Pro Lys
530                 535                 540

Pro Ser Val Tyr Leu Ser Thr Pro Ser Ser Ala Ser Lys Ala Asn Thr
545                 550                 555                 560

Thr Ala Phe Leu Thr Pro Leu Glu Ile Lys Ala Lys Val Glu Thr Asp
                    565                 570                 575

Asp Val Lys Lys Asn Ser Leu Asp Glu Leu Arg Ala Gln Ile Ile Glu
                580                 585                 590

Leu Leu Cys Ile Val Glu Ala Leu Lys Lys Asp His Gly Lys Glu Leu
                595                 600                 605

Glu Lys Leu Arg Lys Asp Leu Glu Glu Lys Thr Met Arg Ser Asn
            610                 615                 620

Leu Glu Met Glu Ile Glu Lys Leu Lys Lys Ala Val Leu Ser Ser
625                 630                 635

<210> SEQ ID NO 3
<211> LENGTH: 21
<212> TYPE: DNA
<213> ORGANISM: Artificial Sequence
<220> FEATURE:
<223> OTHER INFORMATION: siRNA for CD2AP

<400> SEQUENCE: 3
gctggaagga gaactaaatg g                                              21

<210> SEQ ID NO 4
<211> LENGTH: 21
<212> TYPE: DNA
<213> ORGANISM: Artificial Sequence
<220> FEATURE:
<223> OTHER INFORMATION: siRNA/shRNA for human CD2AP

<400> SEQUENCE: 4
ggagaactaa atgggagaag a                                              21

<210> SEQ ID NO 5
<211> LENGTH: 21
<212> TYPE: DNA
<213> ORGANISM: Artificial Sequence
<220> FEATURE:
<223> OTHER INFORMATION: siRNA/shRNA for human CD2AP

<400> SEQUENCE: 5
ggacttccag ctggaggaat t                                              21

<210> SEQ ID NO 6
<211> LENGTH: 21
<212> TYPE: DNA
<213> ORGANISM: Artificial Sequence
<220> FEATURE:
<223> OTHER INFORMATION: siRNA/shRNA for human CD2AP
```

```
<400> SEQUENCE: 6
ggagctgaaa gtgggagata t                                              21

<210> SEQ ID NO 7
<211> LENGTH: 21
<212> TYPE: DNA
<213> ORGANISM: Artificial Sequence
<220> FEATURE:
<223> OTHER INFORMATION: siRNA/shRNA for human CD2AP

<400> SEQUENCE: 7
gctgaaagtg ggagatatta t                                              21

<210> SEQ ID NO 8
<211> LENGTH: 21
<212> TYPE: DNA
<213> ORGANISM: Artificial Sequence
<220> FEATURE:
<223> OTHER INFORMATION: siRNA/shRNA for human CD2AP

<400> SEQUENCE: 8
gctgaaagtg ggagatatta t                                              21

<210> SEQ ID NO 9
<211> LENGTH: 21
<212> TYPE: DNA
<213> ORGANISM: Artificial Sequence
<220> FEATURE:
<223> OTHER INFORMATION: siRNA/shRNA for human CD2AP

<400> SEQUENCE: 9
gcccaggacg attcagaaac t                                              21

<210> SEQ ID NO 10
<211> LENGTH: 21
<212> TYPE: DNA
<213> ORGANISM: Artificial Sequence
<220> FEATURE:
<223> OTHER INFORMATION: siRNA/shRNA for human CD2AP

<400> SEQUENCE: 10
gctgggccta cttcacctat a                                              21

<210> SEQ ID NO 11
<211> LENGTH: 21
<212> TYPE: DNA
<213> ORGANISM: Artificial Sequence
<220> FEATURE:
<223> OTHER INFORMATION: siRNA/shRNA for human CD2AP

<400> SEQUENCE: 11
gccagtaatt tactgagatc t                                              21

<210> SEQ ID NO 12
<211> LENGTH: 21
<212> TYPE: DNA
<213> ORGANISM: Artificial Sequence
<220> FEATURE:
<223> OTHER INFORMATION: siRNA/shRNA for human CD2AP

<400> SEQUENCE: 12
gcttcatctc actgcaaata g                                              21

<210> SEQ ID NO 13
<211> LENGTH: 21
```

```
<212> TYPE: DNA
<213> ORGANISM: Artificial Sequence
<220> FEATURE:
<223> OTHER INFORMATION: siRNA/shRNA for human CD2AP

<400> SEQUENCE: 13
ggaagtttcc agcagatttc a                                              21

<210> SEQ ID NO 14
<211> LENGTH: 19
<212> TYPE: DNA
<213> ORGANISM: Artificial Sequence
<220> FEATURE:
<223> OTHER INFORMATION: siRNA/shRNA for human CD2AP

<400> SEQUENCE: 14
agccgagggt ctgggcaaa                                                 19

<210> SEQ ID NO 15
<211> LENGTH: 19
<212> TYPE: DNA
<213> ORGANISM: Artificial Sequence
<220> FEATURE:
<223> OTHER INFORMATION: siRNA/shRNA for human CD2AP

<400> SEQUENCE: 15
agccgagggt ctgggcaaa                                                 19

<210> SEQ ID NO 16
<211> LENGTH: 19
<212> TYPE: DNA
<213> ORGANISM: Artificial Sequence
<220> FEATURE:
<223> OTHER INFORMATION: siRNA/shRNA for human CD2AP

<400> SEQUENCE: 16
tgaagagact ggtaggaga                                                 19

<210> SEQ ID NO 17
<211> LENGTH: 19
<212> TYPE: DNA
<213> ORGANISM: Artificial Sequence
<220> FEATURE:
<223> OTHER INFORMATION: siRNA/shRNA for human CD2AP

<400> SEQUENCE: 17
ctaaatggga gaagaggaa                                                 19

<210> SEQ ID NO 18
<211> LENGTH: 19
<212> TYPE: DNA
<213> ORGANISM: Artificial Sequence
<220> FEATURE:
<223> OTHER INFORMATION: siRNA/shRNA for human CD2AP

<400> SEQUENCE: 18
aggatgaact ggagctgaa                                                 19

<210> SEQ ID NO 19
<211> LENGTH: 19
<212> TYPE: DNA
<213> ORGANISM: Artificial Sequence
<220> FEATURE:
<223> OTHER INFORMATION: siRNA/shRNA for human CD2AP

<400> SEQUENCE: 19
```

```
ggtaacagat gatggtgaa                                              19

<210> SEQ ID NO 20
<211> LENGTH: 19
<212> TYPE: DNA
<213> ORGANISM: Artificial Sequence
<220> FEATURE:
<223> OTHER INFORMATION: siRNA/shRNA for human CD2AP

<400> SEQUENCE: 20
ggaaacagat gatgtgaaa                                              19

<210> SEQ ID NO 21
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 21
aaaggcgaca ccgtagacta                                             20

<210> SEQ ID NO 22
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 22
cgacaccgta gactaaggtg                                             20

<210> SEQ ID NO 23
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 23
gtgggaaaac cgcggtcggg                                             20

<210> SEQ ID NO 24
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 24
ggcgacaccg tagactaagg                                             20

<210> SEQ ID NO 25
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 25
agggtgggaa aaccgcggtc                                             20

<210> SEQ ID NO 26
<211> LENGTH: 20
<212> TYPE: DNA
<213> ORGANISM: Artificial Sequence
```

```
<220> FEATURE:
<223> OTHER INFORMATION: CRISPR/CAS9 target sequences for human CD2AP

<400> SEQUENCE: 26
tgggaaaacc gcggtcgggc                                                    20

<210> SEQ ID NO 27
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 27
gcgacaccgt agactaaggt                                                    20

<210> SEQ ID NO 28
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 28
cagggtggga aaccgcggt                                                     20

<210> SEQ ID NO 29
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 29
cgaccgcggt tttcccaccc                                                    20

<210> SEQ ID NO 30
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 30
aaaaccgcgg tcgggcgggc                                                    20

<210> SEQ ID NO 31
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 31
cgaggctagg cgggcgctcg                                                    20

<210> SEQ ID NO 32
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 32
gaaaaccgcg gtcgggcggg                                                    20
```

```
<210> SEQ ID NO 33
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 33
gagggtctgg gcaaaccggt                                                   20

<210> SEQ ID NO 34
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 34
tgggtcccca ccttagtcta                                                   20

<210> SEQ ID NO 35
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 35
cgagggtctg gcaaaccgg                                                    20

<210> SEQ ID NO 36
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 36
gcgctcgggg ttggagccga                                                   20

<210> SEQ ID NO 37
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 37
tccgaggcta ggcgggcgct                                                   20

<210> SEQ ID NO 38
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 38
ttttctaact gcgagtgcta                                                   20

<210> SEQ ID NO 39
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP
```

<400> SEQUENCE: 39
ccgaggctag gcgggcgctc                                                   20

<210> SEQ ID NO 40
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 40
aaaccgcggt cgggcgggcg                                                   20

<210> SEQ ID NO 41
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 41
ttagcactcg cagttagaaa                                                   20

<210> SEQ ID NO 42
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 42
gctaggcggg cgctcggggt                                                   20

<210> SEQ ID NO 43
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 43
tccccactgc gggagcggcc                                                   20

<210> SEQ ID NO 44
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 44
cccgagcgcc cgcctagcct                                                   20

<210> SEQ ID NO 45
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 45
accctggccg ctcccgcagt                                                   20

<210> SEQ ID NO 46

```
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 46
cggccagggt gggaaaaccg                                                20

<210> SEQ ID NO 47
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 47
cgagtgctaa ggaagaggcg                                                20

<210> SEQ ID NO 48
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 48
aactgcgagt gctaaggaag                                                20

<210> SEQ ID NO 49
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 49
ggcgggctcc gaggctaggc                                                20

<210> SEQ ID NO 50
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 50
tccccaggag ccacggcggc                                                20

<210> SEQ ID NO 51
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 51
ctaccccgcc cgcccgaccg                                                20

<210> SEQ ID NO 52
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 52
```

```
gtagggccct cccgccgccg                                                  20

<210> SEQ ID NO 53
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 53
caccggtttg cccagaccct                                                  20

<210> SEQ ID NO 54
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 54
ccctggccgc tcccgcagtg                                                  20

<210> SEQ ID NO 55
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 55
agccgagggt ctgggcaaac                                                  20

<210> SEQ ID NO 56
<211> LENGTH: 20
<212> TYPE: DNA
<213> ORGANISM: Artificial Sequence
<220> FEATURE:
<223> OTHER INFORMATION: CRISPR/CAS9 target sequences for human CD2AP

<400> SEQUENCE: 56
tggccgctcc cgcagtgggg                                                  20

<210> SEQ ID NO 57
<211> LENGTH: 2082
<212> TYPE: DNA
<213> ORGANISM: Canis lupus

<400> SEQUENCE: 57
atgcatttta aaagtttgct gaaaaacctg aatggagac aaccaaccag gaggaaaaag       60
acacatagag aacatcagct gaaaaaggtc aaaagaactg gggatggcaa gctcagaaag    120
tgtctacaac ttctccggtg gagtcggatt tctggtcacg ggtcagttga ctatattgtg    180
gagtatgact acgatgctgt acatgatgat gaattaacta ttcgggttgg tgaaataatc    240
aggaatgtga aaaaactaca ggaggaagga tggctagaag gagagctaaa tgggagaaga    300
ggaatgtttc ctgataattt tgttaaggaa attaagagag agacagaacc caaggatgat    360
aatttgccca ttaaacggga aagacatggg aatgtagcaa gccttgtaca acgaataagc    420
acctatggac ttccagctgg aggaattcaa ccacatccac aaaccaaaaa cattaagaag    480
aagaccaaga agcgtcagtg taagttctc tttgagtacc ttccacaaaa tgaggatgaa    540
ttggagctga aagtgggaga tattattgat attaatgatg aggtagaaga aggctggtgg    600
```

| | |
|---|---:|
| agtggaaccc tgaacaacaa gttgggactg tttccctcaa attttgtgaa agaattagag | 660 |
| gtaacagatg atggtgaaac tcatgaagcc caagaggatt cagaaacggt ttttactggg | 720 |
| cctacctcac ctttaccgtc tccggggaat gggaatgaaa ctgcacctgg atcagttaca | 780 |
| cagccaaaga aaattcgagg aattggattt ggagatattt ttaaagaagg ctctgtgaaa | 840 |
| cttagaacaa gaacatctgg tagtgaaata gaagagaaga aaacggaaaa gcccttaatt | 900 |
| atacagtcag taggatccaa aacacagagt ctggatgcaa caaaaacaga cacgaaaat | 960 |
| aaaagtaaag caaggaata ttgtagaaca ttatttgcct atgaaggtac taatgaagac | 1020 |
| gagctttctt ttaaagaggg agagataatt cacttaataa gtaaggagac tggagaagct | 1080 |
| ggctggtgga agggtgaact taatggtaaa gaaggagtat ttccagataa ttttgctatt | 1140 |
| cagatacatg aactggataa agactttcca aaaccaaaga aaccaccacc tcctgctaaa | 1200 |
| ggtccagctc caaaacctga gctaatagct acagagaaga agtatttttcc tataaagcca | 1260 |
| gaagaaaaag atgaaaaatc agtactggaa cagaaaccct ctaaaccagc agctccacaa | 1320 |
| gtcccaccta gaagcctac tccacccacc aaagccaata atttattgag atctcctggg | 1380 |
| acaatatacc caaagcgacc tgaaaaacca gtccctccac cacctcctat agccaagatt | 1440 |
| aatggggaag tatctaccat ttcatcaaaa tttgaaactg agccattatc aaaaccaaag | 1500 |
| ctagattctg aacaattacc acttagacca aaatcagtag acctagattc atttacagtt | 1560 |
| aggagctcta agaaacaga tattgtaaat tttgatgaca tagcttcctc agaaaacttg | 1620 |
| ctacatctta ctgcaaacag accgaagatg cctggaagaa ggttgcctgg acgcttcaat | 1680 |
| ggtggacatt ctccaaccca aagcccagaa aaaaccttga agttaccaaa agaagaagat | 1740 |
| agtgccaact taaagccgtc tgaatttaaa aaggattcaa gctactctcc aaagccatct | 1800 |
| ctgtaccttt caacaccttc aagtgcttcg aaaccaaata cagctgcttt tttaactcca | 1860 |
| ttagaaatca agctaaagt agaatcagat gatgggaaaa aaaccccctt ggatgaactt | 1920 |
| agagctcaga ttattgaatt gctgtgcatt gtagaagcac tgaaaaagga tcatgggaaa | 1980 |
| gaactggaaa aactacgaaa ggatttggaa gaggagaagg caatgagaag taatctagag | 2040 |
| gtggaaatcg agaagctgaa aaaggcagtc ctgtcgtctt ga | 2082 |

<210> SEQ ID NO 58
<211> LENGTH: 693
<212> TYPE: PRT
<213> ORGANISM: Canis lupus

<400> SEQUENCE: 58

```
Met His Phe Lys Ser Leu Leu Lys Asn Leu Glu Trp Arg Gln Pro Thr
1               5                   10                  15

Arg Arg Lys Lys Thr His Arg Glu His Gln Leu Lys Lys Val Lys Arg
            20                  25                  30

Thr Gly Asp Gly Lys Leu Arg Lys Cys Leu Gln Leu Leu Arg Trp Ser
        35                  40                  45

Arg Ile Ser Gly His Gly Ser Val Asp Tyr Ile Val Glu Tyr Asp Tyr
    50                  55                  60

Asp Ala Val His Asp Asp Glu Leu Thr Ile Arg Val Gly Glu Ile Ile
65                  70                  75                  80

Arg Asn Val Lys Lys Leu Gln Glu Glu Gly Trp Leu Glu Gly Glu Leu
                85                  90                  95

Asn Gly Arg Arg Gly Met Phe Pro Asp Asn Phe Val Lys Glu Ile Lys
            100                 105                 110
```

-continued

```
Arg Glu Thr Glu Pro Lys Asp Asp Asn Leu Pro Ile Lys Arg Glu Arg
            115                 120                 125

His Gly Asn Val Ala Ser Leu Val Gln Arg Ile Ser Thr Tyr Gly Leu
        130                 135                 140

Pro Ala Gly Gly Ile Gln Pro His Pro Gln Thr Lys Asn Ile Lys Lys
145                 150                 155                 160

Lys Thr Lys Lys Arg Gln Cys Lys Val Leu Phe Glu Tyr Leu Pro Gln
                165                 170                 175

Asn Glu Asp Glu Leu Glu Leu Lys Val Gly Asp Ile Ile Asp Ile Asn
            180                 185                 190

Asp Glu Val Glu Glu Gly Trp Trp Ser Gly Thr Leu Asn Asn Lys Leu
        195                 200                 205

Gly Leu Phe Pro Ser Asn Phe Val Lys Glu Leu Glu Val Thr Asp Asp
    210                 215                 220

Gly Glu Thr His Glu Ala Gln Glu Asp Ser Glu Thr Val Phe Thr Gly
225                 230                 235                 240

Pro Thr Ser Pro Leu Pro Ser Pro Gly Asn Gly Asn Glu Thr Ala Pro
                245                 250                 255

Gly Ser Val Thr Gln Pro Lys Lys Ile Arg Gly Ile Gly Phe Gly Asp
            260                 265                 270

Ile Phe Lys Glu Gly Ser Val Lys Leu Arg Thr Arg Thr Ser Gly Ser
    275                 280                 285

Glu Ile Glu Glu Lys Lys Thr Glu Lys Pro Leu Ile Ile Gln Ser Val
290                 295                 300

Gly Ser Lys Thr Gln Ser Leu Asp Ala Thr Lys Thr Asp Thr Glu Asn
305                 310                 315                 320

Lys Ser Lys Ala Lys Glu Tyr Cys Arg Thr Leu Phe Ala Tyr Glu Gly
                325                 330                 335

Thr Asn Glu Asp Glu Leu Ser Phe Lys Glu Gly Ile Ile His Leu
            340                 345                 350

Ile Ser Lys Glu Thr Gly Glu Ala Gly Trp Trp Lys Gly Glu Leu Asn
    355                 360                 365

Gly Lys Glu Gly Val Phe Pro Asp Asn Phe Ala Ile Gln Ile His Glu
    370                 375                 380

Leu Asp Lys Asp Phe Pro Lys Pro Lys Lys Pro Pro Pro Pro Ala Lys
385                 390                 395                 400

Gly Pro Ala Pro Lys Pro Glu Leu Ile Ala Thr Glu Lys Lys Tyr Phe
                405                 410                 415

Pro Ile Lys Pro Glu Glu Lys Asp Glu Lys Ser Val Leu Glu Gln Lys
            420                 425                 430

Pro Ser Lys Pro Ala Ala Pro Gln Val Pro Lys Lys Pro Thr Pro
        435                 440                 445

Pro Thr Lys Ala Asn Asn Leu Leu Arg Ser Pro Gly Thr Ile Tyr Pro
450                 455                 460

Lys Arg Pro Glu Lys Pro Val Pro Pro Pro Ile Ala Lys Ile
465                 470                 475                 480

Asn Gly Glu Val Ser Thr Ile Ser Ser Lys Phe Glu Thr Pro Leu
                485                 490                 495

Ser Lys Pro Lys Leu Asp Ser Glu Gln Leu Pro Leu Arg Pro Lys Ser
            500                 505                 510

Val Asp Leu Asp Ser Phe Thr Val Arg Ser Ser Lys Glu Thr Asp Ile
        515                 520                 525

Val Asn Phe Asp Asp Ile Ala Ser Ser Glu Asn Leu Leu His Leu Thr
```

-continued

```
                530               535               540
Ala Asn Arg Pro Lys Met Pro Gly Arg Arg Leu Pro Gly Arg Phe Asn
545                 550                 555                 560

Gly Gly His Ser Pro Thr Gln Ser Pro Glu Lys Thr Leu Lys Leu Pro
                565                 570                 575

Lys Glu Glu Asp Ser Ala Asn Leu Lys Pro Ser Glu Phe Lys Lys Asp
            580                 585                 590

Ser Ser Tyr Ser Pro Lys Pro Ser Leu Tyr Leu Ser Thr Pro Ser Ser
        595                 600                 605

Ala Ser Lys Pro Asn Thr Ala Ala Phe Leu Thr Pro Leu Glu Ile Lys
    610                 615                 620

Ala Lys Val Glu Ser Asp Gly Lys Lys Asn Pro Leu Asp Glu Leu
625                 630                 635                 640

Arg Ala Gln Ile Ile Glu Leu Leu Cys Ile Val Glu Ala Leu Lys Lys
                645                 650                 655

Asp His Gly Lys Glu Leu Glu Lys Leu Arg Lys Asp Leu Glu Glu Glu
            660                 665                 670

Lys Ala Met Arg Ser Asn Leu Glu Val Glu Ile Glu Lys Leu Lys Lys
        675                 680                 685

Ala Val Leu Ser Ser
    690

<210> SEQ ID NO 59
<211> LENGTH: 19
<212> TYPE: DNA
<213> ORGANISM: Artificial Sequence
<220> FEATURE:
<223> OTHER INFORMATION: siRNA/shRNA sequences for canine CD2AP

<400> SEQUENCE: 59
gaggaatgtt tcctgataa                                                19

<210> SEQ ID NO 60
<211> LENGTH: 19
<212> TYPE: DNA
<213> ORGANISM: Artificial Sequence
<220> FEATURE:
<223> OTHER INFORMATION: siRNA/shRNA sequences for canine CD2AP

<400> SEQUENCE: 60
tcagtagacc tagattcat                                                19

<210> SEQ ID NO 61
<211> LENGTH: 19
<212> TYPE: DNA
<213> ORGANISM: Artificial Sequence
<220> FEATURE:
<223> OTHER INFORMATION: siRNA/shRNA sequences for canine CD2AP

<400> SEQUENCE: 61
gcgtcagtgt aaagttctc                                                19

<210> SEQ ID NO 62
<211> LENGTH: 19
<212> TYPE: DNA
<213> ORGANISM: Artificial Sequence
<220> FEATURE:
<223> OTHER INFORMATION: siRNA/shRNA sequences for canine CD2AP

<400> SEQUENCE: 62
tagctacaga gaagaagta                                                19
```

<210> SEQ ID NO 63
<211> LENGTH: 19
<212> TYPE: DNA
<213> ORGANISM: Artificial Sequence
<220> FEATURE:
<223> OTHER INFORMATION: siRNA/shRNA sequences for canine CD2AP

<400> SEQUENCE: 63
agagggagag ataattcac                                               19

<210> SEQ ID NO 64
<211> LENGTH: 19
<212> TYPE: DNA
<213> ORGANISM: Artificial Sequence
<220> FEATURE:
<223> OTHER INFORMATION: siRNA/shRNA sequences for canine CD2AP

<400> SEQUENCE: 64
atcagtagac ctagattca                                               19

<210> SEQ ID NO 65
<211> LENGTH: 19
<212> TYPE: DNA
<213> ORGANISM: Artificial Sequence
<220> FEATURE:
<223> OTHER INFORMATION: siRNA/shRNA sequences for canine CD2AP

<400> SEQUENCE: 65
ggtactaatg aagacgagc                                               19

<210> SEQ ID NO 66
<211> LENGTH: 19
<212> TYPE: DNA
<213> ORGANISM: Artificial Sequence
<220> FEATURE:
<223> OTHER INFORMATION: siRNA/shRNA sequences for canine CD2AP

<400> SEQUENCE: 66
agaagaagat agtgccaac                                               19

<210> SEQ ID NO 67
<211> LENGTH: 19
<212> TYPE: DNA
<213> ORGANISM: Artificial Sequence
<220> FEATURE:
<223> OTHER INFORMATION: siRNA/shRNA sequences for canine CD2AP

<400> SEQUENCE: 67
ctcatgaagc ccaagagga                                               19

<210> SEQ ID NO 68
<211> LENGTH: 19
<212> TYPE: DNA
<213> ORGANISM: Artificial Sequence
<220> FEATURE:
<223> OTHER INFORMATION: siRNA/shRNA sequences for canine CD2AP

<400> SEQUENCE: 68
cgaataagca cctatggac                                               19

<210> SEQ ID NO 69
<211> LENGTH: 19
<212> TYPE: DNA
<213> ORGANISM: Artificial Sequence
<220> FEATURE:

<223> OTHER INFORMATION: siRNA/shRNA sequences for canine CD2AP

<400> SEQUENCE: 69
ctggaatgga gacaaccaa                                                    19

<210> SEQ ID NO 70
<211> LENGTH: 19
<212> TYPE: DNA
<213> ORGANISM: Artificial Sequence
<220> FEATURE:
<223> OTHER INFORMATION: siRNA/shRNA sequences for canine CD2AP

<400> SEQUENCE: 70
gcaagctcag aaagtgtct                                                    19

<210> SEQ ID NO 71
<211> LENGTH: 19
<212> TYPE: DNA
<213> ORGANISM: Artificial Sequence
<220> FEATURE:
<223> OTHER INFORMATION: siRNA/shRNA sequences for canine CD2AP

<400> SEQUENCE: 71
gctcagaaag tgtctacaa                                                    19

<210> SEQ ID NO 72
<211> LENGTH: 19
<212> TYPE: DNA
<213> ORGANISM: Artificial Sequence
<220> FEATURE:
<223> OTHER INFORMATION: siRNA/shRNA sequences for canine CD2AP

<400> SEQUENCE: 72
cagaaagtgt ctacaactt                                                    19

<210> SEQ ID NO 73
<211> LENGTH: 19
<212> TYPE: DNA
<213> ORGANISM: Artificial Sequence
<220> FEATURE:
<223> OTHER INFORMATION: siRNA/shRNA sequences for canine CD2AP

<400> SEQUENCE: 73
gtctacaact tctccggtg                                                    19

<210> SEQ ID NO 74
<211> LENGTH: 19
<212> TYPE: DNA
<213> ORGANISM: Artificial Sequence
<220> FEATURE:
<223> OTHER INFORMATION: siRNA/shRNA sequences for canine CD2AP

<400> SEQUENCE: 74
ggagtcggat ttctggtca                                                    19

<210> SEQ ID NO 75
<211> LENGTH: 19
<212> TYPE: DNA
<213> ORGANISM: Artificial Sequence
<220> FEATURE:
<223> OTHER INFORMATION: siRNA/shRNA sequences for canine CD2AP

<400> SEQUENCE: 75
gtcacgggtc agttgacta                                                    19

```
<210> SEQ ID NO 76
<211> LENGTH: 19
<212> TYPE: DNA
<213> ORGANISM: Artificial Sequence
<220> FEATURE:
<223> OTHER INFORMATION: siRNA/shRNA sequences for canine CD2AP

<400> SEQUENCE: 76
acgggtcagt tgactatat                                                    19

<210> SEQ ID NO 77
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 77
aaaggcagac actcaaccgc cgg                                               23

<210> SEQ ID NO 78
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 78
atgtattgaa gtgagacacc tgg                                               23

<210> SEQ ID NO 79
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 79
atgatgtggg actccatccc agg                                               23

<210> SEQ ID NO 80
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 80
agggcgtgac ccccaagtcc tgg                                               23

<210> SEQ ID NO 81
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 81
tgtattgaag tgagacacct ggg                                               23

<210> SEQ ID NO 82
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP
```

-continued

```
<400> SEQUENCE: 82
gggcgtgacc cccaagtcct ggg                                                23

<210> SEQ ID NO 83
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 83
ccatgcagga agcatgatgt ggg                                                23

<210> SEQ ID NO 84
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 84
ggggtcacgc cctgagccaa agg                                                23

<210> SEQ ID NO 85
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 85
tccatgcagg aagcatgatg tgg                                                23

<210> SEQ ID NO 86
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 86
attgaagtga gacacctggg tgg                                                23

<210> SEQ ID NO 87
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 87
gactccatcc caggacttgg ggg                                                23

<210> SEQ ID NO 88
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 88
gagtgtctgc ctttggctca ggg                                                23

<210> SEQ ID NO 89
<211> LENGTH: 23
```

```
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 89
tgggactcca tcccaggact tgg                                              23

<210> SEQ ID NO 90
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 90
agacacctgg gtggctccgg cgg                                              23

<210> SEQ ID NO 91
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 91
tgagtgtctg cctttggctc agg                                              23

<210> SEQ ID NO 92
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 92
ggactccatc ccaggacttg ggg                                              23

<210> SEQ ID NO 93
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 93
gtgaccccca agtcctggga tgg                                              23

<210> SEQ ID NO 94
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 94
ggcggttgag tgtctgcctt tgg                                              23

<210> SEQ ID NO 95
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 95
```
gtgagacacc tgggtggctc cgg                                              23

<210> SEQ ID NO 96
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 96
cccacatcat gcttcctgca tgg                                              23

<210> SEQ ID NO 97
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 97
gggactccat cccaggactt ggg                                              23

<210> SEQ ID NO 98
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 98
taacgcaact ttctattttt tgg                                              23

<210> SEQ ID NO 99
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 99
ctcacttcaa tacatttta agg                                               23

<210> SEQ ID NO 100
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 100
ccagttaaaa agaaaatcta agg                                              23

<210> SEQ ID NO 101
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 101
ctcaaccgcc ggagccaccc agg                                              23

<210> SEQ ID NO 102
<211> LENGTH: 23
<212> TYPE: DNA
<213> ORGANISM: Artificial Sequence

```
<220> FEATURE:
<223> OTHER INFORMATION: CRISPR/CAS9 target sequences for canine CD2AP

<400> SEQUENCE: 102
taaagcaact ttctattttt tgg                                              23

<210> SEQ ID NO 103
<211> LENGTH: 23
<212> TYPE: DNA
<213> ORGANISM: Artificial Sequence
<220> FEATURE:
<223> OTHER INFORMATION: CRISPR/CAS9 target sequences for canine CD2AP

<400> SEQUENCE: 103
ccttagattt tctttttaac tgg                                              23

<210> SEQ ID NO 104
<211> LENGTH: 1398
<212> TYPE: DNA
<213> ORGANISM: Hepatitis C virus

<400> SEQUENCE: 104
tccggatcct ggctccgcga cgtgtgggac tgggtttgca ccatcttgac agacttcaaa      60
aattggctga cctctaaatt gttccccaag ctgcccggcc tccccttcat ctcttgtcaa     120
aaggggtaca agggtgtgtg ggccggcact ggcatcatga ccacgcgctg cccttgcggc     180
gccaacatct ctggcaatgt ccgcctgggc tctatgagga tcacagggcc taaaacctgc     240
atgaacacct ggcagggac ctttcctatc aattgctaca cggagggcca gtgcgcgccg     300 aaaccccca cgaactacaa gaccgccatc tggagggtgg cggcctcgga gtacgcggag     360
gtgacgcagc atgggtcgta ctcctatgta acaggactga ccactgacaa tctgaaaatt     420
ccttgccaac taccttctcc agagtttttc tcctgggtgg acggtgtgca gatccatagg     480 tttgcacca caccaaagcc gttttttccgg gatgaggtct cgttctgcgt tgggcttaat     540
tcctatgctg tcgggtccca gcttccctgt gaacctgagc ccgacgcaga cgtattgagg     600
tccatgctaa cagatccgcc ccacatcacg gcggagactg cggcgcggcg cttggcacgg     660
ggatcacctc catctgaggc gagctcctca gtgagccagc tatcagcacc gtcgctgcgg     720
gccacctgca cccaccacag caacacctat gacgtggaca tggtcgatgc caacctgctc     780
atggagggcg gtgtggctca gacagagcct gagtccaggg tgcccgttct ggactttctc     840
gagccaatgg ccgaggaaga gagcgacctt gagccctcaa taccatcgga gtgcatgctc     900
cccaggagcg ggtttccacg ggccttaccg gcttgggcac ggcctgacta caaccccgcg     960
ctcgtggaat cgtggaggag gccagattac aaccgccca ccgttgctgg ttgtgctctc    1020
ccccccccca agaaggcccc gacgcctccc caaggagac gccggacagt gggtctgagc    1080
gagagcacca tatcagaagc cctccagcaa ctggccatca agacctttgg ccagccccc    1140 tcgagcggtg atgcaggctc gtccacgggg gcggcgccg ccgaatccgg cggtccgacg    1200 tccccctggtg agccggcccc ctcagagaca ggttccgcct cctctatgcc cccctcgag    1260 ggggagcctg gagatccgga cctggagtct gatcaggtag agcttcaacc tccccccag     1320 gggggggggg tagctcccgg ttcgggctcg ggtcttggt ctacttgctc cgaggaggac     1380
gataccaccg tgtgctgc                                                 1398

<210> SEQ ID NO 105
<211> LENGTH: 466
<212> TYPE: PRT
```

<213> ORGANISM: Hepatitis C virus

<400> SEQUENCE: 105

Ser Gly Ser Trp Leu Arg Asp Val Trp Asp Trp Val Cys Thr Ile Leu
1               5                   10                  15

Thr Asp Phe Lys Asn Trp Leu Thr Ser Lys Leu Phe Pro Lys Leu Pro
            20                  25                  30

Gly Leu Pro Phe Ile Ser Cys Gln Lys Gly Tyr Lys Gly Val Trp Ala
        35                  40                  45

Gly Thr Gly Ile Met Thr Thr Arg Cys Pro Cys Gly Ala Asn Ile Ser
    50                  55                  60

Gly Asn Val Arg Leu Gly Ser Met Arg Ile Thr Gly Pro Lys Thr Cys
65                  70                  75                  80

Met Asn Thr Trp Gln Gly Thr Phe Pro Ile Asn Cys Tyr Thr Glu Gly
                85                  90                  95

Gln Cys Ala Pro Lys Pro Pro Thr Asn Tyr Lys Thr Ala Ile Trp Arg
            100                 105                 110

Val Ala Ala Ser Glu Tyr Ala Glu Val Thr Gln His Gly Ser Tyr Ser
        115                 120                 125

Tyr Val Thr Gly Leu Thr Thr Asp Asn Leu Lys Ile Pro Cys Gln Leu
    130                 135                 140

Pro Ser Pro Glu Phe Phe Ser Trp Val Asp Gly Val Gln Ile His Arg
145                 150                 155                 160

Phe Ala Pro Thr Pro Lys Pro Phe Phe Arg Asp Glu Val Ser Phe Cys
                165                 170                 175

Val Gly Leu Asn Ser Tyr Ala Val Gly Ser Gln Leu Pro Cys Glu Pro
            180                 185                 190

Glu Pro Asp Ala Asp Val Leu Arg Ser Met Leu Thr Asp Pro Pro His
        195                 200                 205

Ile Thr Ala Glu Thr Ala Ala Arg Arg Leu Ala Arg Gly Ser Pro Pro
    210                 215                 220

Ser Glu Ala Ser Ser Ser Val Ser Gln Leu Ser Ala Pro Ser Leu Arg
225                 230                 235                 240

Ala Thr Cys Thr Thr His Ser Asn Thr Tyr Asp Val Asp Met Val Asp
                245                 250                 255

Ala Asn Leu Leu Met Glu Gly Gly Val Ala Gln Thr Glu Pro Glu Ser
            260                 265                 270

Arg Val Pro Val Leu Asp Phe Leu Glu Pro Met Ala Glu Glu Glu Ser
        275                 280                 285

Asp Leu Glu Pro Ser Ile Pro Ser Glu Cys Met Leu Pro Arg Ser Gly
    290                 295                 300

Phe Pro Arg Ala Leu Pro Ala Trp Ala Arg Pro Asp Tyr Asn Pro Pro
305                 310                 315                 320

Leu Val Glu Ser Trp Arg Arg Pro Asp Tyr Gln Pro Pro Thr Val Ala
                325                 330                 335

Gly Cys Ala Leu Pro Pro Lys Lys Ala Pro Thr Pro Pro Pro Arg
            340                 345                 350

Arg Arg Arg Thr Val Gly Leu Ser Glu Ser Thr Ile Ser Glu Ala Leu
        355                 360                 365

Gln Gln Leu Ala Ile Lys Thr Phe Gly Gln Pro Pro Ser Ser Gly Asp
    370                 375                 380

Ala Gly Ser Ser Thr Gly Ala Gly Ala Ala Glu Ser Gly Gly Pro Thr
385                 390                 395                 400

```
Ser Pro Gly Glu Pro Ala Pro Ser Glu Thr Gly Ser Ala Ser Ser Met
            405                 410                 415

Pro Pro Leu Glu Gly Glu Pro Gly Asp Pro Asp Leu Glu Ser Asp Gln
        420                 425                 430

Val Glu Leu Gln Pro Pro Pro Gln Gly Gly Val Ala Pro Gly Ser
                435                 440                 445

Gly Ser Gly Ser Trp Ser Thr Cys Ser Glu Glu Asp Asp Thr Thr Val
    450                 455                 460

Cys Cys
465

<210> SEQ ID NO 106
<211> LENGTH: 3729
<212> TYPE: DNA
<213> ORGANISM: Homo sapiens

<400> SEQUENCE: 106
atggcgagcc ctccggagag cgatggcttc tcggacgtgc gcaaggtggg ctacctgcgc      60
aaacccaaga gcatgcacaa cgcttcttc gtactgcgcg cggccagcga ggctgggggc      120
ccggcgcgcc tcgagtacta cgagaacgag aagaagtggc ggcacaagtc gagcgccccc     180
aaacgctcga tccccttga gctgcttc aacatcaaca agcgggctga ctccaagaac        240
aagcacctgg tggctctcta cacccgggac gagcactttg ccatcgcggc ggacagcgag     300
gccgagcaag acagctggta ccaggctctc ctacagctgc acaaccgtgc taagggccac     360
cacgacggga ctgcggccct cggggcggga ggtggtgggg gcagctgcag cggcagctcc     420
ggccttggtg aggctgggga ggacttgagc tacggtgacg tgcccccagg acccgcattc     480
aaagaggtct ggcaagtgat cctgaagccc aagggcctgg gtcagacaaa gaacctgatt     540
ggtatctacc gcctttgcct gaccagcaag accatcagct tcgtgaagct gaactcggag     600
gcagcggccg tggtgctgca gctgatgaac atcaggcgct gtggccactc ggaaaacttc     660
ttcttcatcg aggtgggccg ttctgccgtg acggggcccg gggagttctg gatgcaggtg     720
gatgactctg tggtggccca gaacatgcac gagaccatcc tggaggccat gcgggccatg     780
agtgatgagt tccgccctcg cagcaagagc cagtcctcgt ccaactgctc taaccccatc     840
agcgtccccc tgcgccggca ccatctcaac aatcccccgc ccagccaggt ggggctgacc     900
cgccgatcac gcactgagag catcaccgcc acctcccggg ccagcatggt gggcgggaag     960
ccaggctcct tccgtgtccg cgcctccagt gacggcgaag gcaccatgtc ccgcccagcc    1020
tcggtggacg gcagccctgt gagtccagc accaacagaa cccacgccca ccggcatcgg    1080
ggcagcgccc ggctgcaccc cccgctcaac acagccgct ccatccccat gccggcttcc     1140
cgctgctcgc cttcggccac cagccgtc agtctgtcgt ccagtagcac cagtggccat    1200
ggctccacct cggattgtct cttcccacgg cgatctagtg cttcggtgtc tggttccccc    1260
agcgatggcg gtttcatctc ctcggatgag tatggctcca gtccctgcga tttccggagt    1320
tccttccgca gtgtcactcc ggattccctg gccacaccc caccagcccg cggtgaggag    1380
gagctaagca actatatctg catgggtggc aaggggccct ccaccctgac cgccccaac    1440 ggtcactaca ttttgtctcg gggtggcaat ggccaccgct gcaccccagg aacaggcttg    1500
ggcacgagtc cagccttggc tggggatgaa gcagccagtg ctgcagatct ggataatcgg    1560
ttccgaaaga gaactcactc ggcaggcaca tcccctacca ttaccaccac gaagaccccg    1620
tcccagtcct cagtggcttc cattgaggag tacacagaga tgatgcctgc ctacccacca    1680
```

```
ggaggtggca gtggaggccg actgccggga cacaggcact ccgccttcgt gcccacccgc    1740
tcctacccag aggagggtct ggaaatgcac cccttggagc gtcgggggg gcaccaccgc     1800 ccagacagct ccaccctcca cacggatgat ggctacatgc ccatgtcccc aggggtggcc    1860
ccagtgccca gtggccgaaa gggcagtgga gactatatgc ccatgagccc caagagcgta    1920
tctgccccac agcagatcat caatcccatc agacgccatc cccagagagt ggaccccaat    1980
ggctacatga tgatgtcccc cagcggtggc tgctctcctg acattggagg tggccccagc    2040
agcagcagca gcagcagcaa cgccgtccct tccgggacca gctatggaaa gctgtggaca    2100
aacggggtag ggggccacca ctctcatgtc ttgcctcacc ccaaaccccc agtggagagc    2160
agcggtggta agctcttacc ttgcacaggt gactacatga acatgtcacc agtgggggac    2220
tccaacacca gcagcccctc cgactgctac tacggccctg aggaccccca gcacaagcca    2280
gtcctctcct actactcatt gccaagatcc tttaagcaca cccagcgccc cggggagccg    2340
gaggagggtg cccggcatca gcacctccgc ctttccacta gctctggtcg ccttctctat    2400
gctgcaacag cagatgattc ttcctcttcc accagcagcg acagcctggg tgggggatac    2460
tgcggggcta ggctggagcc cagccttcca catccccacc atcaggttct gcagccccat    2520
ctgcctcgaa aggtggacac agctgctcag accaatagcc gctggcccg cccacgcgagg    2580 ctgtccctgg gggatcccaa ggccagcacc ttacctcggg cccgagagca gcagcagcag    2640
cagcagccct gctgcacccc tcagagaccc aagagcccgg gggaatatgt caatattgaa    2700
tttgggagtg atcagtctgg ctacttgtct ggcccggtgg cttttccacag ctcaccttct    2760 gtcaggtgtc catcccagct ccagccagct cccagagagg aagagactgg cactgaggag    2820
tacatgaaga tggacctggg gccgggccgg agggcagcct ggcaggagag cactggggtc    2880
gagatgggca gactgggccc tgcacctccc ggggctgcta gcatttgcag gcctacccgg    2940
gcagtgccca gcagccgggg tgactacatg accatgcaga tgagttgtcc ccgtcagagc    3000
tacgtggaca cctcgccagc tgcccctgta agctatgctg acatgcgaac aggcattgct    3060
gcagaggagg tgagcctgcc cagggccacc atggctgctg cctcctcatc ctcagcagcc    3120
tctgcttccc cgactgggcc tcaagggca gcagagctgg ctgcccactc gtccctgctg    3180 ggggcccac aaggacctgg gggcatgagc gccttcaccc gggtgaacct cagtcctaac    3240
cgcaaccaga gtgccaaagt gatccgtgca gacccacaag ggtgccggcg gaggcatagc    3300
tccgagactt tctcctcaac acccagtgcc accgggtgg gcaacacagt gcccttttgga    3360 gcggggggcag cagtagggg cggtggcggt agcagcagca gcagcgagga tgtgaaacgc    3420
cacagctctg cttcctttga aatgtgtgg ctgaggcctg gggagcttgg gggagccccc    3480
aaggagccag ccaaactgtg tgggggctgct ggggtttgg agaatggtct taactacata    3540
gacctggatt tggtcaagga cttcaaacag tgccctcagg agtgcacccc tgaaccgcag    3600 cctccccac ccccacccccc tcatcaaccc ctgggcagcg gtgagagcag ctccacccgc    3660
cgctcaagtg aggatttaag cgcctatgcc agcatcagtt ccagaagca gccagaggac    3720 cgtcagtag                                                            3729
```

<210> SEQ ID NO 107
<211> LENGTH: 1242
<212> TYPE: PRT
<213> ORGANISM: Homo sapiens

<400> SEQUENCE: 107

Met Ala Ser Pro Pro Glu Ser Asp Gly Phe Ser Asp Val Arg Lys Val

```
  1               5                  10                 15
Gly Tyr Leu Arg Lys Pro Lys Ser Met His Lys Arg Phe Phe Val Leu
                20                 25                 30

Arg Ala Ala Ser Glu Ala Gly Gly Pro Ala Arg Leu Glu Tyr Tyr Glu
                35                 40                 45

Asn Glu Lys Lys Trp Arg His Lys Ser Ser Ala Pro Lys Arg Ser Ile
50                 55                 60

Pro Leu Glu Ser Cys Phe Asn Ile Asn Lys Arg Ala Asp Ser Lys Asn
65                 70                 75                 80

Lys His Leu Val Ala Leu Tyr Thr Arg Asp Glu His Phe Ala Ile Ala
                85                 90                 95

Ala Asp Ser Glu Ala Glu Gln Asp Ser Trp Tyr Gln Ala Leu Leu Gln
                100                105                110

Leu His Asn Arg Ala Lys Gly His His Asp Gly Ala Ala Ala Leu Gly
                115                120                125

Ala Gly Gly Gly Gly Ser Cys Ser Gly Ser Ser Gly Leu Gly Glu
                130                135                140

Ala Gly Glu Asp Leu Ser Tyr Gly Asp Val Pro Pro Gly Pro Ala Phe
145                150                155                160

Lys Glu Val Trp Gln Val Ile Leu Lys Pro Lys Gly Leu Gly Gln Thr
                165                170                175

Lys Asn Leu Ile Gly Ile Tyr Arg Leu Cys Leu Thr Ser Lys Thr Ile
                180                185                190

Ser Phe Val Lys Leu Asn Ser Glu Ala Ala Val Val Leu Gln Leu
                195                200                205

Met Asn Ile Arg Arg Cys Gly His Ser Glu Asn Phe Phe Ile Glu
210                215                220

Val Gly Arg Ser Ala Val Thr Gly Pro Gly Glu Phe Trp Met Gln Val
225                230                235                240

Asp Asp Ser Val Val Ala Gln Asn Met His Glu Thr Ile Leu Glu Ala
                245                250                255

Met Arg Ala Met Ser Asp Glu Phe Arg Pro Arg Ser Lys Ser Gln Ser
                260                265                270

Ser Ser Asn Cys Ser Asn Pro Ile Ser Val Pro Leu Arg Arg His His
                275                280                285

Leu Asn Asn Pro Pro Ser Gln Val Gly Leu Thr Arg Arg Ser Arg
                290                295                300

Thr Glu Ser Ile Thr Ala Thr Ser Pro Ala Ser Met Val Gly Lys
305                310                315                320

Pro Gly Ser Phe Arg Val Arg Ala Ser Ser Asp Gly Glu Gly Thr Met
                325                330                335

Ser Arg Pro Ala Ser Val Asp Gly Ser Pro Val Ser Pro Ser Thr Asn
                340                345                350

Arg Thr His Ala His Arg His Arg Gly Ser Ala Arg Leu His Pro Pro
                355                360                365

Leu Asn His Ser Arg Ser Ile Pro Met Pro Ala Ser Arg Cys Ser Pro
                370                375                380

Ser Ala Thr Ser Pro Val Ser Leu Ser Ser Ser Thr Ser Gly His
385                390                395                400

Gly Ser Thr Ser Asp Cys Leu Phe Pro Arg Arg Ser Ser Ala Ser Val
                405                410                415

Ser Gly Ser Pro Ser Asp Gly Gly Phe Ile Ser Ser Asp Glu Tyr Gly
                420                425                430
```

-continued

```
Ser Ser Pro Cys Asp Phe Arg Ser Phe Arg Ser Val Thr Pro Asp
        435                 440                 445
Ser Leu Gly His Thr Pro Ala Arg Gly Glu Glu Glu Leu Ser Asn
    450                 455                 460
Tyr Ile Cys Met Gly Gly Lys Gly Pro Ser Thr Leu Thr Ala Pro Asn
465                 470                 475                 480
Gly His Tyr Ile Leu Ser Arg Gly Gly Asn Gly His Arg Cys Thr Pro
                    485                 490                 495
Gly Thr Gly Leu Gly Thr Ser Pro Ala Leu Ala Gly Asp Glu Ala Ala
                500                 505                 510
Ser Ala Ala Asp Leu Asp Asn Arg Phe Arg Lys Arg Thr His Ser Ala
            515                 520                 525
Gly Thr Ser Pro Thr Ile Thr His Gln Lys Thr Pro Ser Gln Ser Ser
        530                 535                 540
Val Ala Ser Ile Glu Glu Tyr Thr Glu Met Met Pro Ala Tyr Pro Pro
545                 550                 555                 560
Gly Gly Gly Ser Gly Gly Arg Leu Pro Gly His Arg His Ser Ala Phe
                    565                 570                 575
Val Pro Thr Arg Ser Tyr Pro Glu Glu Gly Leu Glu Met His Pro Leu
                580                 585                 590
Glu Arg Arg Gly Gly His His Arg Pro Asp Ser Ser Thr Leu His Thr
            595                 600                 605
Asp Asp Gly Tyr Met Pro Met Ser Pro Gly Val Ala Pro Val Pro Ser
        610                 615                 620
Gly Arg Lys Gly Ser Gly Asp Tyr Met Pro Met Ser Pro Lys Ser Val
625                 630                 635                 640
Ser Ala Pro Gln Gln Ile Ile Asn Pro Ile Arg Arg His Pro Gln Arg
                    645                 650                 655
Val Asp Pro Asn Gly Tyr Met Met Met Ser Pro Ser Gly Gly Cys Ser
                660                 665                 670
Pro Asp Ile Gly Gly Gly Pro Ser Ser Ser Ser Ser Ser Ser Asn Ala
            675                 680                 685
Val Pro Ser Gly Thr Ser Tyr Gly Lys Leu Trp Thr Asn Gly Val Gly
        690                 695                 700
Gly His His Ser His Val Leu Pro His Pro Lys Pro Pro Val Glu Ser
705                 710                 715                 720
Ser Gly Gly Lys Leu Leu Pro Cys Thr Gly Asp Tyr Met Asn Met Ser
                    725                 730                 735
Pro Val Gly Asp Ser Asn Thr Ser Ser Pro Ser Asp Cys Tyr Tyr Gly
                740                 745                 750
Pro Glu Asp Pro Gln His Lys Pro Val Leu Ser Tyr Tyr Ser Leu Pro
            755                 760                 765
Arg Ser Phe Lys His Thr Gln Arg Pro Gly Glu Pro Glu Glu Gly Ala
        770                 775                 780
Arg His Gln His Leu Arg Leu Ser Thr Ser Ser Gly Arg Leu Leu Tyr
785                 790                 795                 800
Ala Ala Thr Ala Asp Asp Ser Ser Ser Ser Thr Ser Ser Asp Ser Leu
                    805                 810                 815
Gly Gly Gly Tyr Cys Gly Ala Arg Leu Glu Pro Ser Leu Pro His Pro
                820                 825                 830
His His Gln Val Leu Gln Pro His Leu Pro Arg Lys Val Asp Thr Ala
            835                 840                 845
```

-continued

```
Ala Gln Thr Asn Ser Arg Leu Ala Arg Pro Thr Arg Leu Ser Leu Gly
    850                 855                 860

Asp Pro Lys Ala Ser Thr Leu Pro Arg Ala Arg Glu Gln Gln Gln Gln
865                 870                 875                 880

Gln Gln Pro Leu Leu His Pro Glu Pro Lys Ser Pro Gly Glu Tyr
                885                 890                 895

Val Asn Ile Glu Phe Gly Ser Asp Gln Ser Gly Tyr Leu Ser Gly Pro
            900                 905                 910

Val Ala Phe His Ser Ser Pro Ser Val Arg Cys Pro Ser Gln Leu Gln
            915                 920                 925

Pro Ala Pro Arg Glu Glu Glu Thr Gly Thr Glu Tyr Met Lys Met
930                 935                 940

Asp Leu Gly Pro Gly Arg Arg Ala Ala Trp Gln Glu Ser Thr Gly Val
945                 950                 955                 960

Glu Met Gly Arg Leu Gly Pro Ala Pro Pro Gly Ala Ala Ser Ile Cys
                965                 970                 975

Arg Pro Thr Arg Ala Val Pro Ser Ser Arg Gly Asp Tyr Met Thr Met
                980                 985                 990

Gln Met Ser Cys Pro Arg Gln Ser  Tyr Val Asp Thr Ser  Pro Ala Ala
                995                 1000                1005

Pro Val  Ser Tyr Ala Asp Met  Arg Thr Gly Ile Ala  Ala Glu Glu
    1010                1015                1020

Val Ser  Leu Pro Arg Ala Thr  Met Ala Ala Ala Ser  Ser Ser Ser
    1025                1030                1035

Ala Ala  Ser Ala Ser Pro Thr  Gly Pro Gln Gly Ala  Ala Glu Leu
    1040                1045                1050

Ala Ala  His Ser Ser Leu Leu  Gly Gly Pro Gln Gly  Pro Gly Gly
    1055                1060                1065

Met Ser  Ala Phe Thr Arg Val  Asn Leu Ser Pro Asn  Arg Asn Gln
    1070                1075                1080

Ser Ala  Lys Val Ile Arg Ala  Asp Pro Gln Gly Cys  Arg Arg Arg
    1085                1090                1095

His Ser  Ser Glu Thr Phe Ser  Ser Thr Pro Ser Ala  Thr Arg Val
    1100                1105                1110

Gly Asn  Thr Val Pro Phe Gly  Ala Gly Ala Ala Val  Gly Gly Gly
    1115                1120                1125

Gly Gly  Ser Ser Ser Ser Ser  Glu Asp Val Lys Arg  His Ser Ser
    1130                1135                1140

Ala Ser  Phe Glu Asn Val Trp  Leu Arg Pro Gly Glu  Leu Gly Gly
    1145                1150                1155

Ala Pro  Lys Glu Pro Ala Lys  Leu Cys Gly Ala Ala  Gly Gly Leu
    1160                1165                1170

Glu Asn  Gly Leu Asn Tyr Ile  Asp Leu Asp Leu Val  Lys Asp Phe
    1175                1180                1185

Lys Gln  Cys Pro Gln Glu Cys  Thr Pro Glu Pro Gln  Pro Pro Pro
    1190                1195                1200

Pro Pro  Pro Pro His Gln Pro  Leu Gly Ser Gly Glu  Ser Ser Ser
    1205                1210                1215

Thr Arg  Arg Ser Ser Glu Asp  Leu Ser Ala Tyr Ala  Ser Ile Ser
    1220                1225                1230

Phe Gln  Lys Gln Pro Glu Asp  Arg Gln
    1235                1240
```

<210> SEQ ID NO 108
<211> LENGTH: 3723
<212> TYPE: DNA
<213> ORGANISM: Canis lupus
<220> FEATURE:
<221> NAME/KEY: misc_feature
<222> LOCATION: (2356)..(2356)
<223> OTHER INFORMATION: n is a, c, g, or t

<400> SEQUENCE: 108

```
atggcgagcc ctccggagac cgacggcttc tcggacgtgc gcaaggtggg ctacctgcgc      60
aaacccaaga gcatgcacaa gcgcttcttc gtgctgcggg cggccagcga ggcgggggc      120
ccggcgcgcc tcgagtacta cgagaacgag aagaagtggc ggcacaagtc gagcgccccc      180
aaacgctcga tcccctcga gctgcttc aacatcaaca agcgggcgga ctccaagaac        240
aagcacctgg tggccttta cacccgggac gagcactttg ccatcgcggc ggacagcgag      300
gccgagcagg acagctggta ccaggccctc ctgcagctgc acaaccgggc caagggccac      360
cacgacggcg cctcggcccc cggggcggga ggcggcgggg gcagctgcag cggcagctcg      420
ggcctcgggg aggccggcga ggacttgagc tacgggacg tgccccccggg acctgcgttc      480
aaggaggtct ggcaggtgat cctgaaaccc aagggcctgg ggcagacaaa gaacctgatt      540
ggcatctacc gcctctgcct gaccagcaag accatcagct tcgtgaagct gaactccgag      600
gcggcggccg tggtgctgca gctgatgaac atccgacgtt gcggccactc ggagaacttc      660
ttcttcatcg aagtgggccg ttccgcagtg acgggacccg gcgagttctg gatgcaggtg      720
gatgactccg tggtggccca gaacatgcac gagaccatcc tggaggccat gcgggccatg      780
agcgacgagt tccgccctcg gagtaagagc cagtcctcct ccaactgctc caaccccatc      840
agcgtccccc tgcgccggca ccacctcaac aaccccctc ccagccaggt ggggctgacg      900
cgccgctcgc gcaccgagag catcaccgcc acctctccgg ccagcatggt gggcgggaag      960
caggcgctcct tccgtgtgcg cgcgtccagc gacggcgagg gcaccatgtc ccgcccggcc    1020
tcggtggacg gcagccccgt gagcccgagc accaccagga cccacgcgca ccggcatcgc    1080
ggcagctccc ggctgcaccc ccgctcaac cacagccgct ccatccccat gccttcctct    1140
cgctgctcgc cttccgccac cagccgtc agcctgtcgt ccagcagcac cagtggccac    1200
ggctccacct cggactgcct cttccccccgg cgctctagtg cctctgtgtc gggttccccc    1260
agcgacggtg gtttcatctc ctctgacgag tacggctcga gtccctgcga tttccgaagt    1320
tccttccgca gtgtcacccc ggattccctg ggccacaccc cccggcccg cggcgaggag    1380
gagctgagca actacatctg catgggaggc aaagggtcct ccaccctcac cgcccccaac    1440
ggtcactaca ttttgcctcg gggtggcaat ggccaccgct acatcccggg ggctggcttg    1500
ggcaccagcc cggccctggc tgcggatgaa gcggccgctg cggccgacct ggataaccgg    1560
ttccgaaagc ggactcactc cgcgggcaca tcccctacca tttcccacca aagaccccg    1620
tcccagtctt ctgtggcttc cattgaggag tacacggaga tgatgcctgc ctacccgcca    1680
ggaggtggca gtggaggccg actgcctggc taccggcact ctgccttcgt gcccacccac    1740
tcctaccccg aggagggtct ggaaatgcac cctctggaca ggcgtggggg ccaccaccgg    1800
ccggacgccc cgcccctcca cacgatgat ggctacatgc ccatgtcccc gggagtggca    1860
ccggtgccca gcagccggaa gggcagtggg gactatatgc ccatgagccc caagagcgtg    1920
tccgcgccgc agcagatcat caaccccatt gacgcgcatc cccagagggt ggaccccaat    1980
ggctacatga tgatgtcccc aagcggcagc tgctctcctg acattggagg tgggcccggc    2040
```

| | | |
|---|---|---|
| agcagcagca gcggcagcgc cgcccttct gggagcagct atggcaagct gtggacaaac | 2100 |
| ggggtagggg gccaccaccc tcacgccctg ccgcaccca aactcccgt ggagagcggg | 2160 |
| agtggcaagc tcctgtcttg taccggcgac tacatgaaca tgtcgccggt gggggactcc | 2220 |
| aacaccagca gcccctccga cggctactac gggcccagagg accccagca caagccagtt | 2280 |
| ctctcctact actcattgcc aaggtccttt aagcacaccc agcgccctgg ggagctggag | 2340 |
| gagagcgccc ggcacnagca cctccgcctc tcctccagct cgggtcgtct tctctacgcc | 2400 |
| gcgacggcgg aagattcctc ctcctccacc agcagcgaca gcctgggccc aggggggatac | 2460 |
| tgtggggtca ggccggatcc cggcctcccg catatccacc atcaggtcct gcagcctcac | 2520 |
| ctgcctcgga aggtggacac ggccgcgcag accaacagcc gcctggctcg gcccacgagg | 2580 |
| ctgtccctgg gggaccccaa ggccagcacc ttacctcggg ttcgagagca gcagcacccg | 2640 |
| ccgcccctgc tgcaccctcc ggagcccaag agccccgggg aatatgtgaa tattgagttc | 2700 |
| gggagcgatc agccgggcta cttatcgggg ccggtggctg cccgcagctc gccttctgtc | 2760 |
| aggtgcccac cccagctcca gccagctccc cgcgaggaag agactggcac cgaggagtac | 2820 |
| atgaacatgg acctggggcc tggccggagg gcagcctggc aggagggtgc tggggtccag | 2880 |
| cccggcaggg tgggccccgc gccccccggg gccgctagcg tgtgcaggcc cacccgggca | 2940 |
| gtgcccagca gccggggcga ctacatgacc atgcaggtgg gctgtcccgg ccagggctac | 3000 |
| gtggacacct cgccagtggc ccccatcagc tacgctgaca tgcggacagg cattgtcgtg | 3060 |
| gaggaggcca gcctgccggg ggccacagcg gccgccccct cctcggcctc ggcagcctcg | 3120 |
| gcttccccca cggcgcctcc aaaagcgggg gagctggtgg cccgctcctc cctgctgggg | 3180 |
| ggcccgcagg gacccggggg catgagcgcc ttcacccggg tgaacctcag ccccaaccgc | 3240 |
| aaccagagtg ccaaagtgat ccgcgccgac ccgcaggggt gccggaggcg gcatagctct | 3300 |
| gagaccttct cctccacgcc cagtgccacc cgggcgggca acgcagtgcc cttcggcggg | 3360 |
| ggggcggccc tgggggggcag cggtggcggc agcagcgcgg aggatatgaa acgccacagt | 3420 |
| tcggcttcct ttgagaacgt gtggctgagg cctggggagc tcggggagc ccccaaggag | 3480 |
| ccggcccgc acgctgggc cgccgggggt ttggagaatg gcttaacta catagacctg | 3540 |
| gatttggtca aggacttcaa acagtgctct caggagcgcc cccctcaacc gcagccgccc | 3600 |
| ccgcccccgg cccctcatca gcctctgggc agcagtgaga gcagttcaac cagccgctcc | 3660 |
| agcgaggatc taagcgccta tgccagcatc agtttccaga agcagccaga ggacctccag | 3720 |
| tag | 3723 |

<210> SEQ ID NO 109
<211> LENGTH: 1240
<212> TYPE: PRT
<213> ORGANISM: Canis lupus
<220> FEATURE:
<221> NAME/KEY: misc_feature
<222> LOCATION: (786)..(786)
<223> OTHER INFORMATION: Xaa can be any naturally occurring amino acid

<400> SEQUENCE: 109

Met Ala Ser Pro Pro Glu Thr Asp Gly Phe Ser Asp Val Arg Lys Val
1               5                   10                  15

Gly Tyr Leu Arg Lys Pro Lys Ser Met His Lys Arg Phe Phe Val Leu
            20                  25                  30

Arg Ala Ala Ser Glu Ala Gly Gly Pro Ala Arg Leu Glu Tyr Tyr Glu
        35                  40                  45

```
Asn Glu Lys Lys Trp Arg His Lys Ser Ser Ala Pro Lys Arg Ser Ile
    50              55                  60

Pro Leu Glu Ser Cys Phe Asn Ile Asn Lys Arg Ala Asp Ser Lys Asn
65              70                  75                  80

Lys His Leu Val Ala Leu Tyr Thr Arg Asp Glu His Phe Ala Ile Ala
                85                  90                  95

Ala Asp Ser Glu Ala Glu Gln Asp Ser Trp Tyr Gln Ala Leu Leu Gln
            100                 105                 110

Leu His Asn Arg Ala Lys Gly His His Asp Gly Ala Ser Ala Pro Gly
            115                 120                 125

Ala Gly Gly Gly Gly Ser Cys Ser Gly Ser Ser Gly Leu Gly Glu
130                 135                 140

Ala Gly Glu Asp Leu Ser Tyr Gly Asp Val Pro Gly Pro Ala Phe
145                 150                 155                 160

Lys Glu Val Trp Gln Val Ile Leu Lys Pro Lys Gly Leu Gly Gln Thr
                165                 170                 175

Lys Asn Leu Ile Gly Ile Tyr Arg Leu Cys Leu Thr Ser Lys Thr Ile
            180                 185                 190

Ser Phe Val Lys Leu Asn Ser Glu Ala Ala Val Val Leu Gln Leu
        195                 200                 205

Met Asn Ile Arg Arg Cys Gly His Ser Glu Asn Phe Phe Ile Glu
210                 215                 220

Val Gly Arg Ser Ala Val Thr Gly Pro Gly Glu Phe Trp Met Gln Val
225                 230                 235                 240

Asp Asp Ser Val Val Ala Gln Asn Met His Glu Thr Ile Leu Glu Ala
                245                 250                 255

Met Arg Ala Met Ser Asp Glu Phe Arg Pro Arg Ser Lys Ser Gln Ser
        260                 265                 270

Ser Ser Asn Cys Ser Asn Pro Ile Ser Val Pro Leu Arg Arg His His
        275                 280                 285

Leu Asn Asn Pro Pro Ser Gln Val Gly Leu Thr Arg Arg Ser Arg
290                 295                 300

Thr Glu Ser Ile Thr Ala Thr Ser Pro Ala Ser Met Val Gly Gly Lys
305                 310                 315                 320

Gln Gly Ser Phe Arg Val Arg Ala Ser Ser Asp Gly Glu Gly Thr Met
                325                 330                 335

Ser Arg Pro Ala Ser Val Asp Gly Ser Pro Val Ser Pro Ser Thr Thr
            340                 345                 350

Arg Thr His Ala His Arg His Arg Gly Ser Ser Arg Leu His Pro Pro
        355                 360                 365

Leu Asn His Ser Arg Ser Ile Pro Met Pro Ser Ser Arg Cys Ser Pro
370                 375                 380

Ser Ala Thr Ser Pro Val Ser Leu Ser Ser Ser Thr Ser Gly His
385                 390                 395                 400

Gly Ser Thr Ser Asp Cys Leu Phe Pro Arg Arg Ser Ser Ala Ser Val
            405                 410                 415

Ser Gly Ser Pro Ser Asp Gly Phe Ile Ser Ser Asp Glu Tyr Gly
        420                 425                 430

Ser Ser Pro Cys Asp Phe Arg Ser Phe Arg Ser Val Thr Pro Asp
            435                 440                 445

Ser Leu Gly His Thr Pro Pro Ala Arg Gly Glu Glu Leu Ser Asn
450                 455                 460

Tyr Ile Cys Met Gly Gly Lys Gly Ser Ser Thr Leu Thr Ala Pro Asn
```

```
            465                 470                 475                 480
        Gly His Tyr Ile Leu Pro Arg Gly Gly Asn Gly His Arg Tyr Ile Pro
                        485                 490                 495
        Gly Ala Gly Leu Gly Thr Ser Pro Ala Leu Ala Ala Asp Glu Ala Ala
                        500                 505                 510
        Ala Ala Ala Asp Leu Asp Asn Arg Phe Arg Lys Arg Thr His Ser Ala
                        515                 520                 525
        Gly Thr Ser Pro Thr Ile Ser His Gln Lys Thr Pro Ser Gln Ser Ser
                        530                 535                 540
        Val Ala Ser Ile Glu Glu Tyr Thr Glu Met Met Pro Ala Tyr Pro Pro
        545                 550                 555                 560
        Gly Gly Gly Ser Gly Gly Arg Leu Pro Gly Tyr Arg His Ser Ala Phe
                        565                 570                 575
        Val Pro Thr His Ser Tyr Pro Glu Glu Gly Leu Glu Met His Pro Leu
                        580                 585                 590
        Asp Arg Arg Gly Gly His His Arg Pro Asp Ala Ala Ala Leu His Thr
                        595                 600                 605
        Asp Asp Gly Tyr Met Pro Met Ser Pro Gly Val Ala Pro Val Pro Ser
                        610                 615                 620
        Ser Arg Lys Gly Ser Gly Asp Tyr Met Pro Met Ser Pro Lys Ser Val
        625                 630                 635                 640
        Ser Ala Pro Gln Gln Ile Ile Asn Pro Ile Arg Arg His Pro Gln Arg
                        645                 650                 655
        Val Asp Pro Asn Gly Tyr Met Met Met Ser Pro Ser Gly Ser Cys Ser
                        660                 665                 670
        Pro Asp Ile Gly Gly Gly Pro Gly Ser Ser Ser Gly Ser Ala Ala
                        675                 680                 685
        Pro Ser Gly Ser Ser Tyr Gly Lys Leu Trp Thr Asn Gly Val Gly Gly
                        690                 695                 700
        His His Pro His Ala Leu Pro His Pro Lys Leu Pro Val Glu Ser Gly
        705                 710                 715                 720
        Ser Gly Lys Leu Leu Ser Cys Thr Gly Asp Tyr Met Asn Met Ser Pro
                        725                 730                 735
        Val Gly Asp Ser Asn Thr Ser Ser Pro Ser Asp Gly Tyr Tyr Gly Pro
                        740                 745                 750
        Glu Asp Pro Gln His Lys Pro Val Leu Ser Tyr Tyr Ser Leu Pro Arg
                        755                 760                 765
        Ser Phe Lys His Thr Gln Arg Pro Gly Glu Leu Glu Glu Ser Ala Arg
        770                 775                 780
        His Xaa His Leu Arg Leu Ser Ser Ser Gly Arg Leu Leu Tyr Ala
        785                 790                 795                 800
        Ala Thr Ala Glu Asp Ser Ser Ser Ser Thr Ser Ser Asp Ser Leu Gly
                        805                 810                 815
        Pro Gly Gly Tyr Cys Gly Val Arg Pro Asp Pro Gly Leu Pro His Ile
                        820                 825                 830
        His His Gln Val Leu Gln Pro His Leu Pro Arg Lys Val Asp Thr Ala
                        835                 840                 845
        Ala Gln Thr Asn Ser Arg Leu Ala Arg Pro Thr Arg Leu Ser Leu Gly
                        850                 855                 860
        Asp Pro Lys Ala Ser Thr Leu Pro Arg Val Arg Glu Gln Gln His Pro
        865                 870                 875                 880
        Pro Pro Leu Leu His Pro Pro Glu Pro Lys Ser Pro Gly Glu Tyr Val
                        885                 890                 895
```

Asn Ile Glu Phe Gly Ser Asp Gln Pro Gly Tyr Leu Ser Gly Pro Val
                900                 905                 910

Ala Ala Arg Ser Ser Pro Ser Val Arg Cys Pro Pro Gln Leu Gln Pro
        915                 920                 925

Ala Pro Arg Glu Glu Thr Gly Thr Glu Tyr Met Asn Met Asp
930                 935                 940

Leu Gly Pro Gly Arg Arg Ala Ala Trp Gln Glu Gly Ala Gly Val Gln
945                 950                 955                 960

Pro Gly Arg Val Gly Pro Ala Pro Pro Gly Ala Ala Ser Val Cys Arg
                965                 970                 975

Pro Thr Arg Ala Val Pro Ser Ser Arg Gly Asp Tyr Met Thr Met Gln
        980                 985                 990

Val Gly Cys Pro Gly Gln Gly Tyr Val Asp Thr Ser Pro Val Ala Pro
        995                 1000                1005

Ile Ser Tyr Ala Asp Met Arg Thr Gly Ile Val Val Glu Glu Ala
    1010                1015                1020

Ser Leu Pro Gly Ala Thr Ala Ala Ala Pro Ser Ser Ala Ser Ala
    1025                1030                1035

Ala Ser Ala Ser Pro Thr Ala Pro Pro Lys Ala Gly Glu Leu Val
    1040                1045                1050

Ala Arg Ser Ser Leu Leu Gly Gly Pro Gln Gly Pro Gly Gly Met
    1055                1060                1065

Ser Ala Phe Thr Arg Val Asn Leu Ser Pro Asn Arg Asn Gln Ser
    1070                1075                1080

Ala Lys Val Ile Arg Ala Asp Pro Gln Gly Cys Arg Arg Arg His
    1085                1090                1095

Ser Ser Glu Thr Phe Ser Ser Thr Pro Ser Ala Thr Arg Ala Gly
    1100                1105                1110

Asn Ala Val Pro Phe Gly Gly Gly Ala Ala Leu Gly Gly Ser Gly
    1115                1120                1125

Gly Gly Ser Ser Ala Glu Asp Met Lys Arg His Ser Ser Ala Ser
    1130                1135                1140

Phe Glu Asn Val Trp Leu Arg Pro Gly Glu Leu Gly Gly Ala Pro
    1145                1150                1155

Lys Glu Pro Ala Pro His Ala Gly Ala Ala Gly Gly Leu Glu Asn
    1160                1165                1170

Gly Leu Asn Tyr Ile Asp Leu Asp Leu Val Lys Asp Phe Lys Gln
    1175                1180                1185

Cys Ser Gln Glu Arg Pro Pro Gln Pro Gln Pro Pro Pro Pro Pro
    1190                1195                1200

Ala Pro His Gln Pro Leu Gly Ser Ser Glu Ser Ser Ser Thr Ser
    1205                1210                1215

Arg Ser Ser Glu Asp Leu Ser Ala Tyr Ala Ser Ile Ser Phe Gln
    1220                1225                1230

Lys Gln Pro Glu Asp Leu Gln
    1235                1240

<210> SEQ ID NO 110
<211> LENGTH: 3033
<212> TYPE: DNA
<213> ORGANISM: Homo sapiens

<400> SEQUENCE: 110
atgggctatt tgtgtgttaa tttcatttgg ttcttgggaa taacgactca ccgcgttgat      60

```
ttaaagaaag aactaaaatt ccagatggca aactcaatga atggcagaaa ccctggtggt    120
cgaggaggaa atccccgaaa aggtcgaatt ttgggtatta ttgatgctat tcaggatgca    180
gttggacccc ctaagcaagc tgccgcagat cgcaggaccg tggagaagac ttggaagctc    240
atggacaaag tggtaagact gtgccaaaat cccaaacttc agttgaaaaa tagcccacca    300
tatatacttg atattttgcc tgatacatat cagcatttac gacttatatt gagtaaatat    360
gatgacaacc agaaacttgc ccaactcagt gagaatgagt actttaaaat ctacattgat    420
agccttatga aaaagtcaaa cgggcaata agactcttta aagaaggcaa ggagagaatg    480
tatgaagaac agtcacagga cagacgaaat ctcacaaaac tgtcccttat cttcagtcac    540
atgctggcag aaatcaaagc aatctttccc aatggtcaat ccagggaga taactttcgt    600 atcacaaaag cagatgctgc tgaattctgg agaaagtttt ttggagacaa aactatcgta    660
ccatggaaag tattcagaca gtgccttcat gaggtccacc agattagctc tggcctggaa    720
gcaatggctc taaaatcaac aattgattta acttgcaatg attacatttc agttttgaa     780 tttgatattt ttaccaggct gtttcagcct tggggctcta ttttgcggaa ttggaatttc    840
ttagctgtga cacatccagg ttacatggca tttctcacat atgatgaagt taaagcacga    900
ctacagaaat atagcaccaa acccggaagc tatattttcc ggttaagttg cactcgattg    960
ggacagtggg ccattggcta tgtgactggg gatgggaata tcttacagac catacctcat    1020
aacaagccct tatttcaagc cctgattgat ggcagcaggg aaggatttta tctttatcct    1080
gatgggagga gttataatcc tgatttaact ggattatgtg aacctacacc tcatgaccat    1140
ataaaagtta cacaggaaca atatgaatta tattgtgaaa tgggctccac ttttcagctc    1200
tgtaagattt gtgcagagaa tgacaaagat gtcaagattg agccttgtgg gcatttgatg    1260
tgcacctctt gccttacggc atggcaggag tcggatggtc agggctgccc tttctgtcgt    1320
tgtgaaataa aaggaactga gcccataatc gtggacccct ttgatccaag agatgaaggc    1380
tccaggtgtt gcagcatcat tgacccctt ggcatgccga tgctagactt ggacgacgat    1440
gatgatcgtg aggagtcctt gatgatgaat cggttggcaa acgtccgaaa gtgcactgac    1500
aggcagaact caccagtcac atcaccagga tcctctcccc ttgcccagag aagaaagcca    1560
cagcctgacc cactccagat cccacatcta agcctgccac ccgtgcctcc tcgcctggat    1620
ctaattcaga aaggcatagt tagatctccc tgtggcagcc aacgggttc accaaagtct    1680 tctccttgca tggtgagaaa acaagataaa ccactcccag caccacctcc tcccttaaga    1740
gatcctcctc caccgccacc tgaaagacct ccaccaatcc caccagacaa tagactgagt    1800
agacacatcc atcatgtgga aagcgtgcct tccagagacc cgccaatgcc tcttgaagca    1860
tggtgccctc gggatgtgtt tgggactaat cagcttgtgg gatgtcgact cctaggggag    1920
ggctctccaa aacctggaat cacagcgagt tcaaatgtca atggaaggca cagtagagtg    1980
ggctctgacc cagtgcttat gcggaaacac agacgccatg atttgccttt agaaggagct    2040
aaggtctttt ccaatggtca ccttggaagt gaagaatatg atgttcctcc ccggctttct    2100
cctcctcctc cagttaccac cctcctccct agcataaagt gtactggtcc gttagcaaat    2160 tctcttttcag agaaaacaag agacccagta gaggaagatg atgatgaata caagattcct    2220
tcatcccacc ctgtttccct gaattcacaa ccatctcatt gtcataatgt aaaacctcct    2280
gttcggtctt gtgataatgg tcactgtatg ctgaatggaa cacatggtcc atcttcagag    2340
aagaaatcaa acatccctga cttaagcata tatttaaagg gagatgtttt tgattcagcc    2400
```

-continued

```
tctgatcccg tgccattacc acctgccagg cctccaactc gggacaatcc aaagcatggt    2460
tcttcactca acaggacgcc ctctgattat gatcttctca tccctccatt aggtgaagat    2520
gcttttgatg ccctccctcc atctctccca cctcccccac ctcctgcaag gcatagtctc    2580
attgaacatt caaaacctcc tggctccagt agccggccat cctcaggaca ggatcttttt    2640
cttcttcctt cagatccctt tgttgatcta gcaagtggcc aagttccttt gcctcctgct    2700
agaaggttac caggtgaaaa tgtcaaaact aacagaacat cacaggacta tgatcagctt    2760
ccttcatgtt cagatggttc acaggcacca gccagacccc ctaaaccacg accgcgcagg    2820
actgcaccag aaattcacca cagaaaaccc catgggcctg aggcggcatt ggaaaatgtc    2880
gatgcaaaaa ttgcaaaact catgggagag ggttatgcct ttgaagaggt gaagagagcc    2940
ttagagatag cccagaataa tgtcgaagtt gcccggagca tcctccgaga atttgccttc    3000
cctcctccag tatccccacg tctaaatcta tag                                 3033
```

<210> SEQ ID NO 111
<211> LENGTH: 1010
<212> TYPE: PRT
<213> ORGANISM: Homo sapiens

<400> SEQUENCE: 111

```
Met Gly Tyr Leu Cys Val Asn Phe Ile Trp Phe Leu Gly Ile Thr Thr
1               5                   10                  15

His Arg Val Asp Leu Lys Lys Glu Leu Lys Phe Gln Met Ala Asn Ser
                20                  25                  30

Met Asn Gly Arg Asn Pro Gly Gly Arg Gly Asn Pro Arg Lys Gly
            35                  40                  45

Arg Ile Leu Gly Ile Ile Asp Ala Ile Gln Asp Ala Val Gly Pro Pro
        50                  55                  60

Lys Gln Ala Ala Ala Asp Arg Arg Thr Val Glu Lys Thr Trp Lys Leu
65                  70                  75                  80

Met Asp Lys Val Val Arg Leu Cys Gln Asn Pro Lys Leu Gln Leu Lys
                85                  90                  95

Asn Ser Pro Pro Tyr Ile Leu Asp Ile Leu Pro Asp Thr Tyr Gln His
            100                 105                 110

Leu Arg Leu Ile Leu Ser Lys Tyr Asp Asp Asn Gln Lys Leu Ala Gln
        115                 120                 125

Leu Ser Glu Asn Glu Tyr Phe Lys Ile Tyr Ile Asp Ser Leu Met Lys
    130                 135                 140

Lys Ser Lys Arg Ala Ile Arg Leu Phe Lys Glu Gly Lys Glu Arg Met
145                 150                 155                 160

Tyr Glu Glu Gln Ser Gln Asp Arg Arg Asn Leu Thr Lys Leu Ser Leu
                165                 170                 175

Ile Phe Ser His Met Leu Ala Glu Ile Lys Ala Ile Phe Pro Asn Gly
            180                 185                 190

Gln Phe Gln Gly Asp Asn Phe Arg Ile Thr Lys Ala Asp Ala Ala Glu
        195                 200                 205

Phe Trp Arg Lys Phe Gly Asp Lys Thr Ile Val Pro Trp Lys Val
    210                 215                 220

Phe Arg Gln Cys Leu His Glu Val His Gln Ile Ser Ser Gly Leu Glu
225                 230                 235                 240

Ala Met Ala Leu Lys Ser Thr Ile Asp Leu Thr Cys Asn Asp Tyr Ile
                245                 250                 255

Ser Val Phe Glu Phe Asp Ile Phe Thr Arg Leu Phe Gln Pro Trp Gly
```

-continued

```
                260                 265                 270
Ser Ile Leu Arg Asn Trp Asn Phe Leu Ala Val Thr His Pro Gly Tyr
                275                 280                 285

Met Ala Phe Leu Thr Tyr Asp Glu Val Lys Ala Arg Leu Gln Lys Tyr
290                 295                 300

Ser Thr Lys Pro Gly Ser Tyr Ile Phe Arg Leu Ser Cys Thr Arg Leu
305                 310                 315                 320

Gly Gln Trp Ala Ile Gly Tyr Val Thr Gly Asp Gly Asn Ile Leu Gln
                325                 330                 335

Thr Ile Pro His Asn Lys Pro Leu Phe Gln Ala Leu Ile Asp Gly Ser
                340                 345                 350

Arg Glu Gly Phe Tyr Leu Tyr Pro Asp Gly Arg Ser Tyr Asn Pro Asp
                355                 360                 365

Leu Thr Gly Leu Cys Glu Pro Thr Pro His Asp His Ile Lys Val Thr
370                 375                 380

Gln Glu Gln Tyr Glu Leu Tyr Cys Glu Met Gly Ser Thr Phe Gln Leu
385                 390                 395                 400

Cys Lys Ile Cys Ala Glu Asn Asp Lys Asp Val Lys Ile Glu Pro Cys
                405                 410                 415

Gly His Leu Met Cys Thr Ser Cys Leu Thr Ala Trp Gln Glu Ser Asp
                420                 425                 430

Gly Gln Gly Cys Pro Phe Cys Arg Cys Glu Ile Lys Gly Thr Glu Pro
                435                 440                 445

Ile Ile Val Asp Pro Phe Asp Pro Arg Asp Glu Gly Ser Arg Cys Cys
450                 455                 460

Ser Ile Ile Asp Pro Phe Gly Met Pro Met Leu Asp Leu Asp Asp Asp
465                 470                 475                 480

Asp Asp Arg Glu Glu Ser Leu Met Met Asn Arg Leu Ala Asn Val Arg
                485                 490                 495

Lys Cys Thr Asp Arg Gln Asn Ser Pro Val Thr Ser Pro Gly Ser Ser
                500                 505                 510

Pro Leu Ala Gln Arg Arg Lys Pro Gln Pro Asp Pro Leu Gln Ile Pro
                515                 520                 525

His Leu Ser Leu Pro Pro Val Pro Pro Arg Leu Asp Leu Ile Gln Lys
                530                 535                 540

Gly Ile Val Arg Ser Pro Cys Gly Ser Pro Thr Gly Ser Pro Lys Ser
545                 550                 555                 560

Ser Pro Cys Met Val Arg Lys Gln Asp Lys Pro Leu Pro Ala Pro Pro
                565                 570                 575

Pro Pro Leu Arg Asp Pro Pro Pro Pro Glu Arg Pro Pro Pro
                580                 585                 590

Ile Pro Pro Asp Asn Arg Leu Ser Arg His Ile His His Val Glu Ser
                595                 600                 605

Val Pro Ser Arg Asp Pro Met Pro Leu Glu Ala Trp Cys Pro Arg
610                 615                 620

Asp Val Phe Gly Thr Asn Gln Leu Val Gly Cys Arg Leu Leu Gly Glu
625                 630                 635                 640

Gly Ser Pro Lys Pro Gly Ile Thr Ala Ser Ser Asn Val Asn Gly Arg
                645                 650                 655

His Ser Arg Val Gly Ser Asp Pro Val Leu Met Arg Lys His Arg Arg
                660                 665                 670

His Asp Leu Pro Leu Glu Gly Ala Lys Val Phe Ser Asn Gly His Leu
                675                 680                 685
```

-continued

Gly Ser Glu Glu Tyr Asp Val Pro Pro Arg Leu Ser Pro Pro Pro
690                 695                 700

Val Thr Thr Leu Leu Pro Ser Ile Lys Cys Thr Gly Pro Leu Ala Asn
705                 710                 715                 720

Ser Leu Ser Glu Lys Thr Arg Asp Pro Val Glu Glu Asp Asp Glu
            725                 730                 735

Tyr Lys Ile Pro Ser Ser His Pro Val Ser Leu Asn Ser Gln Pro Ser
            740                 745                 750

His Cys His Asn Val Lys Pro Pro Val Arg Ser Cys Asp Asn Gly His
            755                 760                 765

Cys Met Leu Asn Gly Thr His Gly Pro Ser Ser Glu Lys Lys Ser Asn
770                 775                 780

Ile Pro Asp Leu Ser Ile Tyr Leu Lys Gly Asp Val Phe Asp Ser Ala
785                 790                 795                 800

Ser Asp Pro Val Pro Leu Pro Ala Arg Pro Pro Thr Arg Asp Asn
            805                 810                 815

Pro Lys His Gly Ser Ser Leu Asn Arg Thr Pro Ser Asp Tyr Asp Leu
            820                 825                 830

Leu Ile Pro Pro Leu Gly Glu Asp Ala Phe Asp Ala Leu Pro Pro Ser
            835                 840                 845

Leu Pro Pro Pro Pro Pro Ala Arg His Ser Leu Ile Glu His Ser
850                 855                 860

Lys Pro Pro Gly Ser Ser Ser Arg Pro Ser Ser Gly Gln Asp Leu Phe
865                 870                 875                 880

Leu Leu Pro Ser Asp Pro Phe Val Asp Leu Ala Ser Gly Gln Val Pro
            885                 890                 895

Leu Pro Pro Ala Arg Arg Leu Pro Gly Glu Asn Val Lys Thr Asn Arg
            900                 905                 910

Thr Ser Gln Asp Tyr Asp Gln Leu Pro Ser Cys Ser Asp Gly Ser Gln
            915                 920                 925

Ala Pro Ala Arg Pro Pro Lys Pro Arg Pro Arg Arg Thr Ala Pro Glu
            930                 935                 940

Ile His His Arg Lys Pro His Gly Pro Glu Ala Ala Leu Glu Asn Val
945                 950                 955                 960

Asp Ala Lys Ile Ala Lys Leu Met Gly Glu Gly Tyr Ala Phe Glu Glu
            965                 970                 975

Val Lys Arg Ala Leu Glu Ile Ala Gln Asn Asn Val Glu Val Ala Arg
            980                 985                 990

Ser Ile Leu Arg Glu Phe Ala Phe Pro Pro Pro Val Ser Pro Arg Leu
            995                 1000                1005

Asn Leu
    1010

<210> SEQ ID NO 112
<211> LENGTH: 19
<212> TYPE: DNA
<213> ORGANISM: Artificial Sequence
<220> FEATURE:
<223> OTHER INFORMATION: siRNA/shRNAi sequences for human Cbl-b

<400> SEQUENCE: 112
gcctgataca tatcagcat                                                    19

<210> SEQ ID NO 113
<211> LENGTH: 19

```
<212> TYPE: DNA
<213> ORGANISM: Artificial Sequence
<220> FEATURE:
<223> OTHER INFORMATION: siRNA/shRNAi sequences for human Cbl-b

<400> SEQUENCE: 113
gcggaattgg aatttctta                                               19

<210> SEQ ID NO 114
<211> LENGTH: 19
<212> TYPE: DNA
<213> ORGANISM: Artificial Sequence
<220> FEATURE:
<223> OTHER INFORMATION: siRNA/shRNAi sequences for human Cbl-b

<400> SEQUENCE: 114
gcatgccgat gctagactt                                               19

<210> SEQ ID NO 115
<211> LENGTH: 19
<212> TYPE: DNA
<213> ORGANISM: Artificial Sequence
<220> FEATURE:
<223> OTHER INFORMATION: siRNA/shRNAi sequences for human Cbl-b

<400> SEQUENCE: 115
gcctgataca tatcagcat                                               19

<210> SEQ ID NO 116
<211> LENGTH: 21
<212> TYPE: DNA
<213> ORGANISM: Artificial Sequence
<220> FEATURE:
<223> OTHER INFORMATION: siRNA/shRNAi sequences for human Cbl-b

<400> SEQUENCE: 116
ggagagaatg tatgaagaac a                                            21

<210> SEQ ID NO 117
<211> LENGTH: 21
<212> TYPE: DNA
<213> ORGANISM: Artificial Sequence
<220> FEATURE:
<223> OTHER INFORMATION: siRNA/shRNAi sequences for human Cbl-b

<400> SEQUENCE: 117
gcggaattgg aatttcttag c                                            21

<210> SEQ ID NO 118
<211> LENGTH: 21
<212> TYPE: DNA
<213> ORGANISM: Artificial Sequence
<220> FEATURE:
<223> OTHER INFORMATION: siRNA/shRNAi sequences for human Cbl-b

<400> SEQUENCE: 118
gcacgactac agaaatatag c                                            21

<210> SEQ ID NO 119
<211> LENGTH: 21
<212> TYPE: DNA
<213> ORGANISM: Artificial Sequence
<220> FEATURE:
<223> OTHER INFORMATION: siRNA/shRNAi sequences for human Cbl-b

<400> SEQUENCE: 119
```
ggaatatctt acagaccata c                                              21

<210> SEQ ID NO 120
<211> LENGTH: 21
<212> TYPE: DNA
<213> ORGANISM: Artificial Sequence
<220> FEATURE:
<223> OTHER INFORMATION: siRNA/shRNAi sequences for human Cbl-b

<400> SEQUENCE: 120
gcaccaaacc cggaagctat a                                              21

<210> SEQ ID NO 121
<211> LENGTH: 21
<212> TYPE: DNA
<213> ORGANISM: Artificial Sequence
<220> FEATURE:
<223> OTHER INFORMATION: siRNA/shRNAi sequences for human Cbl-b

<400> SEQUENCE: 121
gcctggatct aattcagaaa g                                              21

<210> SEQ ID NO 122
<211> LENGTH: 21
<212> TYPE: DNA
<213> ORGANISM: Artificial Sequence
<220> FEATURE:
<223> OTHER INFORMATION: siRNA/shRNAi sequences for human Cbl-b

<400> SEQUENCE: 122
ggaatcacag cgagttcaaa t                                              21

<210> SEQ ID NO 123
<211> LENGTH: 21
<212> TYPE: DNA
<213> ORGANISM: Artificial Sequence
<220> FEATURE:
<223> OTHER INFORMATION: siRNA/shRNAi sequences for human Cbl-b

<400> SEQUENCE: 123
ggaacacatg gtccatcttc a                                              21

<210> SEQ ID NO 124
<211> LENGTH: 21
<212> TYPE: DNA
<213> ORGANISM: Artificial Sequence
<220> FEATURE:
<223> OTHER INFORMATION: siRNA/shRNAi sequences for human Cbl-b

<400> SEQUENCE: 124
gcatagtctc attgaacatt c                                              21

<210> SEQ ID NO 125
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 125
gttgcgtttc cacgtctcgg                                                20

<210> SEQ ID NO 126
<211> LENGTH: 20
<212> TYPE: DNA
<213> ORGANISM: Artificial Sequence

```
<220> FEATURE:
<223> OTHER INFORMATION: CRISPR/CAS9 target sequences for human Cbl-b

<400> SEQUENCE: 126
gaacagctcg ctcccgaaga                                                   20

<210> SEQ ID NO 127
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 127
attgttgcgt ttccacgtct                                                   20

<210> SEQ ID NO 128
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 128
agtgctgctg cggcgtcccg                                                   20

<210> SEQ ID NO 129
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 129
aggaggagga gaccgctcgc                                                   20

<210> SEQ ID NO 130
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 130
gaaggagcaa cccagcgcgc                                                   20

<210> SEQ ID NO 131
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 131
gcgcgcaggc ctccgagacg                                                   20

<210> SEQ ID NO 132
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 132
cgtctcggag gcctgcgcgc                                                   20
```

<210> SEQ ID NO 133
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 133
gtcccgcggc ctccccgagt                                             20

<210> SEQ ID NO 134
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 134
ctcccctccc gcccgactcg                                             20

<210> SEQ ID NO 135
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 135
gacgccgcag cagcactagc                                             20

<210> SEQ ID NO 136
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 136
gtctcggagg cctgcgcgct                                             20

<210> SEQ ID NO 137
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 137
gcggcctccc cgagtcgggc                                             20

<210> SEQ ID NO 138
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 138
ccctcccgcc cgactcgggg                                             20

<210> SEQ ID NO 139
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b -continued

<400> SEQUENCE: 139
cgcggcctcc ccgagtcggg                                           20

<210> SEQ ID NO 140
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 140
ctccccgagt cgggcgggag                                           20

<210> SEQ ID NO 141
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 141
cgggtgtgga tttgtcttga                                           20

<210> SEQ ID NO 142
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 142
gcctccccga gtcgggcggg                                           20

<210> SEQ ID NO 143
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 143
tcccgcggcc tccccgagtc                                           20

<210> SEQ ID NO 144
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 144
cgcccgactc ggggaggccg                                           20

<210> SEQ ID NO 145
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 145
ctctcccctc ccgcccgact                                           20

<210> SEQ ID NO 146

```
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 146
tctcccctcc cgcccgactc                                                    20

<210> SEQ ID NO 147
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 147
agcgatccca ctcccagccg                                                    20

<210> SEQ ID NO 148
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 148
tcagcgatcc cactcccagc                                                    20

<210> SEQ ID NO 149
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 149
cgctgggttg ctccttcttc                                                    20

<210> SEQ ID NO 150
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 150
gcccgactcg gggaggccgc                                                    20

<210> SEQ ID NO 151
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 151
gcgctgggtt gctccttctt                                                    20

<210> SEQ ID NO 152
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 152
```
cctccccgag tcgggcggga                                          20

<210> SEQ ID NO 153
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 153
tgtgtgtggg gagccccggc                                          20

<210> SEQ ID NO 154
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 154
gtgtgtgggg agccccggct                                          20

<210> SEQ ID NO 155
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 155
cgctggacac cccacccctg                                          20

<210> SEQ ID NO 156
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 156
gccgcagcag cactagcagg                                          20

<210> SEQ ID NO 157
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 157
cggggctccc cacacacact                                          20

<210> SEQ ID NO 158
<211> LENGTH: 20
<212> TYPE: DNA
<213> ORGANISM: Artificial Sequence
<220> FEATURE:
<223> OTHER INFORMATION: CRISPR/CAS9 target sequences for human Cbl-b

<400> SEQUENCE: 158
ctgggtcctg tgtgtgccac                                          20

<210> SEQ ID NO 159
<211> LENGTH: 2952
<212> TYPE: DNA

<213> ORGANISM: Canis lupus

<400> SEQUENCE: 159

```
atggcaaatt ctatgaatgg cagaaaccct ggtggtcgag gaggaaaccc ccgaaaagga      60
cggattttgg gtatcattga tgctattcaa gatgcagttg gacctccgaa gcaagcagca     120
gcagatcgca ggacggtgga gaaaacttgg aaactcatgg acaaagtggt cagactgtgt     180
caaaatccca agcttcagtt gaaaaatagc ccaccatata tacttgatat cttacctgat     240
acatatcagc atttacgact tatactgagt aaatatgatg acaaccagaa acttgcccaa     300
ctcagtgaga atgagtattt taaaatctac atcgatagtc taatgaaaaa gtcaaagcgg     360
gcaataagac tctttaaaga aggcaaggag aggatgtatg aagagcagtc acaggacaga     420
cgaaatctca caaactgtc ccttatcttc agtcacatgc tggcagaaat caaagcaatc     480
tttcccaatg ggcagttcca gggagataac tttcgtatca cgaaagcaga tgctgctgaa     540
ttctggagaa agttttttgg agacaaaact attgtaccat ggaaagtatt cagacagtgc     600
cttcatgagg ttcatcaaat tagctctggc ctggaagcaa tggctctgaa atcaacaatt     660
gatttaactt gtaatgatta catttcagtt tttgaatttg atattttac caggctcttt     720
cagccttggg gctctatttt acggaattgg aatttcttag ctgtaacaca tccaggttac     780
atggcatttc tcacatacga tgaagttaaa gcacgactgc agaaatacag caccaaacct     840
ggaagctaca ttttccggtt aagctgcacc agattgggac agtgggccat ggctatgtg      900
acagggatg gcaatatctt acagaccata ccacataaca agcccttgtt tcaagccctg     960
attgatggca gcagggaagg attctatctt tatcctgatg ggaggagtta taatcctgat    1020
ttaactggat tatgtgaacc cacaccacat gaccatataa agttacgca ggaacaatat    1080
gaattatatt gtgaaatggg ctccactttt cagctctgta aaatttgtgc tgagaacgac    1140
aaagatgtca agattgagcc ctgtgggcat ttgatgtgca cctcttgcct tacagcgtgg    1200
caggagtcgg acggccaagg ctgccccttt tgccgctgtg aaataaaagg aacagagccc    1260
ataatcgtgg accctttga tccaagagat gaaggttcca ggtgctgtag catcattgac    1320
cccctttggaa tgccaatgct ggacctggat gatgacgatg accgagaaga gtccttgatg    1380
atgaatcggt tggcaaatgt tcgaaagtgc actgataggc aaaattcacc agtcacatca    1440
ccaggatcct ctccccttgc acagagaaga aagccacatc cagatcctct ccagatccca    1500
catctgagcc tgccaccagt acctcctcgc ctggatctaa ttcagaaagg catagttcgg    1560
tctccctgtg gcagtcccac tggttcacca aagtcttctc cttgcatggt gagaaaacaa    1620
gataaaccac tcccagcacc gcctcctccc ttaagagatc ctcctccacc tccccctgag    1680
agacctcccc cgatcccacc tgacaacaga ctgagtcgac acttccatca cgtggaaagt    1740
gtgccttcta gagaccagcc aatgcctctt gaagcctggt gccctcggga tgtgtttgga    1800
actaatcagt cagtggggtt g tcgacaatta ggggatggct ctccaaagcc tggaatcaca    1860
gcaagttcaa atgtaaatgg aaggcacagt agaatgggct ctgaccctgt gcttctgcga    1920
aaacacagac gccacgattt gcctttagaa ggagccaagg tcttttccaa tggtcacctg    1980
ggaagcgaag agtacgatgt tcctccccgg ctttcacctc ctcctccagc tgccaccctt    2040
gtccctagca tcaagtgtac tggcccgtta gcaaatcccc tttcagagaa accagagac     2100
ccagtcgagg aagatgatga tgaatacaag attccttcat cccatcctgt ttccctgaat    2160
tcacaaccat ctcattgcca taacgtaaaa cctcctctta ggtcttgtga taatggtcat    2220
tgtgtattga atggaacaca tggtacatct tcagaggtga agaaatcaaa catccctgaa    2280
```

-continued

```
ttaggcattt atttaaaggg agatgttttt gattcagcct ctgatccagt gccattacca     2340
cctgccaggc ctccaactcg ggacaatcca aagcatggtt cttcactcaa caggacgccc     2400
tctgattatg atcttctcat ccctccatta ggtgaagatg cttttgatgc cctcccccca     2460
tccctcccgc ctcccccacc tcccgcaagg cacagcctca tcgaacactc taaacctccc     2520
ggctccaata gccgaccatc ctcaggacag gaccttttcc ttcttccttc agacccctcc     2580
tttgatccag taagtggtca agtccctctg cctcctgcta ggagattacc aggggaaaat     2640
gtcaaatcca acagaacatc acaggactat gatcagcttc cttcagcttc agatggttcg     2700
caggcaccag cccggcctcc caagccgcgc ccgcgcagga ccgcccccga ggtccagcac     2760
cggaagcccc acgggcccga ggcagcgtcg gaaaacgtgg acgcgaagat cgccaaactc     2820
atgggggagg gctacgcctt cgaggaagtg aagagggcgc tggagatcgc ccagaacaac     2880
gtcgaggtgg cccggagcat cctgcgcgag ttcgcctacc gccgcccgt ctccccgcgg      2940 ctgcacctct ag                                                        2952
```

<210> SEQ ID NO 160
<211> LENGTH: 983
<212> TYPE: PRT
<213> ORGANISM: Canis lupus

<400> SEQUENCE: 160

```
Met Ala Asn Ser Met Asn Gly Arg Asn Pro Gly Gly Arg Gly Gly Asn
1               5                   10                  15

Pro Arg Lys Gly Arg Ile Leu Gly Ile Ile Asp Ala Ile Gln Asp Ala
            20                  25                  30

Val Gly Pro Pro Lys Gln Ala Ala Asp Arg Arg Thr Val Glu Lys
        35                  40                  45

Thr Trp Lys Leu Met Asp Lys Val Val Arg Leu Cys Gln Asn Pro Lys
    50                  55                  60

Leu Gln Leu Lys Asn Ser Pro Pro Tyr Ile Leu Asp Ile Leu Pro Asp
65                  70                  75                  80

Thr Tyr Gln His Leu Arg Leu Ile Leu Ser Lys Tyr Asp Asp Asn Gln
                85                  90                  95

Lys Leu Ala Gln Leu Ser Glu Asn Glu Tyr Phe Lys Ile Tyr Ile Asp
            100                 105                 110

Ser Leu Met Lys Lys Ser Lys Arg Ala Ile Arg Leu Phe Lys Glu Gly
        115                 120                 125

Lys Glu Arg Met Tyr Glu Glu Gln Ser Gln Asp Arg Arg Asn Leu Thr
    130                 135                 140

Lys Leu Ser Leu Ile Phe Ser His Met Leu Ala Glu Ile Lys Ala Ile
145                 150                 155                 160

Phe Pro Asn Gly Gln Phe Gln Gly Asp Asn Phe Arg Ile Thr Lys Ala
                165                 170                 175

Asp Ala Ala Glu Phe Trp Arg Lys Phe Gly Asp Lys Thr Ile Val
            180                 185                 190

Pro Trp Lys Val Phe Arg Gln Cys Leu His Glu Val His Gln Ile Ser
        195                 200                 205

Ser Gly Leu Glu Ala Met Ala Leu Lys Ser Thr Ile Asp Leu Thr Cys
    210                 215                 220

Asn Asp Tyr Ile Ser Val Phe Glu Phe Asp Ile Phe Thr Arg Leu Phe
225                 230                 235                 240

Gln Pro Trp Gly Ser Ile Leu Arg Asn Trp Asn Phe Leu Ala Val Thr
```

```
            245                 250                 255
His Pro Gly Tyr Met Ala Phe Leu Thr Tyr Asp Glu Val Lys Ala Arg
        260                 265                 270

Leu Gln Lys Tyr Ser Thr Lys Pro Gly Ser Tyr Ile Phe Arg Leu Ser
    275                 280                 285

Cys Thr Arg Leu Gly Gln Trp Ala Ile Gly Tyr Val Thr Gly Asp Gly
290                 295                 300

Asn Ile Leu Gln Thr Ile Pro His Asn Lys Pro Leu Phe Gln Ala Leu
305                 310                 315                 320

Ile Asp Gly Ser Arg Glu Gly Phe Tyr Leu Tyr Pro Asp Gly Arg Ser
                325                 330                 335

Tyr Asn Pro Asp Leu Thr Gly Leu Cys Glu Pro Thr Pro His Asp His
            340                 345                 350

Ile Lys Val Thr Gln Glu Gln Tyr Glu Leu Tyr Cys Glu Met Gly Ser
        355                 360                 365

Thr Phe Gln Leu Cys Lys Ile Cys Ala Glu Asn Asp Lys Asp Val Lys
    370                 375                 380

Ile Glu Pro Cys Gly His Leu Met Cys Thr Ser Cys Leu Thr Ala Trp
385                 390                 395                 400

Gln Glu Ser Asp Gly Gln Gly Cys Pro Phe Cys Arg Cys Glu Ile Lys
                405                 410                 415

Gly Thr Glu Pro Ile Ile Val Asp Pro Phe Asp Pro Arg Asp Glu Gly
            420                 425                 430

Ser Arg Cys Cys Ser Ile Ile Asp Pro Phe Gly Met Pro Met Leu Asp
        435                 440                 445

Leu Asp Asp Asp Asp Arg Glu Glu Ser Leu Met Met Asn Arg Leu
450                 455                 460

Ala Asn Val Arg Lys Cys Thr Asp Arg Gln Asn Ser Pro Val Thr Ser
465                 470                 475                 480

Pro Gly Ser Ser Pro Leu Ala Gln Arg Arg Lys Pro His Pro Asp Pro
                485                 490                 495

Leu Gln Ile Pro His Leu Ser Leu Pro Pro Val Pro Pro Arg Leu Asp
            500                 505                 510

Leu Ile Gln Lys Gly Ile Val Arg Ser Pro Cys Gly Ser Pro Thr Gly
        515                 520                 525

Ser Pro Lys Ser Ser Pro Cys Met Val Arg Lys Gln Asp Lys Pro Leu
    530                 535                 540

Pro Ala Pro Pro Pro Leu Arg Asp Pro Pro Pro Pro Pro Glu
545                 550                 555                 560

Arg Pro Pro Pro Ile Pro Pro Asp Asn Arg Leu Ser Arg His Phe His
                565                 570                 575

His Val Glu Ser Val Pro Ser Arg Asp Gln Pro Met Pro Leu Glu Ala
            580                 585                 590

Trp Cys Pro Arg Asp Val Phe Gly Thr Asn Gln Ser Val Gly Cys Arg
        595                 600                 605

Gln Leu Gly Asp Gly Ser Pro Lys Pro Gly Ile Thr Ala Ser Ser Asn
    610                 615                 620

Val Asn Gly Arg His Ser Arg Met Gly Ser Asp Pro Val Leu Leu Arg
625                 630                 635                 640

Lys His Arg Arg His Asp Leu Pro Leu Glu Gly Ala Lys Val Phe Ser
                645                 650                 655

Asn Gly His Leu Gly Ser Glu Glu Tyr Asp Val Pro Pro Arg Leu Ser
            660                 665                 670
```

```
Pro Pro Pro Ala Ala Thr Leu Val Pro Ser Ile Lys Cys Thr Gly
        675                 680                 685
Pro Leu Ala Asn Pro Leu Ser Glu Lys Thr Arg Asp Pro Val Glu Glu
690                 695                 700
Asp Asp Asp Glu Tyr Lys Ile Pro Ser Ser His Pro Val Ser Leu Asn
705                 710                 715                 720
Ser Gln Pro Ser His Cys His Asn Val Lys Pro Pro Leu Arg Ser Cys
            725                 730                 735
Asp Asn Gly His Cys Val Leu Asn Gly Thr His Gly Thr Ser Ser Glu
            740                 745                 750
Val Lys Lys Ser Asn Ile Pro Glu Leu Gly Ile Tyr Leu Lys Gly Asp
            755                 760                 765
Val Phe Asp Ser Ala Ser Asp Pro Val Pro Leu Pro Ala Arg Pro
770                 775                 780
Pro Thr Arg Asp Asn Pro Lys His Gly Ser Ser Leu Asn Arg Thr Pro
785                 790                 795                 800
Ser Asp Tyr Asp Leu Leu Ile Pro Pro Leu Gly Glu Asp Ala Phe Asp
                805                 810                 815
Ala Leu Pro Pro Ser Leu Pro Pro Pro Pro Ala Arg His Ser
            820                 825                 830
Leu Ile Glu His Ser Lys Pro Pro Gly Ser Asn Ser Arg Pro Ser Ser
            835                 840                 845
Gly Gln Asp Leu Phe Leu Leu Pro Ser Asp Pro Phe Phe Asp Pro Val
850                 855                 860
Ser Gly Gln Val Pro Leu Pro Pro Ala Arg Arg Leu Pro Gly Glu Asn
865                 870                 875                 880
Val Lys Ser Asn Arg Thr Ser Gln Asp Tyr Asp Gln Leu Pro Ser Ala
                885                 890                 895
Ser Asp Gly Ser Gln Ala Pro Ala Arg Pro Pro Lys Pro Arg Pro Arg
                900                 905                 910
Arg Thr Ala Pro Glu Val Gln His Arg Lys Pro His Gly Pro Glu Ala
            915                 920                 925
Ala Ser Glu Asn Val Asp Ala Lys Ile Ala Lys Leu Met Gly Glu Gly
            930                 935                 940
Tyr Ala Phe Glu Glu Val Lys Arg Ala Leu Glu Ile Ala Gln Asn Asn
945                 950                 955                 960
Val Glu Val Ala Arg Ser Ile Leu Arg Glu Phe Ala Tyr Pro Pro Pro
                965                 970                 975
Val Ser Pro Arg Leu His Leu
            980

<210> SEQ ID NO 161
<211> LENGTH: 19
<212> TYPE: DNA
<213> ORGANISM: Artificial Sequence
<220> FEATURE:
<223> OTHER INFORMATION: siRNA/shRNA sequences for canine Cbl-b

<400> SEQUENCE: 161
cccaccatat atacttgat                                              19

<210> SEQ ID NO 162
<211> LENGTH: 19
<212> TYPE: DNA
<213> ORGANISM: Artificial Sequence
<220> FEATURE:
```

<223> OTHER INFORMATION: siRNA/shRNA sequences for canine Cbl-b

<400> SEQUENCE: 162
cctgatacat atcagcatt                                                19

<210> SEQ ID NO 163
<211> LENGTH: 19
<212> TYPE: DNA
<213> ORGANISM: Artificial Sequence
<220> FEATURE:
<223> OTHER INFORMATION: siRNA/shRNA sequences for canine Cbl-b

<400> SEQUENCE: 163
gcgggcaata agactcttt                                                19

<210> SEQ ID NO 164
<211> LENGTH: 19
<212> TYPE: DNA
<213> ORGANISM: Artificial Sequence
<220> FEATURE:
<223> OTHER INFORMATION: siRNA/shRNA sequences for canine Cbl-b

<400> SEQUENCE: 164
gcagaaatac agcaccaaa                                                19

<210> SEQ ID NO 165
<211> LENGTH: 19
<212> TYPE: DNA
<213> ORGANISM: Artificial Sequence
<220> FEATURE:
<223> OTHER INFORMATION: siRNA/shRNA sequences for canine Cbl-b

<400> SEQUENCE: 165
gcaccaaacc tggaagcta                                                19

<210> SEQ ID NO 166
<211> LENGTH: 19
<212> TYPE: DNA
<213> ORGANISM: Artificial Sequence
<220> FEATURE:
<223> OTHER INFORMATION: siRNA/shRNA sequences for canine Cbl-b

<400> SEQUENCE: 166
gcaatatctt acagaccat                                                19

<210> SEQ ID NO 167
<211> LENGTH: 19
<212> TYPE: DNA
<213> ORGANISM: Artificial Sequence
<220> FEATURE:
<223> OTHER INFORMATION: siRNA/shRNA sequences for canine Cbl-b

<400> SEQUENCE: 167
ccacaccaca tgaccatat                                                19

<210> SEQ ID NO 168
<211> LENGTH: 19
<212> TYPE: DNA
<213> ORGANISM: Artificial Sequence
<220> FEATURE:
<223> OTHER INFORMATION: siRNA/shRNA sequences for canine Cbl-b

<400> SEQUENCE: 168
gcctcctccc ttaagagat                                                19

```
<210> SEQ ID NO 169
<211> LENGTH: 19
<212> TYPE: DNA
<213> ORGANISM: Artificial Sequence
<220> FEATURE:
<223> OTHER INFORMATION: siRNA/shRNA sequences for canine Cbl-b

<400> SEQUENCE: 169
ccttcatccc atcctgttt                                                      19

<210> SEQ ID NO 170
<211> LENGTH: 19
<212> TYPE: DNA
<213> ORGANISM: Artificial Sequence
<220> FEATURE:
<223> OTHER INFORMATION: siRNA/shRNA sequences for canine Cbl-b

<400> SEQUENCE: 170
cctctgatcc agtgccatt                                                      19

<210> SEQ ID NO 171
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 171
cccccgaaaa ggacggattt tgg                                                 23

<210> SEQ ID NO 172
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 172
ccccgaaaag gacggatttt ggg                                                 23

<210> SEQ ID NO 173
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 173
ccaaaatccg tcctttcgg ggg                                                  23

<210> SEQ ID NO 174
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 174
cccaaaatcc gtccttttcg ggg                                                 23

<210> SEQ ID NO 175
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b
```

-continued

<400> SEQUENCE: 175
cgaggaggaa acccccgaaa agg                                              23

<210> SEQ ID NO 176
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 176
gggtttcctc ctcgaccacc agg                                              23

<210> SEQ ID NO 177
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 177
tacccaaaat ccgtcctttt cgg                                              23

<210> SEQ ID NO 178
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 178
agcaagcagc agcagatcgc agg                                              23

<210> SEQ ID NO 179
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 179
acccaaaatc cgtccttttc ggg                                              23

<210> SEQ ID NO 180
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 180
ggtttcctcc tcgaccacca ggg                                              23

<210> SEQ ID NO 181
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 181
tctgctgctg cttgcttcgg agg                                              23

<210> SEQ ID NO 182
<211> LENGTH: 23

```
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 182
agaaaccctg gtggtcgagg agg                                            23

<210> SEQ ID NO 183
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 183
ggcagaaacc ctggtggtcg agg                                            23

<210> SEQ ID NO 184
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 184
agcagcagca gatcgcagga cgg                                            23

<210> SEQ ID NO 185
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 185
agcagcagat cgcaggacgg tgg                                            23

<210> SEQ ID NO 186
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 186
gaggaaaccc ccgaaaagga cgg                                            23

<210> SEQ ID NO 187
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 187
gatgctattc aagatgcagt tgg                                            23

<210> SEQ ID NO 188
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 188
```

```
tctatgaatg gcagaaaccc tgg                                              23

<210> SEQ ID NO 189
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 189
cgatctgctg ctgcttgctt cgg                                              23

<210> SEQ ID NO 190
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 190
gcaggacggt ggagaaaact tgg                                              23

<210> SEQ ID NO 191
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 191
atgaatggca gaaaccctgg tgg                                              23

<210> SEQ ID NO 192
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl-b

<400> SEQUENCE: 192
ggagaaaact tggaaactca tgg                                              23

<210> SEQ ID NO 193
<211> LENGTH: 2721
<212> TYPE: DNA
<213> ORGANISM: Homo sapiens

<400> SEQUENCE: 193
atggccggca acgtgaagaa gagctctggg gccgggggcg gcagcggctc cggggggctcg      60 ggttcgggtg gcctgattgg gctcatgaag gacgccttcc agccgcacca ccaccaccac     120
caccacctca gcccccaccc gccggggacg gtggacaaga gatggtggaa gaagtgctgg     180
aagctcatgg acaaggtggt gcggttgtgt cagaacccaa agctgcgcct aaagaatagc     240
ccaccttata tcttagacct gctaccagat acctaccagc atctccgtac tatcttgtca     300
agatatgagg ggaagatgga gacacttgga gaaaatgagt attttagggt gtttatggag     360
aatttgatga gaaaactaa gcaaaccata gcctcttca aggagggaaa agaaagaatg     420
tatgaggaga attctcagcc taggcgaaac ctaaccaaac tgtccctcat cttcagccac     480
atgctggcag aactaaaagg aatctttcca agtggactct ttcagggaga cacatttcgg     540
attactaaag cagatgctgc ggaattttgg agaaaagctt tggggaaaaa gacaatagtc     600
ccttggaaga gctttcgaca ggctctacat gaagtgcatc ccatcagttc tgggctggag     660
```

```
gccatggctc tgaaatccac tattgatctg acctgcaatg attatatttc ggttttttgaa      720 tttgacatct ttacccgact cttttcagccc tggtcctctt tgctcaggaa ttggaacagc      780
cttgctgtaa ctcatcctgg ctacatggct tttttgacgt atgacgaagt gaaagctcgg      840
ctccagaaat tcattcacaa acctggcagt tatatcttcc ggctgagctg tactcgtctg      900
ggtcagtggg ctattgggta tgttactgct gatgggaaca ttctccagac aatccctcac      960
aataaacctc tcttccaagc actgattgat ggcttcaggg aaggcttcta tttgtttcct     1020
gatggacgaa atcagaatcc tgatctgact ggcttatgtg aaccaactcc ccaagaccat     1080
atcaaagtga cccaggaaca atatgaatta tactgtgaga tgggctccac attccaacta     1140
tgtaaaatat gtgctgaaaa tgataaggat gtaaagattg agccctgtgg cacctcatg      1200 tgcacatcct gtcttacatc ctggcaggaa tcagaaggtc agggctgtcc tttctgccga     1260
tgtgaaatta aggtactgaa acccatcgtg gtagatccgt ttgatcctag agggagtggc     1320
agcctgttga ggcaaggagc agagggagct ccctccccaa attatgatga tgatgatgat     1380
gaacgagctg atgatactct cttcatgatg aaggaattgg ctggtgccaa ggtggaacgg     1440
ccgccttctc cattctccat ggccccacaa gcttcccttc cccggtgcc accacgactt      1500 gaccttctgc cgcagcgagt atgtgttccc tcaagtgctt ctgctcttgg aactgcttct     1560
aaggctgctt ctggctccct tcataaagac aaaccattgc cagtacctcc cacacttcga     1620
gatcttccac caccaccgcc tccagaccgg ccatattctg ttggagcaga atcccgacct     1680
caaagacgcc ccttgccttg tacaccaggc gactgtccct ccagagacaa actgcccct      1740 gtccctctctc gccgccttgg agactcatgg ctgccccggc caatccccaa agtaccagta     1800
tctgccccaa gttccagtga tccctggaca ggaagagaat taaccaaccg gcactcactt     1860
ccattttcat tgccctcaca aatggagccc agaccagatg tgcctaggct cggaagcacg     1920
ttcagtctgg atacctccat gagtatgaat agcagcccat tagtaggtcc agagtgtgac     1980
caccccaaaa tcaaaccttc ctcatctgcc aatgccattt attctctggc tgccagacct     2040
cttcctgtgc caaaactgcc acctggggag caatgtgagg gtgaagagga cacagagtac     2100
atgactccct cttccaggcc tctacggcct ttggatacat cccagagttc acgagcatgt     2160
gattgcgacc agcagattga tagctgtacg tatgaagcaa tgtataatat tcagtcccag     2220
gcgccatcta tcaccgagag cagcaccttt ggtgaaggga atttggccgc agcccatgcc     2280
aacactggtc ccgaggagtc agaaaatgag gatgatgggt atgatgtccc aaagccacct     2340
gtgccggccg tgctggcccg ccgaactctc tcagatatct ctaatgccag ctcctccttt     2400
ggctggttgt ctctggatgg tgatcctaca acaaatgtca ctgaaggttc ccaagttccc     2460
gagaggcctc caaaaccatt cccgcggaga atcaactctg aacggaaagc tggcagctgt     2520
cagcaaggta gtggtcctgc cgcctctgct gccaccgcct caccctcagct ctccagtgag     2580 atcgagaacc tcatgagtca ggggtactcc taccaggaca tccagaaagc tttggtcatt     2640
gcccagaaca acatcgagat ggccaaaaac atcctccggg aatttgtttc catttcttct     2700
cctgcccatg tagctaccta g                                              2721
```

<210> SEQ ID NO 194
<211> LENGTH: 906
<212> TYPE: PRT
<213> ORGANISM: Homo sapiens

<400> SEQUENCE: 194

-continued

```
Met Ala Gly Asn Val Lys Lys Ser Ser Gly Ala Gly Gly Ser Gly
1               5                   10                  15

Ser Gly Gly Ser Gly Ser Gly Gly Leu Ile Gly Leu Met Lys Asp Ala
            20                  25                  30

Phe Gln Pro His His His His His His Leu Ser Pro His Pro Pro
            35                  40                  45

Gly Thr Val Asp Lys Lys Met Val Glu Lys Cys Trp Lys Leu Met Asp
50                  55                  60

Lys Val Val Arg Leu Cys Gln Asn Pro Lys Leu Ala Leu Lys Asn Ser
65                  70                  75                  80

Pro Pro Tyr Ile Leu Asp Leu Leu Pro Asp Thr Tyr Gln His Leu Arg
                85                  90                  95

Thr Ile Leu Ser Arg Tyr Glu Gly Lys Met Glu Thr Leu Gly Glu Asn
            100                 105                 110

Glu Tyr Phe Arg Val Phe Met Glu Asn Leu Met Lys Lys Thr Lys Gln
            115                 120                 125

Thr Ile Ser Leu Phe Lys Glu Gly Lys Glu Arg Met Tyr Glu Glu Asn
    130                 135                 140

Ser Gln Pro Arg Arg Asn Leu Thr Lys Leu Ser Leu Ile Phe Ser His
145                 150                 155                 160

Met Leu Ala Glu Leu Lys Gly Ile Phe Pro Ser Gly Leu Phe Gln Gly
                165                 170                 175

Asp Thr Phe Arg Ile Thr Lys Ala Asp Ala Ala Glu Phe Trp Arg Lys
            180                 185                 190

Ala Phe Gly Glu Lys Thr Ile Val Pro Trp Lys Ser Phe Arg Gln Ala
            195                 200                 205

Leu His Glu Val His Pro Ile Ser Ser Gly Leu Glu Ala Met Ala Leu
    210                 215                 220

Lys Ser Thr Ile Asp Leu Thr Cys Asn Asp Tyr Ile Ser Val Phe Glu
225                 230                 235                 240

Phe Asp Ile Phe Thr Arg Leu Phe Gln Pro Trp Ser Ser Leu Leu Arg
                245                 250                 255

Asn Trp Asn Ser Leu Ala Val Thr His Pro Gly Tyr Met Ala Phe Leu
            260                 265                 270

Thr Tyr Asp Glu Val Lys Ala Arg Leu Gln Lys Phe Ile His Lys Pro
            275                 280                 285

Gly Ser Tyr Ile Phe Arg Leu Ser Cys Thr Arg Leu Gly Gln Trp Ala
            290                 295                 300

Ile Gly Tyr Val Thr Ala Asp Gly Asn Ile Leu Gln Thr Ile Pro His
305                 310                 315                 320

Asn Lys Pro Leu Phe Gln Ala Leu Ile Asp Gly Phe Arg Glu Gly Phe
                325                 330                 335

Tyr Leu Phe Pro Asp Gly Arg Asn Gln Asn Pro Asp Leu Thr Gly Leu
            340                 345                 350

Cys Glu Pro Thr Pro Gln Asp His Ile Lys Val Thr Gln Glu Gln Tyr
            355                 360                 365

Glu Leu Tyr Cys Glu Met Gly Ser Thr Phe Gln Leu Cys Lys Ile Cys
    370                 375                 380

Ala Glu Asn Asp Lys Asp Val Lys Ile Glu Pro Cys Gly His Leu Met
385                 390                 395                 400

Cys Thr Ser Cys Leu Thr Ser Trp Gln Glu Ser Glu Gly Gln Gly Cys
                405                 410                 415

Pro Phe Cys Arg Cys Glu Ile Lys Gly Thr Glu Pro Ile Val Val Asp
```

-continued

```
                420                 425                 430
Pro Phe Asp Pro Arg Gly Ser Gly Ser Leu Leu Arg Gln Gly Ala Glu
            435                 440                 445
Gly Ala Pro Ser Pro Asn Tyr Asp Asp Asp Asp Glu Arg Ala Asp
    450                 455                 460
Asp Thr Leu Phe Met Met Lys Glu Leu Ala Gly Ala Lys Val Glu Arg
465                 470                 475                 480
Pro Pro Ser Pro Phe Ser Met Ala Pro Gln Ala Ser Leu Pro Pro Val
                485                 490                 495
Pro Pro Arg Leu Asp Leu Leu Pro Gln Arg Val Cys Val Pro Ser Ser
            500                 505                 510
Ala Ser Ala Leu Gly Thr Ala Ser Lys Ala Ala Ser Gly Ser Leu His
        515                 520                 525
Lys Asp Lys Pro Leu Pro Val Pro Pro Thr Leu Arg Asp Leu Pro Pro
    530                 535                 540
Pro Pro Pro Pro Asp Arg Pro Tyr Ser Val Gly Ala Glu Ser Arg Pro
545                 550                 555                 560
Gln Arg Arg Pro Leu Pro Cys Thr Pro Gly Asp Cys Pro Ser Arg Asp
                565                 570                 575
Lys Leu Pro Pro Val Pro Ser Ser Arg Leu Gly Asp Ser Trp Leu Pro
            580                 585                 590
Arg Pro Ile Pro Lys Val Pro Val Ser Ala Pro Ser Ser Asp Pro
        595                 600                 605
Trp Thr Gly Arg Glu Leu Thr Asn Arg His Ser Leu Pro Phe Ser Leu
    610                 615                 620
Pro Ser Gln Met Glu Pro Arg Pro Asp Val Pro Arg Leu Gly Ser Thr
625                 630                 635                 640
Phe Ser Leu Asp Thr Ser Met Ser Met Asn Ser Ser Pro Leu Val Gly
                645                 650                 655
Pro Glu Cys Asp His Pro Lys Ile Lys Pro Ser Ser Ser Ala Asn Ala
            660                 665                 670
Ile Tyr Ser Leu Ala Ala Arg Pro Leu Pro Val Pro Lys Leu Pro Pro
        675                 680                 685
Gly Glu Gln Cys Glu Gly Glu Glu Asp Thr Glu Tyr Met Thr Pro Ser
    690                 695                 700
Ser Arg Pro Leu Arg Pro Leu Asp Thr Ser Gln Ser Ser Arg Ala Cys
705                 710                 715                 720
Asp Cys Asp Gln Gln Ile Asp Ser Cys Thr Tyr Glu Ala Met Tyr Asn
                725                 730                 735
Ile Gln Ser Gln Ala Pro Ser Ile Thr Glu Ser Ser Thr Phe Gly Glu
            740                 745                 750
Gly Asn Leu Ala Ala Ala His Ala Asn Thr Gly Pro Glu Glu Ser Glu
        755                 760                 765
Asn Glu Asp Asp Gly Tyr Asp Val Pro Lys Pro Pro Val Pro Ala Val
    770                 775                 780
Leu Ala Arg Arg Thr Leu Ser Asp Ile Ser Asn Ala Ser Ser Ser Phe
785                 790                 795                 800
Gly Trp Leu Ser Leu Asp Gly Asp Pro Thr Thr Asn Val Thr Glu Gly
                805                 810                 815
Ser Gln Val Pro Glu Arg Pro Pro Lys Pro Phe Pro Arg Arg Ile Asn
            820                 825                 830
Ser Glu Arg Lys Ala Gly Ser Cys Gln Gln Gly Ser Gly Pro Ala Ala
        835                 840                 845
```

```
Ser Ala Ala Thr Ala Ser Pro Gln Leu Ser Ser Glu Ile Glu Asn Leu
        850                 855                 860

Met Ser Gln Gly Tyr Ser Tyr Gln Asp Ile Gln Lys Ala Leu Val Ile
865                 870                 875                 880

Ala Gln Asn Asn Ile Glu Met Ala Lys Asn Ile Leu Arg Glu Phe Val
            885                 890                 895

Ser Ile Ser Ser Pro Ala His Val Ala Thr
            900                 905

<210> SEQ ID NO 195
<211> LENGTH: 19
<212> TYPE: DNA
<213> ORGANISM: Artificial Sequence
<220> FEATURE:
<223> OTHER INFORMATION: siRNA/shRNAi sequences for human Cbl

<400> SEQUENCE: 195
ccagacaatc cctcacaat                                              19

<210> SEQ ID NO 196
<211> LENGTH: 19
<212> TYPE: DNA
<213> ORGANISM: Artificial Sequence
<220> FEATURE:
<223> OTHER INFORMATION: siRNA/shRNAi sequences for human Cbl

<400> SEQUENCE: 196
ggacacctca tgtgcacat                                              19

<210> SEQ ID NO 197
<211> LENGTH: 19
<212> TYPE: DNA
<213> ORGANISM: Artificial Sequence
<220> FEATURE:
<223> OTHER INFORMATION: siRNA/shRNAi sequences for human Cbl

<400> SEQUENCE: 197
ccaggcctct acggccttt                                              19

<210> SEQ ID NO 198
<211> LENGTH: 19
<212> TYPE: DNA
<213> ORGANISM: Artificial Sequence
<220> FEATURE:
<223> OTHER INFORMATION: siRNA/shRNAi sequences for human Cbl

<400> SEQUENCE: 198
ccagaaagct ttggtcatt                                              19

<210> SEQ ID NO 199
<211> LENGTH: 21
<212> TYPE: DNA
<213> ORGANISM: Artificial Sequence
<220> FEATURE:
<223> OTHER INFORMATION: siRNA/shRNAi sequences for human Cbl

<400> SEQUENCE: 199
gcctgattgg gctcatgaag g                                           21

<210> SEQ ID NO 200
<211> LENGTH: 21
<212> TYPE: DNA
<213> ORGANISM: Artificial Sequence
<220> FEATURE:
```

<223> OTHER INFORMATION: siRNA/shRNAi sequences for human Cbl

<400> SEQUENCE: 200
gggaacattc tccagacaat c                                    21

<210> SEQ ID NO 201
<211> LENGTH: 21
<212> TYPE: DNA
<213> ORGANISM: Artificial Sequence
<220> FEATURE:
<223> OTHER INFORMATION: siRNA/shRNAi sequences for human Cbl

<400> SEQUENCE: 201
gcttcaggga aggcttctat t                                    21

<210> SEQ ID NO 202
<211> LENGTH: 21
<212> TYPE: DNA
<213> ORGANISM: Artificial Sequence
<220> FEATURE:
<223> OTHER INFORMATION: siRNA/shRNAi sequences for human Cbl

<400> SEQUENCE: 202
gggaaggctt ctatttgttt c                                    21

<210> SEQ ID NO 203
<211> LENGTH: 21
<212> TYPE: DNA
<213> ORGANISM: Artificial Sequence
<220> FEATURE:
<223> OTHER INFORMATION: siRNA/shRNAi sequences for human Cbl

<400> SEQUENCE: 203
ggacacctca tgtgcacatc c                                    21

<210> SEQ ID NO 204
<211> LENGTH: 21
<212> TYPE: DNA
<213> ORGANISM: Artificial Sequence
<220> FEATURE:
<223> OTHER INFORMATION: siRNA/shRNAi sequences for human Cbl

<400> SEQUENCE: 204
gcagaatccc gacctcaaag a                                    21

<210> SEQ ID NO 205
<211> LENGTH: 21
<212> TYPE: DNA
<213> ORGANISM: Artificial Sequence
<220> FEATURE:
<223> OTHER INFORMATION: siRNA/shRNAi sequences for human Cbl

<400> SEQUENCE: 205
ggagcaatgt gagggtgaag a                                    21

<210> SEQ ID NO 206
<211> LENGTH: 21
<212> TYPE: DNA
<213> ORGANISM: Artificial Sequence
<220> FEATURE:
<223> OTHER INFORMATION: siRNA/shRNAi sequences for human Cbl

<400> SEQUENCE: 206
gcctctacgg cctttggata c                                    21

```
<210> SEQ ID NO 207
<211> LENGTH: 21
<212> TYPE: DNA
<213> ORGANISM: Artificial Sequence
<220> FEATURE:
<223> OTHER INFORMATION: siRNA/shRNAi sequences for human Cbl

<400> SEQUENCE: 207
gctgtacgta tgaagcaatg t                                              21

<210> SEQ ID NO 208
<211> LENGTH: 21
<212> TYPE: DNA
<213> ORGANISM: Artificial Sequence
<220> FEATURE:
<223> OTHER INFORMATION: siRNA/shRNAi sequences for human Cbl

<400> SEQUENCE: 208
ggtactccta ccaggacatc c                                              21

<210> SEQ ID NO 209
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 209
ctcggctcga ctgcgagcga                                                20

<210> SEQ ID NO 210
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 210
gccgccgccg gctatccggg                                                20

<210> SEQ ID NO 211
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 211
tccgcccgga tagccggcgg                                                20

<210> SEQ ID NO 212
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 212
gctcggctcg actgcgagcg                                                20

<210> SEQ ID NO 213
<211> LENGTH: 20
<212> TYPE: DNA
<213> ORGANISM: Artificial Sequence
<220> FEATURE:
<223> OTHER INFORMATION: CRISPR/CAS9 target sequences for human Cbl
```

```
<400> SEQUENCE: 213
tcgcagtcga gccgagccgg                                              20

<210> SEQ ID NO 214
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 214
cttcttcacg ttgccggcca                                              20

<210> SEQ ID NO 215
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 215
cgggttcggg tggcctgatt                                              20

<210> SEQ ID NO 216
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 216
cgctcgcagt cgagccgagc                                              20

<210> SEQ ID NO 217
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 217
ccgagccggc ggacccgcct                                              20

<210> SEQ ID NO 218
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 218
tcgggttcgg gtggcctgat                                              20

<210> SEQ ID NO 219
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 219
gccgagccgg cggacccgcc                                              20

<210> SEQ ID NO 220
<211> LENGTH: 20
```

```
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 220
agagctcttc ttcacgttgc                                              20

<210> SEQ ID NO 221
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 221
gccgccgccg ccggctatcc                                              20

<210> SEQ ID NO 222
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 222
cccaggcggg tccgccggct                                              20

<210> SEQ ID NO 223
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 223
cgtccttcat gagcccaatc                                              20

<210> SEQ ID NO 224
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 224
cggagcccag gcgggtccgc                                              20

<210> SEQ ID NO 225
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 225
tggcctgatt gggctcatga                                              20

<210> SEQ ID NO 226
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 226
```

-continued

```
tcacgttgcc ggccatggcc                                             20

<210> SEQ ID NO 227
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 227
cgccgccgcc gccggctatc                                             20

<210> SEQ ID NO 228
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 228
ggcaacgtga agaagagctc                                             20

<210> SEQ ID NO 229
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 229
cggctccggg ggctcgggtt                                             20

<210> SEQ ID NO 230
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 230
tccgggggct cgggttcggg                                             20

<210> SEQ ID NO 231
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 231
ggctccgggg gctcgggttc                                             20

<210> SEQ ID NO 232
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 232
gcaacgtgaa gaagagctct                                             20

<210> SEQ ID NO 233
<211> LENGTH: 20
<212> TYPE: DNA
<213> ORGANISM: Artificial Sequence
```

```
<220> FEATURE:
<223> OTHER INFORMATION: CRISPR/CAS9 target sequences for human Cbl

<400> SEQUENCE: 233
gcaacgtgaa gaagagctct                                                    20

<210> SEQ ID NO 234
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 234
gccacccgaa cccgagcccc                                                    20

<210> SEQ ID NO 235
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 235
cacgttgccg gccatggcct                                                    20

<210> SEQ ID NO 236
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 236
gcccggatag ccggcggcgg                                                    20

<210> SEQ ID NO 237
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 237
gaagaagagc tctggggccg                                                    20

<210> SEQ ID NO 238
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 238
caacgtgaag aagagctctg                                                    20

<210> SEQ ID NO 239
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 239
aagaagagct ctggggccgg                                                    20
```

```
<210> SEQ ID NO 240
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 240
gggagagaag cagggcgtga                                                 20

<210> SEQ ID NO 241
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 241
cggcagcggc tccgggggct                                                 20

<210> SEQ ID NO 242
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 242
cctgggcagg gtcggagccc                                                 20

<210> SEQ ID NO 243
<211> LENGTH: 20
<212> TYPE: DNA
<213> ORGANISM: Artificial Sequence
<220> FEATURE:
<223> OTHER INFORMATION: CRISPR/CAS9 target sequences for human Cbl

<400> SEQUENCE: 243
agagaagcag ggcgtgaagg                                                 20

<210> SEQ ID NO 244
<211> LENGTH: 2727
<212> TYPE: DNA
<213> ORGANISM: Canis lupus
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (1876)..(1876)
<223> OTHER INFORMATION: n is a, c, g, or t

<400> SEQUENCE: 244
atggccggca acgtgaagaa gagctccggg gccggggggcg gcggcggctc cgggggctcg    60
ggcggcctca tcgggctcat gaaggacgcc ttccagccgc accaccacca ccaccacctc   120
agcccccacc cgcccggcac cngtgacaag aagatggtgg agaagtgctg gaagctcatg   180
gacaaggtgg tgcggttgtg tcagaaccca agctgcgcg  taaagaatag cccaccttat   240
atcttagacc tgctgccaga tacctaccag catctccgca ctatcttgtc aagatatgag   300
gggaagatgg agacacttgg agaaaatgag tattttaggg tgttcatgga gaatttgatg   360
aagaaaacta agcagaccat aagcctcttc aaggagggga agaaagaat gtatgaggag   420 aattctcagc ctaggcgaaa cctaaccaaa ttgtccctga tcttcagcca catgctggca   480
```

```
gaactaaaag gaatctttcc aagtggactc tttcaaggag acacatttcg gattactaaa     540
gcagatgctg cagaattttg gaggaaagct tttggggaaa agacaatcgt cccttggaag     600
agtttccgcc aggcccttca tgaagtgcat cccatcagtt ctgggctcga ggccatggct     660
ctgaaatcca ctattgatct gacctgcaat gattatattt ctgtttttga atttgacatc     720
ttcacacgac tctttcagcc ctggtcctct ttgctcagga actggaacag tcttgctgta     780
actcatcctg gttacatggc tttcctgacg tatgatgaag tgaaagctcg gctccagaag     840
ttcattcaca aacctggcag ttacattttc cggttgagct gtactcgttt gggacagtgg     900
gctattgggt atgtcactgc tgatgggaac atcctccaga cgatccctca caataaacct     960
ctcttccaag ccctgattga cggcttcagg gaaggcttct atttgtttcc agatggacgg    1020
aatcagaatc ctgacctgac aggcctatgt gaaccaactc ccaagacca catcaaagtg    1080 acccaggaac aatatgaatt atactgtgag atgggctcca ccttccaact gtgtaaaata    1140
tgtgctgaga acgataagga tgtgaaaatt gagccctgtg acacctcat gtgcacatcc    1200 tgtcttacat cctggcagga atcagaaggc caaggctgcc ctttctgccg atgtgaaatt    1260
aaaggtactg agcccattgt ggtagatccg tttgaccctc gaggaagtgg cagcctactg    1320
aggcaaggag ctgagggagc tccctcccca aattatgaag atgatgacga tgaacgagct    1380
gatgattctc tctttatgat gaaggaactg gctggtgcca aggtgaacg gcctccttct    1440 ccgttctcga tggccccaca ggctcccctg ccccagtac caccacgtct tgacctccta    1500
caacagcgag tgtctgttcc ttctagtgct tctggtcttg gaactgcttc taaggtagct    1560
tctggctccc ttcataagga caaaccatta ccaatacccc ccacacttcg agatcttcca    1620 ccaccaccc ctccagaccg accatattct gttggaacag acaccgggcc tcagagacgt    1680
cccttgcctt gtacaccggg cgactgtcca tccagggaca aactgccgcc tgttccctct    1740
agccgtctcg gggaatcatg gctgcctcgg ccaatcccca aagtaccagt ggttgctcca    1800
aactcgagtg acccctggac ctctggtaga gaattaacca acaggcactc acttccattt    1860
tcattgccct cacaaatga acccagaaca gatgtgccta ggcttggagg cacattcaat    1920
gtggatactt ccatgaatgt gaataacagc ccactagcaa gttctgagtg tgagcacccc    1980
aaaatcaaac cttccgcatc tgccaatgcc atttattctc tggctgccag gcctcttcct    2040
gtgccaaagc tgcccctgg ggagcagtgt gaaggtgagg aggacacaga gtatatgacc    2100
ccctcctcta gacctctagg gcttccaaag ccagatggga acggcctttt ggagacaacc    2160
cagagttcac gagcatgtga ttgtgaccag cagatcgata gctgcacata tgaagcaatg    2220
tataatattc agtcccaagc gacaccatct gtcacagaga gcagcacctt tggtgaaggg    2280
agtctggctg cagcccacat cagcaccggc cccgaggaat cagaaaatga ggaggacggg    2340
tatgatgtcc ctaagccgcc catgccagca gtgctggccc gccggactct ctcagacatc    2400
tccaatgcca gttcctcctt tggctggttg tctctggaag gcgatcccac cacaaacttc    2460
actgagggtt cccaagttcc tgaaaggcct cccaaaccgt tccctcggag aatcaactct    2520
gaacgaaaag caggcagctg tcagcagggt ggtgccgctg ctgcctcacc acagctctcc    2580
agtgagattg agaacctcct gagccaggga tactcctacc aggacattca gaaagctctg    2640
gtcattgccc acaacaacat tgaaatggcc aagaacatcc tccgggaatt tgtttctatc    2700
tcttctcccg cccacgtagc cacctag                                       2727
```

<210> SEQ ID NO 245

```
<211> LENGTH: 908
<212> TYPE: PRT
<213> ORGANISM: Canis lupus
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (626)..(626)
<223> OTHER INFORMATION: Xaa can be any naturally occurring amino acid

<400> SEQUENCE: 245
```

Met Ala Gly Asn Val Lys Lys Ser Ser Gly Ala Gly Gly Gly Gly Gly
1               5                   10                  15

Ser Gly Gly Ser Gly Gly Leu Ile Gly Leu Met Lys Asp Ala Phe Gln
                20                  25                  30

Pro His His His His His His Leu Ser Pro His Pro Pro Gly Thr Xaa
            35                  40                  45

Asp Lys Lys Met Val Glu Lys Cys Trp Lys Leu Met Asp Lys Val Val
50                  55                  60

Arg Leu Cys Gln Asn Pro Lys Leu Ala Leu Lys Asn Ser Pro Pro Tyr
65                  70                  75                  80

Ile Leu Asp Leu Leu Pro Asp Thr Tyr Gln His Leu Arg Thr Ile Leu
                85                  90                  95

Ser Arg Tyr Glu Gly Lys Met Glu Thr Leu Gly Glu Asn Glu Tyr Phe
            100                 105                 110

Arg Val Phe Met Glu Asn Leu Met Lys Lys Thr Lys Gln Thr Ile Ser
        115                 120                 125

Leu Phe Lys Glu Gly Lys Glu Arg Met Tyr Glu Glu Asn Ser Gln Pro
130                 135                 140

Arg Arg Asn Leu Thr Lys Leu Ser Leu Ile Phe Ser His Met Leu Ala
145                 150                 155                 160

Glu Leu Lys Gly Ile Phe Pro Ser Gly Leu Phe Gln Gly Asp Thr Phe
                165                 170                 175

Arg Ile Thr Lys Ala Asp Ala Ala Glu Phe Trp Arg Lys Ala Phe Gly
            180                 185                 190

Glu Lys Thr Ile Val Pro Trp Lys Ser Phe Arg Gln Ala Leu His Glu
        195                 200                 205

Val His Pro Ile Ser Ser Gly Leu Glu Ala Met Ala Leu Lys Ser Thr
210                 215                 220

Ile Asp Leu Thr Cys Asn Asp Tyr Ile Ser Val Phe Glu Phe Asp Ile
225                 230                 235                 240

Phe Thr Arg Leu Phe Gln Pro Trp Ser Ser Leu Leu Arg Asn Trp Asn
                245                 250                 255

Ser Leu Ala Val Thr His Pro Gly Tyr Met Ala Phe Leu Thr Tyr Asp
            260                 265                 270

Glu Val Lys Ala Arg Leu Gln Lys Phe Ile His Lys Pro Gly Ser Tyr
        275                 280                 285

Ile Phe Arg Leu Ser Cys Thr Arg Leu Gly Gln Trp Ala Ile Gly Tyr
290                 295                 300

Val Thr Ala Asp Gly Asn Ile Leu Gln Thr Ile Pro His Asn Lys Pro
305                 310                 315                 320

Leu Phe Gln Ala Leu Ile Asp Gly Phe Arg Glu Gly Phe Tyr Leu Phe
                325                 330                 335

Pro Asp Gly Arg Asn Gln Asn Pro Asp Leu Thr Gly Leu Cys Glu Pro
            340                 345                 350

```
Thr Pro Gln Asp His Ile Lys Val Thr Gln Glu Gln Tyr Glu Leu Tyr
        355                 360                 365
Cys Glu Met Gly Ser Thr Phe Gln Leu Cys Lys Ile Cys Ala Glu Asn
    370                 375                 380
Asp Lys Asp Val Lys Ile Glu Pro Cys Gly His Leu Met Cys Thr Ser
385                 390                 395                 400
Cys Leu Thr Ser Trp Gln Glu Ser Gly Gln Gly Cys Pro Phe Cys
            405                 410                 415
Arg Cys Glu Ile Lys Gly Thr Glu Pro Ile Val Val Asp Pro Phe Asp
        420                 425                 430
Pro Arg Gly Ser Gly Ser Leu Leu Arg Gln Gly Ala Glu Gly Ala Pro
        435                 440                 445
Ser Pro Asn Tyr Glu Asp Asp Asp Glu Arg Ala Asp Asp Ser Leu
    450                 455                 460
Phe Met Met Lys Glu Leu Ala Gly Ala Lys Val Glu Arg Pro Pro Ser
465                 470                 475                 480
Pro Phe Ser Met Ala Pro Gln Ala Pro Leu Pro Val Pro Pro Arg
            485                 490                 495
Leu Asp Leu Leu Gln Gln Arg Val Ser Val Pro Ser Ser Ala Ser Gly
        500                 505                 510
Leu Gly Thr Ala Ser Lys Val Ala Ser Gly Ser Leu His Lys Asp Lys
        515                 520                 525
Pro Leu Pro Ile Pro Pro Thr Leu Arg Asp Leu Pro Pro Pro Pro
        530                 535                 540
Pro Asp Arg Pro Tyr Ser Val Gly Thr Asp Thr Arg Pro Gln Arg Arg
545                 550                 555                 560
Pro Leu Pro Cys Thr Pro Gly Asp Cys Pro Ser Arg Asp Lys Leu Pro
            565                 570                 575
Pro Val Pro Ser Ser Arg Leu Gly Glu Ser Trp Leu Pro Arg Pro Ile
            580                 585                 590
Pro Lys Val Pro Val Val Ala Pro Asn Ser Ser Asp Pro Trp Thr Ser
        595                 600                 605
Gly Arg Glu Leu Thr Asn Arg His Ser Leu Pro Phe Ser Leu Pro Ser
        610                 615                 620
Gln Xaa Glu Pro Arg Thr Asp Val Pro Arg Leu Gly Gly Thr Phe Asn
625                 630                 635                 640
Val Asp Thr Ser Met Asn Val Asn Asn Ser Pro Leu Ala Ser Ser Glu
            645                 650                 655
Cys Glu His Pro Lys Ile Lys Pro Ser Ala Ser Ala Asn Ala Ile Tyr
            660                 665                 670
Ser Leu Ala Ala Arg Pro Leu Pro Val Pro Lys Leu Pro Pro Gly Glu
        675                 680                 685
Gln Cys Glu Gly Glu Glu Asp Thr Glu Tyr Met Thr Pro Ser Ser Arg
        690                 695                 700
Pro Leu Gly Leu Pro Lys Pro Asp Gly Lys Arg Pro Leu Glu Thr Thr
705                 710                 715                 720
Gln Ser Ser Arg Ala Cys Asp Cys Asp Gln Gln Ile Asp Ser Cys Thr
            725                 730                 735
Tyr Glu Ala Met Tyr Asn Ile Gln Ser Gln Ala Thr Pro Ser Val Thr
            740                 745                 750
Glu Ser Ser Thr Phe Gly Glu Gly Ser Leu Ala Ala Ala His Ile Ser
        755                 760                 765
```

```
Thr Gly Pro Glu Glu Ser Glu Asn Glu Glu Asp Gly Tyr Asp Val Pro
    770             775                 780
Lys Pro Pro Met Pro Ala Val Leu Ala Arg Arg Thr Leu Ser Asp Ile
785             790                 795                 800
Ser Asn Ala Ser Ser Ser Phe Gly Trp Leu Ser Leu Glu Gly Asp Pro
                805                 810                 815
Thr Thr Asn Phe Thr Glu Gly Ser Gln Val Pro Glu Arg Pro Pro Lys
            820                 825                 830
Pro Phe Pro Arg Arg Ile Asn Ser Glu Arg Lys Ala Gly Ser Cys Gln
                835                 840                 845
Gln Gly Gly Ala Ala Ala Ser Pro Gln Leu Ser Ser Glu Ile Glu
    850                 855                 860
Asn Leu Leu Ser Gln Gly Tyr Ser Tyr Gln Asp Ile Gln Lys Ala Leu
865             870                 875                 880
Val Ile Ala His Asn Asn Ile Glu Met Ala Lys Asn Ile Leu Arg Glu
                885                 890                 895
Phe Val Ser Ile Ser Ser Pro Ala His Val Ala Thr
            900                 905
```

<210> SEQ ID NO 246
<211> LENGTH: 19
<212> TYPE: DNA
<213> ORGANISM: Artificial Sequence
<220> FEATURE:
<223> OTHER INFORMATION: siRNA sequences for canine Cbl

<400> SEQUENCE: 246
ccagaagttc attcacaaa                                            19

<210> SEQ ID NO 247
<211> LENGTH: 19
<212> TYPE: DNA
<213> ORGANISM: Artificial Sequence
<220> FEATURE:
<223> OTHER INFORMATION: siRNA sequences for canine Cbl

<400> SEQUENCE: 247
ggaacatcct ccagacgat                                            19

<210> SEQ ID NO 248
<211> LENGTH: 19
<212> TYPE: DNA
<213> ORGANISM: Artificial Sequence
<220> FEATURE:
<223> OTHER INFORMATION: siRNA sequences for canine Cbl

<400> SEQUENCE: 248
ccagacgatc cctcacaat                                            19

<210> SEQ ID NO 249
<211> LENGTH: 19
<212> TYPE: DNA
<213> ORGANISM: Artificial Sequence
<220> FEATURE:
<223> OTHER INFORMATION: siRNA sequences for canine Cbl

<400> SEQUENCE: 249
gcttcaggga aggcttcta                                            19

<210> SEQ ID NO 250
<211> LENGTH: 19
<212> TYPE: DNA

```
<213> ORGANISM: Artificial Sequence
<220> FEATURE:
<223> OTHER INFORMATION: siRNA sequences for canine Cbl

<400> SEQUENCE: 250
gcaggaatca gaaggccaa                                                    19

<210> SEQ ID NO 251
<211> LENGTH: 19
<212> TYPE: DNA
<213> ORGANISM: Artificial Sequence
<220> FEATURE:
<223> OTHER INFORMATION: siRNA sequences for canine Cbl

<400> SEQUENCE: 251
cctttctgcc gatgtgaaa                                                    19

<210> SEQ ID NO 252
<211> LENGTH: 19
<212> TYPE: DNA
<213> ORGANISM: Artificial Sequence
<220> FEATURE:
<223> OTHER INFORMATION: siRNA sequences for canine Cbl

<400> SEQUENCE: 252
gctgatgatt ctctcttta                                                    19

<210> SEQ ID NO 253
<211> LENGTH: 19
<212> TYPE: DNA
<213> ORGANISM: Artificial Sequence
<220> FEATURE:
<223> OTHER INFORMATION: siRNA sequences for canine Cbl

<400> SEQUENCE: 253
gcttctggct cccttcata                                                    19

<210> SEQ ID NO 254
<211> LENGTH: 19
<212> TYPE: DNA
<213> ORGANISM: Artificial Sequence
<220> FEATURE:
<223> OTHER INFORMATION: siRNA sequences for canine Cbl

<400> SEQUENCE: 254
gcatctgcca atgccattt                                                    19

<210> SEQ ID NO 255
<211> LENGTH: 19
<212> TYPE: DNA
<213> ORGANISM: Artificial Sequence
<220> FEATURE:
<223> OTHER INFORMATION: siRNA sequences for canine Cbl

<400> SEQUENCE: 255
gctgcacata tgaagcaat                                                    19

<210> SEQ ID NO 256
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 256
cccggagccg ccgccgcccc cgg                                               23
```

<210> SEQ ID NO 257
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 257
tgccgggcgg gtgggggctg agg            23

<210> SEQ ID NO 258
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 258
cggcctcatc gggctcatga agg            23

<210> SEQ ID NO 259
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 259
ggagctcttc ttcacgttgc cgg            23

<210> SEQ ID NO 260
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 260
caacgtgaag aagagctccg ggg            23

<210> SEQ ID NO 261
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 261
ggggctcggg cggcctcatc ggg            23

<210> SEQ ID NO 262
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 262
ggcaacgtga agaagagctc cgg            23

<210> SEQ ID NO 263
<211> LENGTH: 23
<212> TYPE: DNA
<213> ORGANISM: Artificial Sequence
<220> FEATURE:

```
<223> OTHER INFORMATION: CRISPR/CAS9 target sequences for canine Cbl

<400> SEQUENCE: 263
gcaacgtgaa gaagagctcc ggg                                           23

<210> SEQ ID NO 264
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 264
gggggctcgg gcggcctcat cgg                                           23

<210> SEQ ID NO 265
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 265
gtgaagaaga gctccggggc cgg                                           23

<210> SEQ ID NO 266
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 266
tgaagaagag ctccggggcc ggg                                           23

<210> SEQ ID NO 267
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 267
cgtccttcat gagcccgatg agg                                           23

<210> SEQ ID NO 268
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 268
aagaagagct ccggggccgg ggg                                           23

<210> SEQ ID NO 269
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 269
gaagaagagc tccggggccg ggg                                           23
```

```
<210> SEQ ID NO 270
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 270
gatgaggccg cccgagcccc cgg                                            23

<210> SEQ ID NO 271
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 271
gtggtggtgg tgcggctgga agg                                            23

<210> SEQ ID NO 272
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 272
aagagctccg gggccggggg cgg                                            23

<210> SEQ ID NO 273
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 273
cacctcagcc cccacccgcc cgg                                            23

<210> SEQ ID NO 274
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 274
cggcggcggc tccgggggct cgg                                            23

<210> SEQ ID NO 275
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 275
agctccgggg ccgggggcgg cgg                                            23

<210> SEQ ID NO 276
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl
```

```
<400> SEQUENCE: 276
gcgggtgggg gctgaggtgg tgg                                           23

<210> SEQ ID NO 277
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 277
tccggggccg ggggcggcgg cgg                                           23

<210> SEQ ID NO 278
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 278
gccgccgccg cccccggccc cgg                                           23

<210> SEQ ID NO 279
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 279
cgggcgggtg ggggctgagg tgg                                           23

<210> SEQ ID NO 280
<211> LENGTH: 23
<212> TYPE: DNA
<213> ORGANISM: Artificial Sequence
<220> FEATURE:
<223> OTHER INFORMATION: CRISPR/CAS9 target sequences for canine Cbl

<400> SEQUENCE: 280 gccggggcg gcggcggctc cgg                                            23

<210> SEQ ID NO 281
<211> LENGTH: 19
<212> TYPE: DNA
<213> ORGANISM: Artificial Sequence
<220> FEATURE:
<223> OTHER INFORMATION: human CD2AP wobble mutant sequence

<400> SEQUENCE: 281
ggagacggac gacgtaaag                                                19
```